United States Patent
Bartolozzi et al.

(10) Patent No.: US 8,580,825 B2
(45) Date of Patent: Nov. 12, 2013

(54) OXADIAZOLE INHIBITORS OF LEUKOTRIENE PRODUCTION

(75) Inventors: Alessandra Bartolozzi, Norwalk, CT (US); Todd Bosanac, New Milford, CT (US); Zhidong Chen, New Milford, CT (US); Stephane De Lombaert, Branford, CT (US); John D. Huber, New York, NY (US); Weimin Liu, Beijing (CN); Ho Yin Lo, Bethel, CT (US); Pui Leng Loke, Abingdon (GB); Doris Riether, Biberach an der Riss (DE); Heather Tye, Abingdon (GB); Lifen Wu, New Milford, CT (US); Renee M. Zindell, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 8 days.

(21) Appl. No.: 13/237,106

(22) Filed: Sep. 20, 2011

(65) Prior Publication Data

US 2012/0245162 A1   Sep. 27, 2012

Related U.S. Application Data

(60) Provisional application No. 61/533,846, filed on Sep. 13, 2011, provisional application No. 61/385,730, filed on Sep. 23, 2010.

(51) Int. Cl.
*A01N 43/40* (2006.01)
*A61K 31/44* (2006.01)

(52) U.S. Cl.
USPC ..................... 514/340; 546/269.1

(58) Field of Classification Search
USPC ..................... 546/269.1; 514/340
See application file for complete search history.

(56) References Cited

U.S. PATENT DOCUMENTS

| | | | |
|---|---|---|---|
| 6,911,444 B2 | 6/2005 | Lacrampe et al. | |
| 7,319,108 B2 | 1/2008 | Schwink et al. | |
| 2007/0105866 A1 | 5/2007 | Hutchinson et al. | |
| 2009/0192171 A1 | 7/2009 | Hutchinson et al. | |
| 2010/0197591 A1 | 8/2010 | Aspnes et al. | |
| 2011/0206652 A1 | 8/2011 | Kayser et al. | |
| 2011/0206783 A1* | 8/2011 | Burgey et al. | 424/722 |
| 2012/0214787 A1* | 8/2012 | Bartolozzi et al. | 514/210.18 |
| 2012/0220561 A1* | 8/2012 | Bartolozzi et al. | 514/210.2 |
| 2012/0245162 A1 | 9/2012 | Bartolozzi et al. | |
| 2012/0295896 A1* | 11/2012 | Bartolozzi et al. | 514/227.8 |

FOREIGN PATENT DOCUMENTS

| | | |
|---|---|---|
| WO | 2006044602 A2 | 4/2006 |
| WO | 2007056228 A2 | 5/2007 |
| WO | 2007120574 A2 | 10/2007 |
| WO | 2008030369 A1 | 3/2008 |
| WO | 2008128335 A1 | 10/2008 |
| WO | 2008156721 A1 | 12/2008 |
| WO | 2009048547 A1 | 4/2009 |
| WO | 2011143466 A1 | 11/2011 |

OTHER PUBLICATIONS

International Search Report for PCT/US2011/047356 mailed on Oct. 28, 2011.
International Search Report for PCT/US2011/048743 mailed on Nov. 2, 2011.
International Search Report for PCT/US2011/052252 mailed on Nov. 2, 2011.
International Search Report for PCT/US2011/052254 mailed on Nov. 16, 2011.
U.S. Appl. No. 13/237,112, filed Sep. 20, 2011. First named inventor: Alessandra Bartolozzi.
Chabner, Bruce A. et al. "Antineoplastic Agents" Chemotherapy of Neoplastic Diseases, Goodman & Gilmans, The Pharmacological Basis of Therapeutics, (2006) 11th edition, pp. 1315-1403.
Poupaert, Jacques H. "Drug Design: Basic Principles and Applications" Encyclopedia of Pharmaceutical Technology, 3rd Edition, (2007) pp. 1362-1369.
Machine Translation of JP05112564 (May 7, 1993).

* cited by examiner

*Primary Examiner* — James O Wilson
*Assistant Examiner* — Alexander R Pagano
(74) *Attorney, Agent, or Firm* — Michael P. Morris; Usha R. Patel

(57) ABSTRACT

The present invention relates to compounds of formula (I):

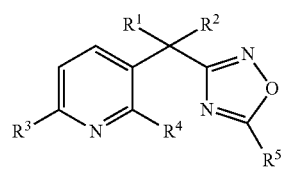

and pharmaceutically acceptable salts thereof, wherein $R^1$-$R^5$ are as defined herein. The invention also relates to pharmaceutical compositions comprising these compounds, methods of using these compounds in the treatment of various diseases and disorders, processes for preparing these compounds and intermediates useful in these processes.

16 Claims, No Drawings

OXADIAZOLE INHIBITORS OF LEUKOTRIENE PRODUCTION

FIELD OF THE INVENTION

This invention relates to oxadiazoles that are useful as inhibitors of five lipoxygenase activating protein (FLAP) and are thus useful for treating a variety of diseases and disorders that are mediated or sustained through the activity of leukotrienes including asthma, allergy, rheumatoid arthritis, multiple sclerosis, inflammatory pain, acute chest syndrome and cardiovascular diseases including atherosclerosis, myocardial infarction and stroke. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LTs) and the biosynthetic pathway from arachidonic acid leading to their production have been the targets of drug discovery efforts for over twenty years. LTs are produced by several cell types including neutrophils, mast cells, eosinophils, basophils monocytes and macrophages. The first committed step in the intracellular synthesis of LTs involves oxidation of arachidonic acid by 5-lipoxygenase (5-LO) to LTA4, a process requiring the presence of the 18 kD integral membrane protein 5-lipoxygenase-activating protein (FLAP) (D. K. Miller et al., Nature, 1990, 343, 278-281; R. A. F. Dixon et al., Nature, 1990, 343, 282-284). Subsequent metabolism of $LTA_4$ leads to $LTB_4$, and the cysteinyl LTs-$LTC_4$, $LTD_4$ and $LTE_4$ (B. Samuelsson, Science, 1983, 220, 568-575). The cysteinyl LTs have potent smooth muscle constricting and bronchoconstricting effects and they stimulate mucous secretion and vascular leakage. $LTB_4$ is a potent chemotactic agent for leukocytes, and stimulates adhesion, aggregation and enzyme release.

Much of the early drug discovery effort in the LT area was directed towards the treatment of allergy, asthma and other inflammatory conditions. Research efforts have been directed towards numerous targets in the pathway including antagonists of $LTB_4$ and the cysteinyl leukotrienes $LTC_4$, $LTD_4$ and $LTE_4$, as well as inhibitors of 5-lipoxygenase (5-LO), $LTA_4$ hydrolase and inhibitors of 5-lipoxygenase activating protein (FLAP) (R. W. Friesen and D. Riendeau, Leukotriene Biosynthesis Inhibitors, Ann. Rep. Med. Chem., 2005, 40, 199-214). Years of effort in the above areas have yielded a few marketed products for the treatment of asthma including a 5-LO inhibitor, zileuton, and LT antagonists, montelukast, pranlukast and zafirlukast.

More recent work has implicated LTs in cardiovascular disease, including myocardial infarction, stroke and atherosclerosis (G. Riccioni et al., J. Leukoc. Biol., 2008, 1374-1378). FLAP and 5-LO were among the components of the 5-LO and LT cascade found in atherosclerotic lesions, suggesting their involvement in atherogenesis (R. Spanbroek et al., Proc. Natl. Acad. Sci. U.S.A., 2003, 100, 1238-1243). Pharmacological inhibition of FLAP has been reported to decrease atherosclerotic lesion size in animal models. In one study, oral dosing of the FLAP inhibitor MK-886 to apoE/LDL-R double knockout mice fed a high-fat diet from 2 months of age to 6 months led to a 56% decrease in plaque coverage in the aorta and a 43% decrease in the aortic root (J. Jawien et al., Eur. J. Clin. Invest., 2006, 36, 141-146). This plaque effect was coupled with a decrease in plaque-macrophage content and a concomitant increase in collagen and smooth muscle content which suggests a conversion to a more stable plaque phenotype. In another study, it was reported that administration of MK-886 via infusion to ApoE$^{-/-}$ xCD4dnTβRII mice (apoE KO mice expressing a dominant-negative TGF-beta receptor which effectively removes all TGF-beta from the system) resulted in about a 40% decrease in plaque area in the aortic root (M. Back et al., Circ. Res., 2007, 100, 946-949). The mice were only treated for four weeks after plaque growth was already somewhat mature (12 weeks) thus raising the possibility of therapeutically treating atherosclerosis via this mechanism. In a study examining human atherosclerotic lesions, it was found that the expression of FLAP, 5-LO and $LTA_4$ hydrolase was significantly increased compared to healthy controls (H. Qiu et al., Proc. Natl. Acad. Sci. U.S.A., 103, 21, 8161-8166). Similar studies suggest that inhibition of the LT pathway, for example by inhibition of FLAP, would be useful for the treatment of atherosclerosis (for reviews, see M. Back Curr. Athero. Reports, 2008 10, 244-251 and Cum Pharm. Des., 2009, 15, 3116-3132).

In addition to the work cited above, many other studies have been directed towards understanding the biological actions of LTs and the role of LTs in disease. These studies have implicated LTs as having a possible role in numerous diseases or conditions (for a review, see M. Peters-Golden and W. R. Henderson, Jr., M.D., N. Engl. J. Med., 2007, 357, 1841-1854). In addition to the specific diseases cited above, LTs have been implicated as having a possible role in numerous allergic, pulmonary, fibrotic, inflammatory and cardiovascular diseases, as well as cancer. Inhibition of FLAP is also reported to be useful for treating renal diseases such as diabetes-induced proteinuria (see for example J. M. Valdivieso et al., Journal of Nephrology, 2003, 16, 85-94 and A Montero et al., Journal of Nephrology, 2003, 16, 682-690).

A number of FLAP inhibitors have been reported in the scientific literature (see for example J. F. Evans et al., Trends in Pharmacological Sciences, 2008, 72-78) and in U.S. patents. Some have been evaluated in clinical trials for asthma, including MK-886, MK-591, and BAY X1005, also known as DG-031. More recently, the FLAP inhibitor AM-103 (J. H. Hutchinson et al., J. Med. Chem. 52, 5803-5815) has been evaluated in clinical trials, based on its anti-inflammatory properties (D. S. Lorrain et al., J. Pharm. Exp. Ther., 2009, DOI:10.1124/jpet.109.158089). Subsequently, it was replaced by the back-up compound AM-803 (GSK-2190915) for the treatment of respiratory diseases. DG-031 has also been in clinical trials to evaluate its effect on biomarkers for myocardial infarction risk and showed a dose-dependent suppression of several biomarkers for the disease (H. Hakonarson et al., JAMA, 2005, 293, 2245-2256). MK-591 was shown in a clinical trial to reduce proteinuria in human glomerulonephritis (see for example A. Guash et al., Kidney International, 1999, 56, 291-267).

However, to date, no FLAP inhibitor has been approved as a marketed drug.

BRIEF SUMMARY OF THE INVENTION

The present invention provides novel compounds which inhibit 5-lipoxygenase activating protein (FLAP) and are thus useful for treating a variety of diseases and disorders that are mediated or sustained through the activity of leukotrienes, including allergic, pulmonary, fibrotic, inflammatory and cardiovascular diseases and cancer. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its first broadest embodiment, the present invention relates to a compound of formula I:

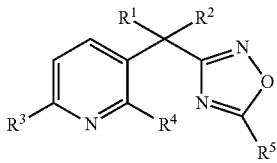

wherein:
$R^1$ and $R^2$ are each independently hydrogen, $C_{1-7}$ alkyl or $C_{3-10}$-carbocycle, with the proviso that both $R^1$ and $R^2$ are not hydrogen;
$R^3$ is a 5-11 membered heteroaryl ring containing one to three heteroatoms selected from nitrogen, oxygen and sulfur, wherein the heteroaryl ring is optionally independently substituted with one to three groups selected from $C_{1-5}$ alkyl, $C_{1-5}$ alkoxy, $C_{1-3}$ alkylhydroxy, amino, $C_{1-3}$ alkylamino, $C_{1-3}$ dialkylamino, oxo, —CN, halogen and 5-6 membered heteroaryl optionally substituted with one to three methyl groups;
$R^4$ is hydrogen, $C_{1-3}$ alkyl, halogen or nitrile;
$R^5$ is $C_{1-6}$ alkyl, $C_{3-10}$ carbocycle, 5-11 membered heterocycle, aryl, 5-11 membered heteroaryl, —C(O)—$R^6$ or —$NR^7R^8$, wherein each $R^5$ is optionally independently substituted with one to three groups selected from $R^9$, $R^{10}$ and $R^{11}$;
$R^6$ is $C_{3-8}$ heterocycle or —NH-5-6 membered heterocycle, each optionally independently substituted with one to three groups selected from $R^9$, $R^{10}$ and $R^{11}$;
$R^7$ and $R^8$ are each independently hydrogen or $C_{1-6}$ alkyl, wherein the alkyl group is optionally substituted with —OH or $C_{1-3}$alkoxy;
$R^9$, $R^{10}$ and $R^{11}$ are independently selected from
(a) —H,
(b) —OH,
(c) halogen,
(d) —CN,
(e) —$CF_3$,
(f) $C_{1-6}$alkyl optionally substituted with one to three —OH, —N($R^{12}$)($R^{13}$), 3-6 membered heterocycle, $C_{1-6}$alkoxy, halogen, CN, —$CO_2R^{12}$, —O—$C_{1-6}$alkyl-O—$C_{1-3}$alkyl, —C(O)N($R^{12}$)($R^{13}$) or —S(O)$_n$$C_{1-6}$alkyl,
(g) $C_{1-6}$alkoxy,
(h) —N($R^{12}$)($R^{13}$),
(i) —S(O)$_n$$C_{1-6}$alkyl,
(j) —$CO_2R^{12}$,
(k) —C(O)N($R^{12}$)($R^{13}$),
(l) —S(O)$_2$N($R^{12}$)($R^{13}$),
(m) a 3-10 membered heterocyclic group optionally substituted with one to three $C_{1-6}$ alkyl groups or oxo,
(n') oxo,
(o) —C(O)—$C_{1-3}$ alkyl;
(p) $C_{1-6}$alkenyl substituted optionally substituted with a —OH;
$R^{12}$ and $R^{13}$ are each independently selected from —H, —$C_{1-6}$alkyl, C(O)$C_{1-6}$alkyl $C_{3-6}$ carbocycle and a 3-6 membered heterocyclic group, each of which is optionally independently substituted with one to three $C_{1-6}$alkyl groups, halogen, —OH, $C_{1-6}$alkoxy, —C(O)N($R^{14}$)($R^{15}$), —S(O)$_n$$C_{1-6}$alkyl, CN, a 3-6 membered heterocyclic group, —O$C_{1-6}$alkyl, $CF_3$, or;
$R^{12}$ and $R^{13}$ taken together with the nitrogen ring to which they are attached form a heterocyclyl ring optionally substituted with one to three —OH, CN, —O$C_{1-6}$alkyl or oxo;
$R^{14}$ and $R^{15}$ are each independently selected from —H and —$C_{1-6}$alkyl;
n is 0, 1 or 2;
or a pharmaceutically acceptable salt thereof.

In a second embodiment, the present invention relates to a compound as described in the broadest embodiment above, wherein:
$R^1$ and $R^2$ are each independently hydrogen, methyl, ethyl, propyl, isopropyl, butyl, isobutyl, tert. butyl, pentyl, hexyl, cyclopropyl, cyclobutyl, cyclopentyl or cylohexyl, with the proviso that both $R^1$ and $R^2$ are not hydrogen;
$R^3$ is pyridinyl, pyrimidinyl, pyrazinyl, pyridazinyl, pyrrolyl, imidazolyl, thienyl, furanyl or thiazolyl, wherein each heteroaryl ring is optionally independently substituted with one to three groups selected from $C_{1-3}$ alkyl, $C_{1-3}$ alkoxy, $C_{1-3}$ alkylhydroxy, amino, $C_{1-3}$ alkylamino and $C_{1-3}$ dialkylamino, oxo, —CN, halogen and 5-6 membered heteroaryl optionally substituted with one to three methyl groups; or
$R^3$ is pyrrolopyrazinyl or pyrido-oxazinyl;
$R^4$ is hydrogen, methyl or fluoro;
$R^5$ is methyl, ethyl, propyl, isopropyl, butyl, isobutyl, tert-butyl, pentyl, hexyl, cyclopropyl, cyclobutyl, cyclopentyl, cyclohexyl, cycloheptyl, cyclooctyl, phenyl, piperidinyl, piperazinyl, morpholinyl, thiomorpholinyl, pyrrolidinyl, tetrahydropyranyl, pyrrolyl, thienyl, furanyl, thiazolyl, oxazolyl, isoxazolyl, pyrazolyl, imidazolyl, triazolyl, pyridinyl, pyrimidinyl, pyrazinyl, pyridazinyl, quinolinyl, isoquinolinyl, indolyl, pyrrolopyridinyl, pyrrolopyrimidinyl, pyrazolopyrimidinyl, pyrazolopyridinyl, —C(O)—$R^6$ or —$NR^7R^8$, wherein each $R^5$ is optionally independently substituted with one to three groups selected from $R^9$, $R^{10}$ and $R^{11}$;
$R^6$ is piperidinyl, piperazinyl, tetrahydropyranyl, morpholinyl, thiomorpholinyl or —NH-piperadinyl each optionally independently substituted with one to three groups selected from $R^9$, $R^{10}$ and $R^{11}$;
$R^7$ and $R^8$ are each independently hydrogen or $C_{1-5}$ alkyl wherein the alkyl group is optionally substituted with —OH or $C_{1-3}$alkoxy;
$R^9$, $R^{10}$ and $R^{11}$ are independently selected from
(a) —H,
(b) —OH,
(c) halogen,
(d) —CN,
(e) —$CF_3$,
(f) $C_{1-6}$alkyl optionally substituted with one to three —OH, —N($R^{12}$)($R^{13}$), 3-6 membered heterocycle, $C_{1-6}$alkoxy, halogen, CN, —$CO_2R^{12}$, —O—$C_{1-6}$alkyl-O—$C_{1-3}$alkyl, —C(O)N($R^{12}$)($R^{13}$) or —S(O)$_n$$C_{1-6}$alkyl,
(g) $C_{1-6}$alkoxy,
(h) —N($R^{12}$)($R^{13}$),
(i) —S(O)$_n$$C_{1-6}$alkyl,
(j) —$CO_2R^{12}$,
(k) —C(O)N($R^{12}$)($R^{13}$),
(l) —S(O)$_2$N($R^{12}$)($R^{13}$),
(m) a 3-8 membered heterocyclic group optionally substituted with one to three $C_{1-6}$ alkyl groups or oxo,
(n') oxo,
(o) —C(O)—$C_{1-3}$ alkyl, (p) $C_{1-6}$alkenyl substituted optionally substituted with a —OH;

$R^{12}$ and $R^{13}$ are each independently selected from —H, —$C_{1-6}$alkyl, C(O)$C_{1-6}$alkyl, $C_{3-6}$ carbocycle, and a 3-6 membered heterocyclic group, each of which is optionally independently substituted with one to three $C_{1-6}$alkyl groups, halogen, —OH, $C_{1-6}$alkoxy, —C(O)N($R^{14}$)($R^{15}$), —S(O)$_n$$C_{1-6}$alkyl, CN, a 3-6 membered heterocyclic group, —O$C_{1-6}$alkyl, CF$_3$; or, $R^{12}$ and $R^{13}$ taken together with the nitrogen ring to which they are attached can form a heterocyclyl ring optionally substituted with one to three —OH, CN, —O$C_{1-6}$alkyl or oxo;

$R^{14}$ and $R^{15}$ are each independently selected from —H and —$C_{1-4}$alkyl;

n is 1 or 2;

or a pharmaceutically acceptable salt thereof.

In a third embodiment, the present invention relates to a compound as described in any of the preceding embodiments above, wherein:

$R^1$ and $R^2$ are each independently hydrogen, methyl, ethyl, propyl, isopropyl, tert-butyl, cyclopropyl or cyclobutyl, with the proviso that both $R^1$ and $R^2$ are not hydrogen;

or a pharmaceutically acceptable salt thereof.

In a fourth embodiment there is provided a compound of formula (I) as described in any of the preceding embodiments above, wherein:

$R^3$ is pyridinyl, pyrazinyl, pyridazinyl or pyrimidinyl, wherein each heteroaryl ring is optionally independently substituted with one to two groups selected from $C_{1-3}$ alkyl, $C_1$-$C_3$ alkoxy, $C_{1-2}$ alkylhydroxy, dimethylpyrrole, oxo, —CN, halogen, $C_{1-3}$ alkylamino and amino; or $R^3$ is pyrrolopyrazinyl or pyrido-oxazinyl;

or a pharmaceutically acceptable salt thereof.

In a fifth embodiment there is provided a compound as described in any of the preceding embodiments above, wherein:

$R^5$ is methyl, ethyl, propyl, isopropyl, butyl, pentyl, hexyl, cyclopropyl, cyclobutyl, cyclopentyl, cyclohexyl, phenyl, piperidinyl, piperazinyl, morpholinyl, tetrahydropyranyl, thiazolyl, oxazolyl, isoxazolyl, pyrazolyl, imidazolyl, pyridinyl, pyrimidinyl, pyrazinyl, pyridazinyl, quinolinyl, isoquinolinyl, pyrrolopyridinyl, pyrrolopyrimidinyl, pyrazolopyrimidinyl, pyrazolopyridinyl, —C(O)-piperizinyl, —C(O)-piperidinyl, —C(O)—NH-piperidinyl or —NR$^7$R$^8$, wherein each $R^5$ is optionally independently substituted with one to three groups selected from $R^9$, $R^{10}$ and $R^{11}$;

$R^7$ and $R^8$ are each independently hydrogen or $C_1$-$C_5$ alkyl wherein the alkyl group is optionally substituted with —OH or $C_{1-3}$alkoxy;

$R^9$, $R^{10}$ and $R^{11}$ are independently selected from (a) —H,
(b) —OH,
(c) halogen,
(d) —CN,
(e) —CF$_3$,
(f) $C_{1-6}$alkyl optionally substituted with one to three —OH, halogen, CN, —CO$_2$R$^{12}$, —O—$C_{1-6}$alkyl-O—$C_{1-3}$alkyl, —N(R$^{12}$)(R$^{13}$), morpholinyl, piperazinyl, $C_{1-6}$alkoxy, —SO$_2$$C_{1-3}$alkyl or —C(O)N(R$^{12}$)(R$^{13}$),
(g) $C_{1-3}$alkoxy,
(h) —N(R$^{12}$)(R$^{13}$),
(i) —S(O)$_2$$C_{1-6}$alkyl,
(j) —CO$_2$R$^{12}$,
(k) —C(O)N(R$^{12}$)(R$^{13}$),
(l) —S(O)$_2$N(R$^{12}$)(R$^{13}$),
(m) morpholinyl, piperazinyl, piperidinyl, tetrahydropyranyl, tetrahydrothienyl, dioxotetrahydrothienyl or oxetanyl each optionally substituted with a methyl group,
(n') oxo,
(o) —C(O)—CH$_3$,
(p) $C_{1-6}$alkenyl substituted optionally substituted with a —OH;

$R^{12}$ and $R^{13}$ are each independently selected from —H, $C_{3-6}$ carbocycle, 3-6 membered heterocycle and —$C_{1-6}$alkyl, wherein the alkyl group is optionally substituted with one to three halogen, —OH, $C_{1-6}$alkoxy, 5-6 membered heterocyclic group, —C(O)N(R$^{14}$)(R$^{15}$) or —S(O)$_2$$C_{1-6}$alkyl; or $R^{12}$ and $R^{13}$ taken together with the nitrogen ring to which they are attached form a heterocyclyl ring selected from pyrrolidinyl, piperidinyl and morpholinyl, wherein each heterocyclic ring is optionally substituted with one to three —OH, CN, —O$C_{1-6}$alkyl or oxo;

$R^{14}$ and $R^{15}$ are each independently selected from —H and —$C_{1-4}$alkyl;

or a pharmaceutically acceptable salt thereof.

In a sixth embodiment there is provided a compound of formula (I) as described in the first or second embodiment above, wherein:

$R^1$ and $R^2$ are each independently hydrogen, methyl, isopropyl, or cyclopropyl, with the proviso that both $R^1$ and $R^2$ are not hydrogen;

$R^3$ is pyridinyl, pyrazinyl, pyridazinyl or pyrimidinyl, wherein each heteroaryl ring is optionally independently substituted with one to two groups selected from $C_{1-3}$ alkyl, methoxy, —CH$_2$OH, amino, —NH—CH$_3$, oxo, —CN, fluoro and 2,5-dimethylpyrrole; or $R^3$ is pyrrolopyrazinyl or pyrido-oxazinyl;

$R^4$ is hydrogen;

$R^5$ is pyrazolyl, imidazolyl, pyridinyl, pyrimidinyl, pyrazinyl, pyridazinyl, piperazinyl, pyrazolopyrimidinyl, phenyl or —NR$^7$R$^8$, wherein each $R^5$ is optionally independently substituted with one to three groups selected from $R^9$, $R^{10}$ and $R^{11}$;

$R^7$ and $R^8$ are each independently hydrogen, methyl or ethyl optionally substituted with hydroxy;

$R^9$, $R^{10}$ and $R^{11}$ are independently selected from (a) —H,
(b) —OH,
(c) halogen,
(d) —CN,
(e) —CF$_3$,
(f) $C_{1-6}$alkyl optionally substituted with one to three —OH, —N(R$^{12}$)(R$^{13}$), morpholinyl, piperazinyl, $C_{1-3}$alkoxy, halogen, CN, —CO$_2$R$^{12}$, —O—$C_{1-6}$alkyl-O—$C_{1-3}$alkyl, —SO$_2$CH$_3$ or —C(O)N(R$^{12}$)(R$^{13}$),
(g) $C_{1-3}$alkoxy,
(h) —N(R$^{12}$)(R$^{13}$),
(i) —S(O)$_2$$C_{1-2}$alkyl,
(j) —CO$_2$R$^{12}$,
(k) —C(O)N(R$^{12}$)(R$^{13}$),
(l) —S(O)$_2$N(R$^{12}$)(R$^{13}$),
(m) morpholinyl, piperazinyl, tetrahydropyranyl, dioxotetrahydrothienyl or oxetanyl each optionally substituted with a methyl group,
(n') oxo,
(o) —C(O)—CH$_3$,
(p) $C_{1-4}$alkenyl substituted optionally substituted with a —OH;

$R^{12}$ and $R^{13}$ are each independently selected from —H, cyclopropyl, tetrahydrofuranyl, tetrahydropyranyl and —$C_{1-6}$alkyl, wherein the alkyl group is optionally independently substituted with one to three halogen, —OH, $C_{1-6}$alkoxy, tetrahydrofuranyl, tetrahydropyranyl, —C(O)N($R^{14}$)($R^{15}$), or —S(O)$_2C_{1-6}$alkyl; or $R^{12}$ and $R^{13}$ taken together with the nitrogen ring to which they are attached form a heterocyclyl ring selected from pyrrolidinyl, piperidinyl and morpholinyl, wherein each heterocyclic ring is optionally substituted with one to three —OH, CN, —OC$_{1-6}$alkyl or oxo;

$R^{14}$ and $R^{15}$ are each independently selected from —H and —C$_{1-4}$alkyl;

or a pharmaceutically acceptable salt thereof.

In a seventh embodiment there is provided a compound as described in the sixth embodiment above, wherein:

$R^1$ is methyl, $R^2$ is selected from methyl, isopropyl and cyclopropyl;

or a pharmaceutically acceptable salt thereof.

In an eighth embodiment there is provided a compound as described in the sixth embodiment above, wherein:

$R^3$ is selected from

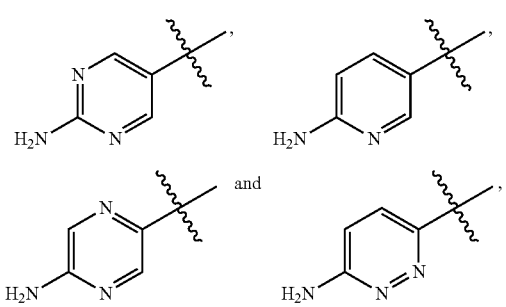 [SMILES: *c1cnc(N)nc1 ; *c1ccc(N)nc1 ; *c1cnc(N)cn1 ; *c1ccc(N)nn1]

or a pharmaceutically acceptable salt thereof.

In a ninth embodiment there is provided a compound as described in the sixth embodiment above, wherein:

$R^5$ is pyrazolyl optionally independently substituted with one to three groups selected from $R^9$, $R^{10}$ and $R^{11}$;

or a pharmaceutically acceptable salt thereof.

In a tenth embodiment there is provided a compound as described in the sixth embodiment above, wherein:

$R^1$ is methyl, $R^2$ is selected from methyl, isopropyl and cyclopropyl;

$R^3$ is selected from

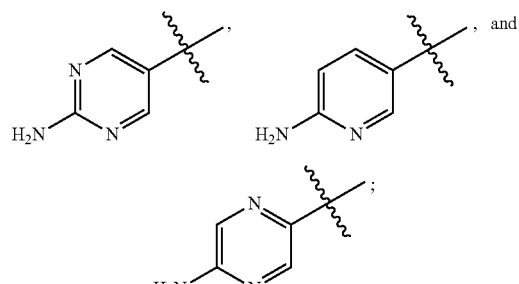

$R^4$ is hydrogen, $R^5$ is selected from

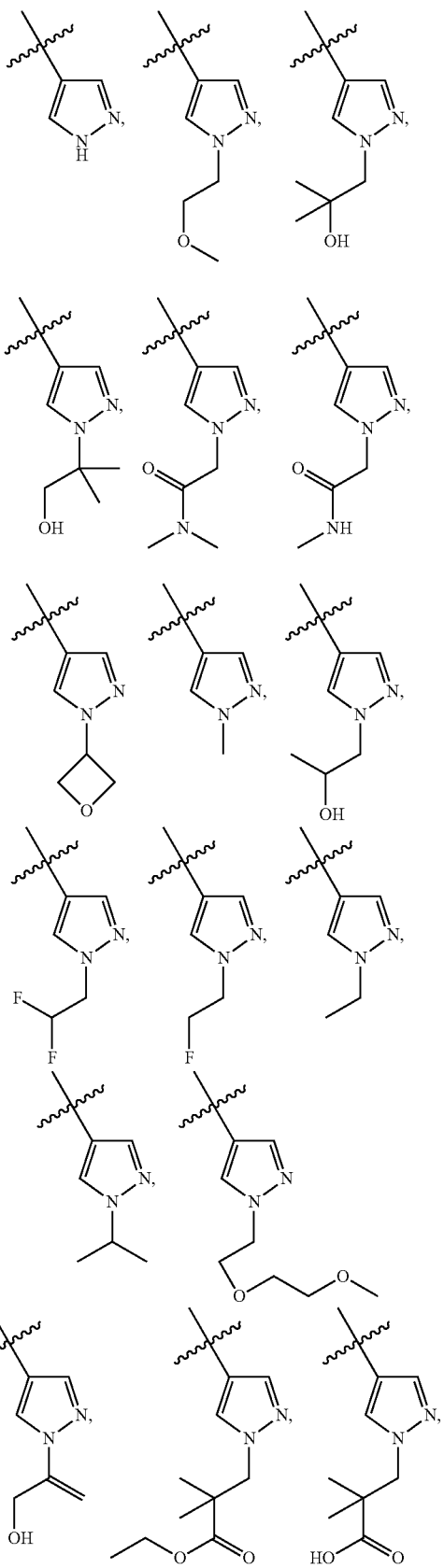

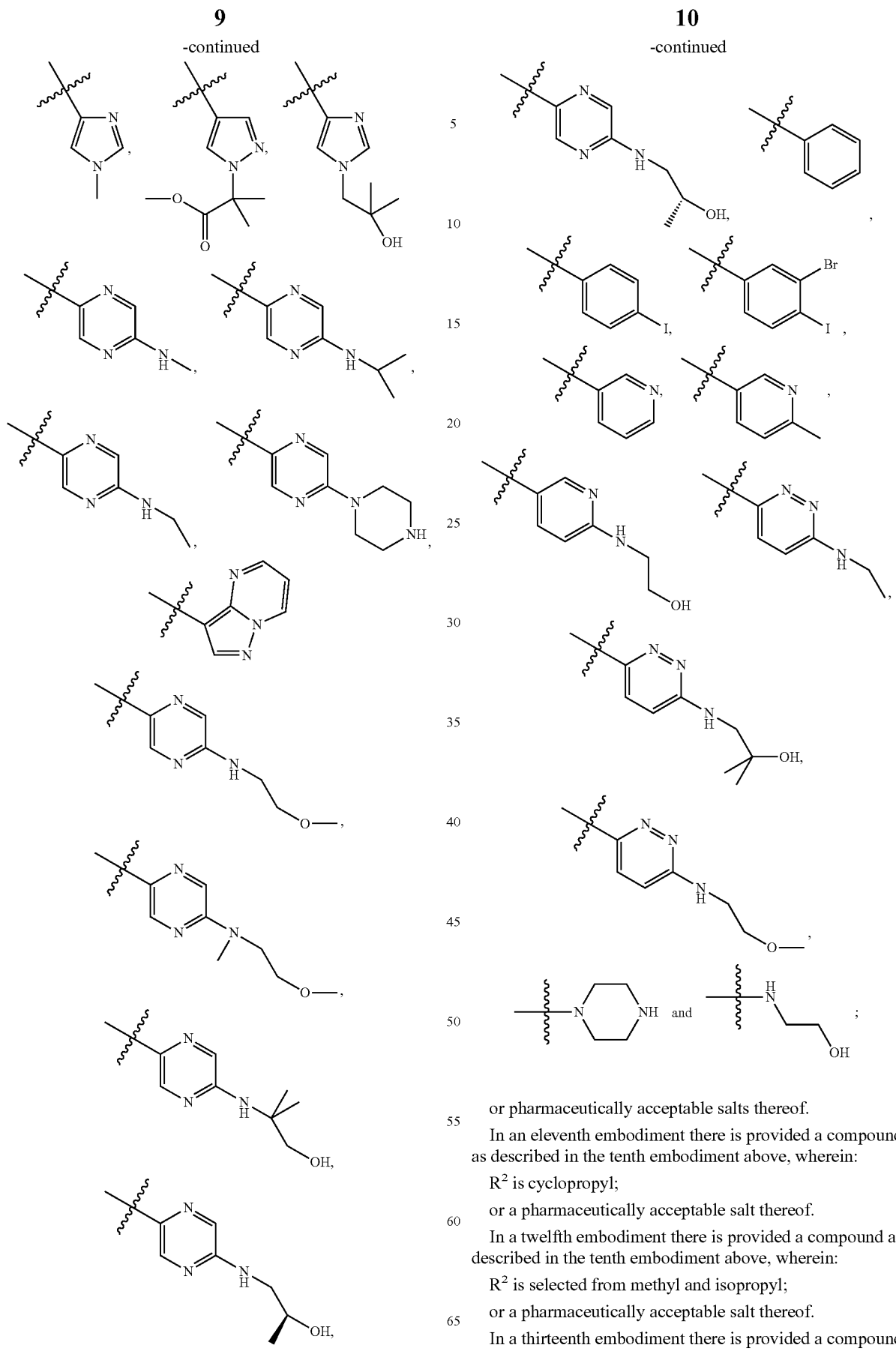

or pharmaceutically acceptable salts thereof.

In an eleventh embodiment there is provided a compound as described in the tenth embodiment above, wherein:

$R^2$ is cyclopropyl;

or a pharmaceutically acceptable salt thereof.

In a twelfth embodiment there is provided a compound as described in the tenth embodiment above, wherein:

$R^2$ is selected from methyl and isopropyl;

or a pharmaceutically acceptable salt thereof.

In a thirteenth embodiment there is provided a compound as described in the sixth embodiment above, wherein:

$R^3$ is selected from various heteroaryl groups shown, or a pharmaceutically acceptable salt thereof.

In a fourteenth embodiment there is provided a compound as described in the sixth embodiment above, wherein:

$R^1$ is methyl,
$R^2$ is selected from methyl, isopropyl and cyclopropyl;
$R^3$ is selected from the structures shown, $R^4$ is hydrogen,
$R^5$ is selected from the pyrazole-based structures shown.

-continued
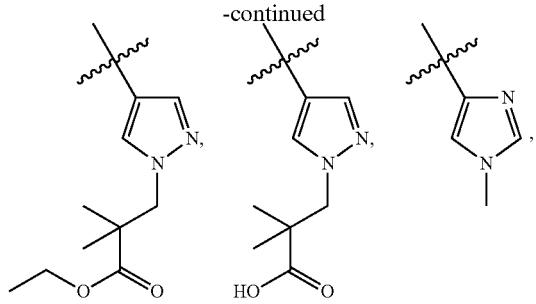
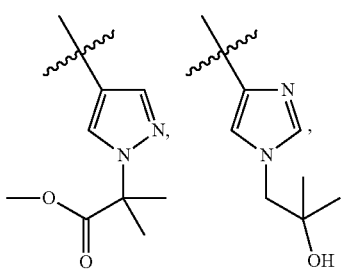
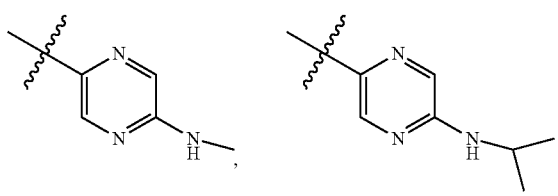
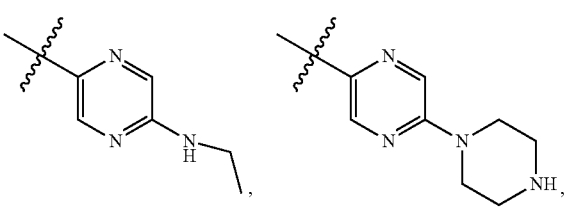
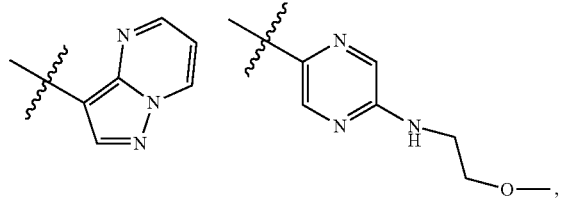
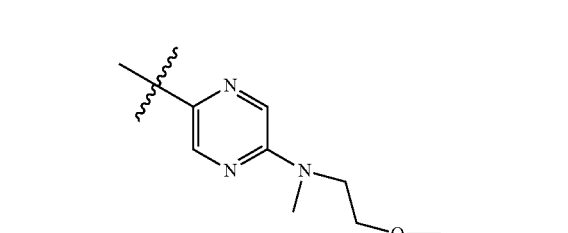
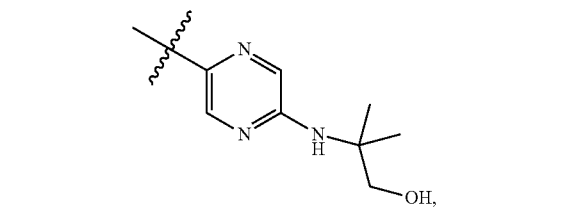
-continued
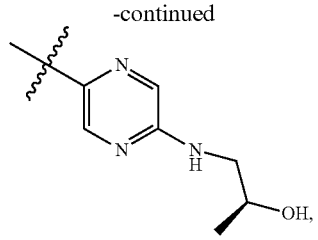
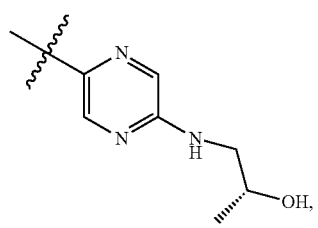
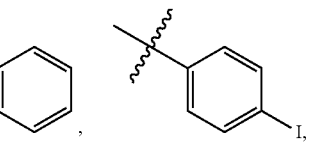
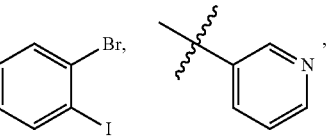
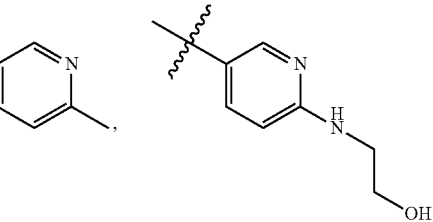
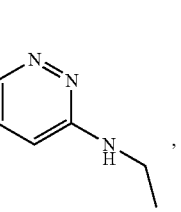
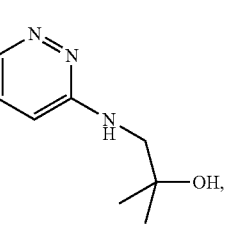

-continued

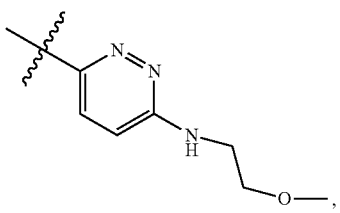

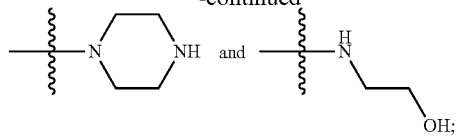

or pharmaceutically acceptable salts thereof.

The following are representative compounds of the invention which can be made by the general synthetic schemes, the examples, and known methods in the art.

TABLE I

| Example | Structure | Name |
| --- | --- | --- |
| 1 | 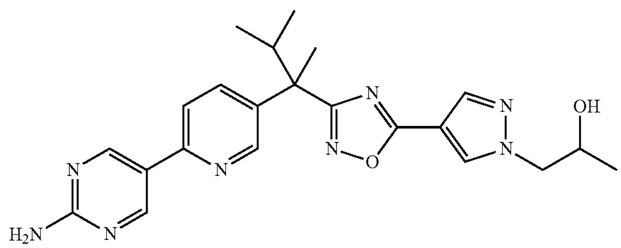 [SMILES: CC(O)Cn1cc(-c2nc(C(C)(c3ccc(-c4cnc(N)nc4)nc3)C(C)C)no2)cn1] | 1-[4-(3-{2-[6-(2-aminopyrimidin-5-yl)pyridin-3-yl]-3-methylbutan-2-yl}-1,2,4-oxadiazol-5-yl)-1H-pyrazol-1-yl]propan-2-ol |
| 2 | 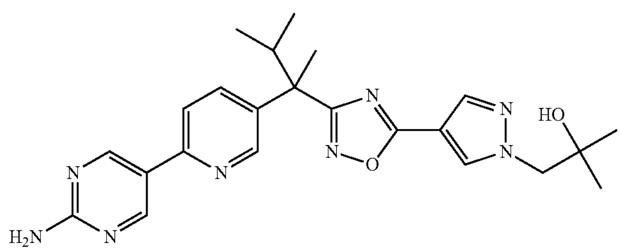 [SMILES: CC(C)C(C)(c1ccc(-c2cnc(N)nc2)nc1)c1noc(-c2cnn(CC(C)(C)O)c2)n1] | 1-[4-(3-{2-[6-(2-aminopyrimidin-5-yl)pyridin-3-yl]-3-methylbutan-2-yl}-1,2,4-oxadiazol-5-yl)-1H-pyrazol-1-yl]-2-methylpropan-2-ol |
| 3 | 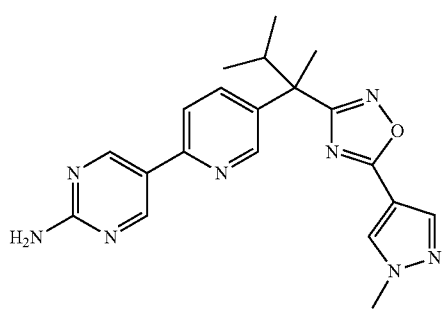 [SMILES: CC(C)C(C)(c1ccc(-c2cnc(N)nc2)nc1)c1noc(-c2cnn(C)c2)n1] | 5-(5-{3-methyl-2-[5-(1-methyl-1H-pyrazol-4-yl)-1,2,4-oxadiazol-3-yl]butan-2-yl}pyridin-2-yl)pyrimidin-2-amine |
| 4 | 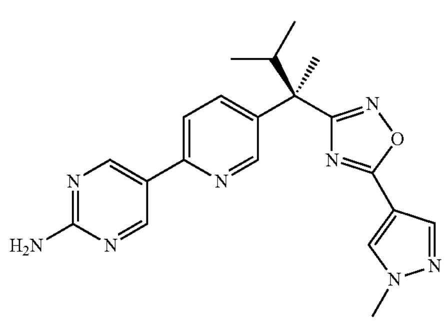 [SMILES: CC(C)[C@](C)(c1ccc(-c2cnc(N)nc2)nc1)c1noc(-c2cnn(C)c2)n1] | 5-(5-{(2R)-3-methyl-2-[5-(1-methyl-1H-pyrazol-4-yl)-1,2,4-oxadiazol-3-yl]butan-2-yl}pyridin-2-yl)pyrimidin-2-amine |

TABLE I-continued

| Example | Structure | Name |
|---|---|---|
| 5 | 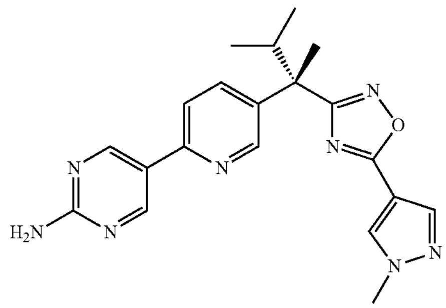 [SMILES: CC(C)[C@@](C)(c1ccc(-c2cnc(N)nc2)nc1)c1noc(-c2cnn(C)c2)n1] | 5-(5-{(2S)-3-methyl-2-[5-(1-methyl-1H-pyrazol-4-yl)-1,2,4-oxadiazol-3-yl]butan-2-yl}pyridin-2-yl)pyrimidin-2-amine |
| 6 | 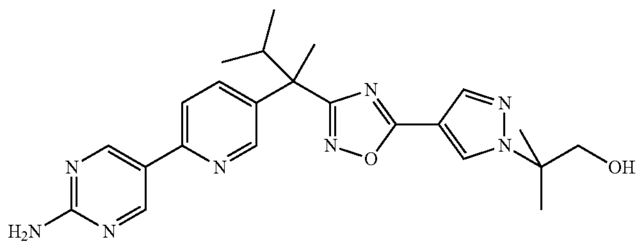 [SMILES: CC(C)C(C)(c1ccc(-c2cnc(N)nc2)nc1)c1noc(-c2cnn(C(C)(C)CO)c2)n1] | 2-[4-(3-{2-[6-(2-aminopyrimidin-5-yl)pyridin-3-yl]-3-methylbutan-2-yl}-1,2,4-oxadiazol-5-yl)-1H-pyrazol-1-yl]-2-methylpropan-1-ol |
| 7 | 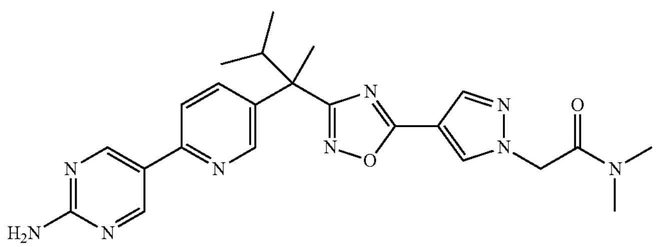 [SMILES: CC(C)C(C)(c1ccc(-c2cnc(N)nc2)nc1)c1noc(-c2cnn(CC(=O)N(C)C)c2)n1] | 2-[4-(3-{2-[6-(2-aminopyrimidin-5-yl)pyridin-3-yl]-3-methylbutan-2-yl}-1,2,4-oxadiazol-5-yl)-1H-pyrazol-1-yl]-N,N-dimethylacetamide |
| 8 | 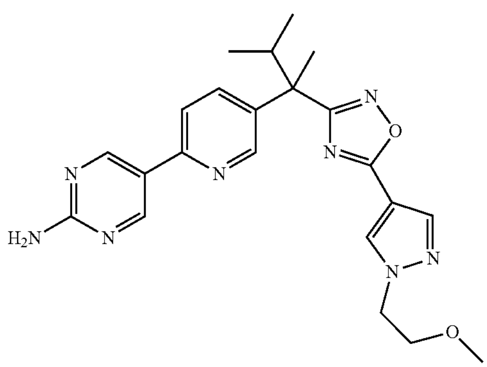 [SMILES: COCCn1cc(-c2nc(C(C)(c3ccc(-c4cnc(N)nc4)nc3)C(C)C)no2)cn1] | 5-[5-(2-{5-[1-(2-methoxyethyl)-1H-pyrazol-4-yl]-1,2,4-oxadiazol-3-yl}-3-methylbutan-2-yl)pyridin-2-yl]pyrimidin-2-amine |
| 9 | 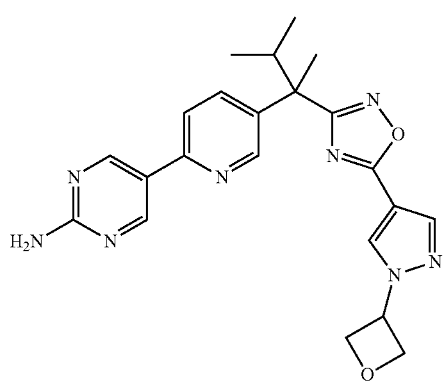 [SMILES: CC(C)C(C)(c1ccc(-c2cnc(N)nc2)nc1)c1noc(-c2cnn(C3COC3)c2)n1] | 5-[5-(3-methyl-2-{5-[1-(oxetan-3-yl)-1H-pyrazol-4-yl]-1,2,4-oxadiazol-3-yl}butan-2-yl)pyridin-2-yl]pyrimidin-2-amine |

TABLE I-continued

| Example | Structure | Name |
|---|---|---|
| 10 | 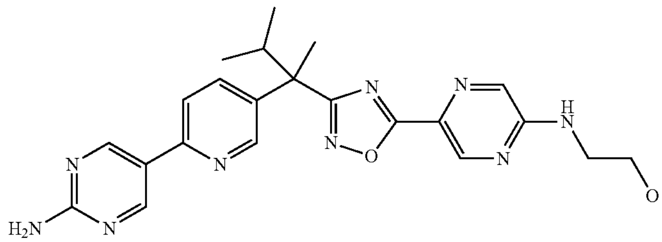 [SMILES: CC(C)C(C)(c1ccc(-c2cnc(N)nc2)nc1)c1noc(-c2cnc(NCCO)cn2)n1] | 5-{5-[2-(5-{5-[(2-methoxyethyl)amino]pyrazin-2-yl}-1,2,4-oxadiazol-3-yl)-3-methylbutan-2-yl]pyridin-2-yl}pyrimidin-2-amine |
| 11 | 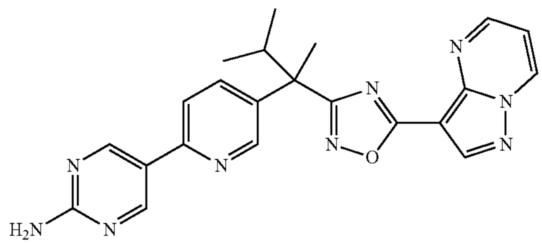 [SMILES: CC(C)C(C)(c1ccc(-c2cnc(N)nc2)nc1)c1noc(-c2cnn3cccnc23)n1] | 5-(5-{3-methyl-2-[5-(pyrazolo[1,5-a]pyrimidin-3-yl)-1,2,4-oxadiazol-3-yl]butan-2-yl}pyridin-2-yl)pyrimidin-2-amine |
| 12 | 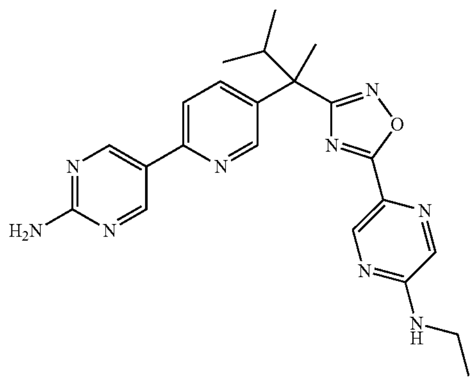 [SMILES: CCNc1cnc(-c2nc(C(C)(c3ccc(-c4cnc(N)nc4)nc3)C(C)C)no2)cn1] | 5-[5-(2-{5-[5-(ethylamino)pyrazin-2-yl]-1,2,4-oxadiazol-3-yl}-3-methylbutan-2-yl)pyridin-2-yl]pyrimidin-2-amine |
| 13 | 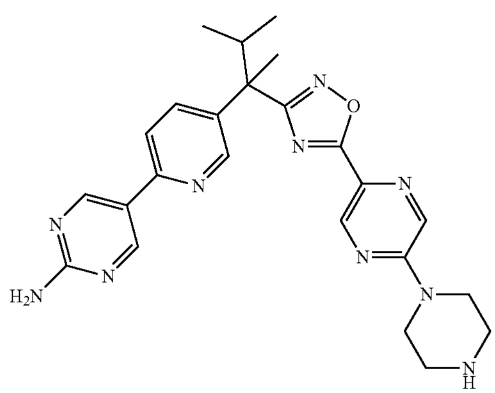 [SMILES: CC(C)C(C)(c1ccc(-c2cnc(N)nc2)nc1)c1noc(-c2cnc(N3CCNCC3)cn2)n1] | 5-[5-(3-methyl-2-{5-[5-(piperazin-1-yl)pyrazin-2-yl]-1,2,4-oxadiazol-3-yl}butan-2-yl)pyridin-2-yl]pyrimidin-2-amine |
| 14 | 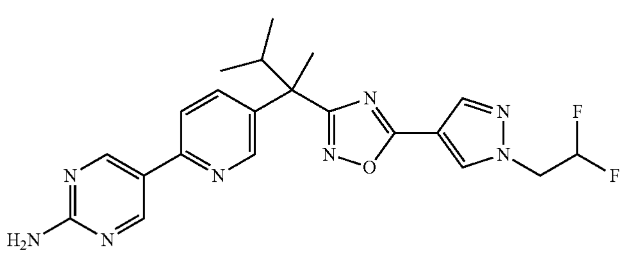 [SMILES: CC(C)C(C)(c1ccc(-c2cnc(N)nc2)nc1)c1noc(-c2cnn(CC(F)F)c2)n1] | 5-[5-(2-{5-[1-(2,2-difluoroethyl)-1H-pyrazol-4-yl]-1,2,4-oxadiazol-3-yl}-3-methylbutan-2-yl)pyridin-2-yl]pyrimidin-2-amine |

TABLE I-continued

| Example | Structure | Name |
|---|---|---|
| 15 | 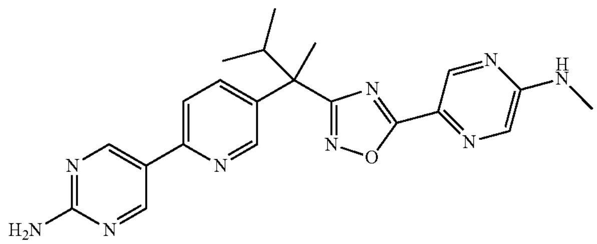 [SMILES: CNc1cnc(-c2nc(C(C)(c3ccc(-c4cnc(N)nc4)nc3)C(C)C)no2)cn1] | 5-[5-(3-methyl-2-{5-[5-(methylamino)pyrazin-2-yl]-1,2,4-oxadiazol-3-yl}butan-2-yl)pyridin-2-yl]pyrimidin-2-amine |
| 16 | 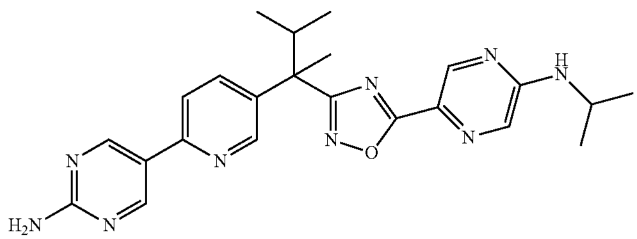 [SMILES: CC(C)Nc1cnc(-c2nc(C(C)(c3ccc(-c4cnc(N)nc4)nc3)C(C)C)no2)cn1] | 5-[5-(3-methyl-2-{5-[5-(propan-2-ylamino)pyrazin-2-yl]-1,2,4-oxadiazol-3-yl}butan-2-yl)pyridin-2-yl]pyrimidin-2-amine |
| 17 | 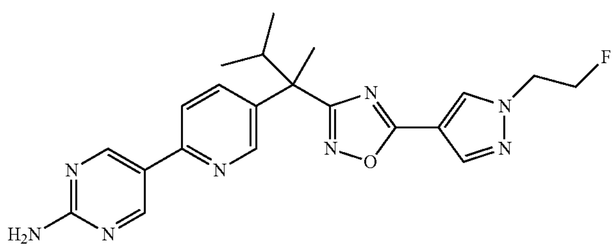 [SMILES: CC(C)C(C)(c1ccc(-c2cnc(N)nc2)nc1)c1noc(-c2cnn(CCF)c2)n1] | 5-[5-(2-{5-[1-(2-fluoroethyl)-1H-pyrazol-4-yl]-1,2,4-oxadiazol-3-yl}-3-methylbutan-2-yl)pyridin-2-yl]pyrimidin-2-amine |
| 18 | 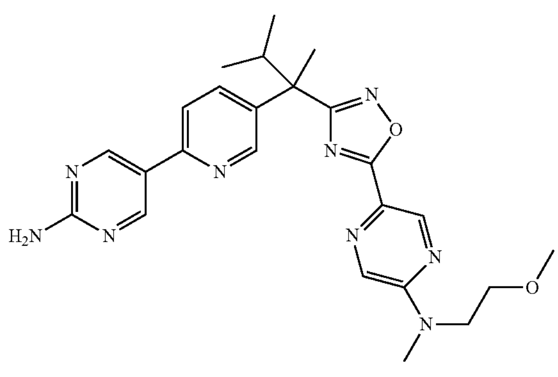 [SMILES: COCCN(C)c1cnc(-c2nc(C(C)(c3ccc(-c4cnc(N)nc4)nc3)C(C)C)no2)cn1] | 5-{5-[2-(5-{5-[(2-methoxyethyl)(methyl)amino]pyrazin-2-yl}-1,2,4-oxadiazol-3-yl)-3-methylbutan-2-yl]pyridin-2-yl}pyrimidin-2-amine |
| 19 | 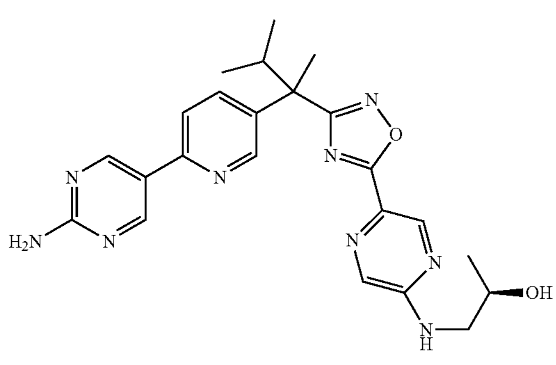 [SMILES: CC(C)C(C)(c1ccc(-c2cnc(N)nc2)nc1)c1noc(-c2cnc(NC[C@@H](C)O)cn2)n1] | (2R)-1-{[5-(3-{2-[6-(2-aminopyrimidin-5-yl)pyridin-3-yl]-3-methylbutan-2-yl}-1,2,4-oxadiazol-5-yl)pyrazin-2-yl]amino}propan-2-ol |

TABLE I-continued

| Example | Structure | Name |
|---|---|---|
| 20 | 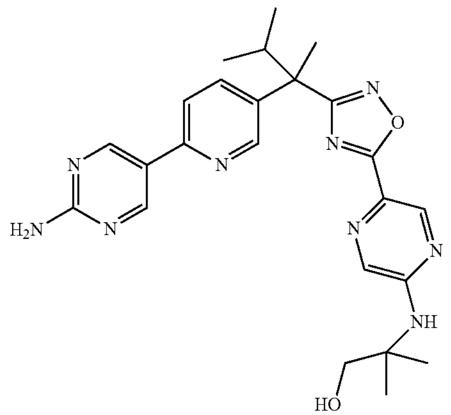 [SMILES: CC(C)C(C)(c1ccc(-c2cnc(N)nc2)nc1)c1noc(-c2cnc(NC(C)(C)CO)cn2)n1] | 2-{[5-(3-{2-[6-(2-aminopyrimidin-5-yl)pyridin-3-yl]-3-methylbutan-2-yl}-1,2,4-oxadiazol-5-yl)pyrazin-2-yl]amino}-2-methylpropan-1-ol |
| 21 | 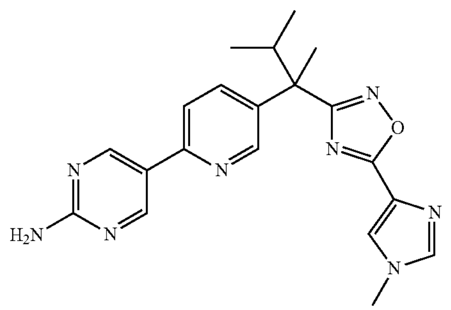 [SMILES: CC(C)C(C)(c1ccc(-c2cnc(N)nc2)nc1)c1noc(-c2cn(C)cn2)n1] | 5-(5-{3-methyl-2-[5-(1-methyl-1H-imidazol-4-yl)-1,2,4-oxadiazol-3-yl]butan-2-yl}pyridin-2-yl)pyrimidin-2-amine |
| 22 | 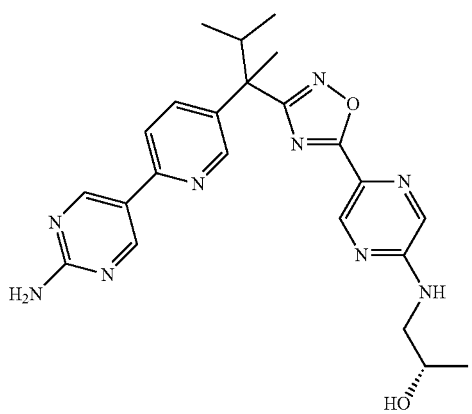 [SMILES: CC(C)C(C)(c1ccc(-c2cnc(N)nc2)nc1)c1noc(-c2cnc(NC[C@H](C)O)cn2)n1] | (2S)-1-{[5-(3-{2-[6-(2-aminopyrimidin-5-yl)pyridin-3-yl]-3-methylbutan-2-yl}-1,2,4-oxadiazol-5-yl)pyrazin-2-yl]amino}propan-2-ol |
| 23 | 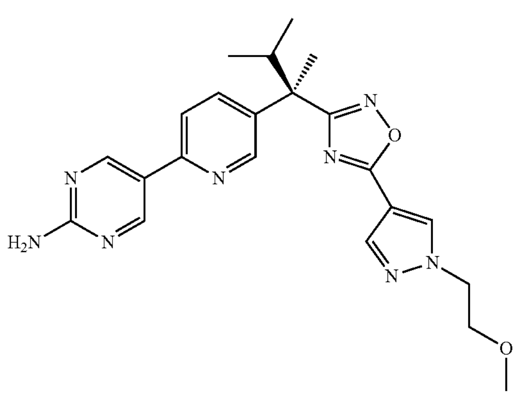 [SMILES: COCCn1cc(-c2nc([C@@](C)(c3ccc(-c4cnc(N)nc4)nc3)C(C)C)no2)cn1] | 5-{5-[(2R)-2-{5-[1-(2-methoxyethyl)-1H-pyrazol-4-yl]-1,2,4-oxadiazol-3-yl}-3-methylbutan-2-yl]pyridin-2-yl}pyrimidin-2-amine |

TABLE I-continued

| Example | Structure | Name |
|---|---|---|
| 24 | 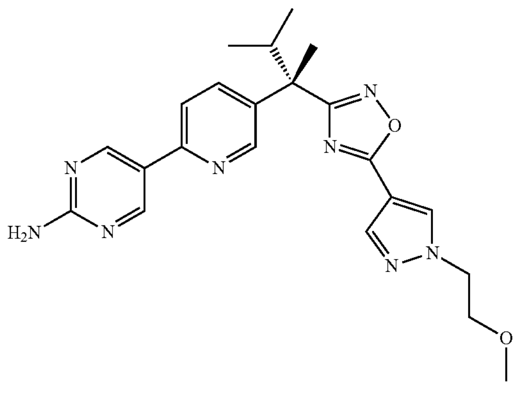 [SMILES: COCCn1cc(-c2nc([C@](C)(c3ccc(-c4cnc(N)nc4)nc3)C(C)C)no2)cn1] | 5-{5-[(2S)-2-{5-[1-(2-methoxyethyl)-1H-pyrazol-4-yl]-1,2,4-oxadiazol-3-yl}-3-methylbutan-2-yl]pyridin-2-yl}pyrimidin-2-amine |
| 25 | 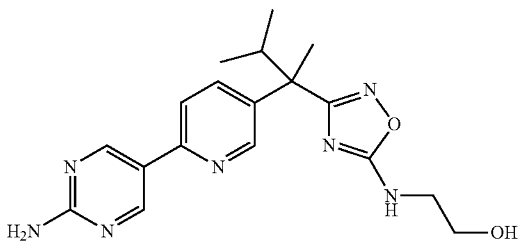 [SMILES: CC(C)C(C)(c1ccc(-c2cnc(N)nc2)nc1)c1noc(NCCO)n1] | 2-[(3-{2-[6-(2-aminopyrimidin-5-yl)pyridin-3-yl]-3-methylbutan-2-yl}-1,2,4-oxadiazol-5-yl)amino]ethanol |
| 26 | 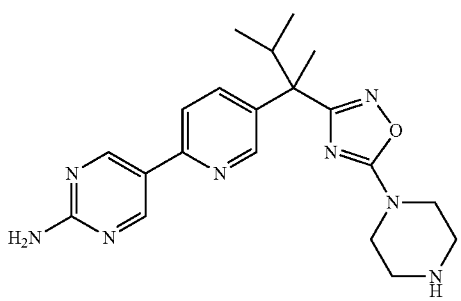 [SMILES: CC(C)C(C)(c1ccc(-c2cnc(N)nc2)nc1)c1noc(N2CCNCC2)n1] | 5-(5-{3-methyl-2-[5-(piperazin-1-yl)-1,2,4-oxadiazol-3-yl]butan-2-yl}pyridin-2-yl)pyrimidin-2-amine |
| 27 | 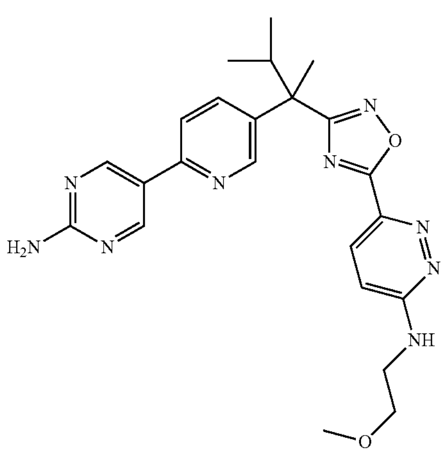 [SMILES: COCCNc1ccc(-c2nc(C(C)(c3ccc(-c4cnc(N)nc4)nc3)C(C)C)no2)nn1] | 6-(3-{2-[6-(2-aminopyrimidin-5-yl)pyridin-3-yl]-3-methylbutan-2-yl}-1,2,4-oxadiazol-5-yl)-N-(2-methoxyethyl)pyridazin-3-amine |

TABLE I-continued

| Example | Structure | Name |
|---|---|---|
| 28 | 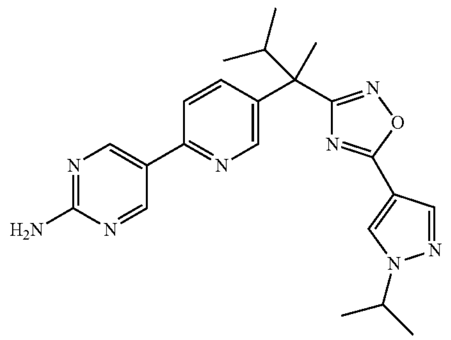 [SMILES: CC(C)n1cc(-c2nc(C(C)(c3ccc(-c4cnc(N)nc4)nc3)C(C)C)no2)cn1] | 5-[5-(3-methyl-2-{5-[1-(propan-2-yl)-1H-pyrazol-4-yl]-1,2,4-oxadiazol-3-yl}butan-2-yl)pyridin-2-yl]pyrimidin-2-amine |
| 29 | 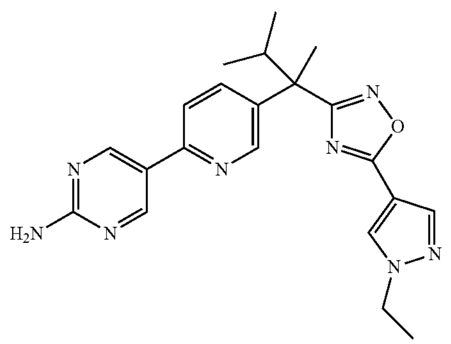 [SMILES: CCn1cc(-c2nc(C(C)(c3ccc(-c4cnc(N)nc4)nc3)C(C)C)no2)cn1] | 5-(5-{2-[5-(1-ethyl-1H-pyrazol-4-yl)-1,2,4-oxadiazol-3-yl]-3-methylbutan-2-yl}pyridin-2-yl)pyrimidin-2-amine |
| 30 | 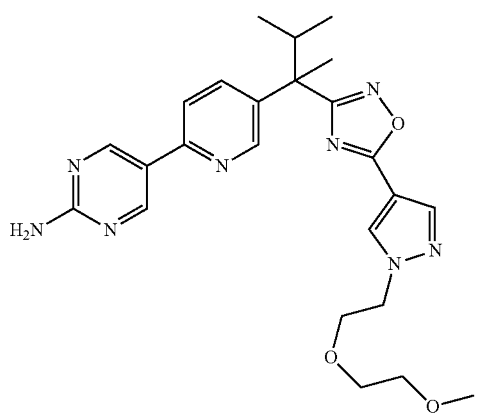 [SMILES: COCCOCCn1cc(-c2nc(C(C)(c3ccc(-c4cnc(N)nc4)nc3)C(C)C)no2)cn1] | 5-{5-[2-(5-{1-[2-(2-methoxyethoxy)ethyl]-1H-pyrazol-4-yl}-1,2,4-oxadiazol-3-yl)-3-methylbutan-2-yl]pyridin-2-yl}pyrimidin-2-amine |
| 31 | 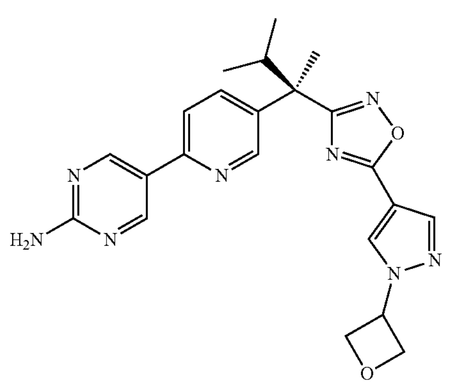 [SMILES: CC(C)[C@](C)(c1ccc(-c2cnc(N)nc2)nc1)c1noc(-c2cnn(C3COC3)c2)n1] | 5-{5-[(2R)-3-methyl-2-{5-[1-(oxetan-3-yl)-1H-pyrazol-4-yl]-1,2,4-oxadiazol-3-yl}butan-2-yl]pyridin-2-yl}pyrimidin-2-amine |

TABLE I-continued

| Example | Structure | Name |
|---|---|---|
| 32 | 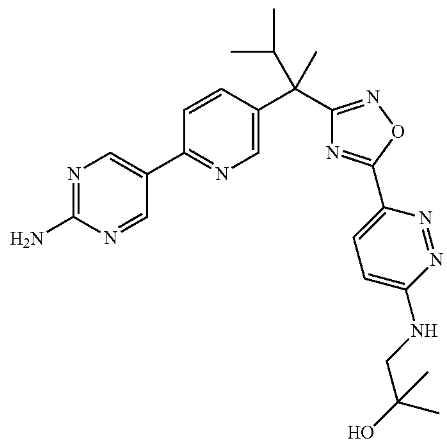 [SMILES: CC(C)C(C)(c1ccc(-c2cnc(N)nc2)nc1)c1noc(-c2ccc(NCC(C)(C)O)nn2)n1] | 1-{[6-(3-{2-[6-(2-aminopyrimidin-5-yl)pyridin-3-yl]-3-methylbutan-2-yl}-1,2,4-oxadiazol-5-yl)pyridazin-3-yl]amino}-2-methylpropan-2-ol |
| 33 | 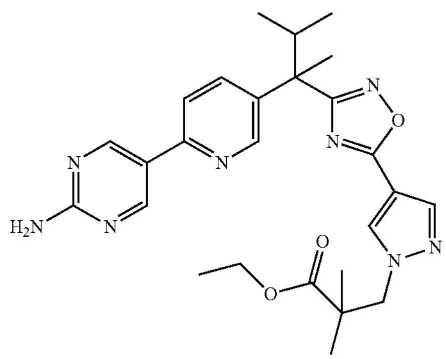 [SMILES: CCOC(=O)C(C)(C)Cn1cc(-c2nc(C(C)(c3ccc(-c4cnc(N)nc4)nc3)C(C)C)no2)cn1] | ethyl 3-[4-(3-{2-[6-(2-aminopyrimidin-5-yl)pyridin-3-yl]-3-methylbutan-2-yl}-1,2,4-oxadiazol-5-yl)-1H-pyrazol-1-yl]-2,2-dimethylpropanoate |
| 34 | 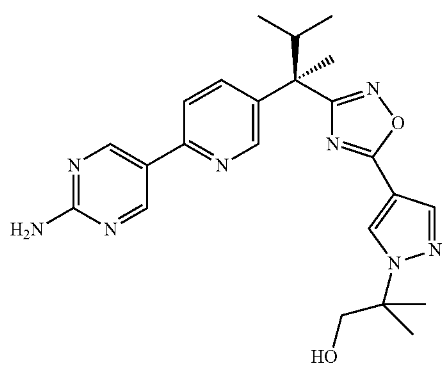 [SMILES: CC(C)[C@](C)(c1ccc(-c2cnc(N)nc2)nc1)c1noc(-c2cnn(C(C)(C)CO)c2)n1] | 2-[4-(3-{(2R)-2-[6-(2-aminopyrimidin-5-yl)pyridin-3-yl]-3-methylbutan-2-yl}-1,2,4-oxadiazol-5-yl)-1H-pyrazol-1-yl]-2-methylpropan-1-ol |
| 35 | 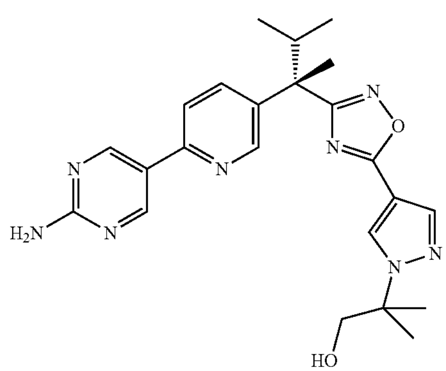 [SMILES: CC(C)[C@@](C)(c1ccc(-c2cnc(N)nc2)nc1)c1noc(-c2cnn(C(C)(C)CO)c2)n1] | 2-[4-(3-{(2S)-2-[6-(2-aminopyrimidin-5-yl)pyridin-3-yl]-3-methylbutan-2-yl}-1,2,4-oxadiazol-5-yl)-1H-pyrazol-1-yl]-2-methylpropan-1-ol |

TABLE I-continued

| Example | Structure | Name |
|---|---|---|
| 36 | 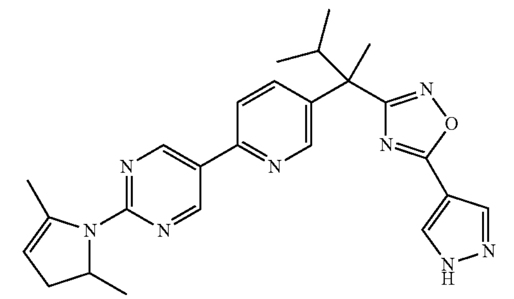 [SMILES: CC1=CCC(C)N1c1ncc(-c2ccc(C(C)(c3noc(-c4cn[nH]c4)n3)C(C)C)cn2)cn1] | 2-(2,5-dimethyl-1H-pyrrol-1-yl)-5-(5-{3-methyl-2-[5-(1H-pyrazol-4-yl)-1,2,4-oxadiazol-3-yl]butan-2-yl}pyridin-2-yl)pyrimidine |
| 37 | 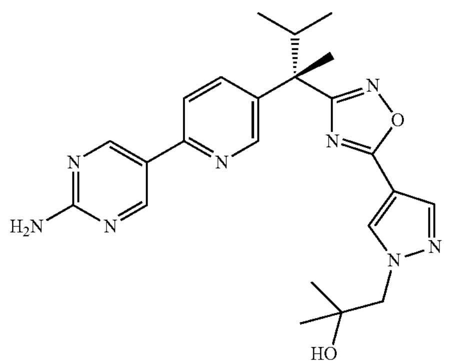 [SMILES: CC(C)[C@@](C)(c1ccc(-c2cnc(N)nc2)nc1)c1noc(-c2cnn(CC(C)(C)O)c2)n1] | 1-[4-(3-{(2S)-2-[6-(2-aminopyrimidin-5-yl)pyridin-3-yl]-3-methylbutan-2-yl}-1,2,4-oxadiazol-5-yl)-1H-pyrazol-1-yl]-2-methylpropan-2-ol |
| 38 | 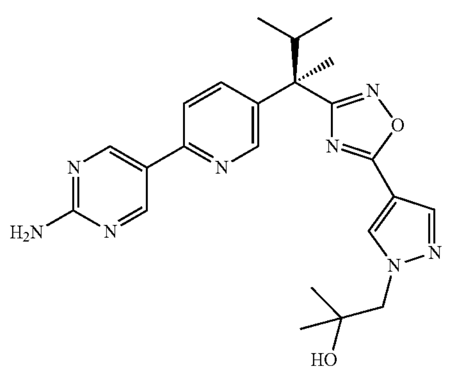 [SMILES: CC(C)[C@](C)(c1ccc(-c2cnc(N)nc2)nc1)c1noc(-c2cnn(CC(C)(C)O)c2)n1] | 1-[4-(3-{(2R)-2-[6-(2-aminopyrimidin-5-yl)pyridin-3-yl]-3-methylbutan-2-yl}-1,2,4-oxadiazol-5-yl)-1H-pyrazol-1-yl]-2-methylpropan-2-ol |
| 39 | 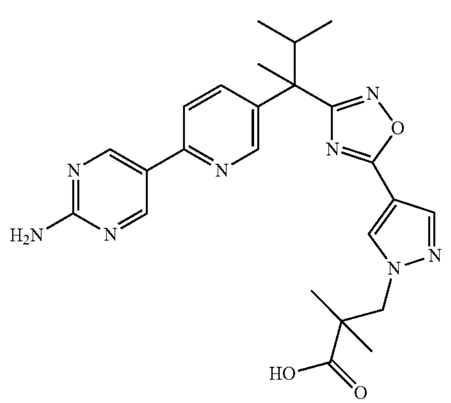 [SMILES: CC(C)C(C)(c1ccc(-c2cnc(N)nc2)nc1)c1noc(-c2cnn(CC(C)(C)C(=O)O)c2)n1] | 3-[4-(3-{2-[6-(2-aminopyrimidin-5-yl)pyridin-3-yl]-3-methylbutan-2-yl}-1,2,4-oxadiazol-5-yl)-1H-pyrazol-1-yl]-2,2-dimethylpropanoic acid |

TABLE I-continued

| Example | Structure | Name |
|---|---|---|
| 40 | 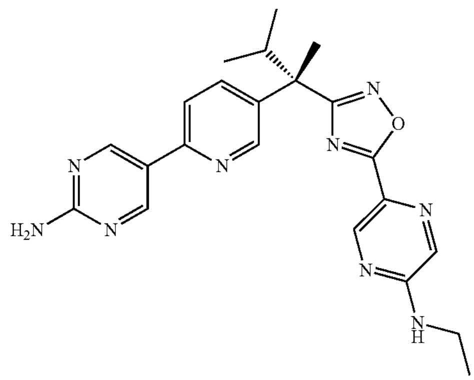 [SMILES: CCNc1cnc(-c2nc([C@](C)(c3ccc(-c4cnc(N)nc4)nc3)C(C)C)no2)cn1] | 5-{5-[(2S)-2-{5-[5-(ethylamino)pyrazin-2-yl]-1,2,4-oxadiazol-3-yl}-3-methylbutan-2-yl]pyridin-2-yl}pyrimidin-2-amine |
| 41 | 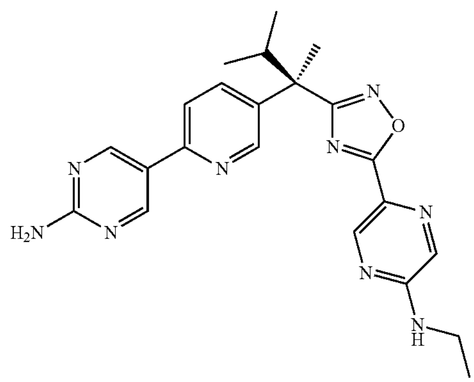 [SMILES: CCNc1cnc(-c2nc([C@@](C)(c3ccc(-c4cnc(N)nc4)nc3)C(C)C)no2)cn1] | 5-{5-[(2R)-2-{5-[5-(ethylamino)pyrazin-2-yl]-1,2,4-oxadiazol-3-yl}-3-methylbutan-2-yl]pyridin-2-yl}pyrimidin-2-amine |
| 42 | 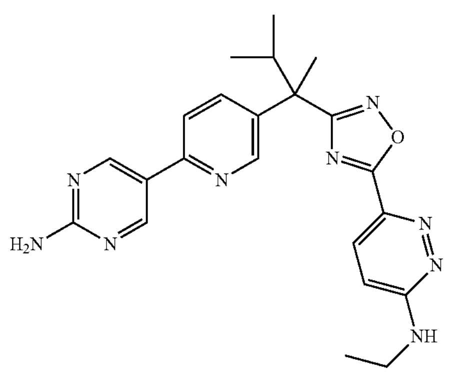 [SMILES: CCNc1ccc(-c2nc(C(C)(c3ccc(-c4cnc(N)nc4)nc3)C(C)C)no2)nn1] | 6-(3-{2-[6-(2-aminopyrimidin-5-yl)pyridin-3-yl]-3-methylbutan-2-yl}-1,2,4-oxadiazol-5-yl)-N-ethylpyridazin-3-amine |
| 43 | 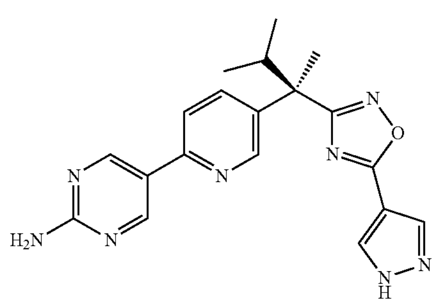 [SMILES: CC(C)[C@](C)(c1ccc(-c2cnc(N)nc2)nc1)c1noc(-c2cn[nH]c2)n1] | 5-(5-{(2R)-3-methyl-2-[5-(1H-pyrazol-4-yl)-1,2,4-oxadiazol-3-yl]butan-2-yl}pyridin-2-yl)pyrimidin-2-amine |

TABLE I-continued

| Example | Structure | Name |
|---|---|---|
| 44 | 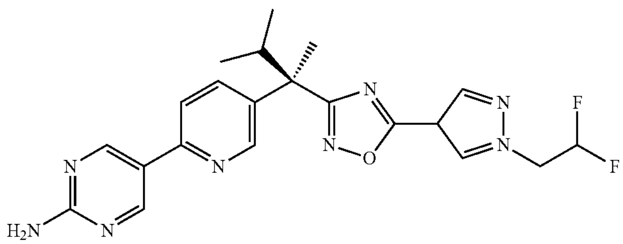 | 5-{5-[(2R)-2-{5-[1-(2,2-difluoroethyl)-1H-pyrazol-4-yl]-1,2,4-oxadiazol-3-yl}-3-methylbutan-2-yl]pyridin-2-yl}pyrimidin-2-amine |
| 45 | 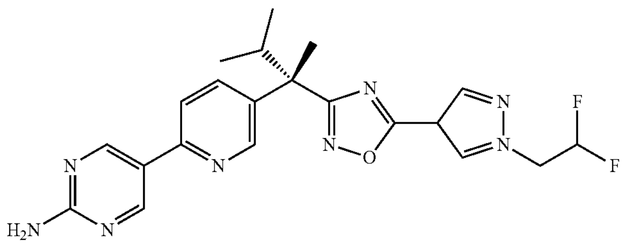 | 5-{5-[(2S)-2-{5-[1-(2,2-difluoroethyl)-1H-pyrazol-4-yl]-1,2,4-oxadiazol-3-yl}-3-methylbutan-2-yl]pyridin-2-yl}pyrimidin-2-amine |
| 46 | 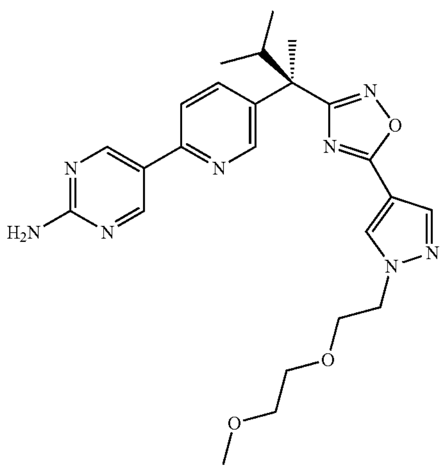 [SMILES: COCCOCCn1cc(-c2nc([C@@](C)(c3ccc(-c4cnc(N)nc4)nc3)C(C)C)no2)cn1] | 5-{5-[(2R)-2-(5-{1-[2-(2-methoxyethoxy)ethyl]-1H-pyrazol-4-yl}-1,2,4-oxadiazol-3-yl)-3-methylbutan-2-yl]pyridin-2-yl}pyrimidin-2-amine |
| 47 | 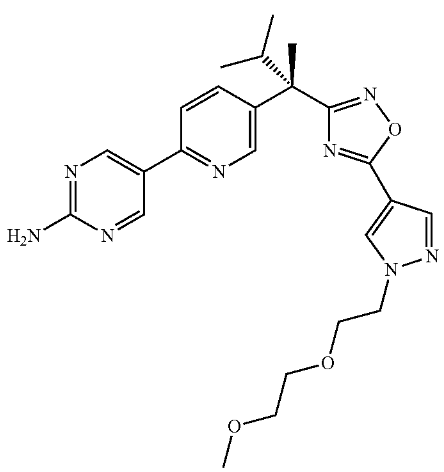 [SMILES: COCCOCCn1cc(-c2nc([C@](C)(c3ccc(-c4cnc(N)nc4)nc3)C(C)C)no2)cn1] | 5-{5-[(2S)-2-(5-{1-[2-(2-methoxyethoxy)ethyl]-1H-pyrazol-4-yl}-1,2,4-oxadiazol-3-yl)-3-methylbutan-2-yl]pyridin-2-yl}pyrimidin-2-amine |

TABLE I-continued

| Example | Structure | Name |
|---|---|---|
| 48 | 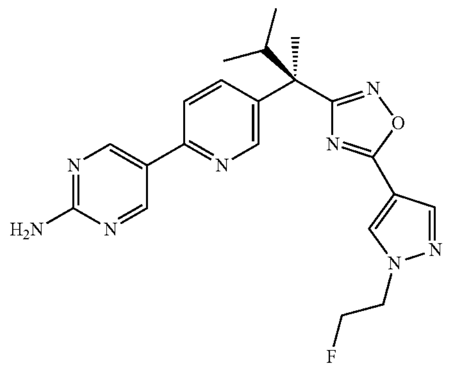 [SMILES: CC(C)[C@](C)(c1ccc(-c2cnc(N)nc2)nc1)c1noc(-c2cnn(CCF)c2)n1] | 5-{5-[(2R)-2-{5-[1-(2-fluoroethyl)-1H-pyrazol-4-yl]-1,2,4-oxadiazol-3-yl}-3-methylbutan-2-yl]pyridin-2-yl}pyrimidin-2-amine |
| 49 | 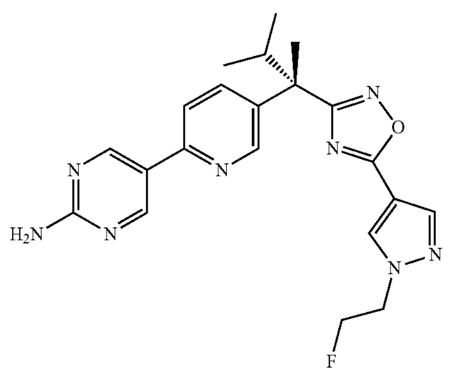 [SMILES: CC(C)[C@@](C)(c1ccc(-c2cnc(N)nc2)nc1)c1noc(-c2cnn(CCF)c2)n1] | 5-{5-[(2S)-2-{5-[1-(2-fluoroethyl)-1H-pyrazol-4-yl]-1,2,4-oxadiazol-3-yl}-3-methylbutan-2-yl]pyridin-2-yl}pyrimidin-2-amine |
| 50 | 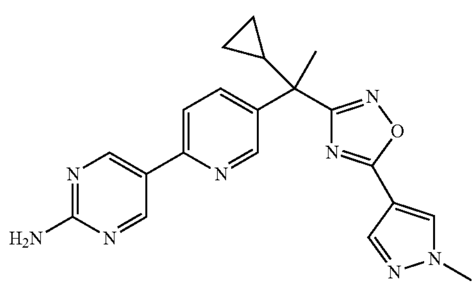 [SMILES: Cn1cc(-c2nc(C(C)(c3ccc(-c4cnc(N)nc4)nc3)C3CC3)no2)cn1] | 5-(5-{1-cyclopropyl-1-[5-(1-methyl-1H-pyrazol-4-yl)-1,2,4-oxadiazol-3-yl]ethyl}pyridin-2-yl)pyrimidin-2-amine |
| 51 | 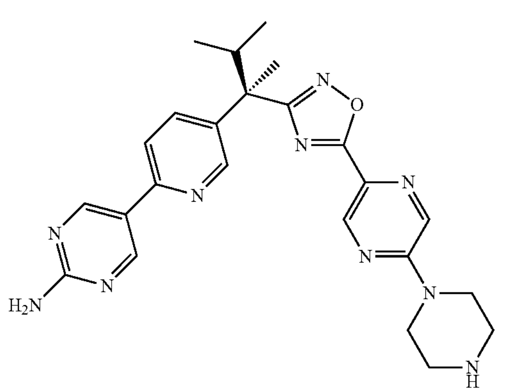 [SMILES: CC(C)[C@](C)(c1ccc(-c2cnc(N)nc2)nc1)c1noc(-c2cnc(N3CCNCC3)cn2)n1] | 5-{5-[(2R)-3-methyl-2-{5-[5-(piperazin-1-yl)pyrazin-2-yl]-1,2,4-oxadiazol-3-yl}butan-2-yl]pyridin-2-yl}pyrimidin-2-amine |

TABLE I-continued

| Example | Structure | Name |
|---|---|---|
| 52 | 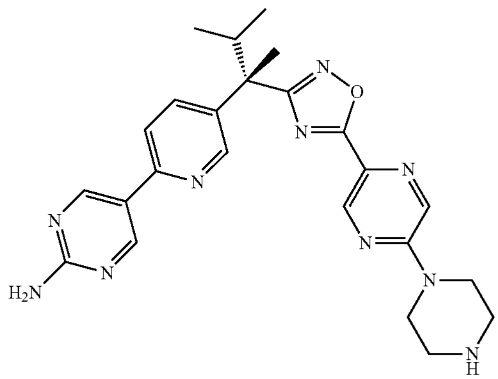 [SMILES: CC(C)[C@@](C)(c1ccc(-c2cnc(N)nc2)nc1)c1noc(-c2cnc(N3CCNCC3)cn2)n1] | 5-{5-[(2S)-3-methyl-2-{5-[5-(piperazin-1-yl)pyrazin-2-yl]-1,2,4-oxadiazol-3-yl}butan-2-yl]pyridin-2-yl}pyrimidin-2-amine |
| 53 | 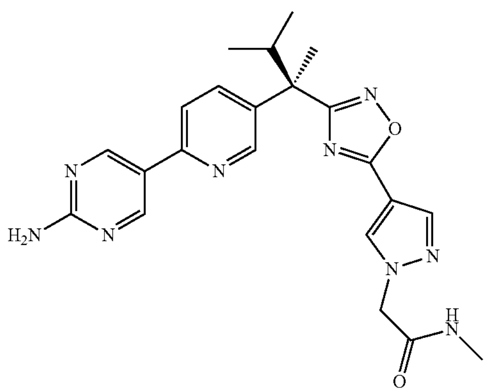 [SMILES: CNC(=O)Cn1cc(-c2nc([C@@](C)(c3ccc(-c4cnc(N)nc4)nc3)C(C)C)no2)cn1] | 2-[4-(3-{(2R)-2-[6-(2-aminopyrimidin-5-yl)pyridin-3-yl]-3-methylbutan-2-yl}-1,2,4-oxadiazol-5-yl)-1H-pyrazol-1-yl]-N-methylacetamide |
| 54 | 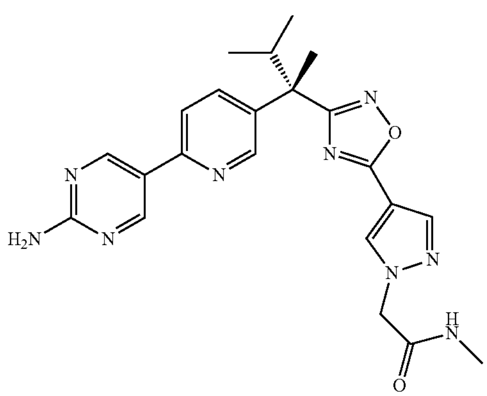 [SMILES: CNC(=O)Cn1cc(-c2nc([C@](C)(c3ccc(-c4cnc(N)nc4)nc3)C(C)C)no2)cn1] | 2-[4-(3-{(2S)-2-[6-(2-aminopyrimidin-5-yl)pyridin-3-yl]-3-methylbutan-2-yl}-1,2,4-oxadiazol-5-yl)-1H-pyrazol-1-yl]-N-methylacetamide |
| 55 | 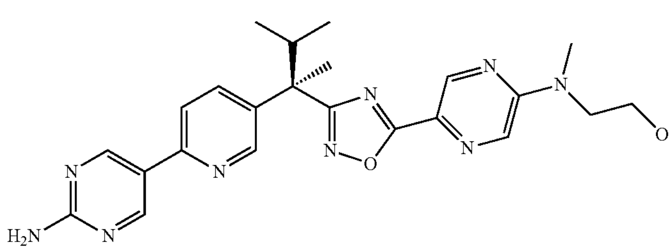 [SMILES: CC(C)[C@](C)(c1ccc(-c2cnc(N)nc2)nc1)c1noc(-c2cnc(N(C)CCO)cn2)n1] | 5-{5-[(2R)-2-(5-{5-[(2-methoxyethyl)(methyl)amino]pyrazin-2-yl}-1,2,4-oxadiazol-3-yl)-3-methylbutan-2-yl]pyridin-2-yl}pyrimidin-2-amine |

TABLE I-continued

| Example | Structure | Name |
|---|---|---|
| 56 | 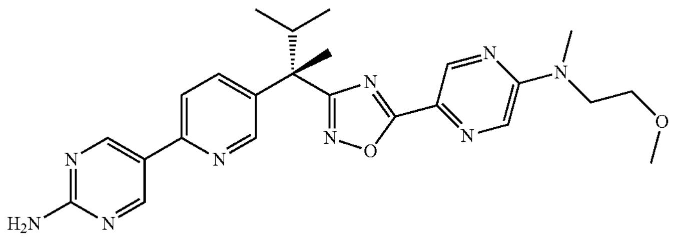 [SMILES: COCCN(C)c1cnc(-c2nc([C@](C)(c3ccc(-c4cnc(N)nc4)nc3)C(C)C)no2)cn1] | 5-{5-[(2S)-2-(5-{5-[(2-methoxyethyl)(methyl)amino]pyrazin-2-yl}-1,2,4-oxadiazol-3-yl)-3-methylbutan-2-yl]pyridin-2-yl}pyrimidin-2-amine |
| 57 | 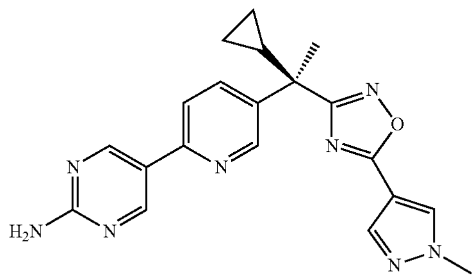 [SMILES: Cn1cc(-c2nc([C@@](C)(c3ccc(-c4cnc(N)nc4)nc3)C3CC3)no2)cn1] | 5-(5-{(1R)-1-cyclopropyl-1-[5-(1-methyl-1H-pyrazol-4-yl)-1,2,4-oxadiazol-3-yl]ethyl}pyridin-2-yl)pyrimidin-2-amine |
| 58 | 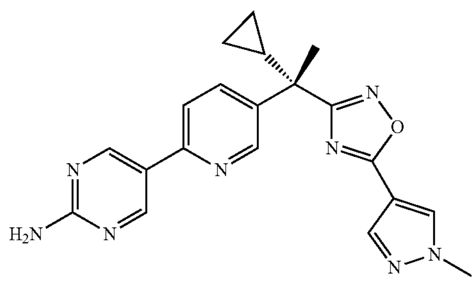 [SMILES: Cn1cc(-c2nc([C@](C)(c3ccc(-c4cnc(N)nc4)nc3)C3CC3)no2)cn1] | 5-(5-{(1S)-1-cyclopropyl-1-[5-(1-methyl-1H-pyrazol-4-yl)-1,2,4-oxadiazol-3-yl]ethyl}pyridin-2-yl)pyrimidin-2-amine |
| 59 | 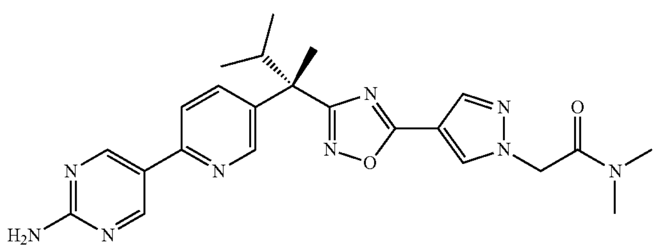 [SMILES: CC(C)[C@@](C)(c1ccc(-c2cnc(N)nc2)nc1)c1noc(-c2cnn(CC(=O)N(C)C)c2)n1] | 2-[4-(3-{(2S)-2-[6-(2-aminopyrimidin-5-yl)pyridin-3-yl]-3-methylbutan-2-yl}-1,2,4-oxadiazol-5-yl)-1H-pyrazol-1-yl]-N,N-dimethylacetamide |
| 60 | 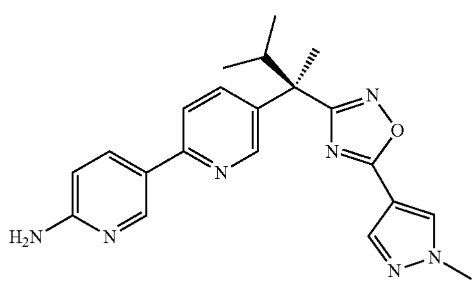 [SMILES: CC(C)[C@](C)(c1ccc(-c2ccc(N)nc2)nc1)c1noc(-c2cnn(C)c2)n1] | 5-{(2R)-3-methyl-2-[5-(1-methyl-1H-pyrazol-4-yl)-1,2,4-oxadiazol-3-yl]butan-2-yl}-2,3'-bipyridin-6'-amine |
| 61 | 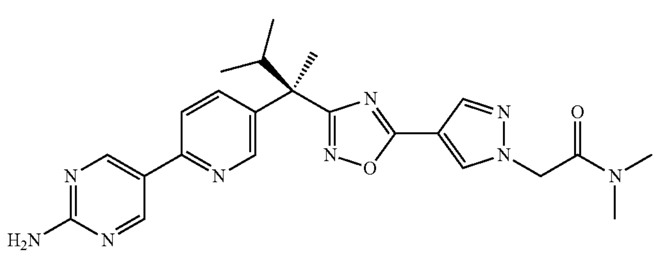 [SMILES: CC(C)[C@](C)(c1ccc(-c2cnc(N)nc2)nc1)c1noc(-c2cnn(CC(=O)N(C)C)c2)n1] | 2-[4-(3-{(2R)-2-[6-(2-aminopyrimidin-5-yl)pyridin-3-yl]-3-methylbutan-2-yl}-1,2,4-oxadiazol-5-yl)-1H-pyrazol-1-yl]-N,N-dimethylacetamid |

TABLE I-continued

| Example | Structure | Name |
|---|---|---|
| 62 | 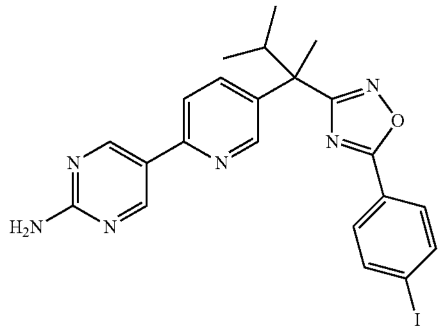 [SMILES: CC(C)C(C)(c1ccc(-c2cnc(N)nc2)nc1)c1noc(-c2ccc(I)cc2)n1] | 5-(5-{2-[5-(4-iodophenyl)-1,2,4-oxadiazol-3-yl]-3-methylbutan-2-yl}pyridin-2-yl)pyrimidin-2-amine |
| 63 | 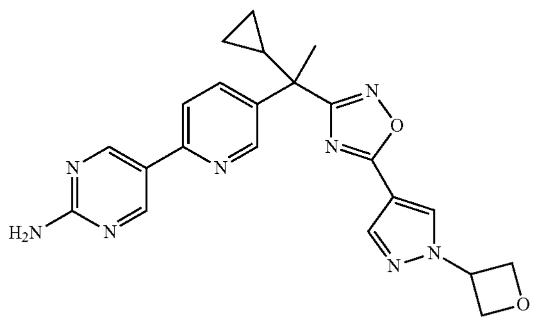 [SMILES: CC(c1ccc(-c2cnc(N)nc2)nc1)(c1noc(-c2cnn(C3COC3)c2)n1)C1CC1] | 5-[5-(1-cyclopropyl-1-{5-[1-(oxetan-3-yl)-1H-pyrazol-4-yl]-1,2,4-oxadiazol-3-yl}ethyl)pyridin-2-yl]pyrimidin-2-amine |
| 64 | 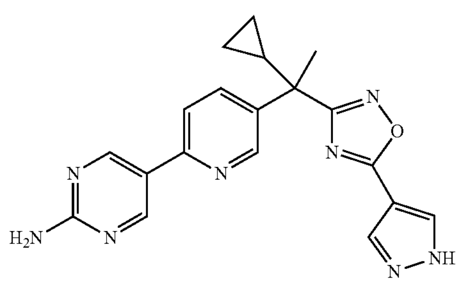 [SMILES: CC(c1ccc(-c2cnc(N)nc2)nc1)(c1noc(-c2cn[nH]c2)n1)C1CC1] | 5-(5-{1-cyclopropyl-1-[5-(1H-pyrazol-4-yl)-1,2,4-oxadiazol-3-yl]ethyl}pyridin-2-yl)pyrimidin-2-amine |
| 65 | 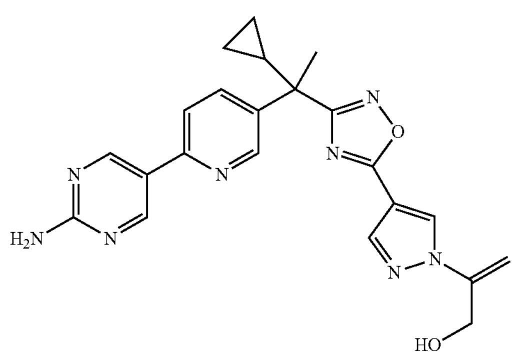 [SMILES: C=C(CO)n1cc(-c2nc(C(C)(c3ccc(-c4cnc(N)nc4)nc3)C3CC3)no2)cn1] | 2-[4-(3-{1-[6-(2-aminopyrimidin-5-yl)pyridin-3-yl]-1-cyclopropylethyl}-1,2,4-oxadiazol-5-yl)-1H-pyrazol-1-yl]prop-2-en-1-ol |

TABLE I-continued

| Example | Structure | Name |
|---|---|---|
| 66 | 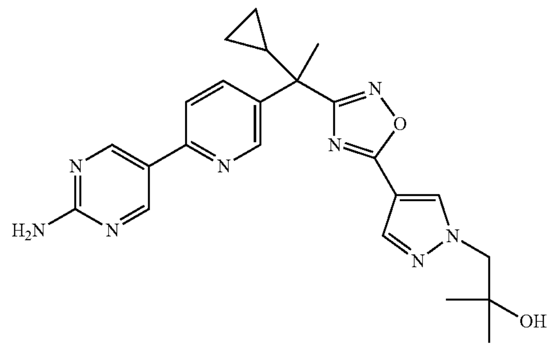 [SMILES: CC(C)(O)Cn1cc(-c2nc(C(C)(c3ccc(-c4cnc(N)nc4)nc3)C3CC3)no2)cn1] | 1-[4-(3-{1-[6-(2-aminopyrimidin-5-yl)pyridin-3-yl]-1-cyclopropylethyl}-1,2,4-oxadiazol-5-yl)-1H-pyrazol-1-yl]-2-methylpropan-2-ol |
| 67 | 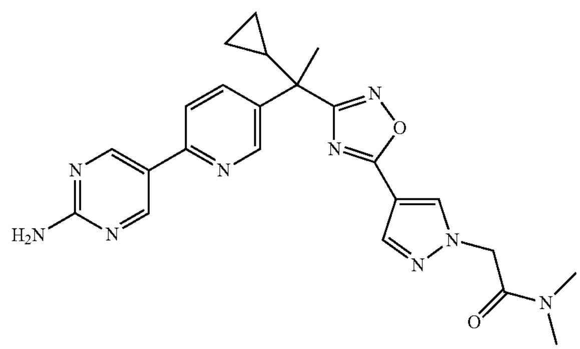 [SMILES: CN(C)C(=O)Cn1cc(-c2nc(C(C)(c3ccc(-c4cnc(N)nc4)nc3)C3CC3)no2)cn1] | 2-[4-(3-{1-[6-(2-aminopyrimidin-5-yl)pyridin-3-yl]-1-cyclopropylethyl}-1,2,4-oxadiazol-5-yl)-1H-pyrazol-1-yl]-N,N-dimethylacetamide |
| 68 | 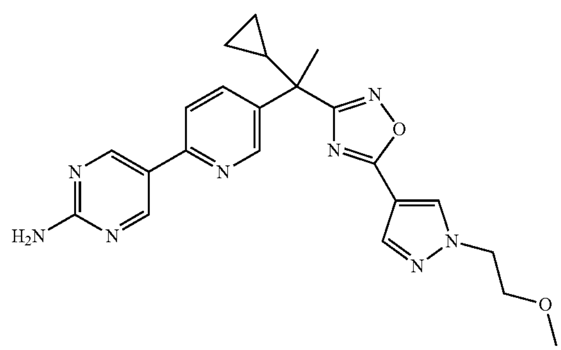 [SMILES: COCCn1cc(-c2nc(C(C)(c3ccc(-c4cnc(N)nc4)nc3)C3CC3)no2)cn1] | 5-[5-(1-cyclopropyl-1-{5[1-(2-methoxyethyl)-1H-pyrazol-4-yl]-1,2,4-oxadiazol-3-yl}ethyl)pyridin-2-yl]pyrimidin-2-amine |
| 69 | 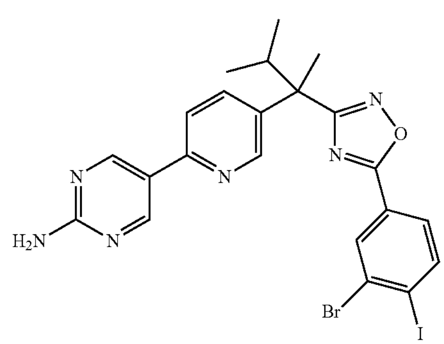 [SMILES: CC(C)C(C)(c1ccc(-c2cnc(N)nc2)nc1)c1noc(-c2ccc(I)c(Br)c2)n1] | 5-(5-{2-[5-(3-bromo-4-iodophenyl)-1,2,4-oxadiazol-3-yl]-3-methylbutan-2-yl}pyridin-2-yl)pyrimidin-2-amine |

TABLE I-continued

| Example | Structure | Name |
|---|---|---|
| 70 | 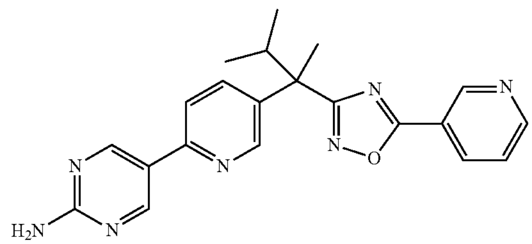 [SMILES: CC(C)C(C)(c1ccc(-c2cnc(N)nc2)nc1)c1noc(-c2cccnc2)n1] | 5-(5-{3-methyl-2-[5-(pyridin-3-yl)-1,2,4-oxadiazol-3-yl]butan-2-yl}pyridin-2-yl)pyrimidin-2-amine |
| 71 | 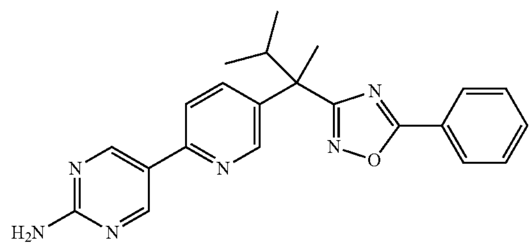 [SMILES: CC(C)C(C)(c1ccc(-c2cnc(N)nc2)nc1)c1noc(-c2ccccc2)n1] | 5-{5-[3-methyl-2-(5-phenyl-1,2,4-oxadiazol-3-yl)butan-2-yl]pyridin-2-yl}pyrimidin-2-amine |
| 72 | 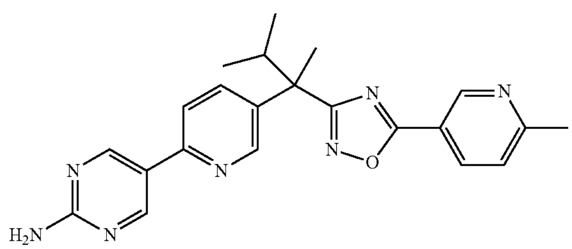 [SMILES: Cc1ccc(-c2nc(C(C)(c3ccc(-c4cnc(N)nc4)nc3)C(C)C)no2)cn1] | 5-(5-{3-methyl-2-[5-(6-methylpyridin-3-yl)-1,2,4-oxadiazol-3-yl]butan-2-yl}pyridin-2-yl)pyrimidin-2-amine |
| 73 | 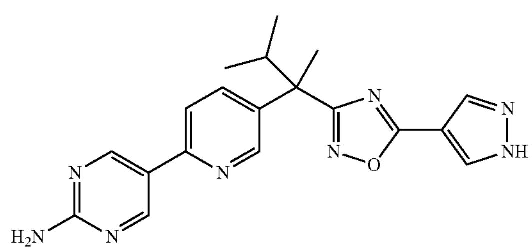 [SMILES: CC(C)C(C)(c1ccc(-c2cnc(N)nc2)nc1)c1noc(-c2cn[nH]c2)n1] | 5-(5-{3-methyl-2-[5-(1H-pyrazol-4-yl)-1,2,4-oxadiazol-3-yl]butan-2-yl}pyridin-2-yl)pyrimidin-2-amine |
| 74 | 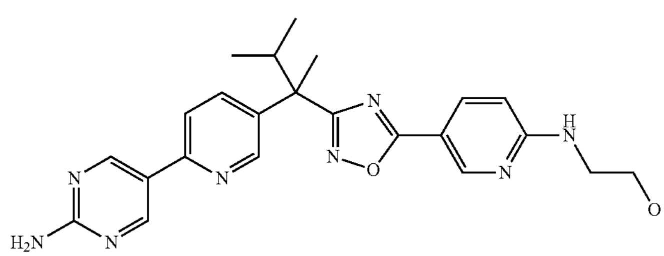 [SMILES: CC(C)C(C)(c1ccc(-c2cnc(N)nc2)nc1)c1noc(-c2ccc(NCCO)nc2)n1] | 2-{[5-(3-{2-[6-(2-aminopyrimidin-5-yl)pyridin-3-yl]-3-methylbutan-2-yl}-1,2,4-oxadiazol-5-yl)pyridin-2-yl]amino}ethanol |

TABLE I-continued

| Example | Structure | Name |
|---|---|---|
| 75 | 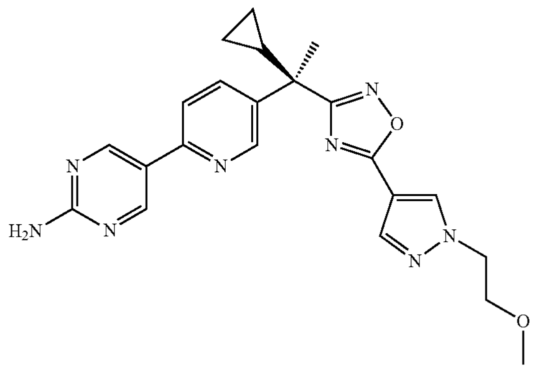 [SMILES: COCCn1cc(-c2nc([C@@](C)(c3ccc(-c4cnc(N)nc4)nc3)C3CC3)no2)cn1] | 5-{5-[(1R)-1-cyclopropyl-1-{5-[1-(2-methoxyethyl)-1H-pyrazol-4-yl]-1,2,4-oxadiazol-3-yl}ethyl]pyridin-2-yl}pyrimidin-2-amine |
| 76 | 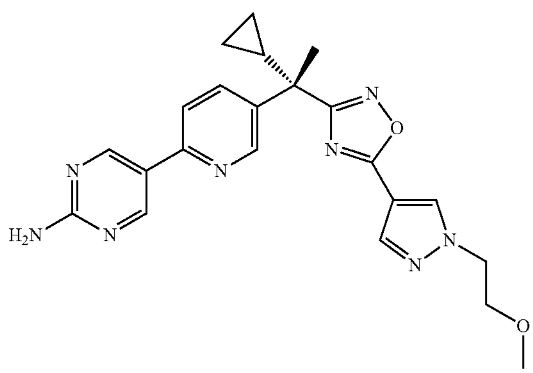 [SMILES: COCCn1cc(-c2nc([C@](C)(c3ccc(-c4cnc(N)nc4)nc3)C3CC3)no2)cn1] | 5-{5-[(1S)-1-cyclopropyl-1-{5-[1-(2-methoxyethyl)-1H-pyrazol-4-yl]-1,2,4-oxadiazol-3-yl}ethyl]pyridin-2-yl}pyrimidin-2-amine |
| 77 | 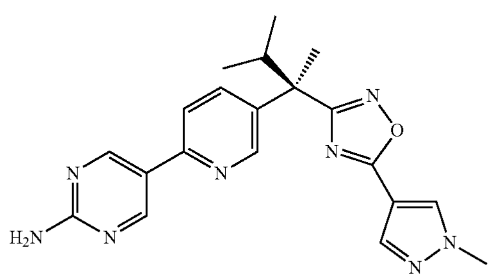 [SMILES: CC(C)[C@](C)(c1ccc(-c2cnc(N)nc2)nc1)c1noc(-c2cnn(C)c2)n1] | 5-(5-{(2R)-3-methyl-2-[5-(1-methyl-1H-pyrazol-4-yl)-1,2,4-oxadiazol-3-yl]butan-2-yl}pyridin-2-yl)pyrazin-2-amine |
| 78 | 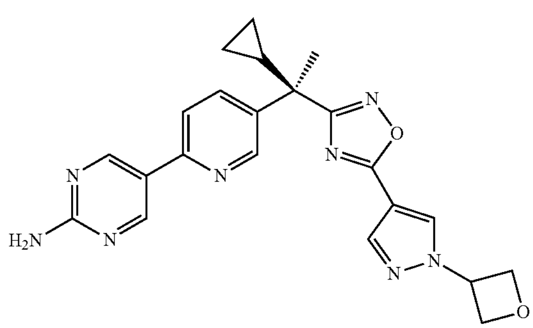 [SMILES: C[C@@](c1ccc(-c2cnc(N)nc2)nc1)(c1noc(-c2cnn(C3COC3)c2)n1)C1CC1] | 5-{5-[(1R)-1-cyclopropyl-1-{5-[1-(oxetan-3-yl)-1H-pyrazol-4-yl]-1,2,4-oxadiazol-3-yl}ethyl]pyridin-2-yl}pyrimidin-2-amine |

TABLE I-continued

| Example | Structure | Name |
|---|---|---|
| 79 | 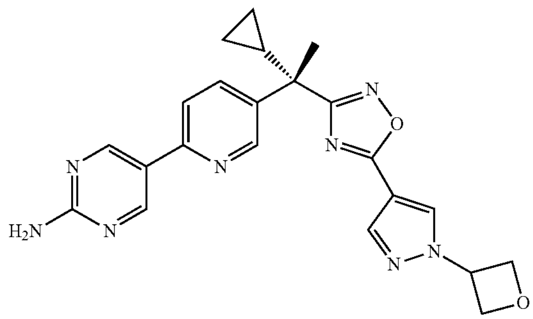 [SMILES: C[C@](c1ccc(-c2cnc(N)nc2)nc1)(c1noc(-c2cnn(C3COC3)c2)n1)C1CC1] | 5-{5-[(1S)-1-cyclopropyl-1-{5-[1-(oxetan-3-yl)-1H-pyrazol-4-yl]-1,2,4-oxadiazol-3-yl}ethyl]pyridin-2-yl}pyrimidin-2-amine |
| 80 | 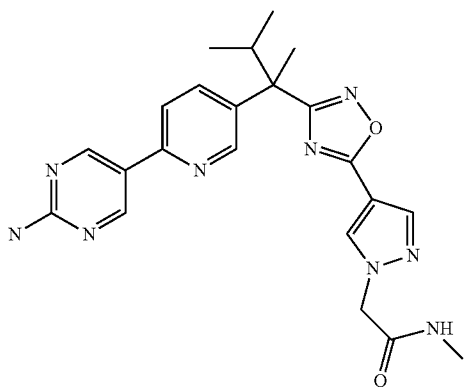 [SMILES: CNC(=O)Cn1cc(-c2nc(C(C)(c3ccc(-c4cnc(N)nc4)nc3)C(C)C)no2)cn1] | 2-[4-(3-{2-[6-(2-aminopyrimidin-5-yl)pyridin-3-yl]-3-methylbutan-2-yl}-1,2,4-oxadiazol-5-yl)-1H-pyrazol-1-yl]-N-methylacetamide |
| 81 | 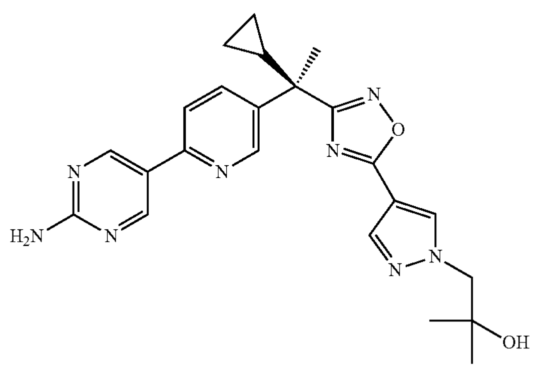 [SMILES: CC(C)(O)Cn1cc(-c2nc([C@@](C)(c3ccc(-c4cnc(N)nc4)nc3)C3CC3)no2)cn1] | 1-[4-(3-{(1R)-1-[6-(2-aminopyrimidin-5-yl)pyridin-3-yl]-1-cyclopropylethyl}-1,2,4-oxadiazol-5-yl)-1H-pyrazol-1-yl]-2-methylpropan-2-ol |
| 82 | 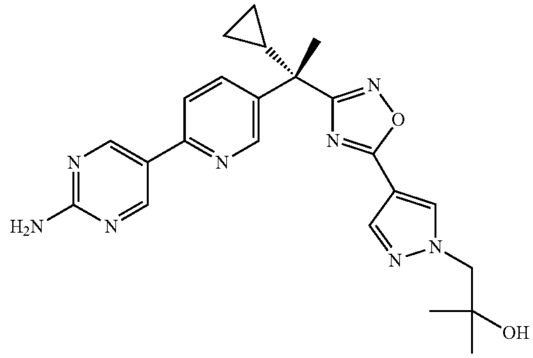 [SMILES: CC(C)(O)Cn1cc(-c2nc([C@](C)(c3ccc(-c4cnc(N)nc4)nc3)C3CC3)no2)cn1] | 1-[4-(3-{(1S)-1-[6-(2-aminopyrimidin-5-yl)pyridin-3-yl]-1-cyclopropylethyl}-1,2,4-oxadiazol-5-yl)-1H-pyrazol-1-yl]-2-methylpropan-2-ol |

TABLE I-continued

| Example | Structure | Name |
|---|---|---|
| 83 | 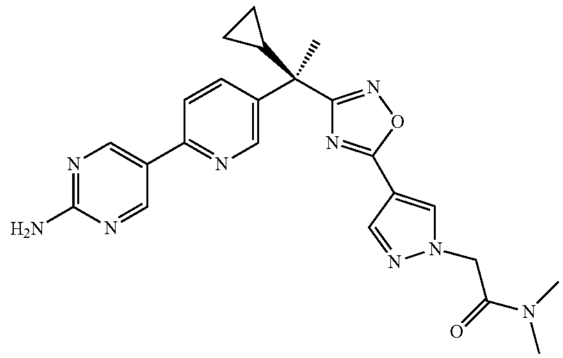 [SMILES: CN(C)C(=O)Cn1cc(-c2nc([C@@](C)(c3ccc(-c4cnc(N)nc4)nc3)C3CC3)no2)cn1] | 2-[4-(3-{(1R)-1-[6-(2-aminopyrimidin-5-yl)pyridin-3-yl]-1-cyclopropylethyl}-1,2,4-oxadiazol-5-yl)-1H-pyrazol-1-yl]-N,N-dimethylacetamide |
| 84 | 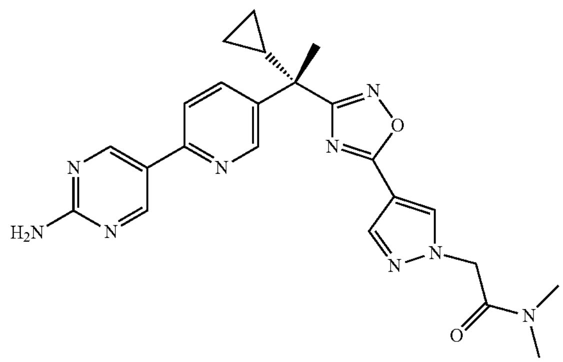 [SMILES: CN(C)C(=O)Cn1cc(-c2nc([C@](C)(c3ccc(-c4cnc(N)nc4)nc3)C3CC3)no2)cn1] | 2-[4-(3-{(1S)-1-[6-(2-aminopyrimidin-5-yl)pyridin-3-yl]-1-cyclopropylethyl}-1,2,4-oxadiazol-5-yl)-1H-pyrazol-1-yl]-N,N-dimethylacetamide |
| 85 | 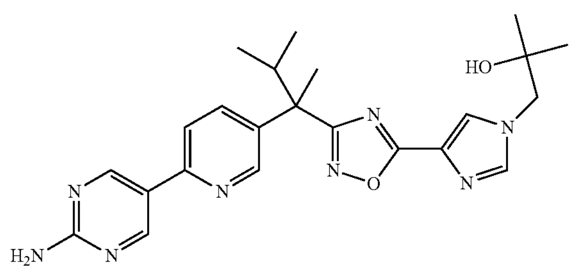 [SMILES: CC(C)C(C)(c1ccc(-c2cnc(N)nc2)nc1)c1noc(-c2cn(CC(C)(C)O)cn2)n1] | 1-[4-(3-{2-[6-(2-aminopyrimidin-5-yl)pyridin-3-yl]-3-methylbutan-2-yl}-1,2,4-oxadiazol-5-yl)-1H-imidazol-1-yl]-2-methylpropan-2-ol |
| 86 | 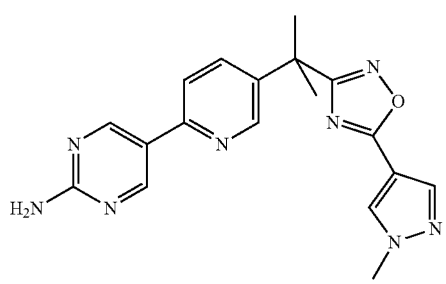 [SMILES: Cn1cc(-c2nc(C(C)(C)c3ccc(-c4cnc(N)nc4)nc3)no2)cn1] | 5-(5-{2-[5-(1-methyl-1H-pyrazol-4-yl)-1,2,4-oxadiazol-3-yl]propan-2-yl}pyridin-2-yl)pyrimidin-2-amine |
| 87 | 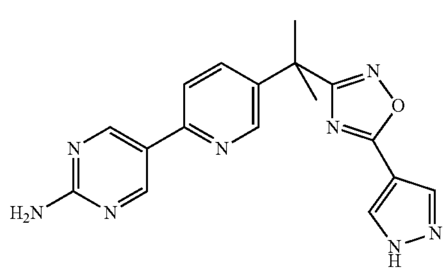 [SMILES: CC(C)(c1ccc(-c2cnc(N)nc2)nc1)c1noc(-c2cn[nH]c2)n1] | 5-(5-{2-[5-(1H-pyrazol-4-yl)-1,2,4-oxadiazol-3-yl]propan-2-yl}pyridin-2-yl)pyrimidin-2-amine |

TABLE I-continued

| Example | Structure | Name |
|---|---|---|
| 88 | 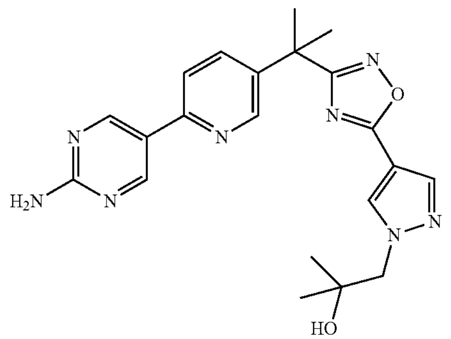 [SMILES: CC(C)(O)Cn1cc(-c2nc(C(C)(C)c3ccc(-c4cnc(N)nc4)nc3)no2)cn1] | 1-[4-(3-{2-[6-(2-aminopyrimidin-5-yl)pyridin-3-yl]propan-2-yl}-1,2,4-oxadiazol-5-yl)-1H-pyrazol-1-yl]-2-methylpropan-2-ol |
| 89 | 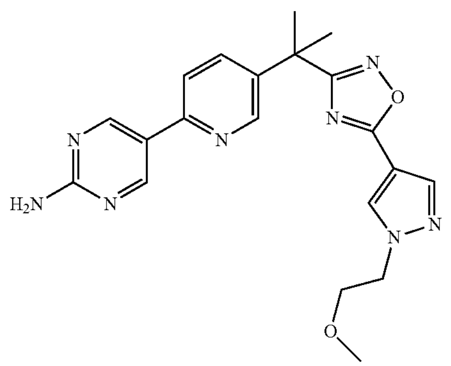 [SMILES: COCCn1cc(-c2nc(C(C)(C)c3ccc(-c4cnc(N)nc4)nc3)no2)cn1] | 5-[5-(2-{5-[1-(2-methoxyethyl)-1H-pyrazol-4-yl]-1,2,4-oxadiazol-3-yl}propan-2-yl)pyridin-2-yl]pyrimidin-2-amine |
| 90 | 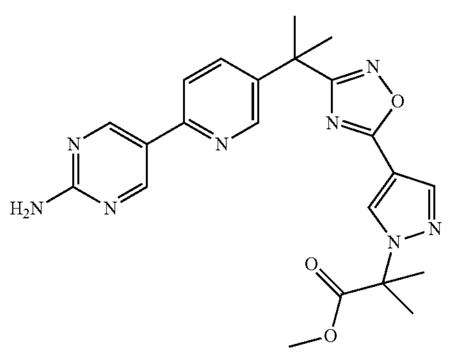 [SMILES: COC(=O)C(C)(C)n1cc(-c2nc(C(C)(C)c3ccc(-c4cnc(N)nc4)nc3)no2)cn1] | methyl 2-[4-(3-{2-[6-(2-aminopyrimidin-5-yl)pyridin-3-yl]propan-2-yl}-1,2,4-oxadiazol-5-yl)-1H-pyrazol-1-yl]-2-methylpropanoate |
| 91 | 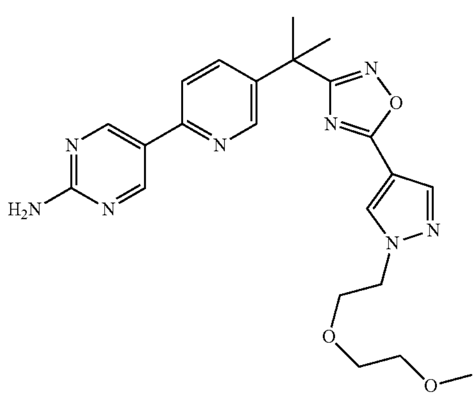 [SMILES: COCCOCCn1cc(-c2nc(C(C)(C)c3ccc(-c4cnc(N)nc4)nc3)no2)cn1] | 5-{5-[2-(5-{1-[2-(2-methoxyethoxy)ethyl]-1H-pyrazol-4-yl}-1,2,4-oxadiazol-3-yl)propan-2-yl]pyridin-2-yl}pyrimidin-2-amine |

TABLE I-continued

| Example | Structure | Name |
|---|---|---|
| 92 | 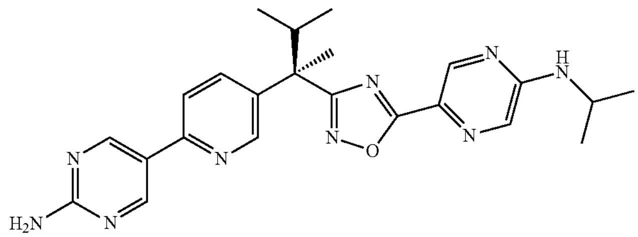 [SMILES: CC(C)Nc1cnc(-c2nc([C@@](C)(c3ccc(-c4cnc(N)nc4)nc3)C(C)C)no2)cn1] | 5-[5-{(R)-1-[5-(5-Isopropylamino-pyrazin-2-yl)-[1,2,4]oxadiazol-3-yl]-1,2-dimethyl-propyl}-pridin-2-yl)-pyrimidin-2-ylamine |
| 93 | 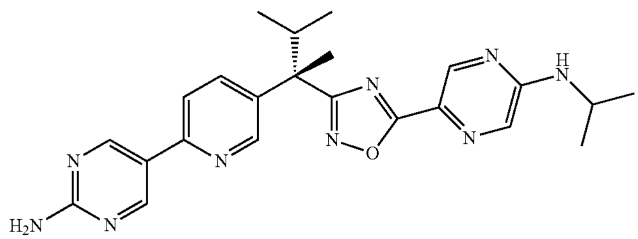 [SMILES: CC(C)Nc1cnc(-c2nc([C@](C)(c3ccc(-c4cnc(N)nc4)nc3)C(C)C)no2)cn1] | 5-(5-{(S)-1-[5-(5-Isopropylamino-pyrazin-2-yl)-[1,2,4]oxadiazol-3-yl]-1,2-dimethyl-propyl}-pyridin-2-yl)-pyrimidin-2-ylamine |
| 94 | 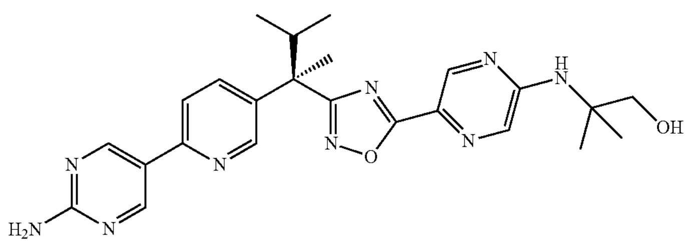 [SMILES: CC(C)[C@](C)(c1ccc(-c2cnc(N)nc2)nc1)c1noc(-c2cnc(NC(C)(C)CO)cn2)n1] | 2-[5-(3-{(R)-1-[6-(2-Amino-pyrimidin-5-yl)-pyridin-3-yl]-1,2-dimethyl-propyl}-[1,2,4]oxadiazol-5-yl)-pyrazin-2-ylamino]-2-methyl-propan-1-ol |
| 95 | 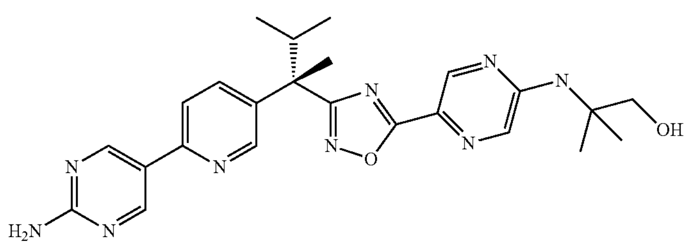 [SMILES: CC(C)[C@@](C)(c1ccc(-c2cnc(N)nc2)nc1)c1noc(-c2cnc(NC(C)(C)CO)cn2)n1] | 2-[5-(3-{(S)-1-[6-(2-Amino-pyrimidin-5-yl)-pyridin-3-yl]-1,2-dimethyl-propyl}-[1,2,4]oxadiazol-5-yl)-pyrazin-2-ylamino]-2-methyl-propan-1-ol |
| 96 | 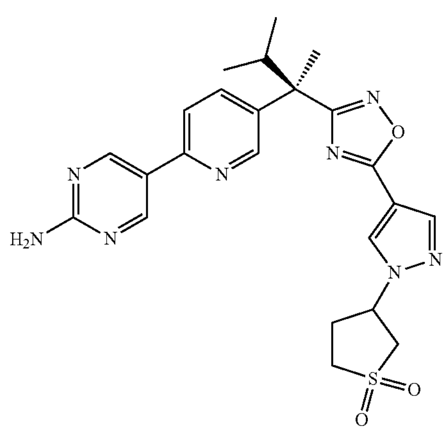 [SMILES: CC(C)[C@](C)(c1ccc(-c2cnc(N)nc2)nc1)c1noc(-c2cnn(C3CCS(=O)(=O)C3)c2)n1] | 5-[5-((R)-1-{5-[1-(1,1-Dioxo-tetrahydro-1l6-thiophen-3-yl)-1H-pyrazol-4-yl]-[1,2,4]oxadiazol-3-yl}-1,2-dimethyl-propyl)-pyridin-2-yl]-pyrimidin-2-ylamine |

TABLE I-continued

| Example | Structure | Name |
|---|---|---|
| 97 | 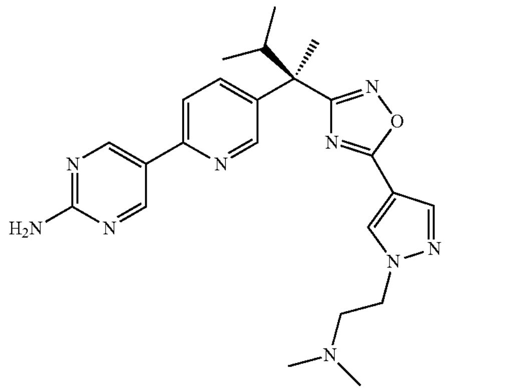 [SMILES: CC(C)[C@](C)(c1ccc(-c2cnc(N)nc2)nc1)c1noc(-c2cnn(CCN(C)C)c2)n1] | 5-[5-((R)-1-{5-[1-(2-Dimethylamino-ethyl)-1H-pyrazol-4-yl]-[1,2,4]oxadiazol-3-yl}-1,2-dimethyl-propyl)-pyridin-2-yl]-pyrimidin-2-ylamine |
| 98 | 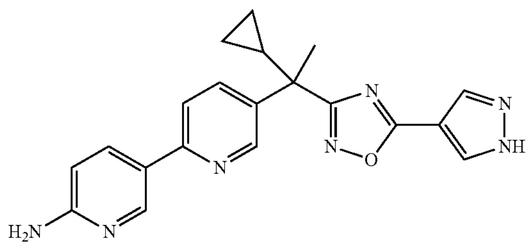 [SMILES: CC(c1ccc(-c2ccc(N)nc2)nc1)(c1noc(-c2cn[nH]c2)n1)C1CC1] | 5-{1-Cyclopropyl-1-[5-(1H-pyrazol-4-yl)-[1,2,4]oxadiazol-3-yl]-ethyl}-[2,3']bipyridinyl-6'-ylamie |
| 99 | Chiral | 5-[5-((R)-1-Cyclopropyl-1-{5-[1-(2-dimethylamino-ethyl)-1H-pyrazol-4-yl]-[1,2,4]oxadiazol-3-yl}-ethyl)-pyridin-2-yl]-pyrimidin-2-ylamine |
| 100 | 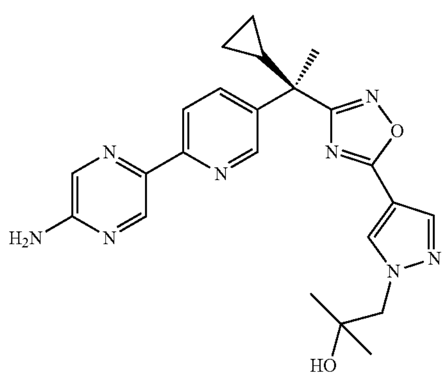 [SMILES: CC(C)(O)Cn1cc(-c2nc([C@@](C)(c3ccc(-c4cnc(N)cn4)nc3)C3CC3)no2)cn1] | 1-[4-(3-{(R)-1-[6-(5-Amino-pyrazin-2-yl)-pyridin-3-yl]-1-cyclopropyl-ethyl}-[1,2,4]oxadiazol-5-yl)-pyrazol-1-yl]-2-methyl-propan-2-ol |

TABLE I-continued

| Example | Structure | Name |
|---|---|---|
| 101 | 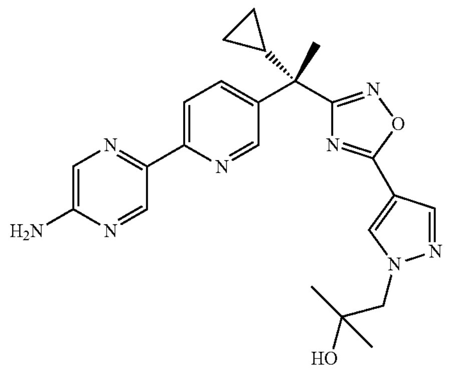 [SMILES: CC(C)(O)Cn1cc(-c2nc([C@](C)(c3ccc(-c4cnc(N)cn4)nc3)C3CC3)no2)cn1] | 1-[4-(3-{(S)-1-[6-(5-Amino-pyrazin-2-yl)-pyridin-3-yl]-1-cyclopropyl-ethyl}-[1,2,4]oxadiazol-5-yl)-pyrazol-1-yl]-2-methyl-propan-2-ol |
| 102 | 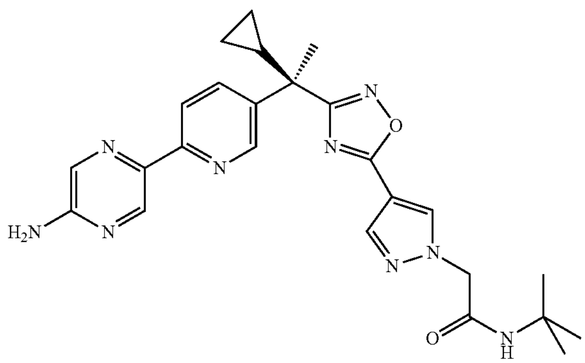 [SMILES: CC(C)(C)NC(=O)Cn1cc(-c2nc([C@@](C)(c3ccc(-c4cnc(N)cn4)nc3)C3CC3)no2)cn1] | 2-[4-(3-{(R)-1-[6-(2-Amino-pyrimidin-5-yl)-pyridin-3-yl]-1-cyclopropyl-ethyl}-[1,2,4]oxadiazol-5-yl)-pyrazol-1-yl]-N-tert-butyl-acetamide |
| 103 | Chiral | [4-(3-{(R)-1-[6-(2-Amino-pyrimidin-5-yl)-pyridin-3-yl]-1-cyclopropyl-ethyl}-[1,2,4]oxadiazol-5-yl)-pyrazol-1-yl]-acetnitrile |
| 104 | 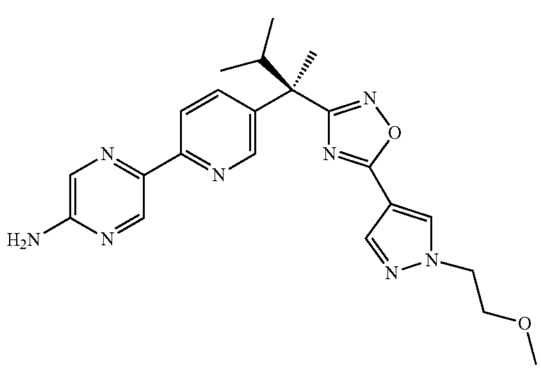 [SMILES: COCCn1cc(-c2nc([C@@](C)(c3ccc(-c4cnc(N)cn4)nc3)C(C)C)no2)cn1] | 5-[5-((R)-1-{5-[1-(2-Methoxy-ethyl)-1H-pyrazol-4-yl]-[1,2,4]oxadiazol-3-yl}-1,2-dimethyl-propyl)-pyridin-2-yl]-pyrazin-2-ylamine |

TABLE I-continued

| Example | Structure | Name |
|---|---|---|
| 105 | 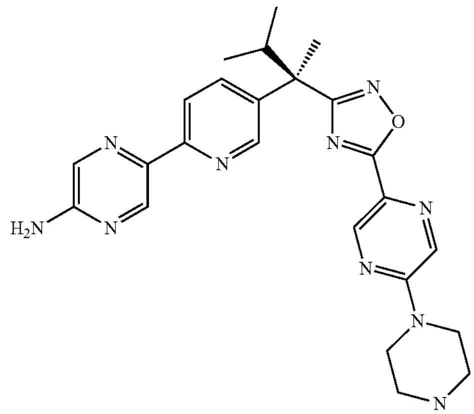 [SMILES: CC(C)[C@](C)(c1ccc(-c2cnc(N)cn2)nc1)c1noc(-c2cnc(N3CCNCC3)cn2)n1] | 5-(5-{(R)-1,2-Dimethyl-1-[5-(3,4,5,6-tetrahydro-2H-[1,2']bipyrazinyl-5'-yl)-[1,2,4]oxadiazol-3-yl]-propyl}-pyridin-2-yl)-pyrazin-2-ylamine |
| 106 | 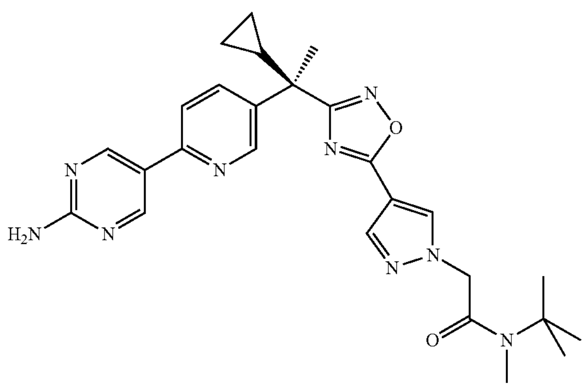 [SMILES: CN(C(=O)Cn1cc(-c2nc([C@@](C)(c3ccc(-c4cnc(N)nc4)nc3)C3CC3)no2)cn1)C(C)(C)C] | 2-[4-(3-{(R)-1-[6-(2-Amino-pyrimidin-5-yl)-pyridin-3-yl]-1-cyclopropyl-ethyl}-[1,2,4]oxadiazol-5-yl)-pyrazol-1-yl]-N-tert-butyl-N-methyl-acetamide |
| 107 | 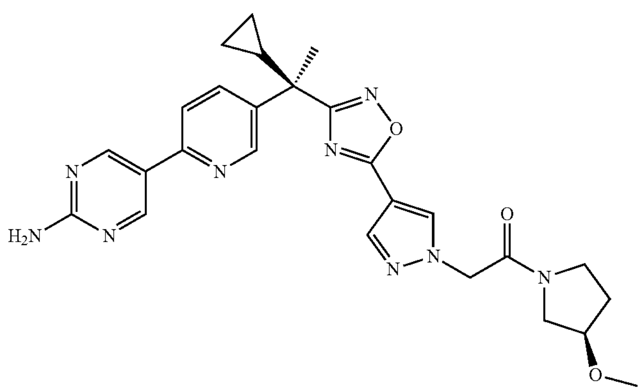 [SMILES: CO[C@@H]1CCN(C(=O)Cn2cc(-c3nc([C@@](C)(c4ccc(-c5cnc(N)nc5)nc4)C4CC4)no3)cn2)C1] | 2-[4-(3-{(R)-1-[6-(2-Amino-pyrimidin-5-yl)-pyridin-3-yl]-1-cyclopropyl-ethyl}-[1,2,4]oxadiazol-5-yl)-pyrazol-1-yl]-1-((R)-3-methoxy-pyrrolidin-1-yl)-ethanone |
| 108 | 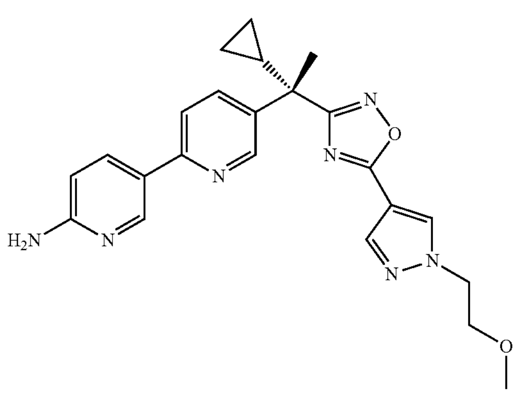 [SMILES: COCCn1cc(-c2nc([C@](C)(c3ccc(-c4ccc(N)nc4)nc3)C3CC3)no2)cn1] | 5-((S)-1-Cyclopropyl-1-{5-[1-(2-methoxy-ethyl)-1H-pyrazol-4-yl]-[1,2,4]oxadiazol-3-yl]-ethyl)-[2,3']bipyridinyl-6'-ylamine |

TABLE I-continued

| Example | Structure | Name |
| --- | --- | --- |
| 109 | 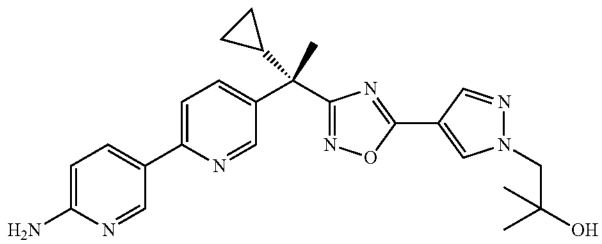 [SMILES: CC(C)(O)Cn1cc(-c2nc([C@](C)(c3ccc(-c4ccc(N)nc4)nc3)C3CC3)no2)cn1] | 1-(4-{3-[(S)-1-(6'-Amino-[2,3']bipyridinyl-5-yl)-1-cyclopropyl-ethyl]-[1,2,4]oxadiazol-5-yl}-pyrazol-1-yl)-2-methyl-propan-2-ol |
| 110 | 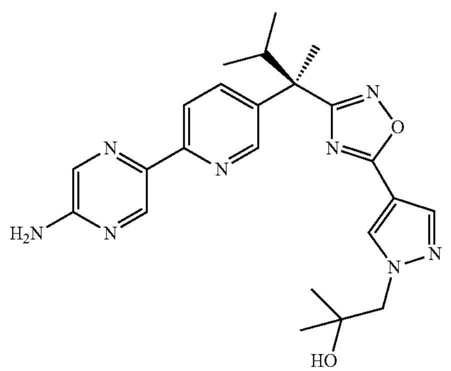 [SMILES: CC(C)[C@](C)(c1ccc(-c2cnc(N)cn2)nc1)c1noc(-c2cnn(CC(C)(C)O)c2)n1] | 1-[4-(3-{(R)-1-[6-(5-Amino-pyrazin-2-yl)-pyridin-3-yl]-1,2-dimethyl-propyl}-[1,2,4]oxadiazol-5-yl)-pyrazol-1-yl]-2-methyl-propan-2-ol |
| 111 | 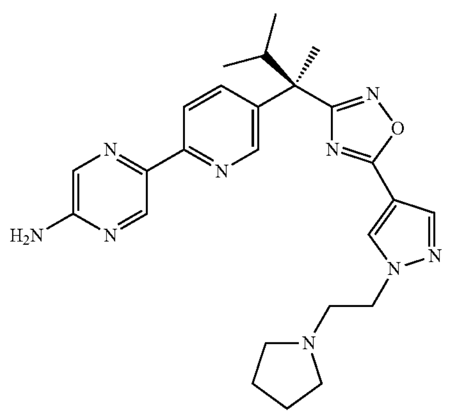 [SMILES: CC(C)[C@](C)(c1ccc(-c2cnc(N)cn2)nc1)c1noc(-c2cnn(CCN3CCCC3)c2)n1] | 5-[5-((R)-1,2-Dimethyl-1-{5-[1-(2-pyrrolidin-1-yl-ethyl)-1H-pyrazol-4-yl]-[1,2,4]oxadiazol-3-yl}-propyl)-pyridin-2-yl]-pyrimidin-2-ylamine |
| 112 | 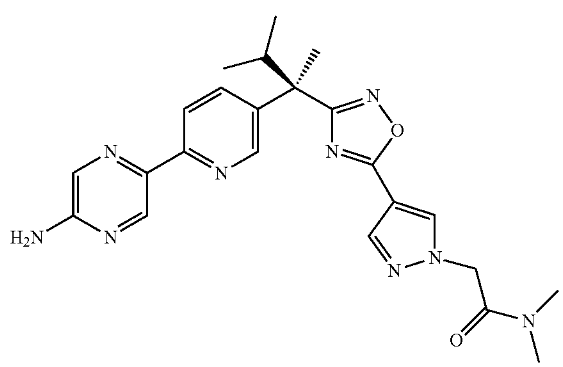 [SMILES: CC(C)[C@](C)(c1ccc(-c2cnc(N)cn2)nc1)c1noc(-c2cnn(CC(=O)N(C)C)c2)n1] | 2-[4-(3-{(R)-1-[6-(5-Amino-pyrazin-2-yl)-pyridin-3-yl]-1,2-dimethyl-propyl}-[1,2,4]oxadiazol-5-yl)-pyrazol-1-yl]-N,N-dimethyl-acetamide |

TABLE I-continued

| Example | Structure | Name |
|---|---|---|
| 113 | 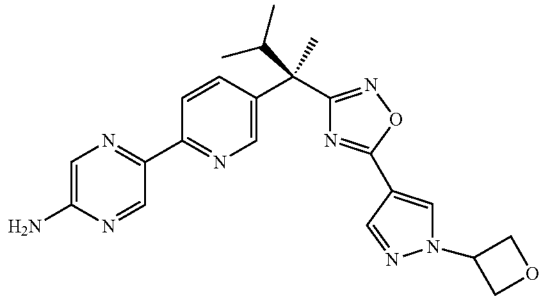 [SMILES: CC(C)[C@](C)(c1ccc(-c2cnc(N)cn2)nc1)c1noc(-c2cnn(C3COC3)c2)n1] | 5-(5-{(R)-1,2-Dimethyl-1-[5-(1-oxetan-3-yl-1H-pyrazol-4-yl)-[1,2,4]oxadiazol-3-yl]-propyl}-pyridin-2-yl)-pyrazin-2-ylamine |
| 114 | 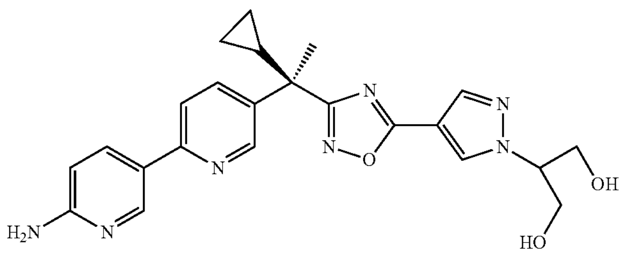 [SMILES: C[C@@](c1ccc(-c2ccc(N)nc2)nc1)(c1noc(-c2cnn(C(CO)CO)c2)n1)C1CC1] | 2-(4-{3-[(R)-1-(6'-Amino-[2,3']bipyridinyl-5-yl)-1-cyclopropyl-ethyl]-[1,2,4]oxadiazol-5-yl}-pyrazol-1-yl)-propane-1,3-diol |
| 115 | 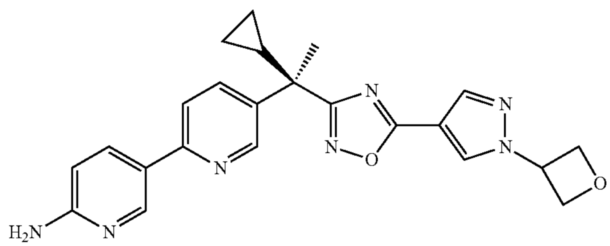 [SMILES: C[C@@](c1ccc(-c2ccc(N)nc2)nc1)(c1noc(-c2cnn(C3COC3)c2)n1)C1CC1] | 5-{(R)-1-Cyclopropyl-1-[5-(1-oxetan-3-yl-1H-pyrazol-4-yl)-[1,2,4]oxadiazol-3-yl]ethyl}-[2,3']bipyridinyl-6'-ylamine |
| 116 | 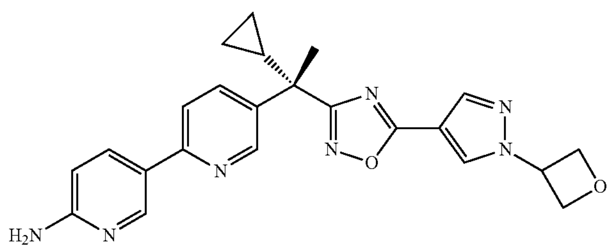 [SMILES: C[C@](c1ccc(-c2ccc(N)nc2)nc1)(c1noc(-c2cnn(C3COC3)c2)n1)C1CC1] | 5-{(S)-1-Cyclopropyl-1-[5-(1-oxetan-3-yl-1H-pyrazol-4-yl)-[1,2,4]oxadiazol-3-yl]ethyl}-[2,3']bipyridinyl-6'-ylamine |
| 117 | 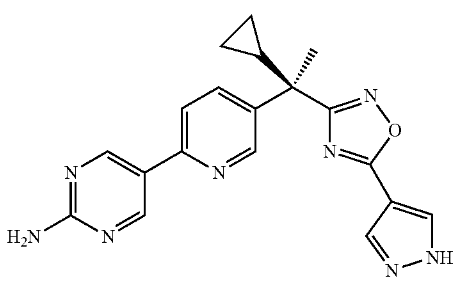 [SMILES: C[C@@](c1ccc(-c2cnc(N)nc2)nc1)(c1noc(-c2cn[nH]c2)n1)C1CC1] | 5-(5-{(R)-1-Cyclopropyl-1-[5-(1H-pyrazol-4-yl)-[1,2,4]oxadiazol-3-yl]-ethyl}-pyridin-2-yl)-pyrimidin-2-ylamine |
| 118 | 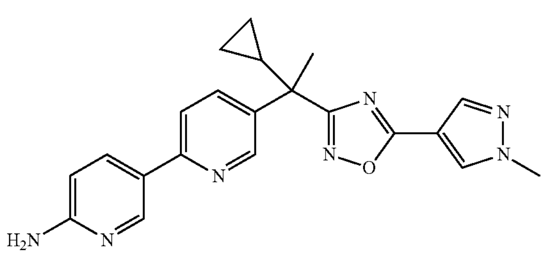 [SMILES: Cn1cc(-c2nc(C(C)(c3ccc(-c4ccc(N)nc4)nc3)C3CC3)no2)cn1] | 5-{1-Cyclopropyl-1-[5-(1-methyl-1H-pyrazol-4-yl)-[1,2,4]oxadiazol-3-yl]-ethyl}-[2,3']bipyridinyl-6'-ylamine |

TABLE I-continued

| Example | Structure | Name |
|---|---|---|
| 119 | 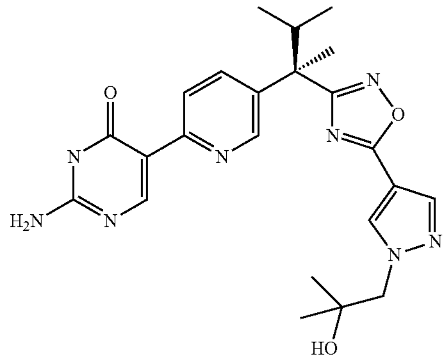 [SMILES: CC(C)[C@](C)(c1ccc(-c2cnc(N)[nH]c2=O)nc1)c1noc(-c2cnn(CC(C)(C)O)c2)n1] | 2-Amino-5-[5-((R)-1-{5-[1-(2-hydroxy-2-methyl-propyl)-1H-pyrazol-4-yl]-[1,2,4]oxadiazol-3-yl}-1,2-dimethyl-propyl)-pyridin-2-yl]-3H-pyrimidin-4-one |
| 120 | 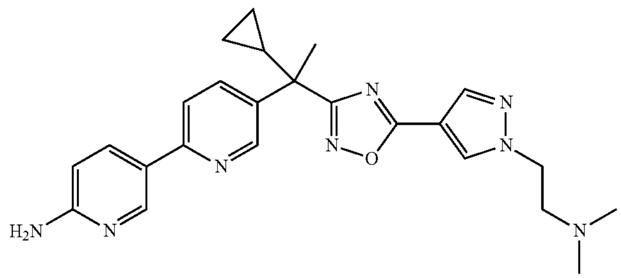 [SMILES: CN(C)CCn1cc(-c2nc(C(C)(c3ccc(-c4ccc(N)nc4)nc3)C3CC3)no2)cn1] | 5-(1-Cyclopropyl-1-{5-[1-(2-dimethylamino-ethyl)-1H-pyrazol-4-yl]-[1,2,4]oxadiazol-3-yl}-ethyl)-[2,3']bipyridinyl-6'-ylamine |
| 121 | 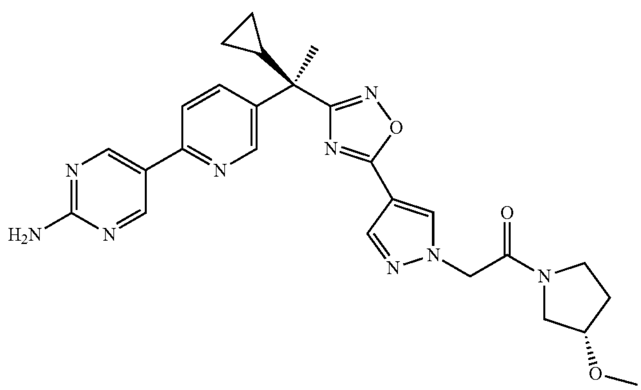 [SMILES: CO[C@H]1CCN(C(=O)Cn2cc(-c3nc([C@@](C)(c4ccc(-c5cnc(N)nc5)nc4)C4CC4)no3)cn2)C1] | 2-[4-(3-{(R)-1-[6-(2-Amino-pyrimidin-5-yl)-pyridin-3-yl]-1-cyclopropyl-ethyl}-[1,2,4]oxadiazol-5-yl)-pyrazol-1-yl]-1-((S)-3-methoxy-pyrrolidin-1-yl)-ethanone |
| 122 | 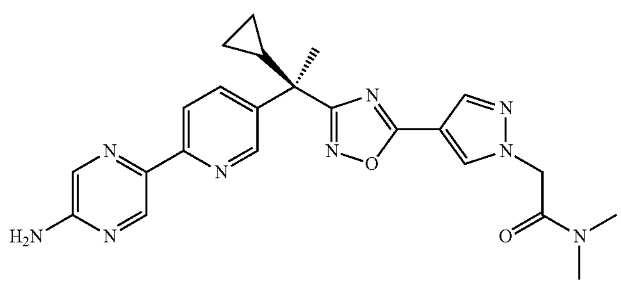 [SMILES: CN(C)C(=O)Cn1cc(-c2nc([C@@](C)(c3ccc(-c4cnc(N)cn4)nc3)C3CC3)no2)cn1] | 2-[4-(3-{(R)-1-[6-(5-Amino-pyrazin-2-yl)-pyridin-3-yl]-1-cyclopropyl-ethyl}-[1,2,4]oxadiazol-5-yl)-pyrazol-1-yl]-N,N-dimethyl-acetamide |
| 123 | 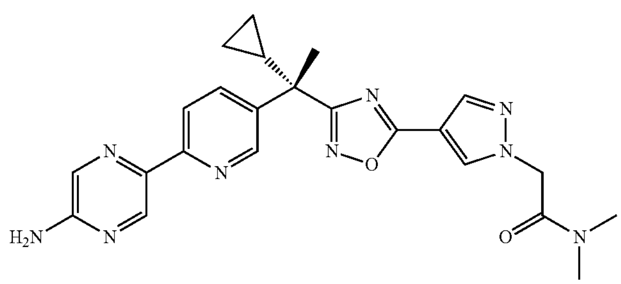 [SMILES: CN(C)C(=O)Cn1cc(-c2nc([C@](C)(c3ccc(-c4cnc(N)cn4)nc3)C3CC3)no2)cn1] | 2-[4-(3-{(S)-1-[6-(5-Amino-pyrazin-2-yl)-pyridin-3-yl]-1-cyclopropyl-ethyl}-[1,2,4]oxadiazol-5-yl)-pyrazol-1-yl]-N,N-dimethyl-acetamide |

TABLE I-continued

| Example | Structure | Name |
|---|---|---|
| 124 | 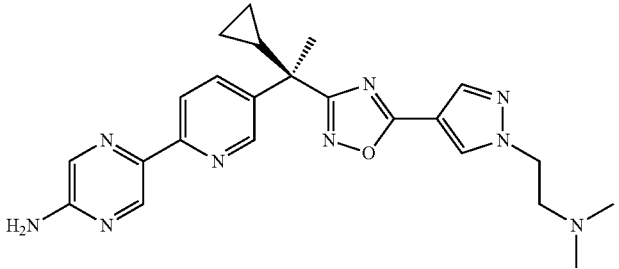 [SMILES: CN(C)CCn1cc(-c2nc([C@@](C)(c3ccc(-c4cnc(N)cn4)nc3)C3CC3)no2)cn1] | 5-[5-((R)-1-Cyclopropyl-1-{5-[1-(2-dimethylamino-ethyl)-1H-pyrazol-4-yl]-[1,2,4]oxadiazol-3-yl}-ethyl)-pyridin-2-yl]-pyrazin-2-ylamine |
| 125 | 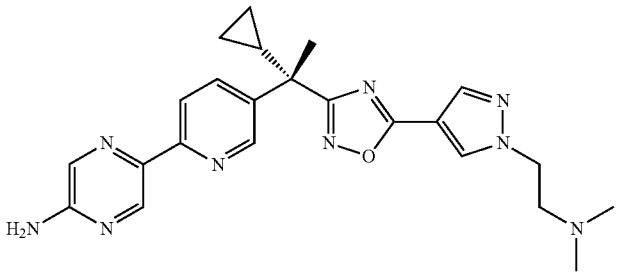 [SMILES: CN(C)CCn1cc(-c2nc([C@](C)(c3ccc(-c4cnc(N)cn4)nc3)C3CC3)no2)cn1] | 5-[5-((S)-1-Cyclopropyl-1-{5-[1-(2-dimethylamino-ethyl)-1H-pyrazol-4-yl]-[1,2,4]oxadiazol-3-yl}-ethyl)-pyridin-2-yl]-pyrazin-2-ylamine |
| 126 | 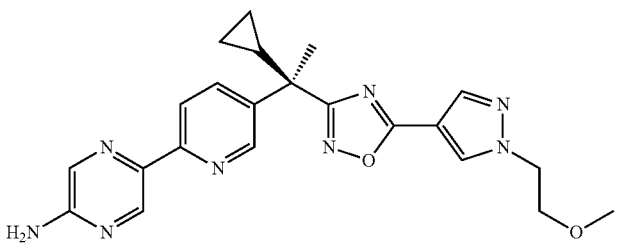 | 5-[5-((R)-1-Cyclopropyl-1-{5-[1-(2-methoxy-ethyl)-1H-pyrazol-4-yl]-[1,2,4]oxadiazol-3-yl}-ethyl)-pyridin-2-yl]-pyrazin-2-ylamine |
| 127 | 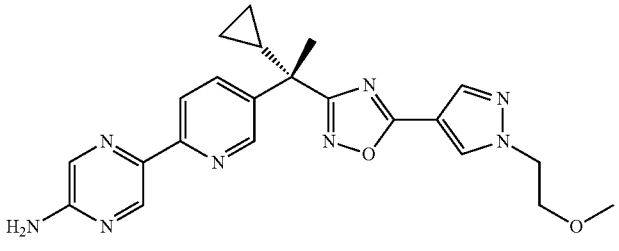 [SMILES: COCCn1cc(-c2nc([C@](C)(c3ccc(-c4cnc(N)cn4)nc3)C3CC3)no2)cn1] | 5-[5-((S)-1-Cyclopropyl-1-{5-[1-(2-methoxy-ethyl)-1H-pyrazol-4-yl]-[1,2,4]oxadiazol-3-yl}-ethyl)-pyridin-2-yl]-pyrazin-2-ylamine |
| 128 | 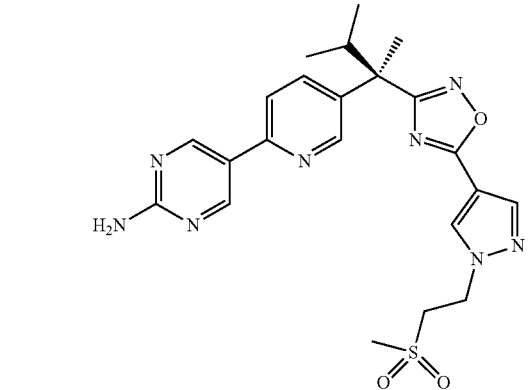 [SMILES: CC(C)[C@](C)(c1ccc(-c2cnc(N)nc2)nc1)c1noc(-c2cnn(CCS(C)(=O)=O)c2)n1] | 5-[5-((R)-1-{5-[1-(2-Methanesulfonyl-ethyl)-1H-pyrazol-4-yl]-[1,2,4]oxadiazol-3-yl}-1,2-dimethyl-propyl)-pyridin-2-yl]-pyrimidin-2-ylamine |

TABLE I-continued

| Example | Structure | Name |
|---|---|---|
| 129 | 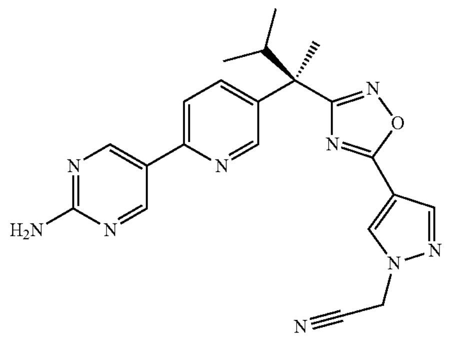 [SMILES: CC(C)[C@](C)(c1ccc(-c2cnc(N)nc2)nc1)c1noc(-c2cnn(CC#N)c2)n1] | [4-(3-{(R)-1-[6-(2-Amino-pyrimidin-5-yl)-pyridin-3-yl]-1,2-dimethyl-propyl}-[1,2,4]oxadiazol-5-yl)-pyrazl-1-yl]-acetonitrile |
| 130 | 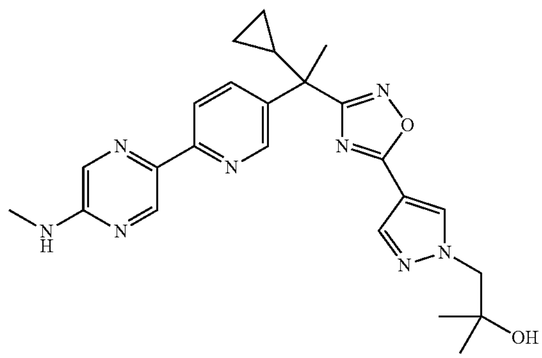 [SMILES: CNc1cnc(-c2ccc(C(C)(c3noc(-c4cnn(CC(C)(C)O)c4)n3)C3CC3)cn2)cn1] | 1-[4-(3-{1-Cyclopropyl-1-[6-(5-methylamino-pyrazin-2-yl)-pyridin-3-yl]-ethyl}-[1,2,4]oxadiazol-5-yl)-pyrazol-1-yl]-2-methyl-propan-2-ol |
| 131 | 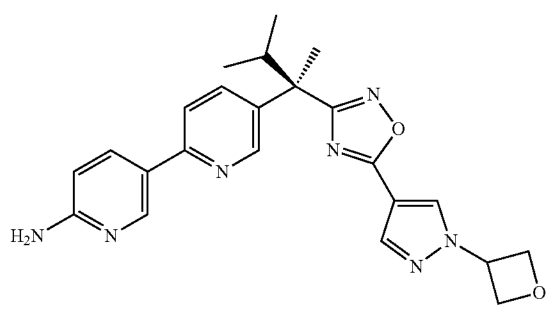 [SMILES: CC(C)[C@](C)(c1ccc(-c2ccc(N)nc2)nc1)c1noc(-c2cnn(C3COC3)c2)n1] | 5-{(R)-1,2-Dimethyl-1-[5-(1-oxetan-3-yl-1H-pyrazol-4-yl)-[1,2,4]oxadiazol-3-yl]-propyl}-[2,3']bipyridinyl-6'-ylamine |
| 132 | 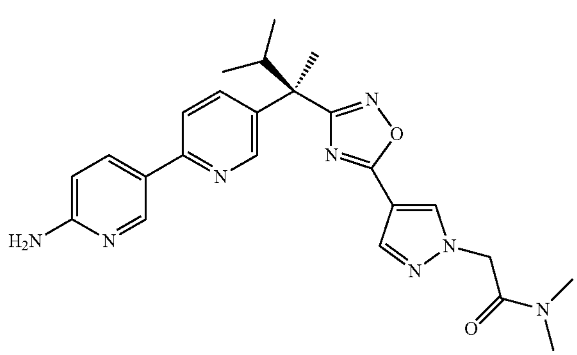 [SMILES: CC(C)[C@](C)(c1ccc(-c2ccc(N)nc2)nc1)c1noc(-c2cnn(CC(=O)N(C)C)c2)n1] | 2-(4-{3-[(R)-1-(6'-Amino-[2,3']bipyridinyl-5-yl)-1,2-dimethyl-propyl]-[1,2,4]oxadiazol-5-yl}-pyrazol-1-yl)-N,N-dimethyl-acetamide |

TABLE I-continued

| Example | Structure | Name |
|---|---|---|
| 133 | 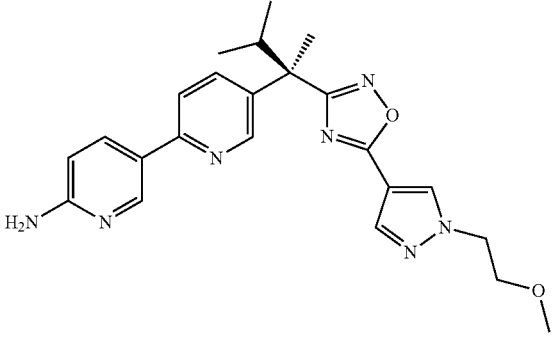 [SMILES: COCCn1cc(-c2nc([C@@](C)(c3ccc(-c4ccc(N)nc4)nc3)C(C)C)no2)cn1] | 5-((R)-1-{5-[1-(2-Methoxy-ethyl)-1H-pyrazol-4-yl]-[1,2,4]oxadiazol-3-yl}-1,2-dimethyl-propyl)-[2,3']bipyridinyl-6'-ylamine |
| 134 | 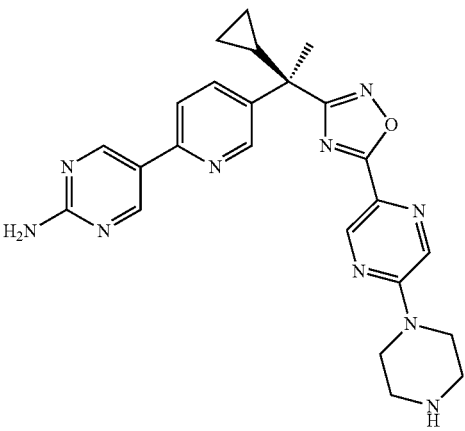 [SMILES: C[C@@](c1ccc(-c2cnc(N)nc2)nc1)(c1noc(-c2cnc(N3CCNCC3)cn2)n1)C1CC1] | 5-(5-{(R)-1-Cyclopropyl-1-[5-(3,4,5,6-tetrahydro-2H-[1,2']bipyrazinyl-5'-yl)-[1,2,4]oxadiazol-3-yl]-ethyl}-pyridin-2-yl)-pyrimidin-2-ylamine |
| 135 | 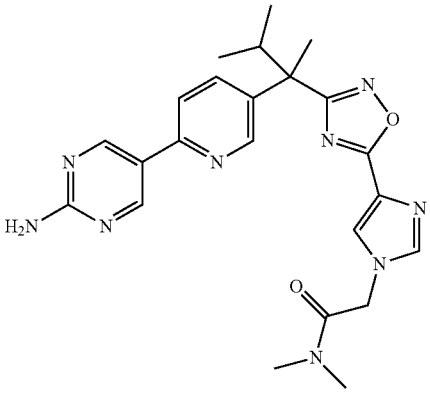 [SMILES: CC(C)C(C)(c1ccc(-c2cnc(N)nc2)nc1)c1noc(-c2cn(CC(=O)N(C)C)cn2)n1] | 2-[4-(3-{1-[6-(2-Amino-pyrimidin-5-yl)-pyridin-3-yl]-1,2-dimethyl-propyl}-[1,2,4]oxadiazol-5-yl)-imidazol-1-yl]-N,N-dimethyl-acetamide |
| 136 | 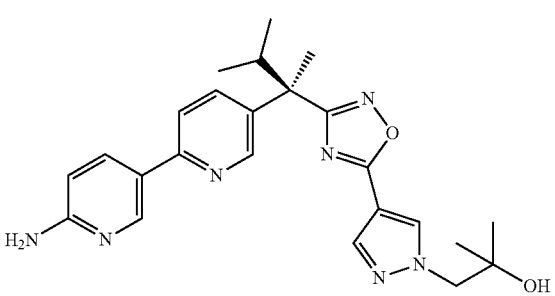 [SMILES: CC(C)[C@](C)(c1ccc(-c2ccc(N)nc2)nc1)c1noc(-c2cnn(CC(C)(C)O)c2)n1] | 1-(4-{3-[(R)-1-(6'-Amino-[2,3']bipyridinyl-5-yl)-1,2-dimethyl-propyl]-[1,2,4]oxadiazol-5-yl}-pyrazol-1-yl)-2-methyl-propan-2-ol |

TABLE I-continued

| Example | Structure | Name |
|---|---|---|
| 137 | 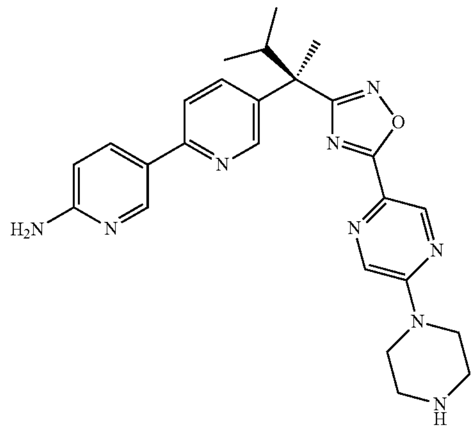 [SMILES: CC(C)[C@](C)(c1ccc(-c2ccc(N)nc2)nc1)c1noc(-c2cnc(N3CCNCC3)cn2)n1] | 5-{(R)-1,2-Dimethyl-1-[5-(3,4,5,6-tetrahydro-2H-[1,2']bipyrazinyl-5'-yl)-[1,2,4]oxadiazol-3-yl]-propyl}-[2,3']bipyridinyl-6'-ylamine |
| 138 | 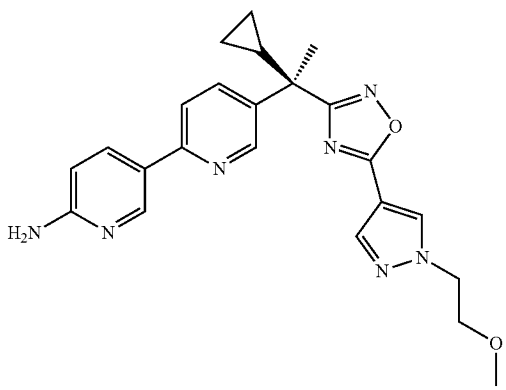 [SMILES: COCCn1cc(-c2nc([C@@](C)(c3ccc(-c4ccc(N)nc4)nc3)C3CC3)no2)cn1] | 5-((R)-1-Cyclopropyl-1-{5-[1-(2-methoxy-ethyl)-1H-pyrazol-4-yl]-[1,2,4]oxadiazol-3-yl}-ethyl)-[2,3']bipyridinyl-6'-ylamine |
| 139 | 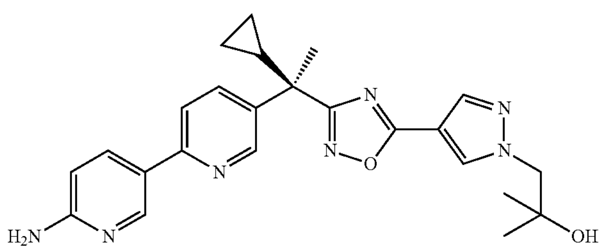 [SMILES: CC(C)(O)Cn1cc(-c2nc([C@@](C)(c3ccc(-c4ccc(N)nc4)nc3)C3CC3)no2)cn1] | 1-(4-{3-[(R)-1-(6'-Amino-[2,3']bipyridinyl-5-yl)-1-cyclopropyl-ethyl]-[1,2,4]oxadiazol-5-yl}-pyrazol-1-yl)-2-methyl-propan-2-ol |
| 140 | 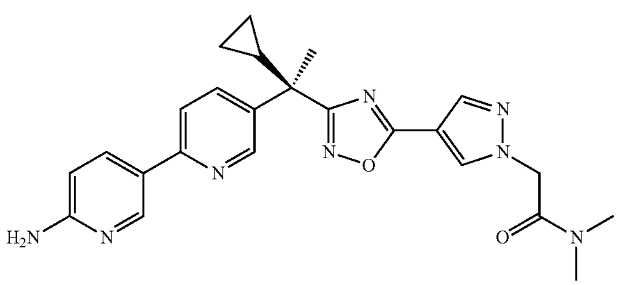 [SMILES: CN(C)C(=O)Cn1cc(-c2nc([C@@](C)(c3ccc(-c4ccc(N)nc4)nc3)C3CC3)no2)cn1] | 2-(4-{3-[(R)-1-(6'-Amino-[2,3']bipyridinyl-5-yl)-1-cyclopropyl-ethyl]-[1,2,4]oxadiazol-5-yl}-pyrazol-1-yl)-N,N-dimethyl-acetamide |
| 141 | 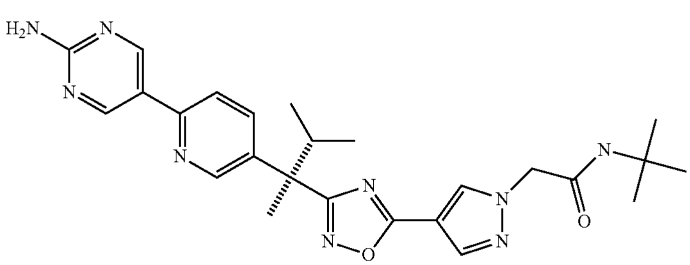 [SMILES: CC(C)[C@](C)(c1ccc(-c2cnc(N)nc2)nc1)c1noc(-c2cnn(CC(=O)NC(C)(C)C)c2)n1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-N-tert-butyl-acetamide |

TABLE I-continued

| Example | Structure | Name |
|---|---|---|
| 142 | 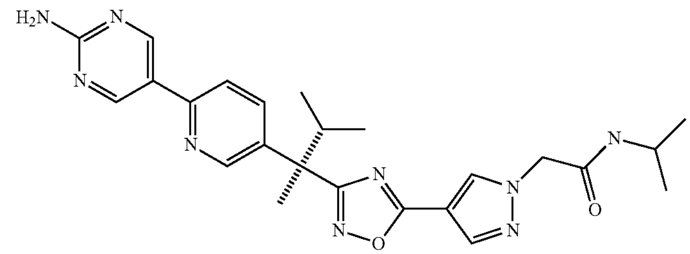 [SMILES: CC(C)NC(=O)Cn1cc(-c2nc([C@@](C)(c3ccc(-c4cnc(N)nc4)nc3)C(C)C)no2)cn1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-N-isopropyl-acetamide |
| 143 | 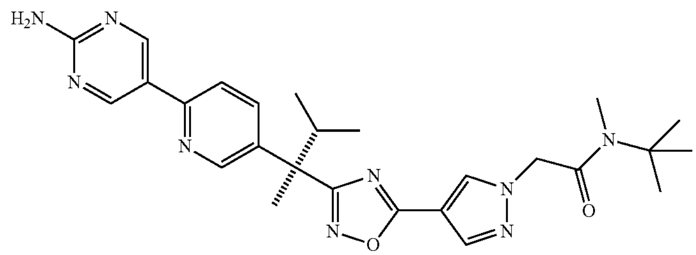 [SMILES: CC(C)[C@](C)(c1ccc(-c2cnc(N)nc2)nc1)c1noc(-c2cnn(CC(=O)N(C)C(C)(C)C)c2)n1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-N-tert-butyl-N-methyl-acetamide |
| 144 | 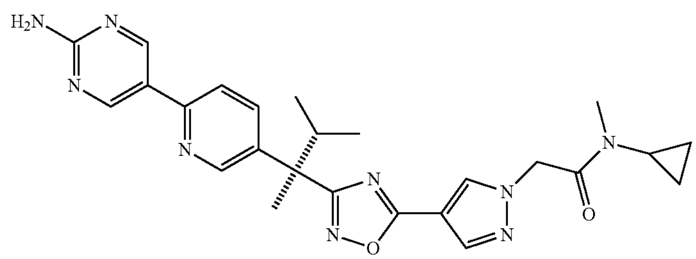 [SMILES: CC(C)[C@](C)(c1ccc(-c2cnc(N)nc2)nc1)c1noc(-c2cnn(CC(=O)N(C)C3CC3)c2)n1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-N-cyclopropyl-N-methyl-acetamide |
| 145 | 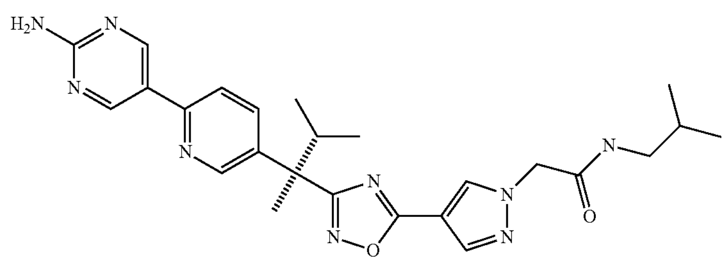 [SMILES: CC(C)CNC(=O)Cn1cc(-c2nc([C@@](C)(c3ccc(-c4cnc(N)nc4)nc3)C(C)C)no2)cn1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-N-isobutyl-acetamide |
| 146 | 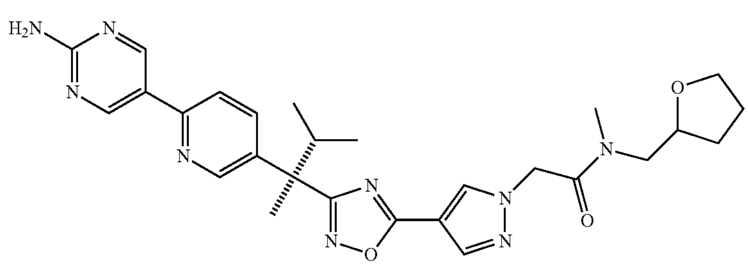 [SMILES: CC(C)[C@](C)(c1ccc(-c2cnc(N)nc2)nc1)c1noc(-c2cnn(CC(=O)N(C)CC3CCCO3)c2)n1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-N-methyl-N-(tetrahydro-furan-2-ylmethyl)-acetamide |
| 147 | 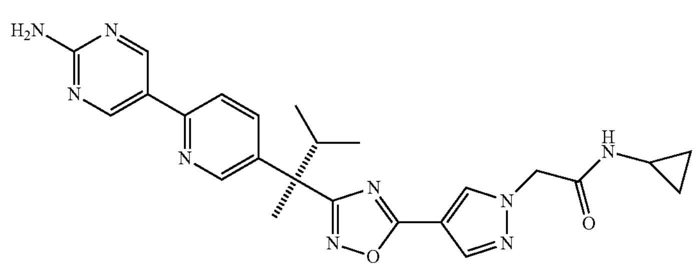 [SMILES: CC(C)[C@](C)(c1ccc(-c2cnc(N)nc2)nc1)c1noc(-c2cnn(CC(=O)NC3CC3)c2)n1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-N-cyclopropyl-acetamide |

TABLE I-continued

| Example | Structure | Name |
|---|---|---|
| 148 | 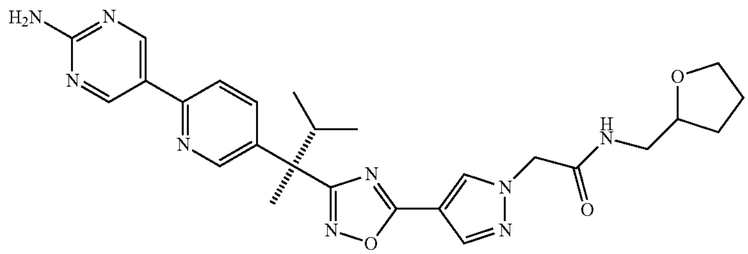 [SMILES: CC(C)[C@](C)(c1ccc(-c2cnc(N)nc2)nc1)c1noc(-c2cnn(CC(=O)NCC3CCCO3)c2)n1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-N-(tetrahydro-furan-2-ylmethyl)-acetamide |
| 149 | 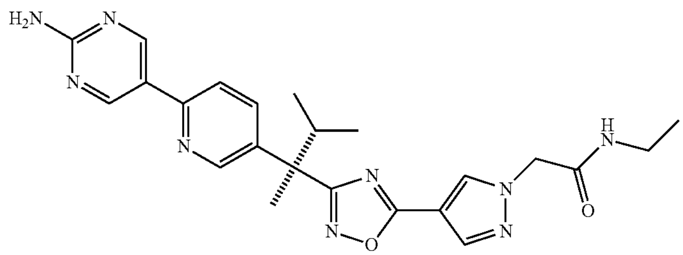 [SMILES: CCNC(=O)Cn1cc(-c2nc([C@@](C)(c3ccc(-c4cnc(N)nc4)nc3)C(C)C)no2)cn1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-N-ethyl-acetamide |
| 150 | 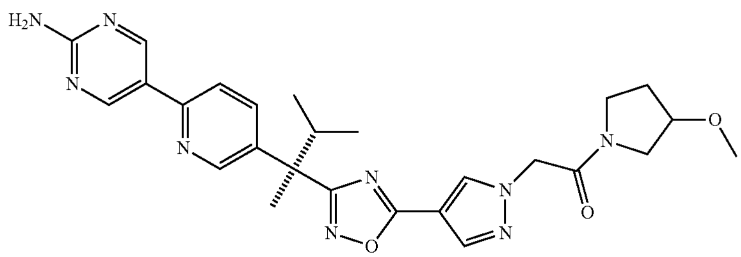 [SMILES: COC1CCN(C(=O)Cn2cc(-c3nc([C@@](C)(c4ccc(-c5cnc(N)nc5)nc4)C(C)C)no3)cn2)C1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-1-(3-methoxy-pyrrolidin-1-yl)-ethanone |
| 151 | 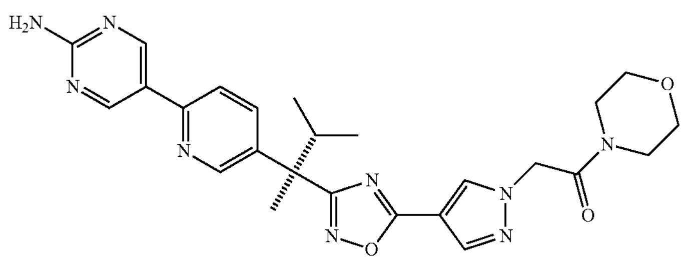 [SMILES: CC(C)[C@](C)(c1ccc(-c2cnc(N)nc2)nc1)c1noc(-c2cnn(CC(=O)N3CCOCC3)c2)n1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-1-morpholin-4-yl-ethanone |
| 152 | 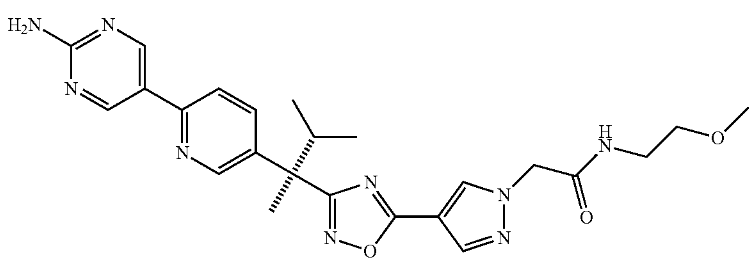 [SMILES: COCCNC(=O)Cn1cc(-c2nc([C@@](C)(c3ccc(-c4cnc(N)nc4)nc3)C(C)C)no2)cn1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-N-(2-methoxy-ethyl)-acetamide |
| 153 | 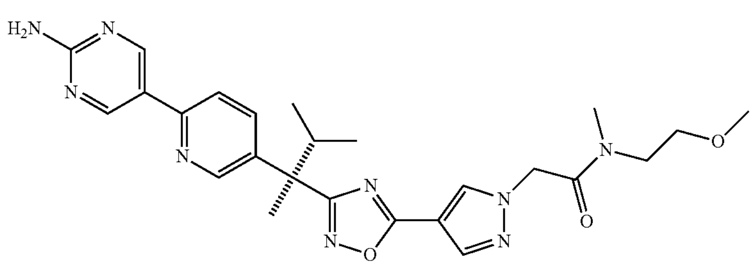 [SMILES: COCCN(C)C(=O)Cn1cc(-c2nc([C@@](C)(c3ccc(-c4cnc(N)nc4)nc3)C(C)C)no2)cn1] | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-N-(2-methoxy-ethyl)-N-methyl-acetamide |

TABLE I-continued

| Example | Structure | Name |
|---|---|---|
| 154 | 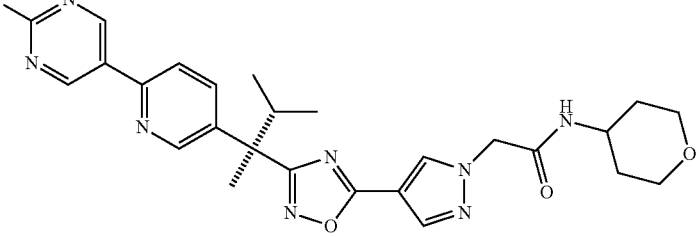 | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-N-(tetrahydro-pyran-4-yl)-acetamide |
| 155 | 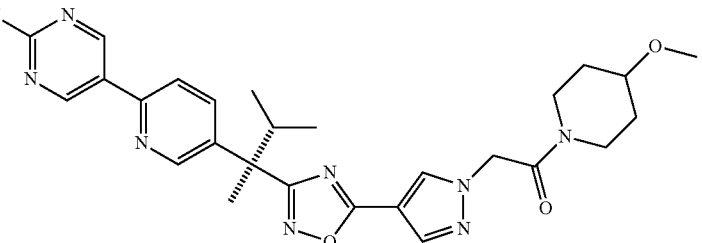 | 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-1-(4-methoxy-piperidin-1-yl)-ethanone |
| 156 | 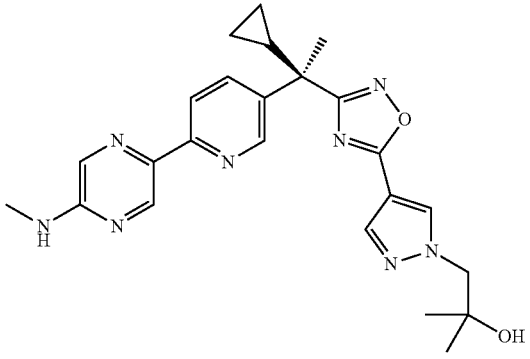 [SMILES: CNc1cnc(-c2ccc([C@](C)(c3noc(-c4cnn(CC(C)(C)O)c4)n3)C3CC3)cn2)cn1] | 1-[4-(3-{(R)-1-Cyclopropyl-1-[6-(5-methylamino-pyrazin-2-yl)-pyridin-3-yl]-ethyl}-[1,2,4]oxadiazol-5-yl)-pyrazol-1-yl]-2-methyl-propan-2-ol |
| 157 | 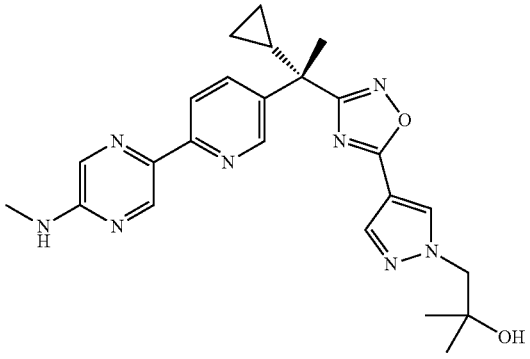 [SMILES: CNc1cnc(-c2ccc([C@@](C)(c3noc(-c4cnn(CC(C)(C)O)c4)n3)C3CC3)cn2)cn1] | 1-[4-(3-{(S)-1-Cyclopropyl-1-[6-(5-methylamino-pyrazin-2-yl)-pyridin-3-yl]-ethyl}-[1,2,4]oxadiazol-5-yl)-pyrazol-1-yl]-2-methyl-propan-2-ol |
| 158 | 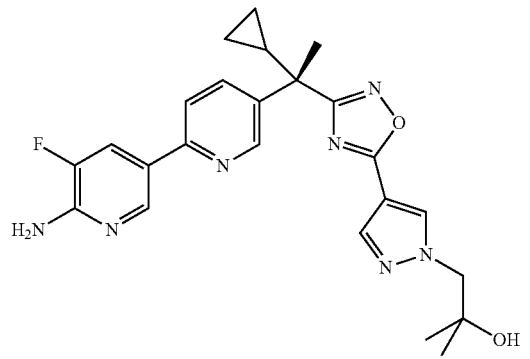 [SMILES: CC(C)(O)Cn1cc(-c2nc([C@](C)(c3ccc(-c4cnc(N)c(F)c4)nc3)C3CC3)no2)cn1] | 1-(4-{3-[1-(6'-Amino-5'-fluoro-[2,3']bipyridinyl-5-yl)-1-cyclopropyl-ethyl]-[1,2,4]oxadiazol-5-yl}-pyrazol-1-yl)-2-methyl-propan-2-ol |

TABLE I-continued

| Example | Structure | Name |
|---|---|---|
| 159 | 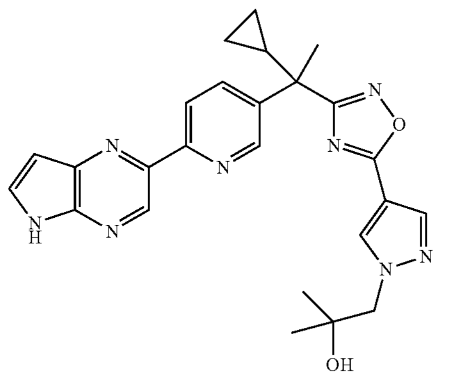 [SMILES: CC(C)(O)Cn1cc(-c2nc(C(C)(c3ccc(-c4cnc5[nH]ccc5n4)nc3)C3CC3)no2)cn1] | 1-[4-(3-{1-Cyclopropyl-1-[6-(5H-pyrrolo[2,3-b]pyrazin-2-yl)-pyridin-3-yl]-ethyl}-[1,2,4]oxadiazol-5-yl)-pyrazol-1-yl]-2-methyl-propan-2-ol |
| 160 | 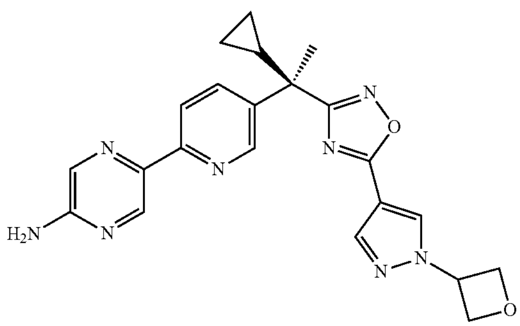 [SMILES: C[C@@](c1ccc(-c2cnc(N)cn2)nc1)(c1noc(-c2cnn(C3COC3)c2)n1)C1CC1] | 5-(5-{(R)-1-Cyclopropyl-1[5-(1-oxetan-3-yl-1H-pyrazol-4-yl)-[1,2,4]oxadiazol-3-yl]-ethyl}-pyridin-2-yl)-pyrazin-2-ylamine |
| 161 | 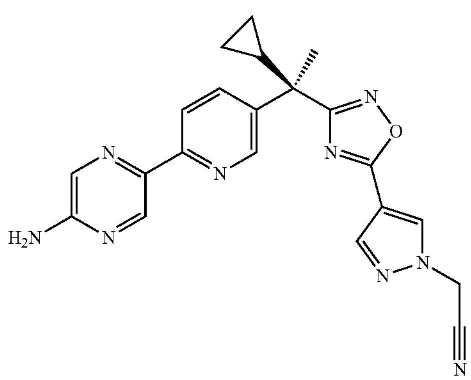 [SMILES: C[C@@](c1ccc(-c2cnc(N)cn2)nc1)(c1noc(-c2cnn(CC#N)c2)n1)C1CC1] | [4-(3-{(R)-1-[6-(5-Amino-pyrazin-2-yl)-pyridin-3-yl]-1-cyclopropyl-ethyl}-[1,2,4]oxadiazol-5-yl)-pyrazol-1-yl]-acetonitrile |
| 162 | 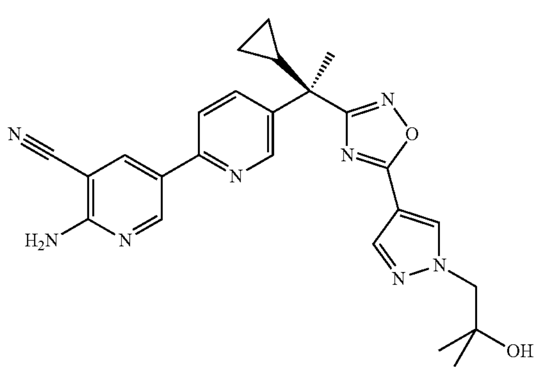 [SMILES: CC(C)(O)Cn1cc(-c2nc([C@@](C)(c3ccc(-c4cnc(N)c(C#N)c4)nc3)C3CC3)no2)cn1] | 6'-Amino-5-((R)-1-cyclopropyl-1-{5-[1-(2-hydroxy-2-methyl-propyl)-1H-pyrazol-4-yl]-[1,2,4]oxadiazol-3-yl}-ethyl)-[2,3']bipyridinyl-5'-carbonitrile |

TABLE I-continued

| Example | Structure | Name |
|---|---|---|
| 163 | 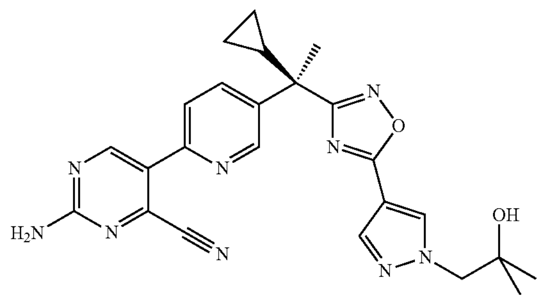 [SMILES: CC(C)(O)Cn1cc(-c2nc([C@@](C)(c3ccc(-c4cnc(N)nc4C#N)nc3)C3CC3)no2)cn1] | 2-Amino-5-[5-((R)-1-cyclopropyl-1-{5-[1-(2-hydroxy-2-methyl-propyl)-1H-pyrazol-4-yl]-[1,2,4]oxadiazol-3-yl}-ethyl)-pyridin-2-yl]-pyrimidine-4-carbonitrile |
| 164 | 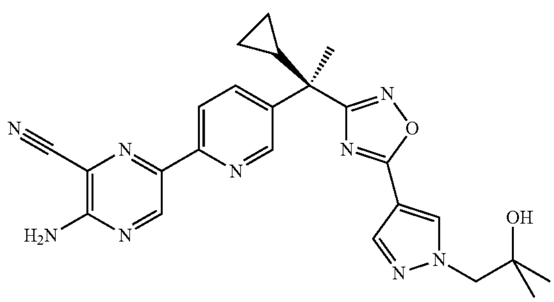 [SMILES: CC(C)(O)Cn1cc(-c2nc([C@@](C)(c3ccc(-c4cnc(N)c(C#N)n4)nc3)C3CC3)no2)cn1] | 3-Amino-6-[5-((R)-1-cyclopropyl-1-{5-[1-(2-hydroxy-2-methyl-propyl)-1H-pyrazol-4-yl]-[1,2,4]oxadiazol-3-yl}-ethyl)-pyridin-2-yl]-pyrazine-2-carbonitrile |
| 165 | 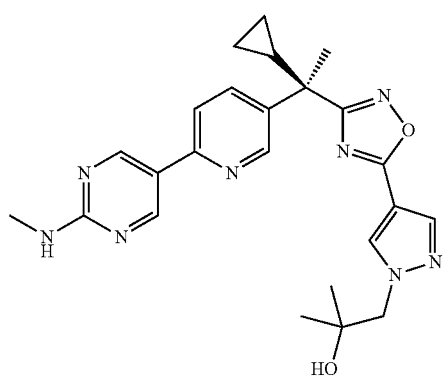 [SMILES: CNc1ncc(-c2ccc([C@](C)(c3noc(-c4cnn(CC(C)(C)O)c4)n3)C3CC3)cn2)cn1] | 1-[4-(3-{(R)-1-Cyclopropyl-1-[6-(2-methylamino-pyrimidin-5-yl)-pyridin-3-yl]-ethyl}-[1,2,4]oxadiazol-5-yl)-pyrazol-1-yl]-2-methyl-propan-2-ol |
| 166 | 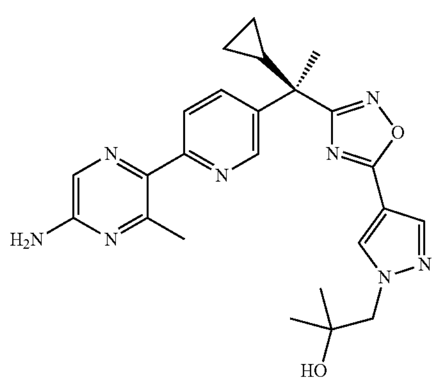 [SMILES: Cc1nc(N)cnc1-c1ccc([C@](C)(c2noc(-c3cnn(CC(C)(C)O)c3)n2)C2CC2)cn1] | 1-[4-(3-{(R)-1-[6-(5-Amino-3-methyl-pyrazin-2-yl)-pyridin-3-yl]-1-cyclopropyl-ethyl}-[1,2,4]oxadiazol-5-yl)-pyrazol-1-yl]-2-methyl-propan-2-ol |

TABLE I-continued

| Example | Structure | Name |
|---|---|---|
| 167 | 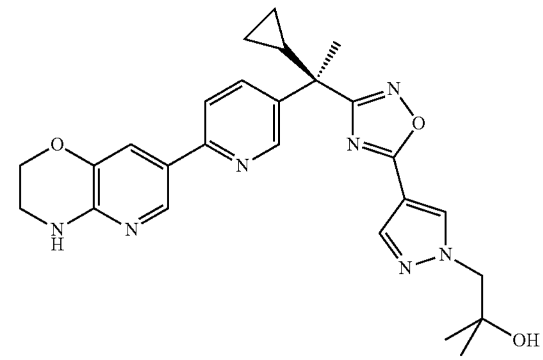 [SMILES: CC(C)(O)Cn1cc(-c2nc([C@@](C)(c3ccc(-c4cnc5c(c4)OCCN5)nc3)C3CC3)no2)cn1] | 1-[4-(3-{(R)-1-Cyclopropyl-1-[6-(3,4-dihydro-2H-pyrido [3,2-b][1,4]oxazin-7-yl)-pyridin-3-ethyl}[1,2,4]oxadiazol-5-yl)-pyrazol-1-yl]-2-methyl-propan-2-ol |
| 168 | 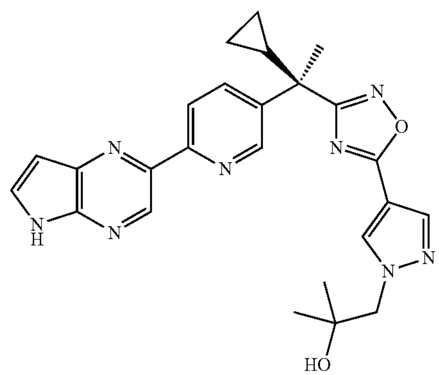 [SMILES: CC(C)(O)Cn1cc(-c2nc([C@@](C)(c3ccc(-c4cnc5[nH]ccc5n4)nc3)C3CC3)no2)cn1] | 1-[4-(3-{(R)-1-Cyclopropyl-1-[6-(5H-pyrrolo[2,3-b]pyrazin-2-yl)-pyridin-3-yl]-ethyl}-[1,2,4]oxadiazol-5-yl)-pyrazol-1-yl]-2-methyl-propan-2-ol |
| 169 | 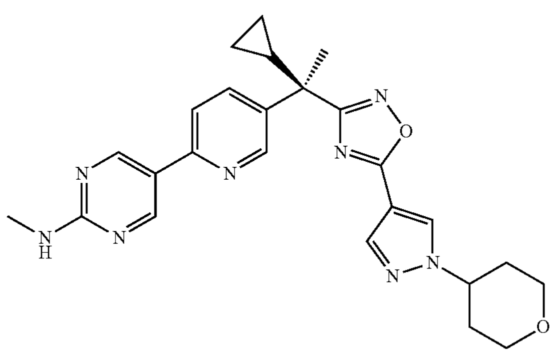 [SMILES: CNc1ncc(-c2ccc([C@](C)(c3noc(-c4cnn(C5CCOCC5)c4)n3)C3CC3)cn2)cn1] | {5-[5-((R)-1-Cyclopropyl-1-{5-[1-(tetrahydro-pyran-4-yl)-1H-pyrazol-4-yl]-[1,2,4]oxadiazol-3-yl}-ethyl)-pyridin-2-yl]-pyrimidin-2-yl}-methyl-amine |
| 170 | 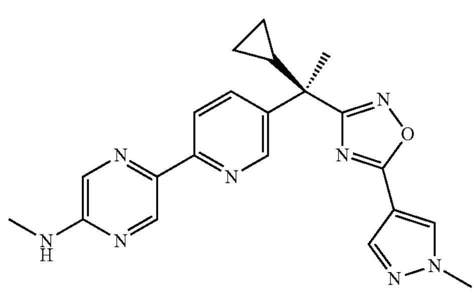 | [5-(5-{(R)-1-Cyclopropyl-1-[5-(1-methyl-1H-pyrazol-4-yl)-[1,2,4]oxadiazol-3-yl]-ethyl}-pyridin-2-yl)-pyrazin-2-yl]-methyl-amine |

TABLE I-continued

| Example | Structure | Name |
|---|---|---|
| 171 | 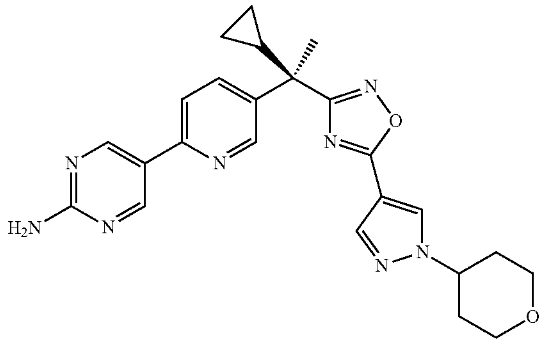 [SMILES: C[C@@](c1ccc(-c2cnc(N)nc2)nc1)(c1noc(-c2cnn(C3CCOCC3)c2)n1)C1CC1] | 5-[5-((R)-1-Cyclopropyl-1-{5-[1-(tetrahydro-pyran-4-yl)-1H-pyrazol-4-yl]-[1,2,4]oxadiazol-3-yl}ethyl)-pyridin-2-yl]-pyrimidin-2-ylamine |
| 172 | 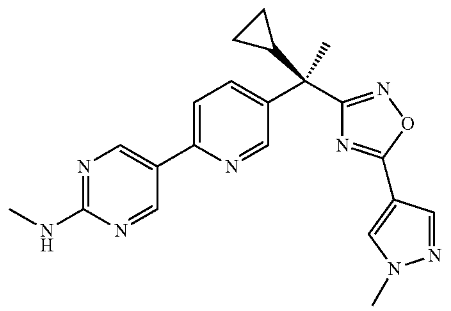 [SMILES: CNc1ncc(-c2ccc([C@](C)(c3noc(-c4cnn(C)c4)n3)C3CC3)cn2)cn1] | [5-(5-{(R)-1-Cyclopropyl-1-[5-(1-methyl-1H-pyrazol-4-yl)-[1,2,4]oxadiazol-3-yl]ethyl}-pyridin-2-yl)-pyrimidin-2-yl]-methyl-amine |
| 173 | 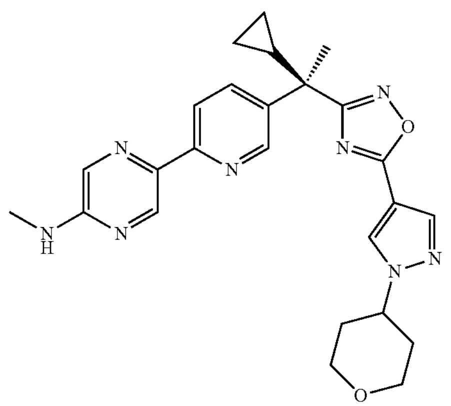 [SMILES: CNc1cnc(-c2ccc([C@](C)(c3noc(-c4cnn(C5CCOCC5)c4)n3)C3CC3)cn2)cn1] | {5-[5-((R)-1-Cyclopropyl-1-{5-[1-(tetrahydro-pyran-4-yl)-1H-pyrazol-4-yl]-[1,2,4]oxadiazol-3-yl}-ethyl)-pyridin-2-yl]-pyrazin-2-yl}-methyl-amine |
| 174 | 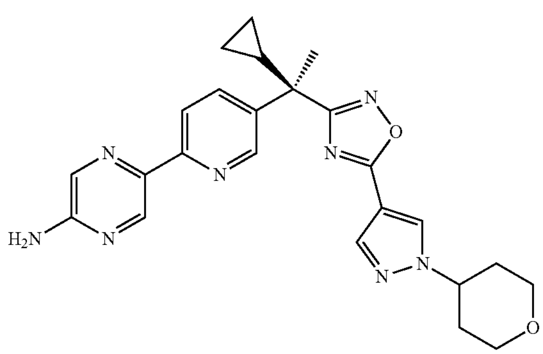 [SMILES: C[C@@](c1ccc(-c2cnc(N)cn2)nc1)(c1noc(-c2cnn(C3CCOCC3)c2)n1)C1CC1] | 5-[5-(R)-1-Cyclopropyl-1-{5-[1-(tetrahydro-pyran-4-yl)-1H-pyrazol-4-yl]-[1,2,4]oxadiazol-3-yl}-ethyl)-pyridin-2-yl]-pyrazin-2-ylamine |

TABLE I-continued

| Example | Structure | Name |
|---|---|---|
| 175 | 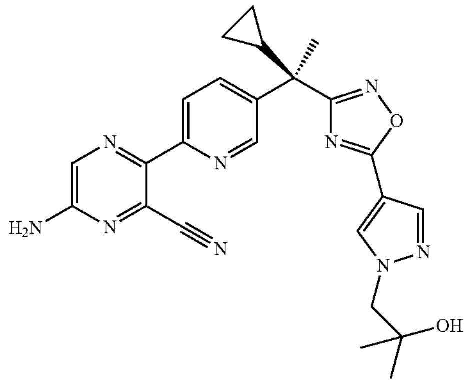 [SMILES: CC(C)(O)Cn1cc(-c2nc([C@@](C)(c3ccc(-c4ncc(N)nc4C#N)nc3)C3CC3)no2)cn1] | 6-Amino-3-[5-((R)-1-cyclopropyl-1-{5-[1-(2-hydroxy-2-methyl-propyl)-1H-pyrazol-4-yl]-[1,2,4]oxadiazol-3-yl}-ethyl)-pyridin-2-yl]-pyrazine-2-carbonitrile |
| 176 | 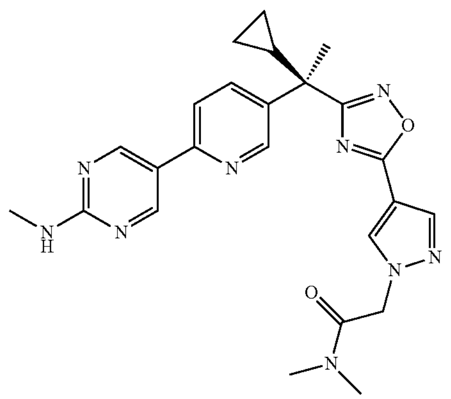 [SMILES: CNc1ncc(-c2ccc([C@](C)(c3noc(-c4cnn(CC(=O)N(C)C)c4)n3)C3CC3)cn2)cn1] | 2-[4-(3-{(R)-1-Cyclopropyl-1-[6-(2-methylamino-pyrimidin-5-yl)-pyridin-3-yl]-ethyl}-[1,2,4]oxadiazol-5-yl)-pyrazol-1-yl]-N,N-dimethyl-acetamide |
| 177 | 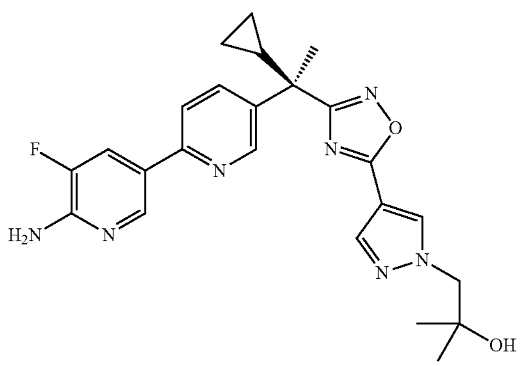 [SMILES: CC(C)(O)Cn1cc(-c2nc([C@@](C)(c3ccc(-c4cnc(N)c(F)c4)nc3)C3CC3)no2)cn1] | 1-(4-{3-[(R)-1-(6'-Amino-5'-fluoro-[2,3']bipyridinyl-5-yl)-1-cyclopropyl-ethyl]-[1,2,4]oxadiazol-5-yl}-pyrazol-1-yl)-2-methyl-propan-2-ol |
| 178 | 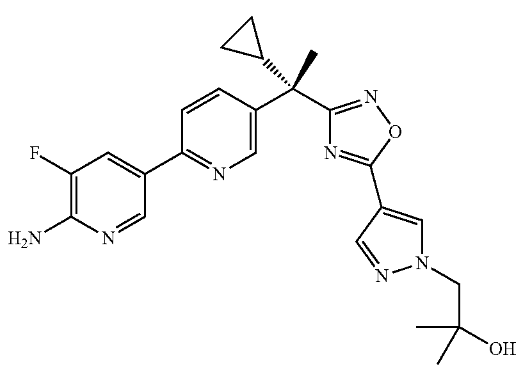 [SMILES: CC(C)(O)Cn1cc(-c2nc([C@](C)(c3ccc(-c4cnc(N)c(F)c4)nc3)C3CC3)no2)cn1] | 1-(4-{3-[(S)-1-(6'-Amino-5'-fluoro-[2,3']bipyridinyl-5-yl)-1-cyclopropyl-ethyl]-[1,2,4]oxadiazol-5-yl}-pyrazol-1-yl)-2-methyl-propan-2-ol |

TABLE I-continued

| Example | Structure | Name |
|---|---|---|
| 179 | 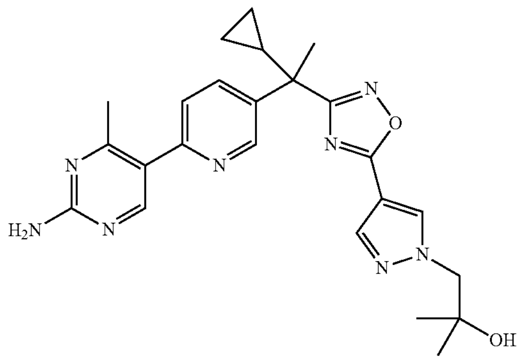 [SMILES: Cc1nc(N)ncc1-c1ccc(C(C)(c2noc(-c3cnn(CC(C)(C)O)c3)n2)C2CC2)cn1] | 1-[4-(3-{1-[6-(2-Amino-4-methyl-pyrimidin-5-yl)-pyridin-3-yl]-1-cyclopropyl-ethyl}-[1,2,4]oxadiazol-5-yl)-pyrazol-1-yl]-2-methyl-propan-2-ol |
| 180 | 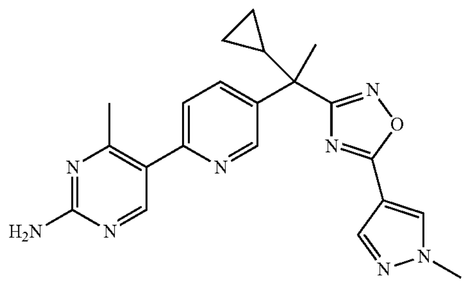 [SMILES: Cc1nc(N)ncc1-c1ccc(C(C)(c2noc(-c3cnn(C)c3)n2)C2CC2)cn1] | 5-(5-{1-Cyclopropyl-1-[5-(1-methyl-1H-pyrazol-4-yl)-[1,2,4]oxadiazol-3-yl]-ethyl}-pyridin-2-yl)-4-methyl-pyrimidin-2-ylamine |
| 181 | 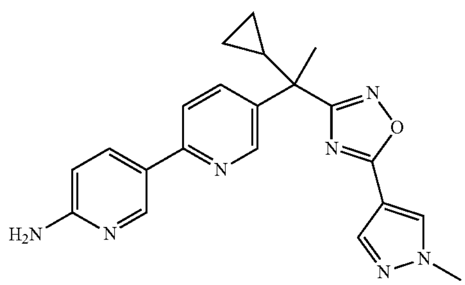 [SMILES: Cn1cc(-c2nc(C(C)(c3ccc(-c4ccc(N)nc4)nc3)C3CC3)no2)cn1] | 5-(5-{1-Cyclopropyl-1-[5-(1-methyl-1H-pyrazol-4-yl)-[1,2,4]oxadiazol-3-yl]-ethyl}-pyridin-2-yl)-pyrazin-2-ylamine |

In one embodiment, the invention relates to any of the compounds depicted in Table I above and the pharmaceutically acceptable salt thereof.

Representative compounds of the invention show activity in the FLAP binding assay and in the human whole blood $LTB_4$ production inhibition assay, described in the assessment of biological properties section, as shown in Table II.

TABLE II

| Example | FLAP SPA $IC_{50}$ (nM) | hWB $LTB_4$ $IC_{50}$ (nM) |
|---|---|---|
| 1 | 8.3 | 54 |
| 2 | 10.0 | 74 |
| 3 | 4.7 | 68 |
| 4 | 3.0 | 20 |
| 5 | 76.2 | 750 |
| 6 | 8.6 | 220 |
| 7 | 14.4 | 180 |
| 8 | 6.3 | 68 |
| 9 | 5.9 | 25 |
| 10 | 4.9 | 60 |
| 11 | 2.9 | 40 |
| 12 | 3.6 | 55 |
| 13 | 10.9 | 490 |
| 14 | 6.5 | 45 |
| 15 | 2.3 | 75 |

TABLE II-continued

| Example | FLAP SPA $IC_{50}$ (nM) | hWB $LTB_4$ $IC_{50}$ (nM) |
|---|---|---|
| 16 | 2.3 | 65 |
| 17 | 4.5 | 53 |
| 18 | 2.7 | 83 |
| 19 | 4.8 | 140 |
| 20 | 4.0 | 140 |
| 21 | 51.2 | 570 |
| 22 | 3.6 | 140 |
| 23 | 3.9 | 39 |
| 24 | 170 | 990 |
| 25 | 520 | >5000 |
| 26 | 400 | 3900 |
| 27 | 7.5 | 71 |
| 28 | 3.8 | 72 |
| 29 | 4.0 | 40 |
| 30 | 12.0 | 160 |
| 31 | 1.4 | 12 |
| 32 | 17.3 | 860 |
| 33 | 5.2 | 210 |
| 34 | 6.6 | 94 |
| 35 | 210 | 3200 |
| 36 | 30% inhibition at 1 uM | >5000 |
| 37 | 167.8 | >5000 |
| 38 | 6.4 | 33 |
| 39 | 20.4 | >5000 |

TABLE II-continued

| Example | FLAP SPA IC$_{50}$ (nM) | hWB LTB$_4$ IC$_{50}$ (nM) |
|---|---|---|
| 40 | 7.9 | 100 |
| 41 | 1.8 | 34 |
| 42 | 8.3 | 210 |
| 43 | 1.2 | 32 |
| 44 | 0.9 | 24 |
| 45 | 140.7 | 1400 |
| 46 | 5.0 | 98 |
| 47 | 180 | 2000 |
| 48 | 2.6 | 20 |
| 49 | 80.9 | 1100 |
| 50 | 9.5 | 110 |
| 51 | 3.0 | 160 |
| 52 | 14.0 | 270 |
| 53 | 12.7 | 230 |
| 54 | 70.7 | 750 |
| 55 | 2.5 | 46 |
| 56 | 11.8 | 230 |
| 57 | 16.0 | 33 |
| 58 | 230 | 980 |
| 59 | 450 | 1800 |
| 60 | 3.4 | 17 |
| 61 | 3.0 | 48 |
| 62 | 19.4 | 420 |
| 63 | 8.7 | 29 |
| 64 | 6.3 | 80 |
| 65 | 1.6 | 28 |
| 66 | 19.7 | 52 |
| 67 | 110 | 290 |
| 68 | 24 | 80 |
| 69 | 64.8 | 840 |
| 70 | 12.4 | 240 |
| 71 | 8.1 | 840 |
| 72 | 26.4 | 440 |
| 73 | 3.9 | 110 |
| 74 | 3.1 | 220 |
| 75 | 32.0 | 52 |
| 76 | 190 | 2000 |
| 77 | 0.14 | 15 |
| 78 | 8.0 | 29 |
| 79 | 140 | 650 |
| 80 | 5.6 | 230 |
| 81 | 16 | 41 |
| 82 | 340 | 1200 |
| 83 | 76 | 200 |
| 84 | 45% inhibition at 1 uM | 2900 |
| 85 | 350 | 1900 |
| 86 | 140 | 790 |
| 87 | 670 | >5000 |
| 88 | 370 | 1500 |
| 89 | 230 | 880 |
| 90 | 140 | 950 |
| 91 | 300 | 1500 |
| 92 | 15 | 92 |
| 93 | 21 | 28 |
| 94 | 26 | 74 |
| 95 | 92 | 210 |
| 96 | 9.9 | 240 |
| 97 | 7.9 | 30 |
| 98 | 26 | 500 |
| 99 | 32 | 150 |
| 100 | 53 | 210 |
| 101 | 280 | 990 |
| 102 | 13 | 89 |
| 103 | 6.3 | 32 |
| 104 | 5.7 | 17 |
| 105 | 7.8 | 450 |
| 106 | 10 | 30 |
| 107 | 72 | 220 |
| 108 | 360 | 2300 |
| 109 | 350 | 1100 |
| 110 | 5.9 | 31 |
| 111 | 13 | 30 |
| 112 | 4.8 | 71 |
| 113 | 4 | 12 |
| 114 | 52 | 850 |
| 115 | 24 | 110 |
| 116 | 360 | 2000 |
| 117 | 8.7 | 86 |
| 118 | 47 | 210 |
| 119 | 3.4 | 2200 |
| 120 | 42 | 300 |
| 121 | 67 | 220 |
| 122 | 34 | 450 |
| 123 | 300 | 3300 |
| 124 | 18 | 60 |
| 125 | 120 | 370 |
| 126 | 8.8 | 25 |
| 127 | 220 | 410 |
| 128 | 10 | 270 |
| 129 | 8.1 | 19 |
| 130 | 15 | 94 |
| 131 | 5.6 | 39 |
| 132 | 12 | 130 |
| 133 | 7.5 | 30 |
| 134 | 7.2 | 310 |
| 135 | 700 | >5000 |
| 136 | 9.9 | 61 |
| 137 | 11 | 590 |
| 138 | 22 | 100 |
| 139 | 33 | 68 |
| 140 | 44 | 150 |
| 141 | 8.3 | 68 |
| 142 | 16 | 85 |
| 143 | 9.2 | 51 |
| 144 | 13 | 68 |
| 145 | 14 | 110 |
| 146 | 9.4 | 53 |
| 147 | 8.6 | 170 |
| 148 | 22 | 290 |
| 149 | 15 | 140 |
| 150 | 42 | 180 |
| 151 | 32 | 190 |
| 152 | 24 | 190 |
| 153 | 16 | 150 |
| 154 | 21 | 550 |
| 155 | 19 | 110 |
| 156 | 27 | 54 |
| 157 | 420 | 969 |
| 158 | 230 | 502 |
| 159 | 27 | 167 |
| 160 | 15 | 23 |
| 161 | 21 | 32 |
| 162 |  | 319 |
| 163 | 290 | 348 |
| 164 | 40 | 97 |
| 165 | 56 | 82 |
| 166 | 41 | 57 |
| 167 |  | 171 |
| 168 |  | 63 |
| 169 |  | 105 |
| 170 |  | 112 |
| 171 |  | 119 |
| 172 |  | 104 |
| 173 |  | 221 |
| 174 |  | 53 |
| 175 |  | 144 |
| 176 |  | 267 |
| 177 | 65 | 256 |
| 178 | 2000 | 2349 |
| 179 | 450 | 483 |
| 180 | 190 | 309 |
| 181 | 34 | 65 |

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form.

The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term $C_{1-3}$ hydroxy also means $C_{1-3}$alkylhydroxy or $C_{1-3}$alkyl-OH.

The term "$C_{3-10}$ carbocycle" or $C_{3-10}$ cycloalkyl refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl(decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "$C_{6-10}$ aryl" or "aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "5 to 11-membered heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, tetrahydropyranyl, oxetanyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "5 to 11-membered heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S, Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, pyrrolopyrimidinyl, pyrazolopyridinyl, pyrrolopyridazinyl, pyrrolopyrazinyl, pyrido-oxazinyl, pyrazolopyrimidinyl indolyl, isoindolyl, benzofuranyl, benzopyranyl, benzodioxolyl, benzoxazolyl and benzothiazolyl.

It will be understood that one to three carbon ring moieties in the each of the $C_{3-10}$ carbocyclic rings, the 5 to 11-membered heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above.

The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —$CH_2CHF_2$, —$CF_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1-C_4$ alkyl$)_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention also provides processes for making compounds of Formula (I). In all Schemes, unless specified otherwise, $R^1$, $R^2$, $R^3$, $R^4$ and $R^5$ in the Formulas below shall have the meaning of $R^1$, $R^2$, $R^3$, $R^4$ and $R^5$ in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, recrystallization and/or preparative HPLC.

The examples which follow are illustrative and, as recognized by one skilled in the art, particular reagents or conditions could be modified as needed for individual compounds without undue experimentation. Starting materials and intermediates used, in the Schemes below, are either commercially available or easily prepared from commercially available materials by those skilled in the art.

The compounds of Formula (I) may be synthesized according to Scheme 1:

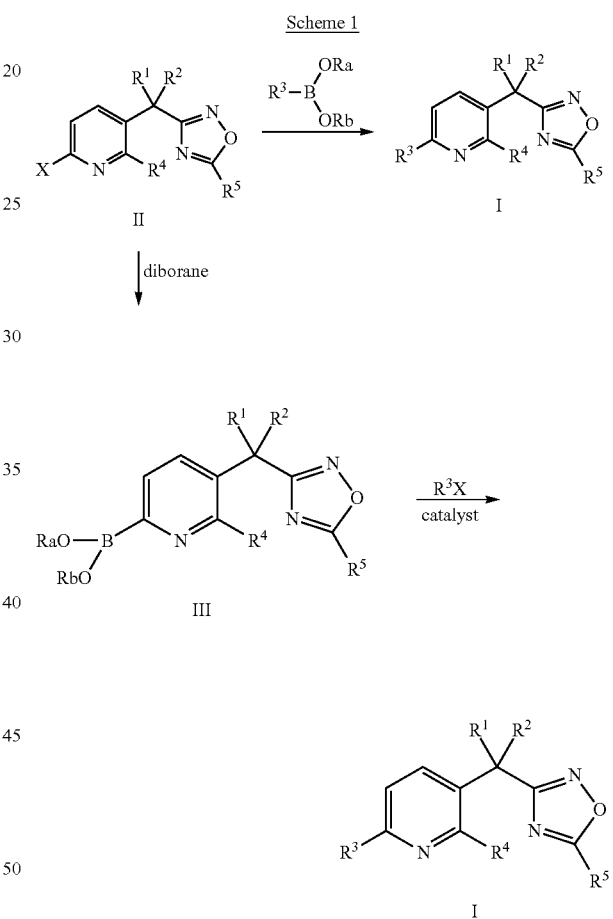

As illustrated in scheme 1, reaction of a compound of formula II with a boronic acid or the corresponding boronic acid ester shown in the above scheme, in a suitable solvent, in the presence of a suitable catalyst, provides a compound of formula (I). Ra and Rb are hydrogen or Ra and Rb together with the oxygen atoms to which they are attached form a 5-6 membered ring optionally substituted with 2-4 methyl groups. Alternatively, reaction of a compound of formula II with a diborane, under standard reaction conditions, provides a compound of formula III. Coupling the intermediate of formula III with a halide or triflate $R^3X$, in a suitable solvent, in the presence of a suitable catalyst, provides a compound of formula (I). X is chloro, bromo, triflate, or iodo.

The compounds of Formula (I) may be prepared according to Scheme 2:

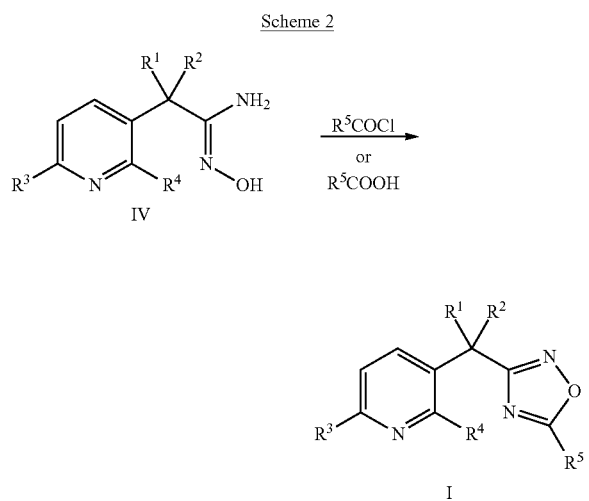

Scheme 2

As illustrated in scheme 2, reaction of a compound of formula IV with an acid chloride $R^5COCl$, in a suitable solvent, in the presence of a suitable base, provides a compound of formula (I).

Alternatively, reaction of a compound of formula IV with an acid $R^5COOH$, in a suitable solvent, in the presence of carbonyl diimidazole, or other suitable amide coupling reagent, provides a compound of formula (I).

Reaction of a compound of formula IV with trichloroacetic anhydride, under standard conditions, provides a compound of formula (I) wherein $R^5$ is trichloromethyl. The trichloromethyl group may be converted to another $R^5$ group by reactions known to one of skilled in the art.

The intermediate of formula II may be synthesized as outlined in Scheme 3:

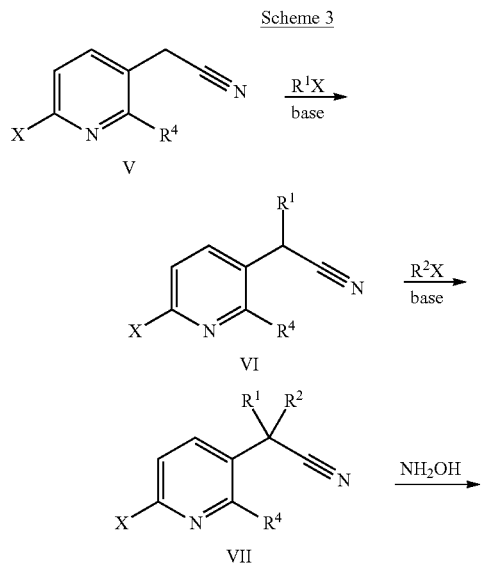

Scheme 3

As illustrated in scheme 3, reaction of a nitrile of formula V with a halide $R^1X$, in a suitable solvent, in the presence of a suitable base such as sodium hydride, provides a substituted nitrile of formula VI. Further reaction of the intermediate of formula VI with a halide $R^2X$, in a suitable solvent, in the presence of a suitable base, provides the corresponding disubstituted nitrile of formula VII. X is chloro, bromo, or iodo. Reaction of the compound of formula VII with hydroxylamine, under standard reaction conditions, provides a compound of formula VIII. Reaction of the compound of formula VIII with an acid chloride $R^5COCl$, in a suitable solvent, in the presence of a suitable base, provides a compound of formula II. Alternatively, reaction of a compound of formula VIII with an acid $R^5COOH$, in a suitable solvent, in the presence of carbonyl diimidazole, or other suitable amide coupling reagent, provides a compound of formula II.

Alternatively, reaction of a compound of formula VIII with a reagent such as carbonyldiimidazole provides a compound of formula II wherein $R^5$ is —OH. Further transformation of this —OH may be carried out by procedures known in the art, to provide additional compounds of formula II.

The intermediate of formula II may also be synthesized as shown in Scheme 4:

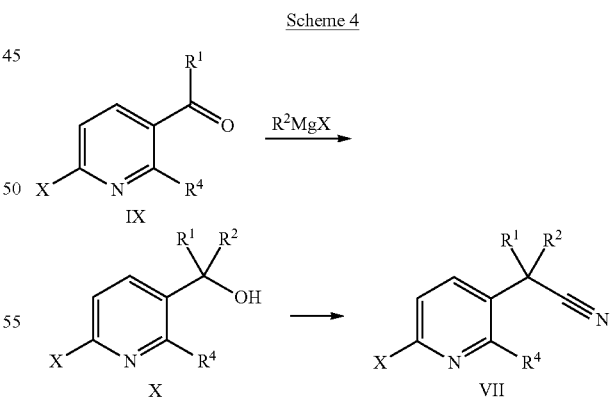

Scheme 4

As shown in scheme 4, reaction of a carbonyl compound of formula IX with a grignard reagent $R^2MgX$, in a suitable solvent, provides a hydroxy compound of formula X. Conversion of the hydroxyl group in compound of formula X to a cyano group, using standard procedures, provides a compound of formula VII. The compound of formula VII is converted to the intermediate of formula II by the reactions shown in scheme 3. X in $R^2MgX$ is chloro, bromo or iodo.

The intermediate of formula IV may be synthesized according to Scheme 5:

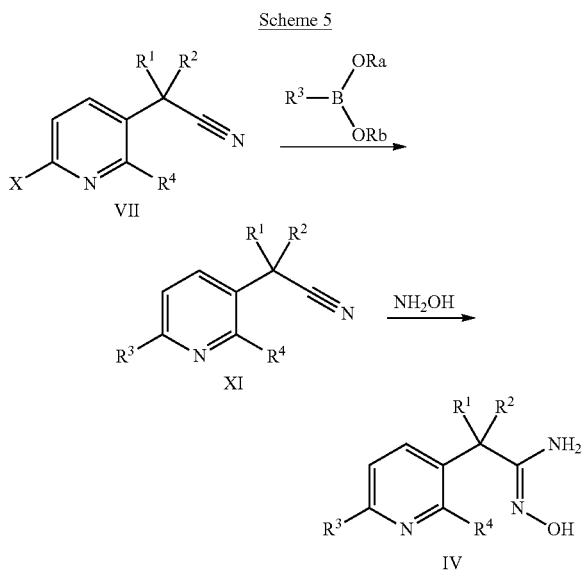

As illustrated above in scheme 5, reaction of a nitrile of formula VII with a boronic acid or the corresponding boronic acid ester shown in the above scheme, in a suitable solvent, in the presence of a suitable catalyst, provides a compound of formula XI. Ra and Rb are hydrogen or Ra and Rb together with the oxygen atoms to which they are attached form a 5-6 membered ring optionally substituted with 2-4 methyl groups. Reaction of a compound of formula XI with hydroxylamine, under standard reaction conditions, provides a compound of formula IV.

The intermediate of formula XI may be synthesized according to Scheme 6:

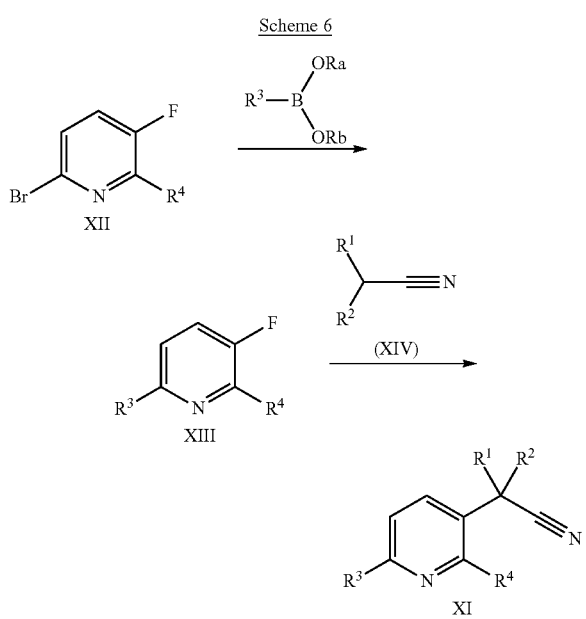

As illustrated above in scheme 6, reaction of a dihalide of formula XII with a boronic acid or the corresponding boronic acid ester shown in the above scheme, in a suitable solvent, in the presence of a suitable catalyst, provides a compound of formula XIII. Ra and Rb are hydrogen or Ra and Rb together with the oxygen atoms to which they are attached form a 5-6 membered ring optionally substituted with 2-4 methyl groups. Reaction of a compound of formula XIII with a nitrile of formula XIV, under standard reaction conditions, in the prence of a suitable base, provides a compound of formula XI.

Compounds of formula I as well as intermediates prepared by the above methods may be further converted to additional intermediates or compounds of formula I by methods known in the art and exemplified in the Synthetic Examples section below.

SYNTHETIC EXAMPLES

The following are representative compounds of the invention which can be made by the general synthetic schemes, the examples, and known methods in the art.

LCMS retention time and observed m/z data for the compounds below are obtained by one of the following methods:

| LC-MS Method A | | |
|---|---|---|
| Column | Waters Atlantis dC18 | |
| | 100 × 2.1 mm, 3 μm column | |
| | 40° C. | |
| Mobile phase | A = Formic acid (aq) 0.1% | |
| | B = Formic acid (acetonitrile) 0.1% | |
| Flow rate | 0.6 ml/min | |
| Injection volume | 3 μl | |
| Detector | 215 nm (nominal) | |
| Gradient | Time (mins) | % B |
| | 0 | 5 |
| | 5 | 100 |
| | 5.4 | 100 |
| | 5.42 | 5 |

| LC-MS Method B | | |
|---|---|---|
| Column | Atlantis dC18 | |
| | 2.1 × 50 mm, 3 μm column | |
| Mobile phase | A = Formic acid (aq) 0.1% | |
| | B = Formic acid (acetonitrile) 0.1% | |
| Flow rate | 1 ml/min | |
| Injection volume | 3 μl | |
| Detector | 215 nm (nominal) | |
| Gradient | Time (mins) | % B |
| | 0 | 5 |
| | 2.5 | 100 |
| | 2.7 | 100 |
| | 2.71 | 5 |
| | 3 | 5 |

| LC-MS Method C | |
|---|---|
| Column | Agilent SB-C18 |
| | 1.8 μm, 3 × 50 mm column |
| | Ambient temperature |

-continued

LC-MS Method C

| | | |
|---|---|---|
| Mobile phase | A = Formic acid (aq) 0.1% | |
| | B = Formic acid (acetonitrile) 0.1% | |
| Flow rate | 1.5 ml/min | |
| Injection volume | 3 μl | |
| Detector | 220 nm and 254 nm | |

| Gradient | Time (mins) | % B |
|---|---|---|
| | 0 | 5 |
| | 3.8 | 90 |
| | 4.5 | 100 |

LC-MS Method D

| | | |
|---|---|---|
| Column | Agilent SB-C18 | |
| | 1.8 μm, 3 × 50 mm column | |
| | Ambient temperature | |
| Mobile phase | A = Formic acid (aq) 0.1% | |
| | B = Formic acid (acetonitrile) 0.1% | |
| Flow rate | 1.5 ml/min | |
| Injection volume | 3 μl | |
| Detector | 220 nm and 254 nm | |

| Gradient | Time (mins) | % B |
|---|---|---|
| | 0 | 12 |
| | 0.25 | 30 |
| | 0.3 | 40 |
| | 1.19 | 95 |
| | 1.75 | 100 |

LC-MS Method E

| | | |
|---|---|---|
| Column | Agilent Zorbax Eclipse XDB-C8 | |
| | 5 μm, 4.6 × 150 mm column | |
| | Ambient temperature | |
| Mobile phase | A = Formic acid (aq) 0.1% | |
| | B = Formic acid (acetonitrile) 0.1% | |
| Flow rate | 1.5 ml/min | |
| Injection volume | 7 μl | |
| Detector | 210 nm-400 nm | |

| Gradient | Time (mins) | % B |
|---|---|---|
| | 0 | 5 |
| | 7 | 95 |
| | 9 | 95 |
| | 9.3 | 5 |
| | 10 | 5 |

LC-MS Method F

| | | |
|---|---|---|
| Column | Waters BEH C18 | |
| | 1.7 μm, 2.1 × 50 mm column | |
| | Ambient temperature | |
| Mobile phase | A = Formic acid (aq) 0.1% | |
| | B = Formic acid (acetonitrile) 0.1% | |
| Flow rate | 0.8 ml/min | |
| Injection volume | 7 μl | |
| Detector | 210 nm-400 nm | |

-continued

LC-MS Method F

| Gradient | Time (mins) | % B |
|---|---|---|
| | 0 | 10 |
| | 4.5 | 95 |
| | 4.58 | 95 |

LC-MS Method G

| | | |
|---|---|---|
| Column | Agilent SB-AQ | |
| | 1.8 μm, 3 × 50 mm column | |
| | Ambient temperature | |
| Mobile phase | A = Formic acid (aq) 0.1% | |
| | B = Formic acid (acetonitrile) 0.1% | |
| Flow rate | 1.5 ml/min | |
| Injection volume | 1 μl | |
| Detector | 210 nm-400 nm | |

| Gradient | Time (mins) | % B |
|---|---|---|
| | 0 | 5 |
| | 0.25 | 50 |
| | 0.3 | 70 |
| | 1.3 | 90 |
| | 1.7 | 100 |

LC-MS Method H

| | | |
|---|---|---|
| Column | Agilent Zorbax C18 SB | |
| | 3.5 μm, 4.6 × 30 mm column | |
| | Ambient temperature | |
| Mobile phase | A = Formic acid (aq) 0.1% | |
| | B = Formic acid (acetonitrile) 0.1% | |
| Flow rate | 2.5 ml/min | |
| Injection volume | 7 μl | |
| Detector | 210 nm-400 nm | |

| Gradient | Time (mins) | % B |
|---|---|---|
| | 0 | 5 |
| | 1.7 | 95 |
| | 2 | 95 |
| | 2.1 | 5 |
| | 2.3 | 5 |

LC-MS Method I

| | | |
|---|---|---|
| Column | Waters BEH C18 | |
| | 1.7 μm, 2.1 × 50 mm column | |
| | Ambient temperature | |
| Mobile phase | A = Formic acid (aq) 0.05% | |
| | B = Formic acid (acetonitrile) 0.05% | |
| Flow rate | 0.8 ml/min | |
| Injection volume | 1 μl | |
| Detector | 210 nm-400 nm | |

| Gradient | Time (mins) | % B |
|---|---|---|
| | 0 | 10 |
| | 1.19 | 100 |
| | 1.7 | 100 |

HPLC purification methods used anywhere from 0-100% acetonitrile in water and may contain 0.1% formic acid, 0.1% TFA or 0.2% ammonium hydroxide and used one of the following columns:

a) Waters Sunfire OBD C18 5 μm 30×150 mm column
b) Waters XBridge OBD C18 5 μm 30×150 mm column
c) Waters ODB C8 5 μm 19×150 mm column
d) Waters Atlantis ODB C18 5 μm 19×50 mm column
e) Waters Atlantis T3 OBD 5 μM 30×100 mm column
f) Phenomenex Gemini Axia C18 5 μm 30×100 mm column
g) Waters SunFire C18 Prep OBD 5 μm 19×100 mm column
h) Waters XBridge Prep C18 5 μm 19×100 mm column Starting materials and reagents are either commercially available or may be prepared by one skilled in the art using methods described in the chemical literature.

Method A: Synthesis of Intermediate I-2.1

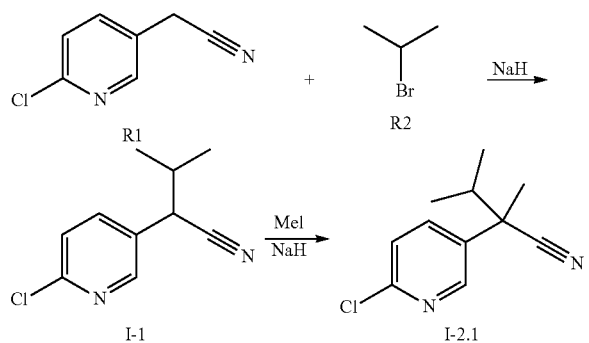

Step 1: Synthesis of I-1

To a solution of compound R1 (30.0 g, 0.20 mol) in DMF (500 mL) at 0° C. is slowly added NaH (60% in oil suspension, 8.26 g, 0.21 mol). The mixture is stirred for a further 15 minutes and R2 (18.5 mL, 0.20 mol) is added. The reaction mixture is allowed to warm up to room temperature and stirring continued for 2 hours. The reaction mixture is concentrated in vacuo. The residue is partitioned between DCM and brine. The combined organics are dried over anhydrous $Na_2SO_4$, filtered and concentrated in vacuo. The residue is purified by silica gel column chromatography (0-15% EtOAc in heptane) to yield I-1 (26.9 g); m/z 195 [M+H].

Step 2: Synthesis of Intermediate I-2.1

To a solution of I-1 (10.3 g, 52.81 mmol) in THF (100 mL) at 0° C. is added MeI (3.8 mL, 60.91 mmol) followed by the addition of NaH (60% in oil suspension, 2.4 g, 59.98 mmol) portionwise. The reaction mixture is allowed to warm up to room temperature and stirring is continued for 18 hours. The reaction mixture is concentrated in vacuo. The residue is diluted with EtOAc and washed with water then brine, dried over anhydrous $Na_2SO_4$, filtered and concentrated in vacuo. The residue is purified by silica gel column chromatography (0-40% EtOAc in heptane) to yield I-2.1 (10.5 g).

The following intermediates were synthesized in a similar fashion from the appropriate reagents:

TABLE 1

| Intermediate | Structure | m/z [M + H] |
|---|---|---|
| I-2.1 | 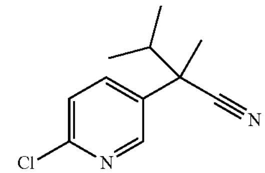 | 209 |
| I-2.2[a] | 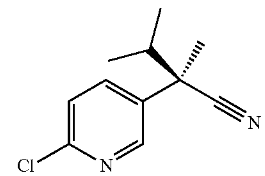 | 209 |
| I-2.3[a] | 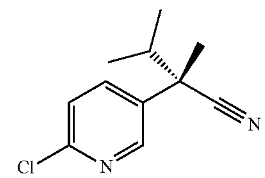 | 209 |
| I-2.4 | 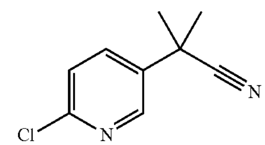 | NA[b] |

[a]Intermediates I-2.2 and I-2.3 were obtained by SFC chiral separation on ChiralPak AD-H, 250 × 50 mm I.D., $CO_2$:MeOH 85:15, flow: 160 mL/min, racemic mixture loaded in MeOH.
[b]1H-NMR (CDCl3, 400 MHz) 8.49 (1H, d, J = 2.8 Hz), 7.76 (1H, q, J = 3.6, 2.8 Hz), 7.35 (1H, d, J = 8 Hz), 1.74 (6H, s).

Method B: Intermediate I-3.1: Synthesis of 2-[6-(2-amino-pyrimidin-5-yl)-pyridin-3-yl]-2,3-dimethyl-butyronitrile

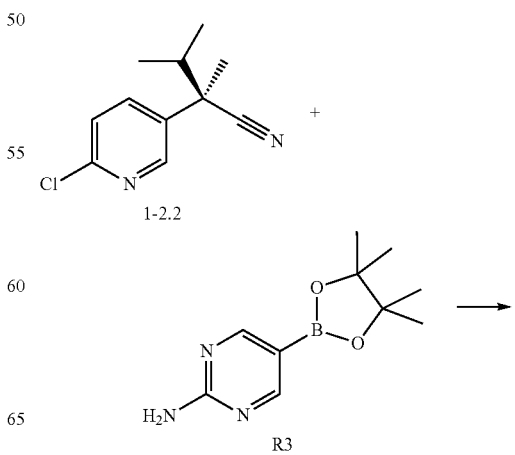

-continued

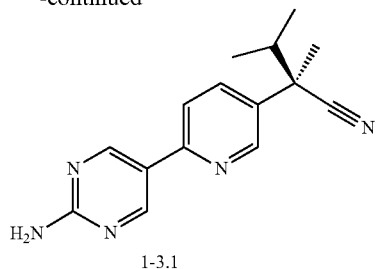
I-3.1

In a pressure tube, Pd(PPh$_3$)$_4$ (2.77 g, 2.40 mmol) and 2M Na$_2$CO$_3$ aqueous solution (40.0 mL, 80.0 mmol) are added to a suspension of I-2.2 (10.0 g, 47.92 mmol) and R3 (12.2 g, 55.1 mmol) in THF (100 mL). The mixture is heated at 90° C. for 3 hours, cooled to room temperature and filtered. The solid is washed with water and cold EtOAc, additional solid is formed in the filtrate and it is filtered. The combined cakes are then diluted with EtOAc and washed with water and brine. The organic phase is dried over anhydrous Na$_2$SO$_4$ and filtered. The solvent is removed under reduced pressure to afford the crude product that is purified via silica gel column chromatography to afford I-3.1 (11.0 g).

The following intermediates were synthesized in a similar fashion from the appropriate reagents:

TABLE 2

| Intermediate | Structure | m/z [M + H] |
|---|---|---|
| I-3.1 | 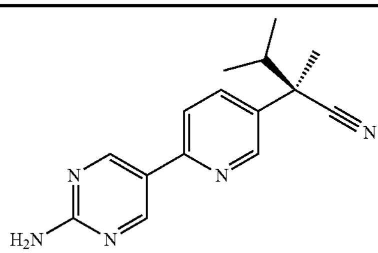 | 268 |
| I-3.2[a] | 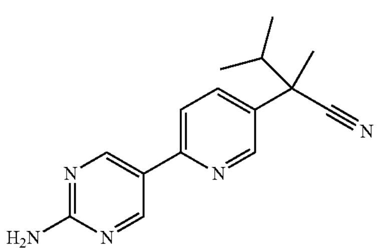 [SMILES: CC(C)C(C)(C#N)c1ccc(-c2cnc(N)nc2)nc1] | 268 |
| I-3.3 | 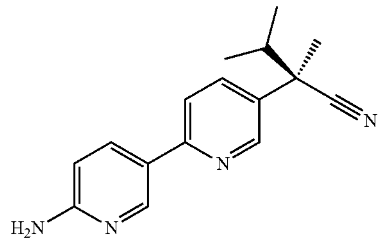 [SMILES: CC(C)[C@@](C)(C#N)c1ccc(-c2ccc(N)nc2)nc1] | 267 |
| I-3.4[b] | 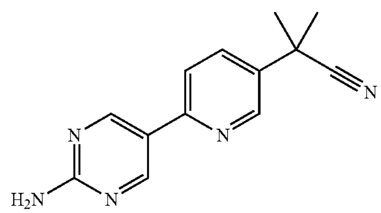 [SMILES: CC(C)(C#N)c1ccc(-c2cnc(N)nc2)nc1] | 252 |
| I-3.5 | 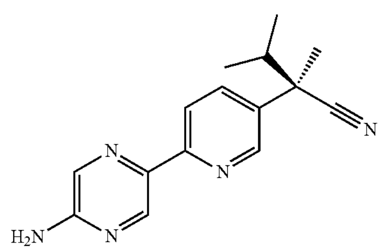 [SMILES: CC(C)[C@@](C)(C#N)c1ccc(-c2cnc(N)cn2)nc1] | 268 |

[a] The reaction is run in DMF, using PdCl$_2$(PPh$_3$)$_2$ as catalyst, heating at 80° C. overnight.
[b] The reaction is run at reflux overnight.

Method C: Synthesis of Intermediate I-7

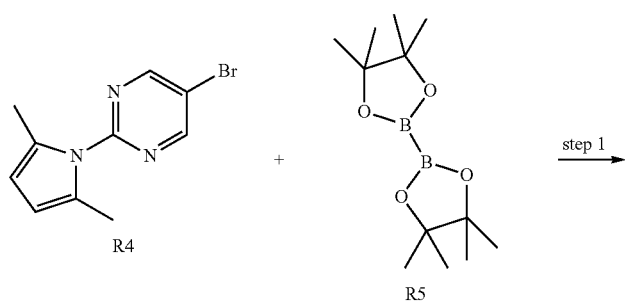

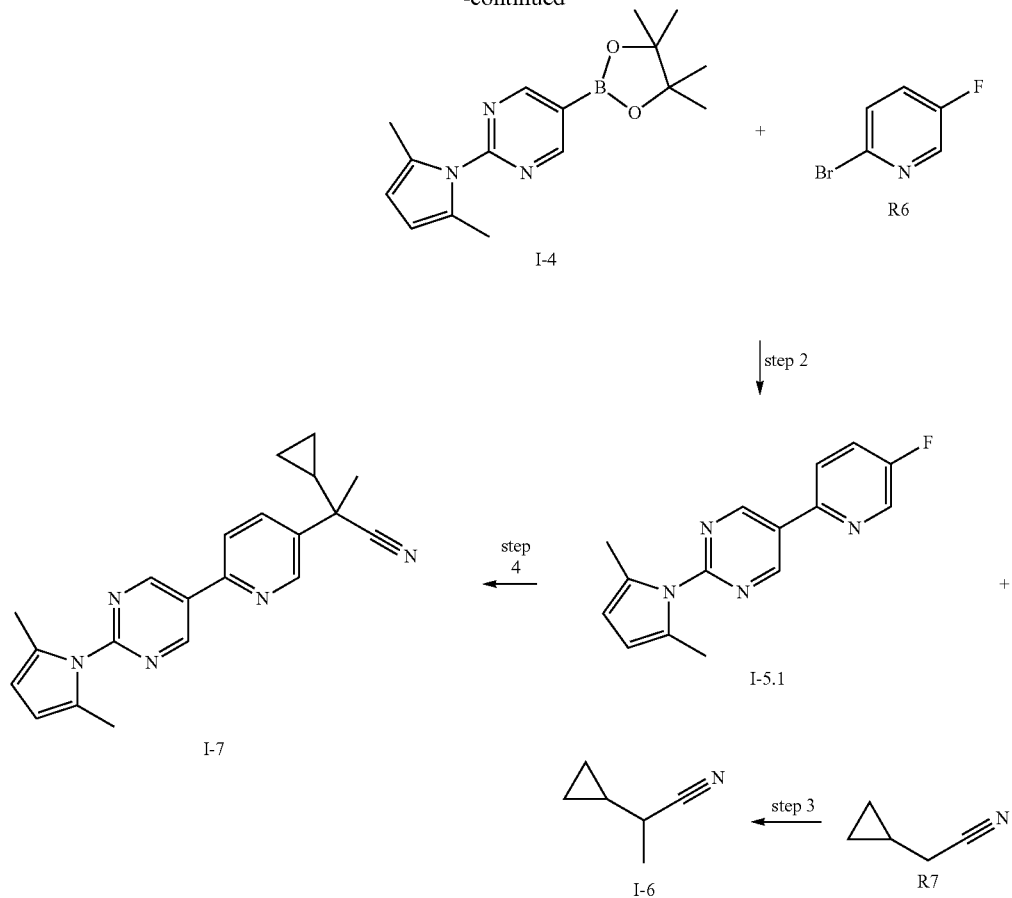

Step 1: Synthesis of Intermediate I-4

To a sealed flask is added R4 (8.83 g, 35.02 mmol), R5 (17.78 g, 70.00 mmol), dppf (0.97 g, 1.75 mmol), PdCl$_2$(dppf)CH$_2$Cl$_2$ (1.43 g, 1.75 mmol) and KOAc (13.74 g, 140.0 mmol) in 1,4-Dioxane (100 mL). The reaction mixture is stirred at 110° C. for 16 hours. After this time, the reaction mixture is concentrated in vacuo. The residue is diluted with EtOAc and washed with saturated NaHCO$_3$ aqueous solution and brine, dried over anhydrous Na$_2$SO$_4$, filtered and concentrated in vacuo. The residue is purified by silica gel column chromatography (0-20% EtOAc in heptane) then triturated in cold hexane to yield I-4 (9.0 g); m/z 300 [M+H].

Step 2: Synthesis of Intermediate I-5.1

To a suspension of R6 (15.0 g, 85.23 mmol), I-4 (28.05 g, 93.76 mmol) and Pd(PPh$_3$)$_4$ (1.97 g, 1.71 mmol) in DMF (250 mL) is added 2M Na$_2$CO$_3$ aqueous solution (85.23 mL, 170.47 mmol) and the reaction mixture is stirred at 90° C. for 4 hours. After cooling, the reaction mixture is diluted with water (1.5 L) and EtOAc (1 L). The layers are separated and the aqueous layer is extracted with EtOAc. The organic layers are combined and dried over anhydrous Na$_2$SO$_4$, filtered and concentrated in vacuo. The residue is recrystallized from EtOAc/heptane to yield I-5.1 (19.3 g).

The following intermediates were synthesized in a similar fashion from the appropriate reagents:

TABLE 3

| Intermediate | Structure | m/z [M + H] |
|---|---|---|
| I-5.1 | 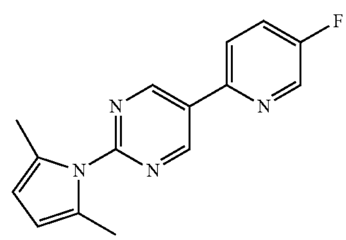 [SMILES: Cc1ccc(C)n1-c1ncc(-c2ccc(F)cn2)cn1] | 269 |
| I-5.2[a] | 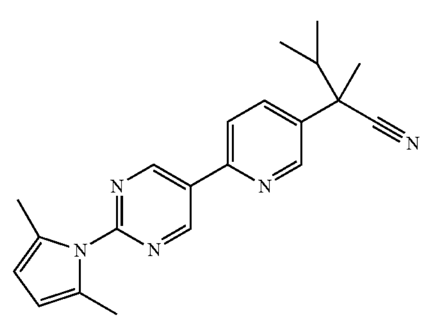 [SMILES: Cc1ccc(C)n1-c1ncc(-c2ccc(C(C)(C#N)C(C)C)cn2)cn1] | 346 |

TABLE 3-continued

| Intermediate | Structure | m/z [M + H] |
|---|---|---|
| I-5.3 | 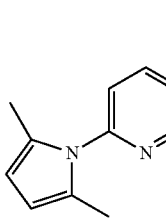 | 268 |

<sup>a</sup>Intermediate I-5.2 is synthesized using I-2.1.

Step 3: Synthesis of Intermediate I-6

LDA (2M in heptane/THF/ethylbenzene, 74 mL, 148.00 mmol) is added slowly into the cooled solution of R7 (10 g, 123.28 mmol) in THF (170 mL) at −78° C. under $N_2$. After the addition, the reaction mixture is stirred at −78° C. for 2 hours. MeI (21 g, 147.95 mmol) is then added and the reaction mixture is allowed to warm up to room temperature and stirred for 2 hours. After this time, the reaction mixture is quenched with saturated $NH_4Cl$ solution and extracted with ether. The layers are separated and the organic layer is washed with water then brine, dried over anhydrous $Na_2SO_4$, filtered and concentrated in vacuo. The residue is purified through distillation to afford I-6 (10.7 g); (400 MHz, DMSO-d) δ ppm 2.41-2.48 (1H, m), 1.26-1.3 (3H, d, J=7.1 Hz), 0.98-1.05 (1H, m), 0.51-0.55 (2H, m), 0.23-0.37 (2H, m),

Step 4: Synthesis of Intermediate I-7

To a solution of I-5.1 (500.00 mg, 1.86 mmol) in toluene (1.0 mL) is added I-6 (1.00 g, 10.51 mol) and KHMDS (0.5 M in toluene, 6.0 mL, 3.00 mmol). The reaction mixture is heated at 100° C. for 18 hours. After cooling, the reaction mixture is diluted with EtOAc and washed with water and brine, dried over anhydrous $Na_2SO_4$, filtered and concentrated in vacuo. The residue is purified by silica gel column chromatography (0-20% EtOAc in heptane) to yield I-7 (350.0 mg); m/z 344 [M+H].

| Intermediate | Structure | m/z [M + H] |
|---|---|---|
| I-7.1 | 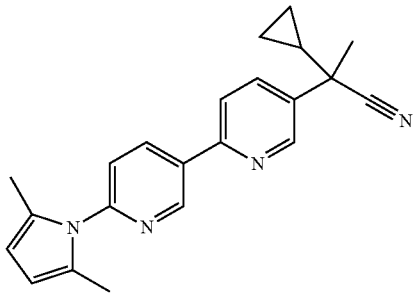 [SMILES: Cc1ccc(C)n1-c1ccc(-c2ccc(C(C)(C#N)C3CC3)cn2)cn1] | 343 |
| I-7.2 | 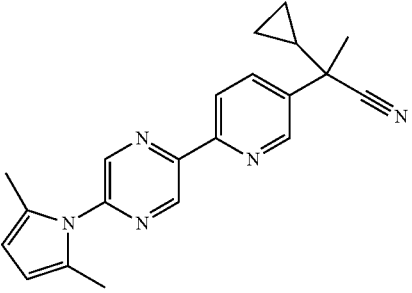 [SMILES: Cc1ccc(C)n1-c1cnc(-c2ccc(C(C)(C#N)C3CC3)cn2)cn1] | 344 |

Method D: Synthesis of Intermediate I-8.1

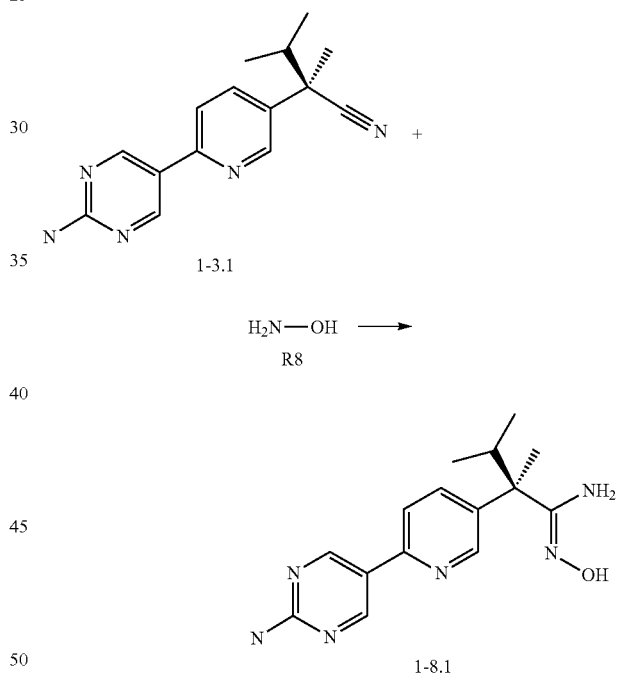

In a pressure tube, R8 (50% aqueous solution, 90.0 mL) is added to a solution of I-3.1 (12.1 g, 45.19 mmol) in ethanol (120 mL). The reaction mixture is stirred at 90° C. for 18 hours. After allowing the reaction mixture to cool to room temperature, the solvent is removed under reduced pressure, the crude is diluted with EtOAc and washed with water and brine. The organic phase is dried over anhydrous $Na_2SO_4$ and filtered. The solvent is removed under reduced pressure and the obtained material is triturated with $CH_3CN$. The solid is filtered and washed with $CH_3CN$ to afford I-8.1 (11.3 g).

The following intermediates were synthesized in a similar fashion from the appropriate reagents. In some cases hydroxylamine hydrochloride in EtOH has been used instead of the aqueous solution of hydroxylamine in EtOH.

TABLE 4

| Intermediate | Structure | m/z [M + H] |
|---|---|---|
| I-8.1 | 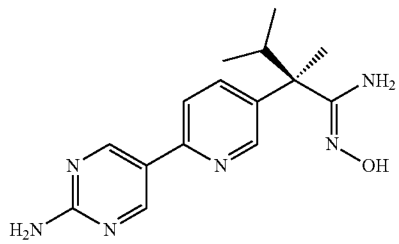 [SMILES: CC(C)[C@@](C)(/C(N)=N/O)c1ccc(-c2cnc(N)nc2)nc1] | 301 |
| I-8.2 | 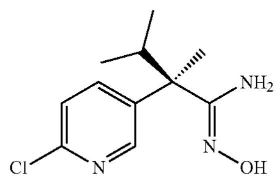 [SMILES: CC(C)[C@@](C)(/C(N)=N/O)c1ccc(Cl)nc1] | 242 |
| I-8.3 | 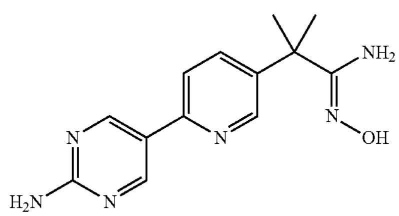 [SMILES: CC(C)(/C(N)=N/O)c1ccc(-c2cnc(N)nc2)nc1] | 273 |
| I-8.4 | 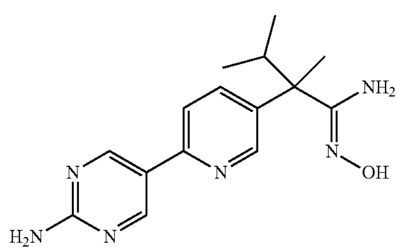 [SMILES: CC(C)C(C)(/C(N)=N/O)c1ccc(-c2cnc(N)nc2)nc1] | 301 |
| I-8.5 | 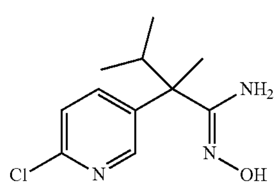 [SMILES: CC(C)C(C)(/C(N)=N/O)c1ccc(Cl)nc1] | 242 |
| I-8.6 | 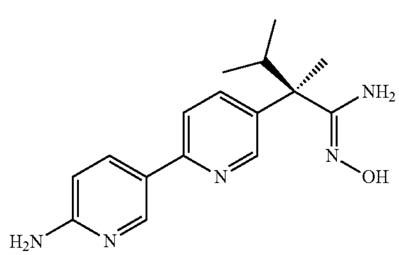 [SMILES: CC(C)[C@@](C)(/C(N)=N/O)c1ccc(-c2ccc(N)nc2)nc1] | 300 |
| I-8.7 | | 377 |
| I-8.8 | | 379 |
| I-8.9 | | 301 |
| I-8.10 | | 378 |
| I-8.11 | | 376 |

TABLE 4-continued

| Intermediate | Structure | m/z [M + H] |
|---|---|---|
| I-8.12 | 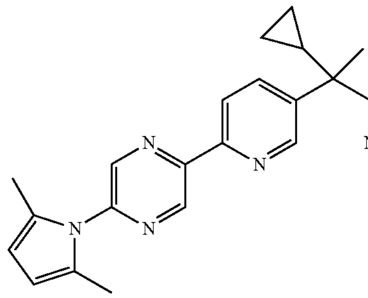 | 377 |

Method E: Synthesis of Intermediate I-9.1

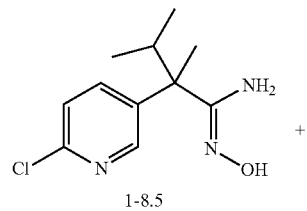

I-8.5

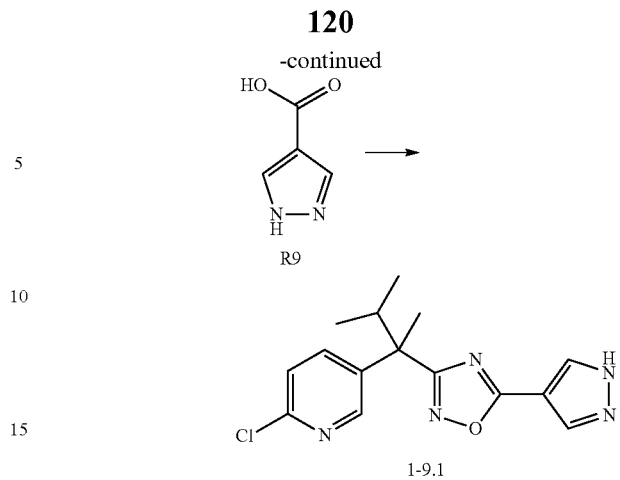

R9

I-9.1

A solution of I-8.5 (3.00 g, 12.4 mmol), R9 (1.4 g, 12.4 mmol), triethylamine (1.7 mL, 12.4 mmol) and HATU (4.7 g, 12.4 mmol) in DMF (20.0 mL) is stirred at room temperature overnight and then at 110° C. until completion. The solvent is removed under reduced pressure, the crude diluted in DCM and washed with saturated NaHCO$_3$ solution. After drying the organic phase over anhydrous Na$_2$SO$_4$ and filtering, the solvent is removed under vacuum and the crude is purified via silica gel column chromatography (DCM/MeOH) to afford I-9.1 (4.2 g).

The following intermediates were synthesized in a similar fashion from the appropriate reagents:

TABLE 5

| Intermediate | Structure | m/z [M + H] |
|---|---|---|
| I-9.1 | 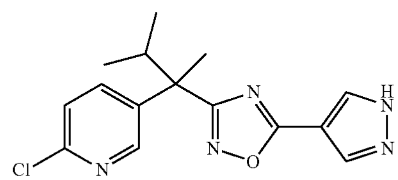 [SMILES: CC(C)C(C)(c1ccc(Cl)nc1)c1noc(-c2cn[nH]c2)n1] | 348 |
| I-9.2[a] | 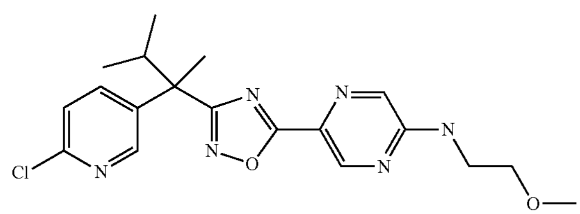 [SMILES: COCCNc1cnc(-c2nc(C(C)(c3ccc(Cl)nc3)C(C)C)no2)cn1] | 403 |
| I-9.3 | 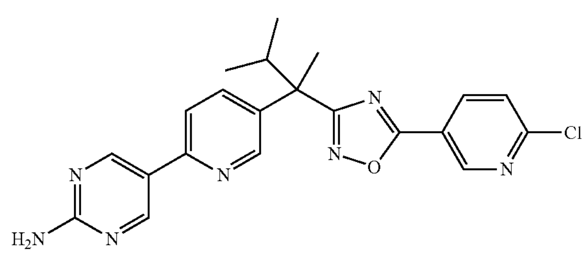 [SMILES: CC(C)C(C)(c1ccc(-c2cnc(N)nc2)nc1)c1noc(-c2ccc(Cl)nc2)n1] | 422 |

[a]Prepared from I-18.2.

Method F: Synthesis of Intermediate I-10.1

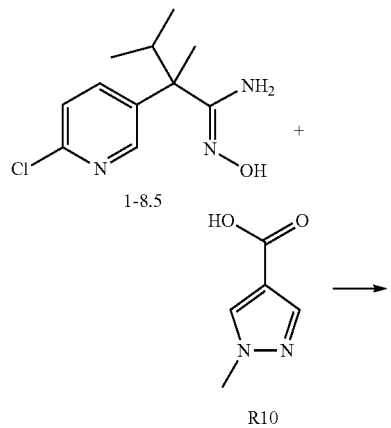

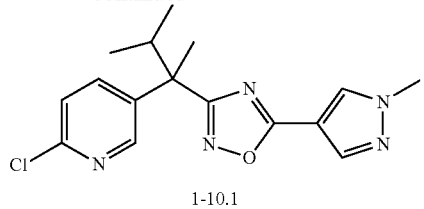

I-10.1

A suspension of R10 (187.7 mg, 1.46 mmol) and 1,1'-carbonyldiimidazole. (237.5 mg, 1.46 mmol) in THF (2.0 mL) is heated at 50° C. for 20 minutes. I-8.5 (322.0 mg, 1.33 mmol) is added and the solution is heated at 55° C. for one hour in an oil bath and at 150° C. in the microwave for 40 minutes. The solvent is removed under reduced pressure and the crude is purified by silica gel column chromatography (DCM/MeOH) to afford I-10.1 (416 mg).

The following intermediates were synthesized in a similar fashion from the appropriate reagents:

TABLE 6

| Intermediate | Structure | m/z [M + H] |
| --- | --- | --- |
| I-10.1 | 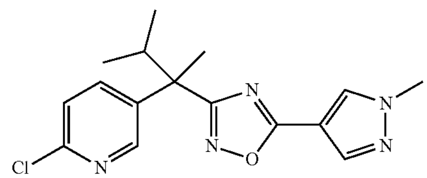 [SMILES: CC(C)C(C)(c1ccc(Cl)nc1)c1noc(-c2cnn(C)c2)n1] | 332 |
| I-10.2[a] | 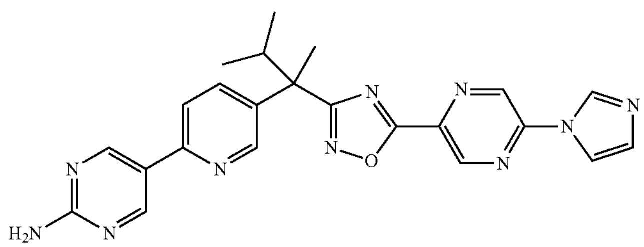 [SMILES: CC(C)C(C)(c1ccc(-c2cnc(N)nc2)nc1)c1noc(-c2cnc(-n3ccnc3)cn2)n1] | 455 |
| I-10.3 | 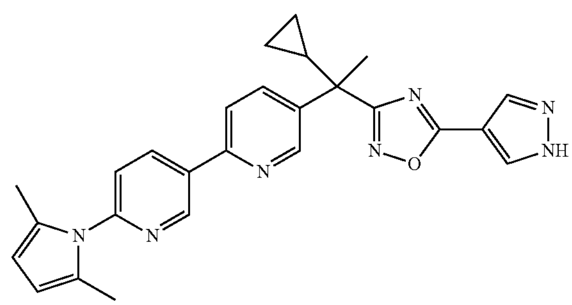 [SMILES: Cc1ccc(C)n1-c1ccc(-c2ccc(C(C)(c3noc(-c4cn[nH]c4)n3)C3CC3)cn2)cn1] | 452 |
| I-10.4 | 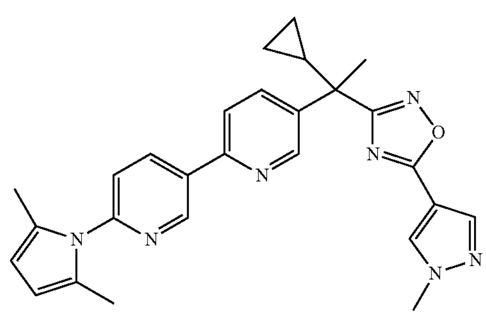 [SMILES: Cc1ccc(C)n1-c1ccc(-c2ccc(C(C)(c3noc(-c4cnn(C)c4)n3)C3CC3)cn2)cn1] | 466 |

TABLE 6-continued

| Intermediate | Structure | m/z [M + H] |
|---|---|---|
| I-10.5 | 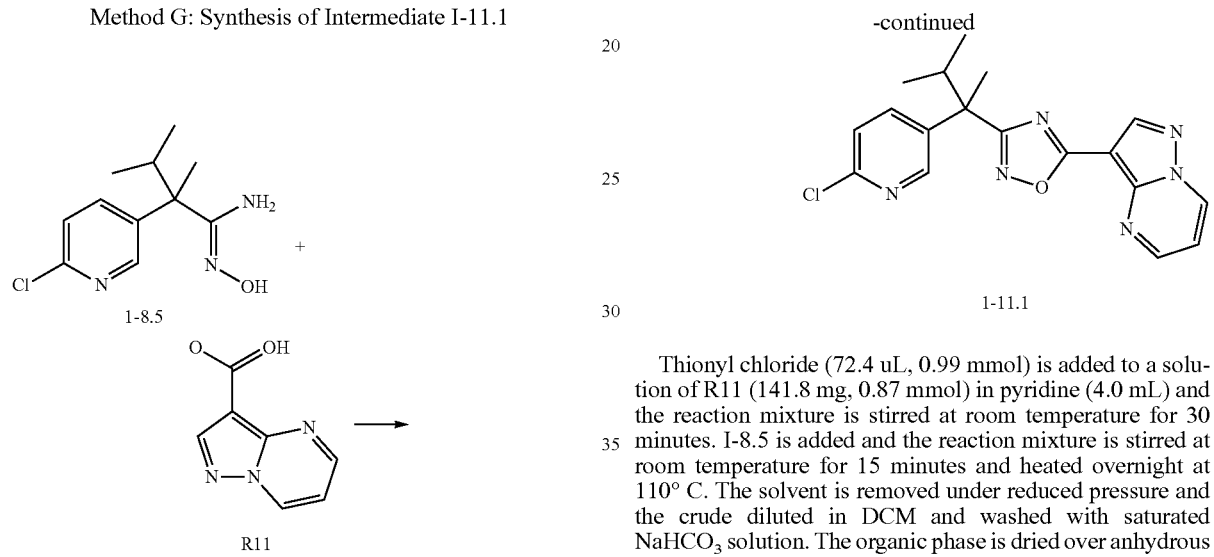 | 453 |

<sup>a</sup>The reaction is run in DMF using 5-chloro-pyrazine-2-carboxylic acid and after the addition of I-8.4 it is heated at 110° C. for 2 hours in an oil bath.

Method G: Synthesis of Intermediate I-11.1

Thionyl chloride (72.4 uL, 0.99 mmol) is added to a solution of R11 (141.8 mg, 0.87 mmol) in pyridine (4.0 mL) and the reaction mixture is stirred at room temperature for 30 minutes. I-8.5 is added and the reaction mixture is stirred at room temperature for 15 minutes and heated overnight at 110° C. The solvent is removed under reduced pressure and the crude diluted in DCM and washed with saturated NaHCO₃ solution. The organic phase is dried over anhydrous Na₂SO₄ to afford I-11.1 (142 mg).

The following intermediates were synthesized in a similar fashion from the appropriate reagents:

TABLE 7

| Intermediate | Structure | m/z [M + H] |
|---|---|---|
| I-11.1 | 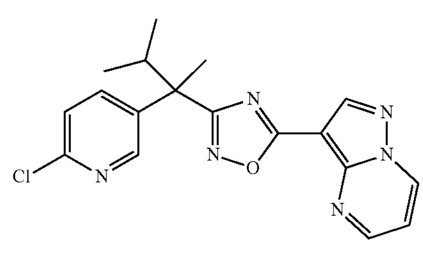 [SMILES: CC(C)C(C)(c1ccc(Cl)nc1)c1noc(-c2cnn3cccnc23)n1] | 369 |
| I-11.2 | 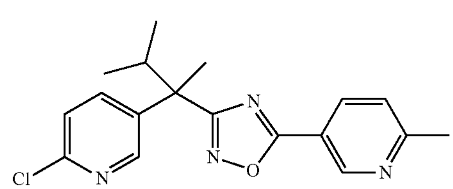 [SMILES: Cc1ccc(-c2nc(C(C)(c3ccc(Cl)nc3)C(C)C)no2)cn1] | 343/345 [M/M + 2H] |

TABLE 7-continued

| Intermediate | Structure | m/z [M + H] |
|---|---|---|
| I-11.3 | 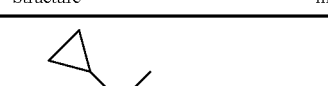 | 467 |

Method H: Synthesis of Intermediate I-12.1

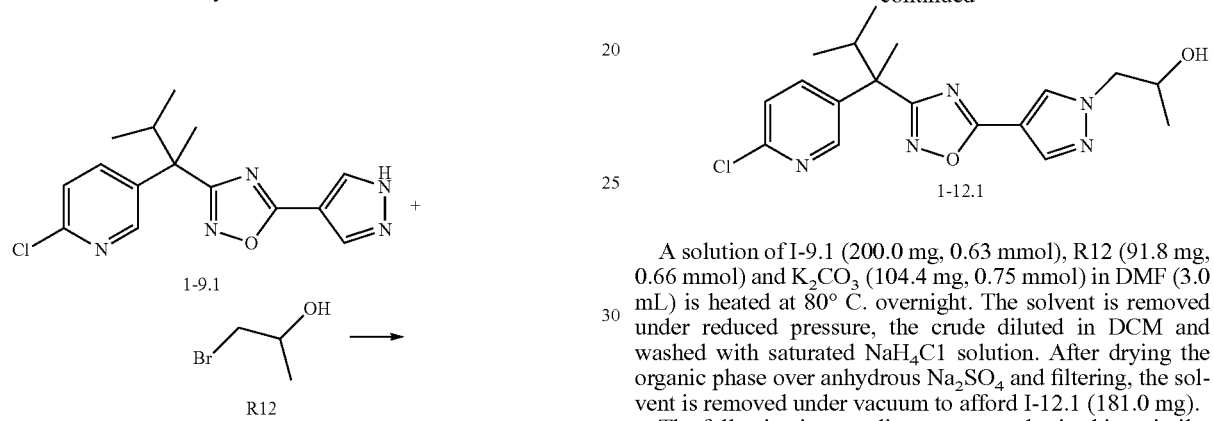

A solution of I-9.1 (200.0 mg, 0.63 mmol), R12 (91.8 mg, 0.66 mmol) and $K_2CO_3$ (104.4 mg, 0.75 mmol) in DMF (3.0 mL) is heated at 80° C. overnight. The solvent is removed under reduced pressure, the crude diluted in DCM and washed with saturated $NaH_4Cl$ solution. After drying the organic phase over anhydrous $Na_2SO_4$ and filtering, the solvent is removed under vacuum to afford I-12.1 (181.0 mg).

The following intermediates were synthesized in a similar fashion from the appropriate reagents:

TABLE 8

| Intermediate | Structure | m/z [M + H] |
|---|---|---|
| I-12.1 | 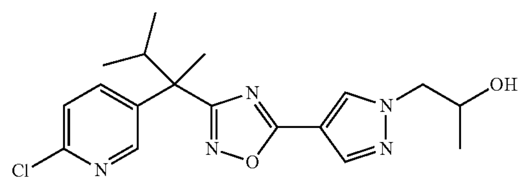 [SMILES: CC(O)Cn1cc(-c2nc(C(C)(c3ccc(Cl)nc3)C(C)C)no2)cn1] | 376 |
| I-12.2 | 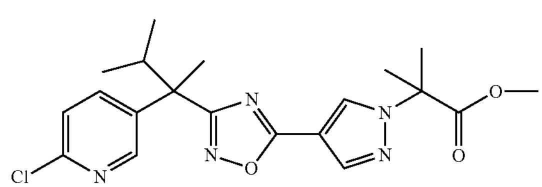 [SMILES: COC(=O)C(C)(C)n1cc(-c2nc(C(C)(c3ccc(Cl)nc3)C(C)C)no2)cn1] | 418 |
| I-12.3[a] | 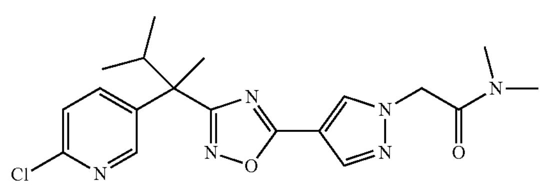 [SMILES: CC(C)C(C)(c1ccc(Cl)nc1)c1noc(-c2cnn(CC(=O)N(C)C)c2)n1] | 403 |

TABLE 8-continued

| Intermediate | Structure | m/z [M + H] |
|---|---|---|
| I-12.4 | 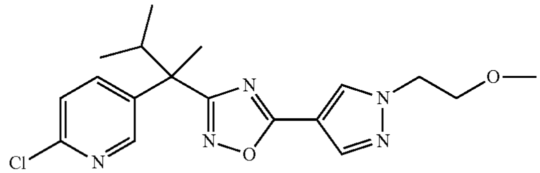 [SMILES: COCCn1cc(-c2nc(C(C)(c3ccc(Cl)nc3)C(C)C)no2)cn1] | 376 |
| I-12.5[b] | 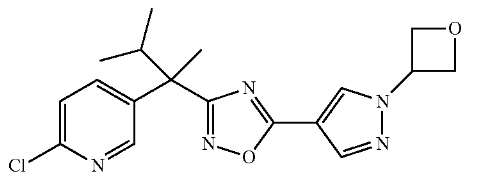 [SMILES: CC(C)C(C)(c1ccc(Cl)nc1)c1noc(-c2cnn(C3COC3)c2)n1] | 374 |
| I-12.6[c] | 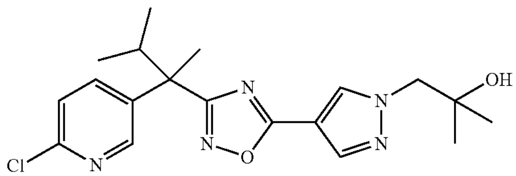 [SMILES: CC(C)C(C)(c1ccc(Cl)nc1)c1noc(-c2cnn(CC(C)(C)O)c2)n1] | 390 |
| I-12.7 | 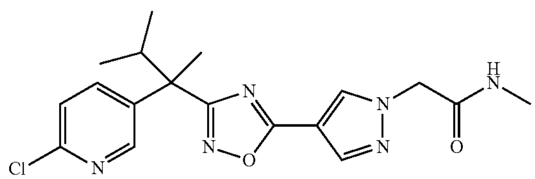 [SMILES: CNC(=O)Cn1cc(-c2nc(C(C)(c3ccc(Cl)nc3)C(C)C)no2)cn1] | 389 |
| I-12.8[a] | 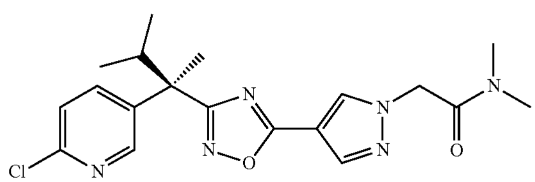 [SMILES: CC(C)[C@](C)(c1ccc(Cl)nc1)c1noc(-c2cnn(CC(=O)N(C)C)c2)n1] | 403 |

[a]The reaction is run using the cdorresponding chloride and in the presence of 0.1 eq NaI.
[b]The reaction is run using the corresponding iodide.
[c]The reaction is run at room temperature using the corresponding chloride and 1.1 eq of NaH in DMF.

Method I: Synthesis of Intermediate 13.1

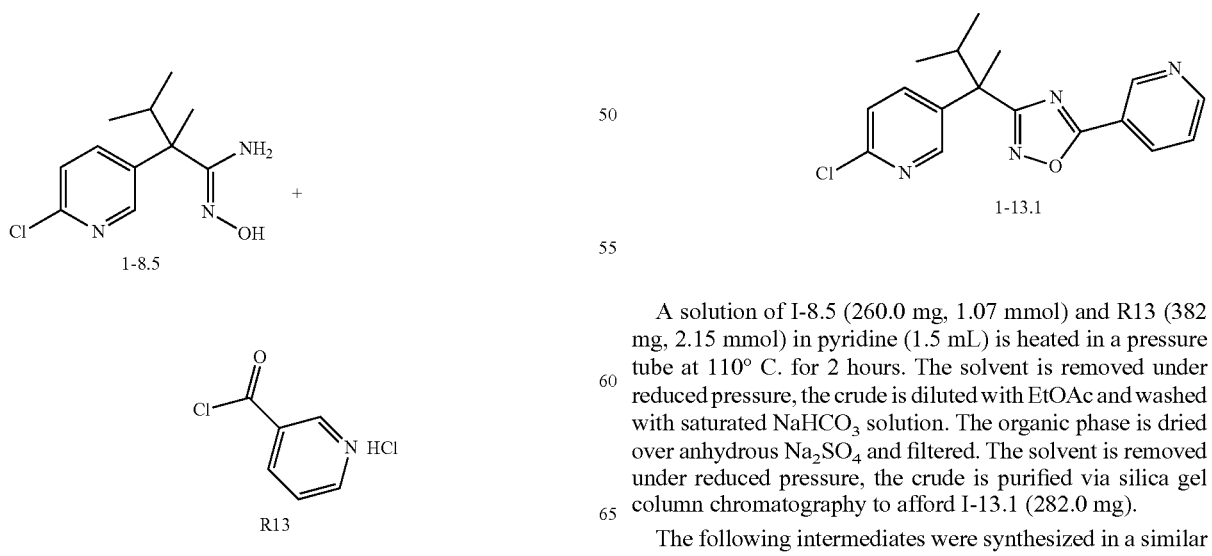

A solution of I-8.5 (260.0 mg, 1.07 mmol) and R13 (382 mg, 2.15 mmol) in pyridine (1.5 mL) is heated in a pressure tube at 110° C. for 2 hours. The solvent is removed under reduced pressure, the crude is diluted with EtOAc and washed with saturated NaHCO$_3$ solution. The organic phase is dried over anhydrous Na$_2$SO$_4$ and filtered. The solvent is removed under reduced pressure, the crude is purified via silica gel column chromatography to afford I-13.1 (282.0 mg).

The following intermediates were synthesized in a similar fashion from the appropriate reagents:

TABLE 9

| Intermediate | Structure | m/z [M + H] |
|---|---|---|
| I-13.1 | 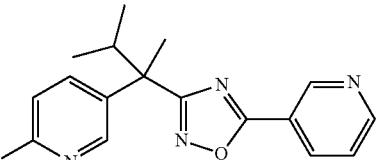 | 329 |
| I-13.2 | 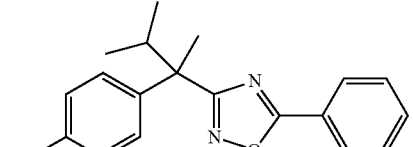 | 328 |

Method J: Synthesis of Intermediate I-14.1

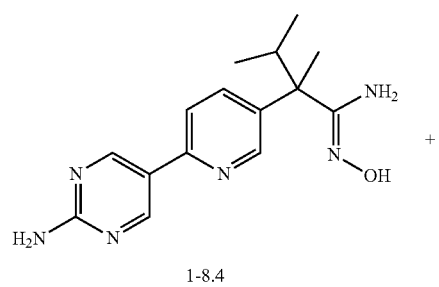

I-8.4

+

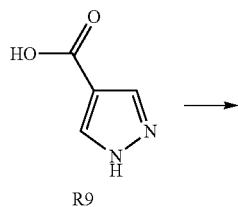

R9

→

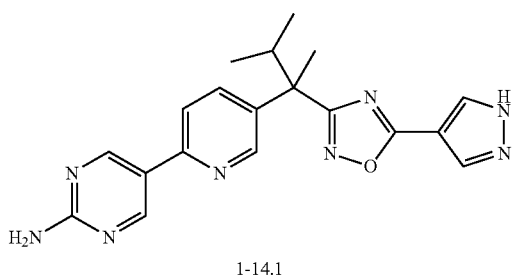

I-14.1

A suspension of R9 (0.3 g, 4.58 mmol) and 1,1'-carbonyldiimidazole. (0.74 g, 4.58 mmol) in NMP (4.0 mL) is heated at 50° C. for 20 min. I-8.4 is added (1.25 g, 4.16 mmol) and the solution is heated at 130° C. for 2 hours. The reaction mixture is cooled to room temperature, water is added and it is stirred overnight. A gooey residue is formed, the liquid is decanted and the crude is purified via silica gel column chromatography (DCM/MeOH) affords I-14.1 (1.41 g).

The following intermediates were synthesized in a similar fashion from the appropriate reagents:

TABLE 10

| Intermediate | Structure | m/z [M + H] |
|---|---|---|
| I-14.1 | 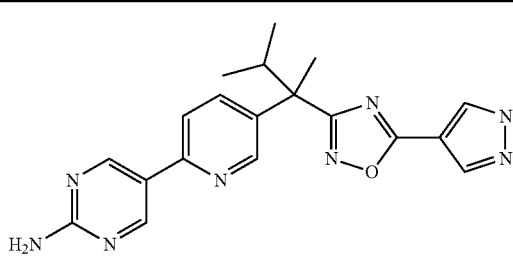 | 377 |
| I-14.2 | 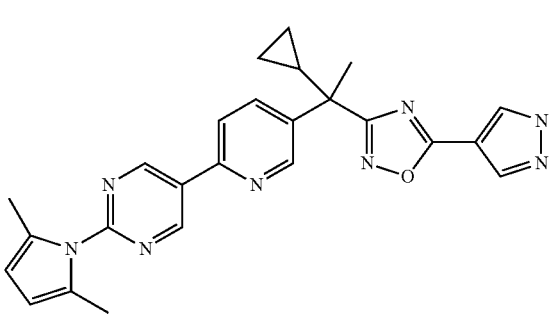 [SMILES: Cc1ccc(C)n1-c1ncc(-c2ccc(C(C)(c3noc(-c4cn[nH]c4)n3)C3CC3)cn2)cn1] | 453 |

| Intermediate | Structure | m/z [M + H] |
|---|---|---|
| I-14.3 | 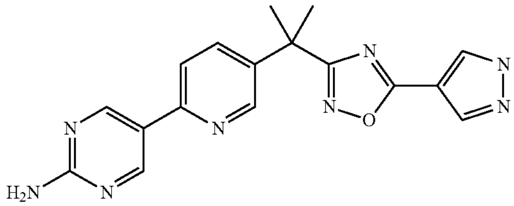 [SMILES: CC(C)(c1ccc(-c2cnc(N)nc2)nc1)c1noc(-c2cn[nH]c2)n1] | 349 |
| I-14.4 | 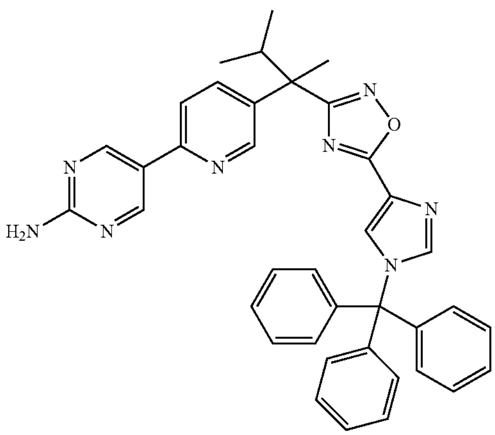 | 377 [M + H] − trityl |

TABLE 10-continued

Method K: Synthesis of Intermediate I-15

Method L: Synthesis of Intermediate I-18

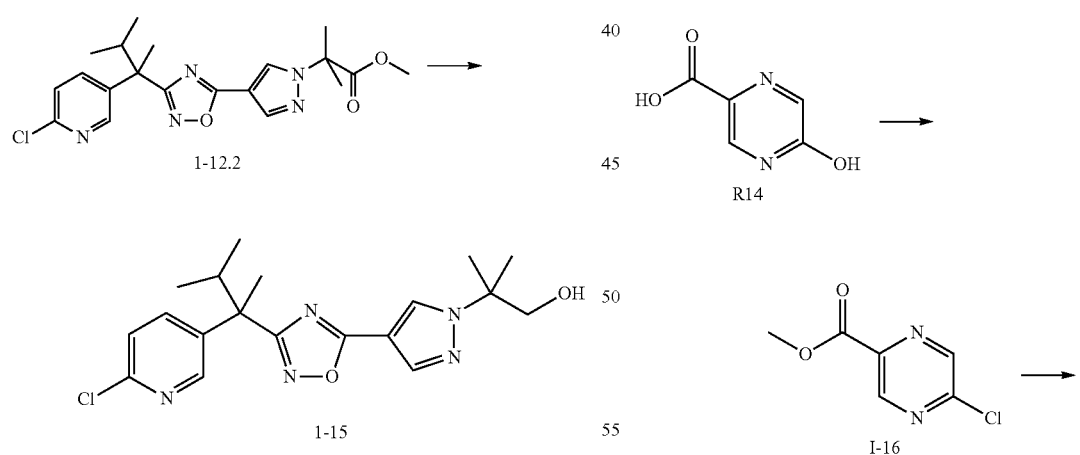

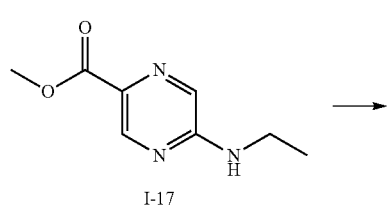

Lithium borohydride (104.1 mg, 4.78 mmol) is added to a solution of I-12.2 (679.0 mg, 1.62 mmol) in THF (20.0 mL) at 0° C. The reaction mixture is allowed to warm to room temperature and then stirred for 2 hours. The solvent is removed under reduced pressure, the crude diluted in EtOAc and washed with saturated NaHCO₃ solution. The organic phase is dried over anhydrous Na₂SO₄ and filtered. The solvent is removed under reduced pressure to afford I-15 (650 mg, 83% pure); m/z 390 [M+H].

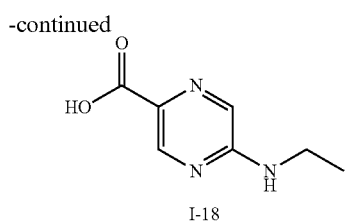

I-18

Step 1: Synthesis of I-16

A solution of R14 (2.0 g, 14.3 mmol) and thionyl chloride (10.0 mL) with a catalytic amount of DMF is refluxed for 4 hours. The solvent is removed under reduced pressure, MeOH (10.0 mL) and pyridine (1.4 mL, 17.1 mmol) are slowly added and the mixture is stirred overnight at room temperature. The solvent is removed under reduced pressure, the crude is purified via silica gel column chromatography to afford I-16 (1.12 g); m/z 173 [M+H].

Step 2: Synthesis of I-17.1

Ethylamine (1.7 mL, 3.48 mmol) is added to a solution of I-16 (500.0 mg, 2.90 mmol) in DMSO (4.0 mL) and the mixture is heated at 80° C. overnight. The reaction mixture is cooled to room temperature, water (5.0 mL) is added and the solution is acidified to pH~2.0 with 2N HCl. The mixture is extracted with EtOAc, the organic layers are combined, dried over anhydrous $Na_2SO_4$ and filtered. The solvent is removed to afford I-17.1 (451.0 mg).

The following intermediates were synthesized in a similar fashion from the appropriate reagents:

TABLE 11

| Intermediate | Structure | m/z [M + H] |
|---|---|---|
| I-17.1 | 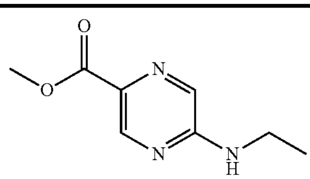 | 182 |
| I-17.2 | 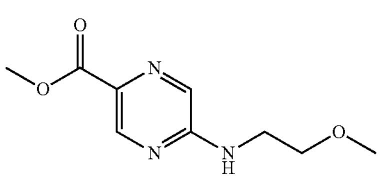 | 212 |
| I-17.3 | 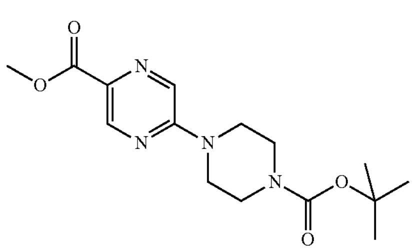 [SMILES: COC(=O)c1cnc(N2CCN(C(=O)OC(C)(C)C)CC2)cn1] | 323 |

Step 3: Synthesis of Intermediate I-18.1

Lithium hydroxide (87.4 mg, 3.65 mmol) is added to a solution of I-17.1 (441.0 mg, 2.43 mmol) in THF/water (6.0 mL/6.0 mL). The solution is stirred at room temperature for 2 days, acidified to pH~3.0 with 2N HCl and extracted with EtOAc. The organic layers are combined, dried over anhydrous $Na_2SO_4$ and filtered. The solvent is removed under vacuum to afford I-18.1 (367.0 mg).

The following intermediates were synthesized in a similar fashion from the appropriate reagents:

TABLE 12

| Intermediate | Structure | m/z [M + H] |
|---|---|---|
| I-18.1 | 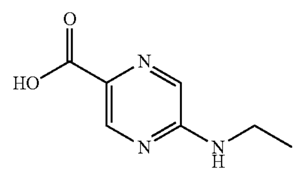 | 168 |
| I-18.2 | 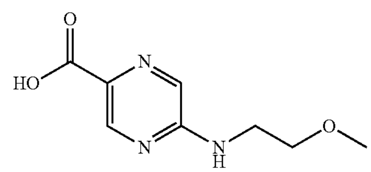 | 196 [M − H] |
| I-18.3 | 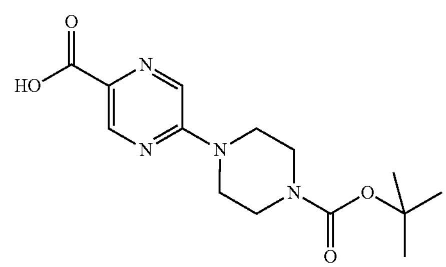 [SMILES: CC(C)(C)OC(=O)N1CCN(c2cnc(C(=O)O)cn2)CC1] | 309 |

Method M: Synthesis of Intermediate I-19

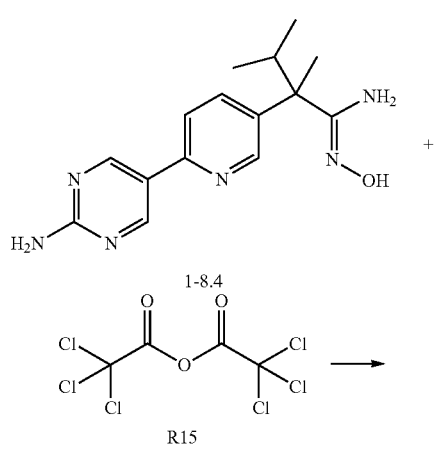

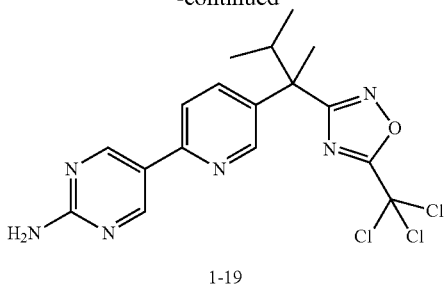

I-19

To a mixture of I-8.4 (1.3 g, 1.328 mmol) in toluene (50 mL) is added R15 (0.949 mL, 5.194 mmol). The reaction mixture is heated to reflux for 3.5 hours. After allowing the reaction mixture to cool to room temperature, the precipitate formed is collected through filtration. The solid is washed with EtOAc to give the title intermediate I-19 (1.89 g); m/z 427 [M+H].

Method N: Synthesis of Intermediate I-24

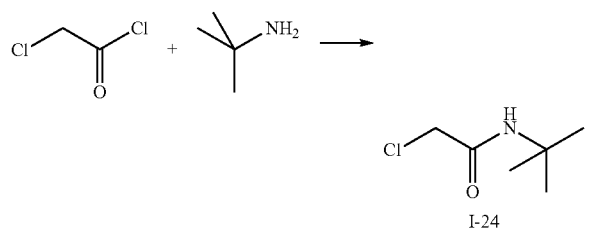

I-24

To a vial was added chloroacetyl chloride (500 mg, 4.43 mmol) in THF (6 ml), followed by the addition of tert-butylamine (485 mg, 6.63 mmol) and triethylamine (672 mg, 6.64 mmol) slowly. The reaction mixture was stirred at room temperature for 18 hours. The reaction mixture was concentrated in vacuo. The residue was dissolved in EtOAc, washed with water, brine, dried under anhy. $Na_2SO_4$, filtered and concentrated to afford title compound (500 mg), m/z: 150 [M+H]

The following intermediates were synthesized in a similar fashion from the appropriate reagents:

TABLE 13

| Intermediate | Structure | m/z [M + H] |
|---|---|---|
| I-24.1 | 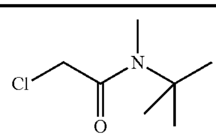 | 164 |
| I-24.2 | 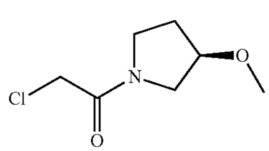 | 178 |
| I-24.3 | 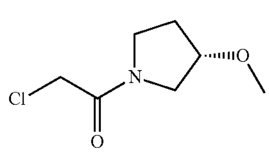 | 178 |

Method O: Synthesis of Intermediate I-28

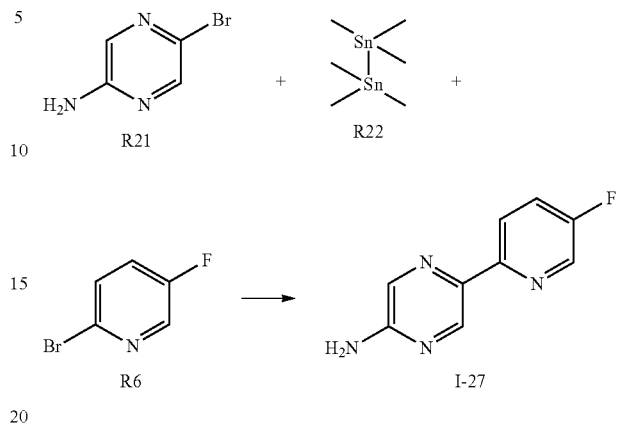

Step 1: Synthesis of Intermediate I-27

R21 (1.00 g, 5.75 mmol) in a pressure flask is treated with degassed toluene (16 mL), $Pd(Ph_3P)_4$ (398 mg, 0.345 mmol), and R22 (1.25 mL, 6.04 mmol) and the resulting mixture is heated at 115° C. for 1 hour. The mixture is then cooled to room temperature and R6 (1.42 g, 8.05 mmol) is added followed by $Pd(Ph_3P)_4$ (332 mg, 0.287 mmol) and the resulting mixture is heated at 115° C. for 1 hour. The resulting mixture is cooled to room temperature and is concentrated. The residue is purified by silica gel column chromatography (0-10% methanol in $CH_2Cl_2$) to yield I-27 (432 mg); m/z: 191 [M+H].

Step 2: Synthesis of Intermediate I-28

I-27 (432 mg, 2.27 mmol) is treated with R23 (374 mL, 3.18 mmol), R24 (8.6 mg, 0.045 mmol), and toluene (15 mL) and refluxed with a Dean-Stark trap for 24 hours. The reaction is then concentrated and the residue is purified by silica gel column chromatography (0-20% EtOAc in heptanes) to yield I-28 (414 mg); m/z: 269 [M+H].

Method P: Synthesis of Intermediate I-35.3

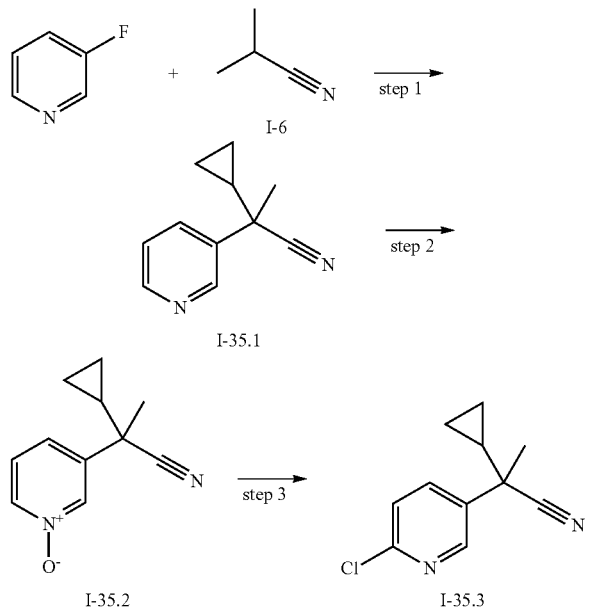

Step 1: Synthesis of Intermediate I-35.1

To a pressure reactor is added 3-fluoropyridine (2 g, 20.6 mmol), followed by the addition of I-6 (5.39 g, 56.7 mmol) and potassium bis(trimethylsilyl)amide (0.5M in toluene) (61.8 ml, 30.9 mmol). The reaction mixture is stirred at 100° C. for 10 hours. The reaction mixture is diluted with EtOAc, is washed with water, brine, is dried under anhy. $Na_2SO_4$, and is filtered and is concentrated. The residue is purified by flash chromatography ($SiO_2$, 0-3% $MeOH/CH_2Cl_2$) to afford I-35.1 (3.18 g); m/z 172.4 [M+1]

Step 2: Synthesis of Intermediate I-35.2

To a round bottom flask is added I-29.1 (3.18 g, 18.5 mmol) in $CH_2Cl_2$ (70 ml), follows by the addition of 3-chloroperoxybenzoic acid (4.4 g, 25.5 mmol). The reaction mixture is stirred at room temperature for 3 hours. The reaction mixture is queched with sat. sodium thiosulfate solution and is stirred for 1 hour. The organic phase is separated, is washed with water, brine, is dried under anhy. $Na_2SO_4$, is filtered and is concentrated. The residue is purified by flash chromatography ($SiO_2$, 0-5% $MeOH/CH_2Cl_2$) to afford I-35.2 (3.31 g); m/z 189.4 [M+1]

Step 3: Synthesis of Intermediate I-35.3

A solution of $POCl_3$ (3.3 ml, 35.4 mmol)) in $CH_2Cl_2$ (10 ml) is added dropwise at 0° C. to a stirred solution of I-29.2 (3.31 mg, 17.6 mmol)) and $Et_3N$ (4.9 ml, 35.2 mmol)) in $CH_2Cl_2$ (50 ml). The reaction mixture is stirred at room temperature for 1 hour, then at 40° C. for 3 hours. The reaction mixture is queched with sat. $NaHCO_3$. The organic layer is separated, is washed with brine, is dried under anhy. $Na_2SO_4$, is filtered and is concentrated. The residue is purified by flash chromatography ($SiO_2$, 0-25% EtOAc/heptane) to afford I-35.3 (1.34 g); m/z 207.1 [M+1]

The following intermediates were synthesized in a similar fashion from the appropriate reagents:

TABLE 15

| Intermediate | Structure | m/z [M + H] |
|---|---|---|
| I-35.4 | 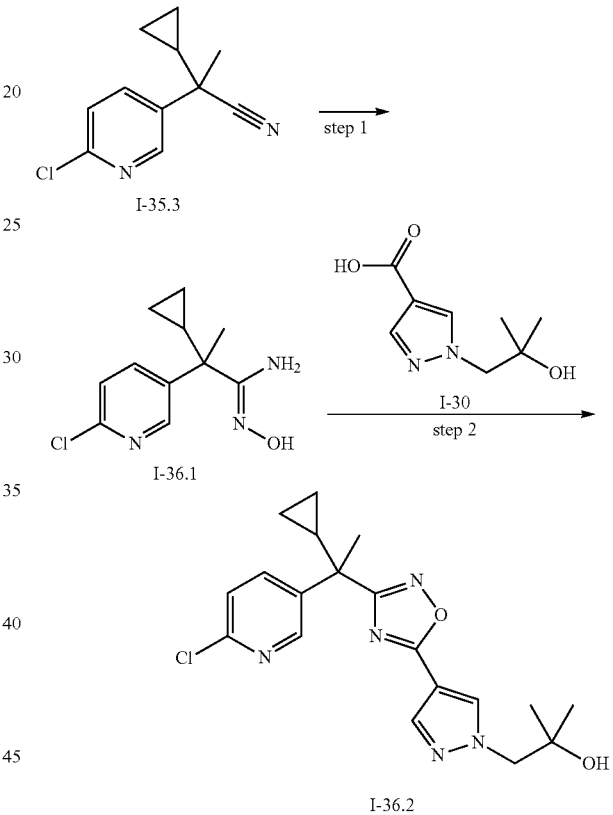 | 207 |

Method Q: Synthesis of Intermediate of I-36.2

Step 1: Synthesis of Intermediate I-36.1

To a pressure reactor is added I-35.3 (500 mg, 2.42 mmol) in EtOH (3 ml), follows by the addition of hydroxylamine (3 ml, 49 mmol). The reaction mixture is stirred at 90° C. for 3 hours. The reaction mixture is concentrated in vacuo. The residue is diluted with EtOAc, is washed with water, brine, is dried under anhy. $Na_2SO_4$, is filtered and is concentrated. The residue is purified by flash chromatography ($SiO_2$, 0-5% $MeOH/CH_2Cl_2$) to afford I-36.1 (567 mg); m/z 240.1 [M+1]

Step 2: Synthesis of Intermediate I-36.2

To a pressure tube is added I-36.1 (250 mg, 1.04 mmol) in 1,4-dioxane (5 ml), follows by the addition of 1,1'-carbonyldiimidazole (186 mg, 1.15 mmol). The reaction mixture is stirred at 55° C. for 60 minutes, followed by the addition of I-30 (211 mg, 1.15 mmol). The reaction mixture is stirred at 110° C. for 16 hours. The reaction mixture is concentrated in vacuo. The residue is diluted with EtOAc, is washed with water, brine, is dried under anhy. Na₂SO₄, is filtered and is concentrated. The residues is purified by flash chromatography (SiO₂, 0-5% MeOH/CH₂Cl₂) to afford I-36.2 (352 mg); m/z 388.2 [M+1]

The following intermediates were synthesized in a similar fashion from the appropriate reagents:

TABLE 16

| Intermediate | Structure | m/z [M + H] |
|---|---|---|
| I-36.3 | 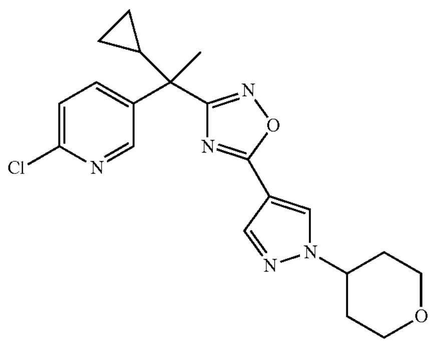 [SMILES: CC(c1ccc(Cl)nc1)(c1noc(-c2cnn(C3CCOCC3)c2)n1)C1CC1] | 400 |
| I-36.4 | 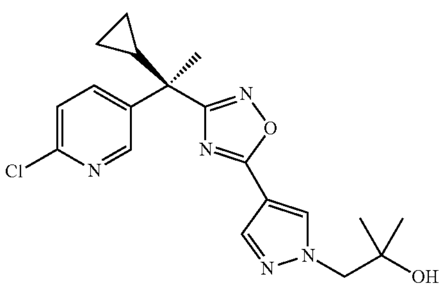 [SMILES: CC(C)(O)Cn1cc(-c2nc([C@@](C)(c3ccc(Cl)nc3)C3CC3)no2)cn1] | 390 |
| I-36.5 | 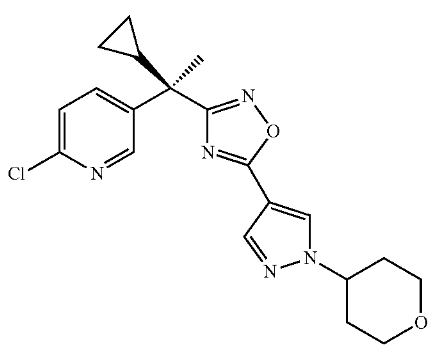 [SMILES: C[C@@](c1ccc(Cl)nc1)(c1noc(-c2cnn(C3CCOCC3)c2)n1)C1CC1] | 402 |
| I-36.6 | 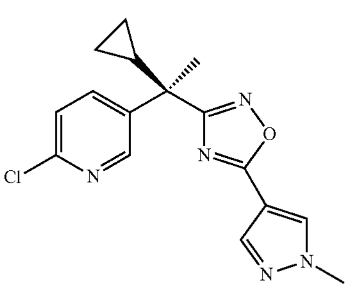 [SMILES: Cn1cc(-c2nc([C@@](C)(c3ccc(Cl)nc3)C3CC3)no2)cn1] | 332 |

Method R: Synthesis of Intermediate I-37.2

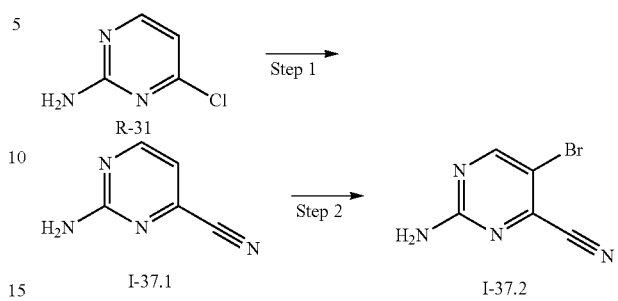

Step 1: Synthesis of I-37.1

To a solution of R-31 (200 mg, 1.5 mmol) in DMF (10 mL) are added ZnCN₂ (217 mg, 1.8 mmol) and Pd(PPh₃)₄ (178 mg, 0.15 mmol) at room temperature. The solution is heated at 120° C. in a microwave reactor for 2 hours. The solution is cooled down and water (10 mL) is added. The solution is extracted with EtOAc (30 mL) and the combined organic layer is dried with MgSO₄ and is filtered. The filtrate is concentrated and the residue (I-37.1: m/z: 120 [M⁺]) is used in the next step of the synthesis without further purification.

Step 2: Synthesis of I-37.2

To a solution of I-37.1 (100 mg, 0.83 mmol) in CH₃CN (10 mL) is added NBS (222 mg, 1.2 mmol) at room temperature. The solution is stirred at the same temperature for 12 hours. The solution is concentrated and the residue is purified by silica gel flash column chromatography with 10% MeOH in CH₂Cl₂ as the eluent to afford I-37.2 (100 mg); m/z: 200 [M⁺+1]

The following intermediates were synthesized in a similar fashion from the appropriate reagents:

TABLE 17

| Intermediate | Structure | m/z [M + H] |
|---|---|---|
| I-37.3 | 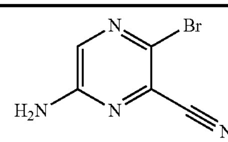 | 200 |

Method S: Synthesis of Intermediate I-38.2

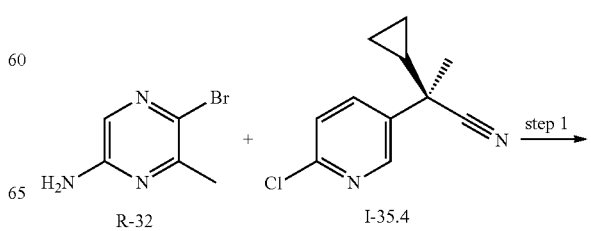

-continued

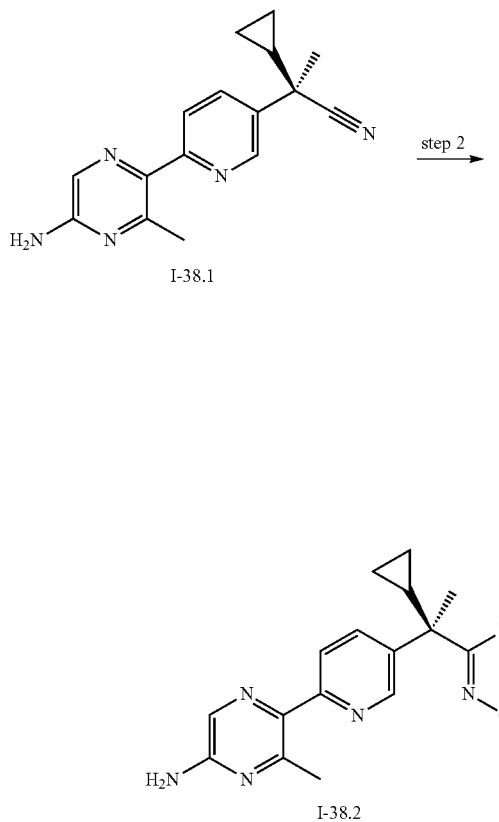

I-38.1

I-38.2

Step 1: Synthesis of I-38.1

To a solution of I-35.4 (495 mg, 2.39 mmol) in THF (5 ml) in a microwave vial is added hexamethyldistannane (0.55 ml, 2.64 mmol) followed by bis(triphenylphosphine)palladium (II) chloride (168 mg, 0.239 mmol). The reaction mixture is degassed with argon, capped, and stirred at 85° C. for 16 hrs. R-32 (450 mg, 2.39 mmol) is added followed by tetrakis (triphenylphosphine)palladium (0) (276 mg, 0.239 mmol). The reaction vessel is degassed with argon, then capped and heated at 85° C. for 16 hours. The reaction mixture is passed through a plug of Celite and rinsed with DCM. The filtrate is concentrated in vacuo and purified by flash chromatography ($SiO_2$, 0-5% MeOH/DCM) to afford the title intermediate (160 mg); m/z 281.3 [M+1]

Step 2: Synthesis of I-38.2

To a solution of I-38.1 (160 mg, 0.57 mmol) in 4 ml of EtOH stifling in a roundbottom flask with a condenser is added hydroxylamine (50% solution in water) (2.5 ml, 81.6 mmol) and stirred at 90° C. for 3 hours. The reaction mixture is concentrated in vacuo. The residue is diluted with EtOAc, is washed with water, brine, is dried under anhy. $Na_2SO_4$, is filtered and is concentrated to afford title intermediate (169 mg); m/z 313.2 [M+1]

Method 1: Synthesis of 1-[4-(3-{2-[6-(2-aminopyrimidin-5-yl)pyridin-3-yl]-3-methylbutan-2-yl}-1,2,4-oxadiazol-5-yl)-1H-pyrazol-1-yl]propan-2-ol (Example 1)

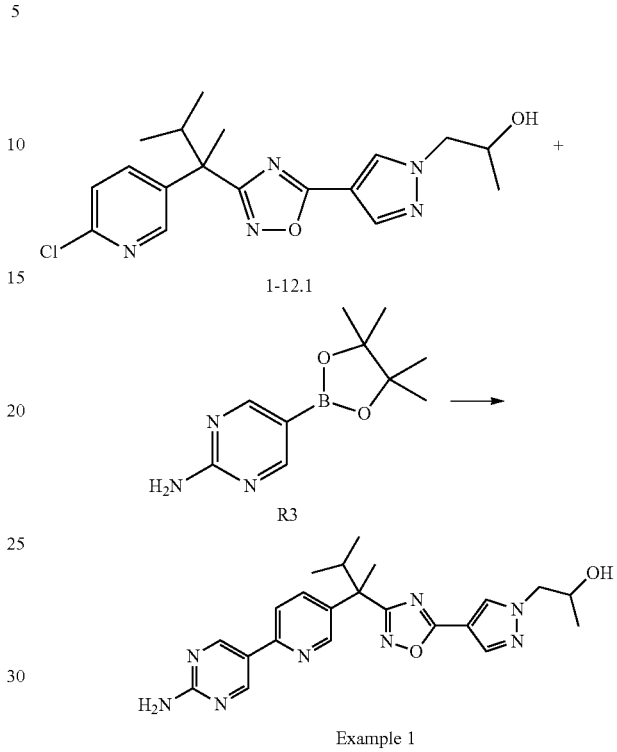

I-12.1

R3

Example 1

A solution of I-12.1 (181.0 mg, 0.48 mmol), R3 (319.5 mg, 1.45 mmol), bis(triphenylphosphine)palladium(II)chloride (67.6 mg, 0.096 mmol) and 2M $Na_2CO_3$ solution (0.48 mL) in DMF (3.0 mL) is heated at 80° C. until completion. The reaction mixture is cooled to room temperature, filtered, the solvent is removed under vacuum, the crude diluted in DCM and washed with saturated $NaHCO_3$ solution. The organic phase is dried over anhydrous $Na_2SO_4$ and filtered. The solvent is removed under vacuum and the crude is purified via preparative HPLC to afford Example 1 (26.5 mg).

Examples listed in Table 13 have been synthesized in a similar manner, with the exception of some that were purified via silica gel column chromatography; Example 3 for which tetrakis(triphenylphosphine)palladium(0) in THF is used; Example 5 that derived from chiral resolution of Example 3 via a Chiracel AD column in 80% (EtOH+0.1% diethylamine) in Heptane @ 75 mL/min; Example 23 and Example 24 derived from chiral resolution of Example 8 via a Chiracel AD column in 95% (EtOH+0.4% diethylamine) in Heptane @ 55 mL/min; Example 34 and Example 35 derived from chiral resolution of Example 6 via a chiral column AD-H in 95% (EtOH+0.4% diethylamine) in Heptane @ 55 mL/min; Example 53 and Example 54 derived from chiral resolution of Example 80 on 4.6×100 mm Regis Pack from Regis Technologies, $CO_2$ cosolvent EtOH:IPA+0.1% isopropilamine, 65% cosolvent at 4 mL/min, P=100 bar, T=25° C.; Example 59 and Example 61 derived from chiral resolution of Example 7 on 4.6×100 mm Chiral Pack AD from Chiral Technologies, $CO_2$ cosolvent IPA:MeOH 7:3+0.1% isopropilamine, 50% cosolvent at 4 mL/min, P=125 bar, T=25° C.; Example 70, Example 71 and Example 72 for which 1,1'-bis(diphenylphosphino)ferrocene]dichloropalladium and catalytic amount of 1,1'-bis(diphenylphosphino)ferrocene are used.

Method 2: Synthesis of 5-(5-{(2R)-3-methyl-2-[5-(1-methyl-1H-pyrazol-4-yl)-1,2,4-oxadiazol-3-yl]butan-2-yl}pyridin-2-yl)pyrimidin-2-amine (Example 4)

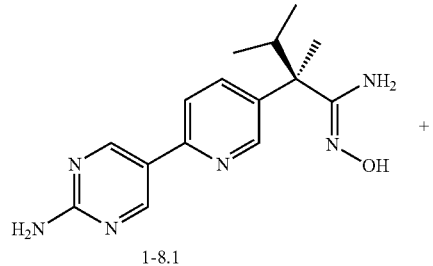

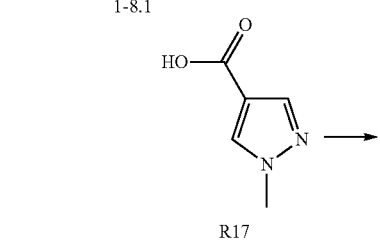

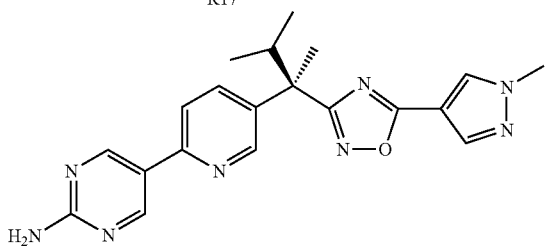

Example 4

This method is performed in accordance to the procedure reported for Method G, using 1.1 eq of acid and CDI.

Examples listed in Table 13 have been synthesized in a similar manner, in some cases compounds were purified via prep HPLC, in some others via silica gel column chromatography. For Example 21 the reaction is carried out in DMF and heating at 110° C. for 7 hours after the addition of I-8.4.

Method 3: Synthesis of 5-(5-{(2R)-3-methyl-2-[5-(1H-pyrazol-4-yl)-1,2,4-oxadiazol-3-yl]butan-2-yl}pyridin-2-yl)pyrimidin-2-amine (Example 43)

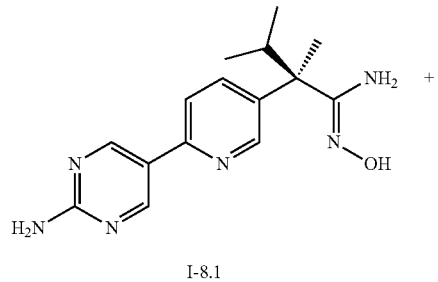

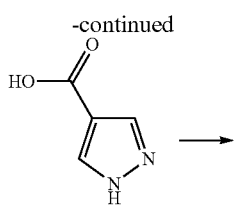

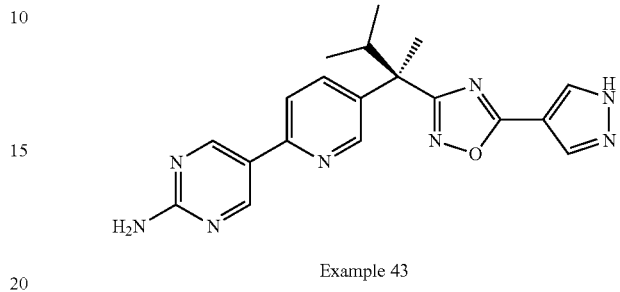

Example 43

In a sealed tube R9 (4.4 g, 37.9 mmol) is added in 1,4-dioxane (100.0 mL), followed by the addition of 1,1'-carbonyldiimidazole (6.1 g, 37.9 mmol). The reaction mixture is stirred at 55° C. for 30 minutes. The reaction mixture first becomes a clear solution, then cloudy. A solution of I-8.1 (10.8 g, 32.1 mmol) in 1,4-dioxane (10.0 mL) is added. The reaction mixture is stirred at 120° C. for 8 hours. The solvent is removed under reduced pressure, the crude is purified by silica gel column chromatography (DCM/MeOH) to afford Example 43 (11.9 g).

Method 4: Synthesis of 1-[4-(3-{(2R)-2-[6-(2-aminopyrimidin-5-yl)pyridin-3-yl]-3-methylbutan-2-yl}-1,2,4-oxadiazol-5-yl)-1H-pyrazol-1-yl]-2-methylpropan-2-ol (Example 38)

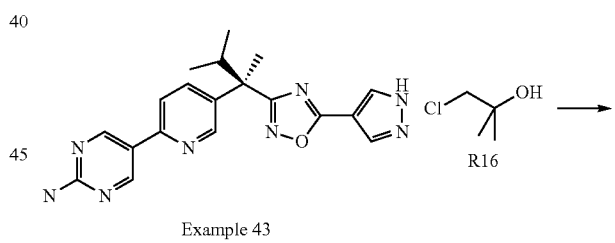

Example 43

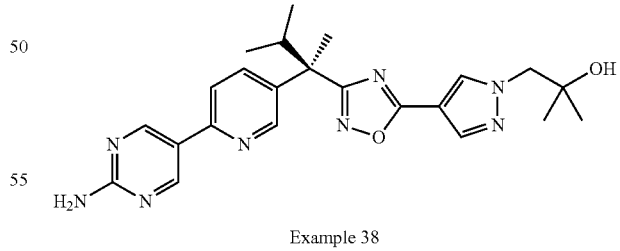

Example 38

A solution of Example 43 (2.0 g, 5.14 mmol), $K_2CO_3$ (1.06 g, 7.71 mmol) and R16 (1.05 mL, 10.28 mmol) in DMF (10.0 mL) is stirred at 80° C. for 3 days. $K_2CO_3$ (355 mg, 2.57 mmol) is added and the reaction mixture is heated for additional 2 hours. The reaction mixture is diluted with EtOAc and washed with water. The water layer is extracted with EtOAc. The organic phase is dried over anhydrous $Na_2SO_4$ and filtered; the solvent removed under vacuum and the crude purified via silica gel column chromatography (DCM/MeOH) to afford Example 38 (1.99 g).

Examples listed in Table 13 have been synthesized in a similar manner, with the exception of Example 14 for which 1.0 eq of base and 1.0 eq of iodide are used; for Example 17 the corresponding iodide is used; for Example 28 1.5 eq of the corresponding bromide are used and the reaction is run at room temperature overnight; for Example 29 1.5 eq of the corresponding iodide are used and the reaction is run at room temperature overnight; for Example 30 1.2 eq of the corresponding bromide are used and the reaction is heated at 100° C. over three days; for Example 31 1.5 eq of the corresponding iodide in DMF at room temperature for 12 hours; Example 33 1.1 .eq of the corresponding chloride is used and the reaction is run at 100° C. over three days in the presence of a catalytic amount of TBAI; Example 37 derived from chiral resolution of Example 2 via a chiral column AD-H in 95% (EtOH+0.4% diethylamine) in Heptane @ 8 mL/min; Example 44 and Example 45 derived from chiral resolution of Example 14 on 4.6×100 mm Regis Pack from Regis Technologies, $CO_2$ cosolvent+0.1% isopropilamine in isopropanol, 30% cosolvent at 4 mL/min, P=100 bar, T=25° C.; Example 46 and Example 47 derived from chiral resolution of Example 30 via a chiral column AD-H in 95% (EtOH+0.4% diethylamine) in Heptane at 55 mL/min; Example 48 and Example 49 derived from chiral resolution of Example 17 via a chiral column AD-H in 95% (EtOH+0.4% diethylamine) in Heptane 55 mL/min; Example 88 the reaction is run in the presence of catalytic amount of TBAI and it is heated at 100° C. for three days; for Example 89 the corresponding bromide is used the reaction is run at 100° C. for three days; for Example 90 the corresponding bromide is used the reaction is run at 100° C. for three days.

The following compounds are made in a similar manner to method 4:

Example 96 uses the corresponding bromide, $Cs_2CO_3$ in place of $K_2CO_3$, and is carried out at 70° C. for 3 hours followed by a second addition of bromide and base and heating for another 1 hour at 70° C.

Examples 97 and 129 use $Cs_2CO_3$ in place of $K_2CO_3$, and are carried out at 60° C. for 1 hour with purification by reverse-phase preparative HPLC.

Example 111 uses $Cs_2CO_3$ in place of $K_2CO_3$, and is carried out at 50° C. for 2 hours then room temperature overnight with purification by reverse-phase preparative HPLC.

Example 140 uses $Cs_2CO_3$ in place of $K_2CO_3$, and is carried out at 50° C. for 2 hours with purification by reverse-phase preparative HPLC.

Method 5: Synthesis of 5-[5-(2-{5-[5-(ethylamino)pyrazin-2-yl]-1,2,4-oxadiazol-3-yl}-3-methylbutan-2-yl)pyridin-2-yl]pyrimidin-2-amine (Example 12)

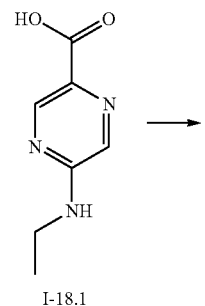

I-18.1

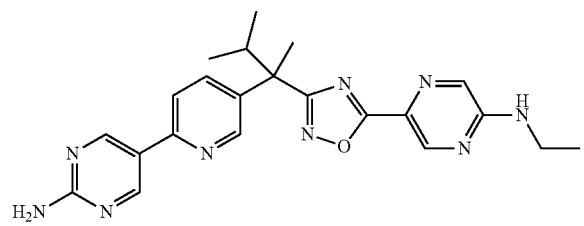

Example 12

This method is performed in accordance to the procedure reported for Method F.

Examples listed in Table 13 have been synthesized in a similar manner with the exception of Example 40 and Example 41 that derived from chiral separation of Example 12 on a 4.6×100 mm ChiralPak OD-H column from Chiral Technologies, isopropanol/35% $CO_2$+0.1% isopropilamine at 4 mL/min, P=100 bar, T=25° C., sample dissolved in MeOH.

Method 6: Synthesis of 5-[5-(3-methyl-2-{5-[5-(piperazin-1-yl)pyrazin-2-yl]-1,2,4-oxadiazol-3-yl}butan-2-yl)pyridin-2-yl]pyrimidin-2-amine (Example 13)

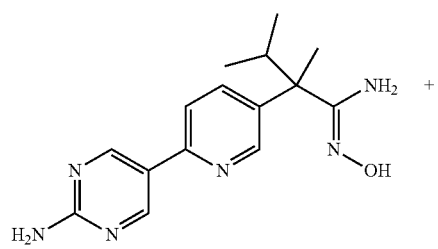

I-8.4

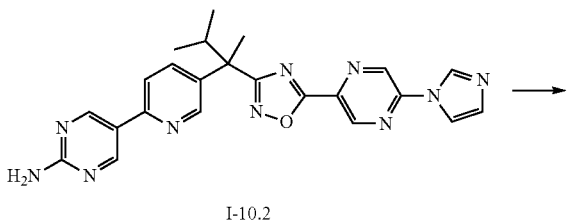

I-10.2

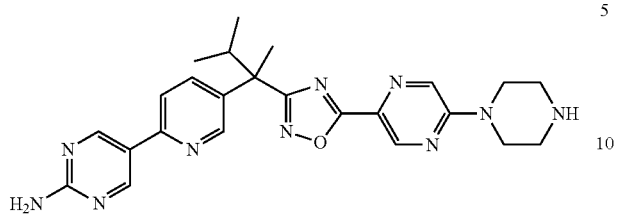

Example 13 piperazine (175.1 mg, 2.03 mmol) is added to a solution of I-10.2 (700 mg, 88% pure, 1.35 mmol) in DMSO (3.0 mL) and the reaction mixture is heated at 80° C. for 2 hours. The mixture is cooled to room temperature, diluted with water and the pH is adjusted to ~12 with 1N NaOH. The mixture is extracted with EtOAc, the combined extracts are washed with brine. The organic phase is dried over anhydrous $Na_2SO_4$ and filtered. The solvent removed under vacuum to afford the crude product that is purified by silica gel column chromatography (DCM/MeOH) to afford Example 13 (183.0 mg).

Examples listed in Table 13 have been synthesized in a similar manner, with the exception of the following compounds for which the second step is carried out with the indicated modifications: Example 15 in 2M Methylamine in THF at 80° C. in sealed tube for 18 hours; Example 16 in NMP (4.2 eq.) employing 15 eq of the corresponding amine; Example 18 in NMP (4.6 eq.) with 20.0 eq. of the corresponding amine; Example 19 in NMP (4.6 eq.) with 12.3 eq. of the corresponding amine; Example 20 in NMP (4.2 eq.) with 5.0 eq. of the corresponding amine; Example 22 in NMP (4.6 eq.) with 20.0 eq of the corresponding amine; Example 27 in THF with 13.0 eq of corresponding amine at 50° C. over three days; Example 32 in THF/NMP 1/1 with 9.0 eq of corresponding amine at 50° C. over three days; Example 42 in THF and 3.0 eq of the corresponding amine (2.0M solution in THF) at room temperature over three days; Example 51 and Example 52 are derived from chiral resolution of Example 13 on 4.6×100 mm Regis Pack column from Regis Technologies, $CO_2$ cosolvent+0.1% isopropilamine in isopropanol, 40% cosolvent at 4 mL/min, P=100 bar, T=25° C.; Example 55 and Example 56 derived from chiral resolution of Example 18 on 4.6×100 mm Chiral Pack AD column from Chiral Technologies, $CO_2$ cosolvent IPA/MeOH 7/3+0.1% isopropilamine, 50% cosolvent at 4 mL/min, P=125 bar, T=40° C.; some of the compounds were purified via prep HPLC; Example 92 and 93 are derived from chiral resolution of Example 16 on 4.6×100 mm Chiral Pack OD-H column from Chiral Technologies, T=40° C.; $CO_2$ cosolvent (Solvent B) 0.1% isopropylamine in isopropanol isocratic method: 30% co-solvent at 4 mL/min; system pressure 125 bar; column temperature: 25° C.; sample diluent: methanol; Example 94 and 95 are derived from resolution on Example 20 on 4.6×100 mm ChiralPak AD-H from Chiral Technologies, $CO_2$ cosolvent (Solvent B) 0.1% isopropylamine in isopropanol; isocratic method: 15% co-solvent at 80 mL/min; system pressure 100 bar; column temperature: 25° C.; sample diluent: methanol.

Method 7: Synthesis of 2-[(3-{2-[6-(2-aminopyrimidin-5-yl)pyridin-3-yl]-3-methylbutan-2-yl}-1,2,4-oxadiazol-5-yl)amino]ethanol (Example 25)

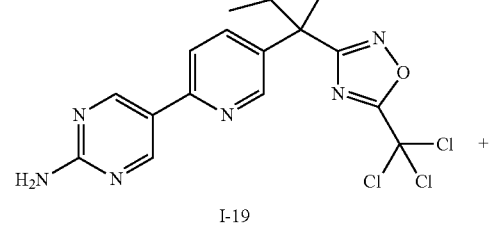

I-19

$H_2N$⁀⁀OH

R17

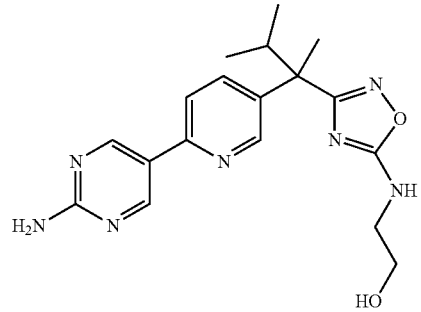

Example 25

To a stirred solution of R17 (0.021 mL, 0.351 mmol) and KOH (23.17 mg, 0.351 mmol) in DMSO (1 mL) is added I-19 (100 mg, 0.234 mmol). The reaction mixture is stirred at room temperature for 1.5 hours. After this time, the reaction mixture is quenched with water and extracted with EtOAc twice. The organics are combined and washed with water then brine, dried over anhydrous $Na_2SO_4$, filtered and concentrated in vacuo. The residue is purified by silica gel column chromatography (1-10% MeOH in DCM) to yield Example 25 (38.0 mg).

Examples listed in Table 13 have been synthesized in a similar manner, with the exception of Example 26 for which KOH and piperazine (7.0 eq) are employed in DMF and the compound is purified via silica gel column chromatography (10% MeOH/DCM with 3% 2N $NH_3$ in MeOH)

Method 8: Synthesis of 3-[4-(3-{2-[6-(2-aminopyrimidin-5-yl)pyridin-3-yl]-3-methylbutan-2-yl}-1,2,4-oxadiazol-5-yl)-1H-pyrazol-1-yl]-2,2-dimethylpropanoic acid (Example 39)

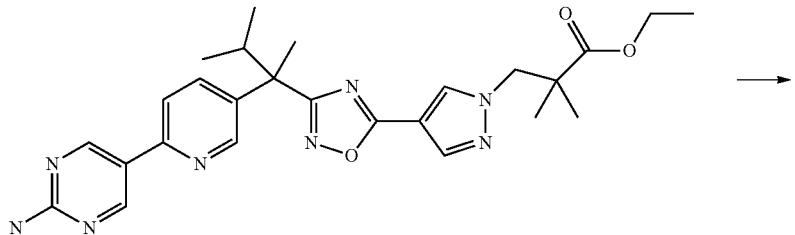

Example 33

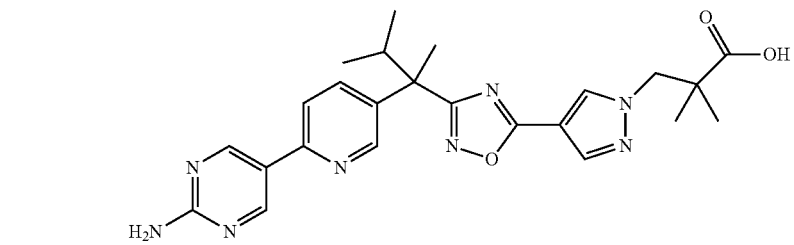

Example 39

A solution of Example 33 (45.0 mg, 0.089 mmol) in THF (3.0 mL), LiOH (4.0 mg, 0.178 mmol) and water (1.0 mL) is stirred at room temperature until complete disappearance of the starting material. The solvent is removed under reduced pressure, the crude is diluted with EtOAc, washed with water. The water phase is brought to pH=2-3 and extracted with EtOAc. The organic layers are combined, dried over anhydrous $Na_2SO_4$ and filtered. After removal of the solvent under reduced pressure, the crude is purified via prep HPLC to afford Example 39 (15.0 mg).

Method 9: Synthesis of 5-(5-{1-cyclopropyl-1-[5-(1-methyl-1H-pyrazol-4-yl)-1,2,4-oxadiazol-3-yl]ethyl}pyridin-2-yl)pyrimidin-2-amine (Example 50)

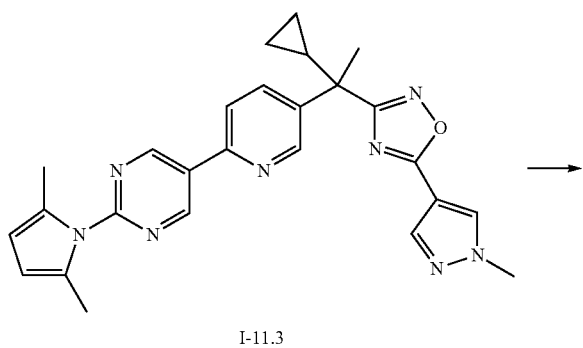

I-11.3

-continued

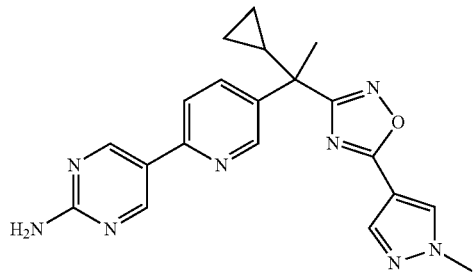

Example 50

A solution of I-11.3 (86.0 mg, 0.18 mmol) and hydroxylamine hydrochloride (128 mg, 1.84 mmol) in EtOH (1.5 mL), water (0.7 mL) and TEA (19 mg, 0.19 mmol) is stirred at 90° C. for 18 hours. The reaction mixture is diluted with EtOAc, washed with water, brine, dried over anhydrous $Na_2SO_4$, filtered and concentrated. The crude is purified via silica gel column chromatography (DCM/MeOH) to afford Example 50 (48.0 mg).

Examples listed in Table 13 have been synthesized in a similar manner, with the exception of Example 57 and Example 58 that are derived from chiral resolution of Example 50 AD-H column (4.6×250 mm) and 95% (EtOH+0.1% diethylamine):heptane at 0.4 ml/min and 40° C., or more recently a 2.1×250 mm column at 0.5 ml/min.

Method 10: Synthesis of 5-(5-{2-[5-(4-iodophenyl)-1,2,4-oxadiazol-3-yl]-3-methylbutan-2-yl}pyridin-2-yl)pyrimidin-2-amine (Example 62)

Method 11: Synthesis of 5-[5-(1-cyclopropyl-1-{5-[1-(oxetan-3-yl)-1H-pyrazol-4-yl]-1,2,4-oxadiazol-3-yl}-ethyl)pyridin-2-yl]pyrimidin-2-amine (Example 63)

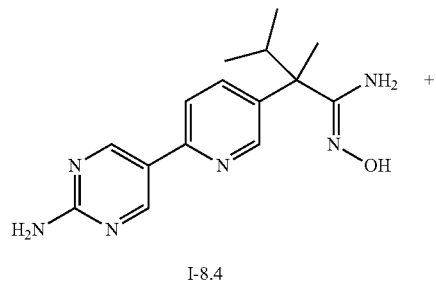

I-8.4

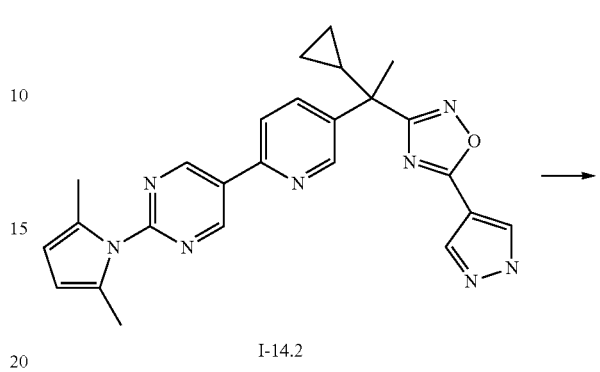

I-14.2

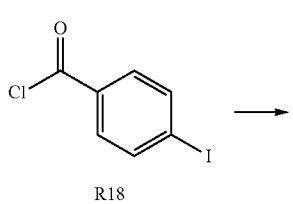

R18

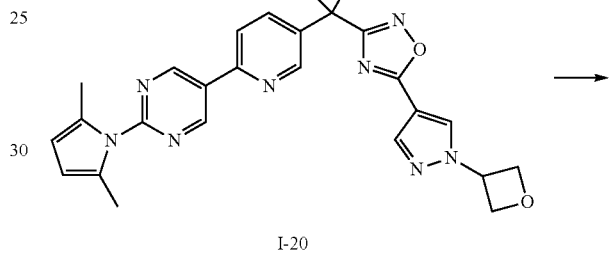

I-20

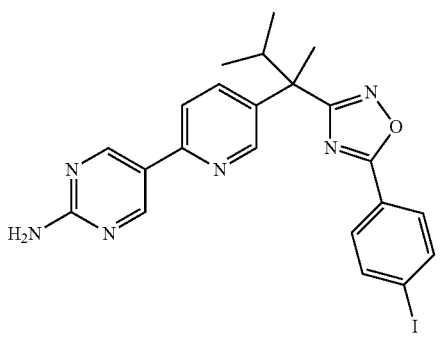

Example 62

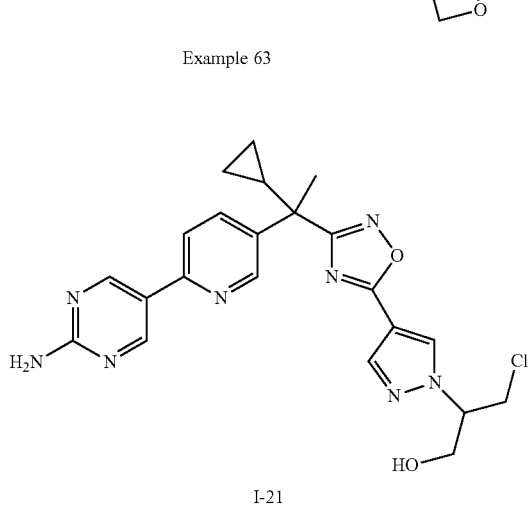

Example 63

I-21

I-8.4 (150.0 mg, 0.499 mmol) is dissolved in DMF (2.0 ml) and treated with DIEA (0.59 mL, 3.20 mmol) and R18 (160.0 mg, 0.599 mmol). The resulting mixture is heated at 110° C. After 1 h no product is detected by LC-MS check (it is possible that the acyl chloride is hydrolyzed to the corresponding acid), the reaction mixture is cooled to room temperature and HATU (0.25 g) is added. The reaction mixture is warmed to 80° C. and stirred over night. After this time, the reaction appeared to be ~50% complete (checked by LC-MS). The reaction mixture is cooled to room temperature, poured into water and extracted twice with EtOAc. The combined organics are washed with brine, dried over anhydrous Na$_2$SO$_4$ and concentrated after filtration. The crude is purified via silica gel column chromatography (DCM/MeOH) to afford Example 62 (256.0 mg).

Step 1: Synthesis of Intermediate I-20.

Performed according to Method 4. I-20, m/z: 509 [M+H]

Step 2: Synthesis of Example 63

Performed according to Method 9, I-21, m/z: 467 [M+H] is formed as a byproduct. Examples listed in Table 13 have been synthesized in a similar manner, with the exception of Example 78 and Example 79 that are derived from chiral resolution of Example 63 on 4.6×100 mm ChiralPak AD-H from Chiral Technologies, $CO_2$ cosolvent+0.1% isopropilamine in methanol:isopropanol 3:1, 55% cosolvent at 4 mL/min, P=125 bar, T=25° C.

The following compounds are made in a similar manner to method 11:

Examples 108 and 138 are derived from chiral resolution on an AD-H column (20×250 mm) and 70% (EtOH+0.1% diethylamine):heptane at 8.5 ml/min and 45° C.

Examples 122 and 123 are derived from chiral resolution on a AD-H column (20×250 mm) and 95% (EtOH+0.1% diethylamine):heptane at 7.0 ml/min and 40° C.

Examples 109 and 139 use $Cs_2CO_3$ in place of $K_2CO_3$, are carried out at 60° C. for step 1, and are derived from chiral resolution AD-H column (20×250 mm) and 74% (EtOH+0.1% diethylamine):heptane at 9.0 ml/min and 45° C.

Example 120 uses $Cs_2CO_3$ in place of $K_2CO_3$ and is carried out at 60° C. for step 1

Examples 124 and 125 use $Cs_2CO_3$ in place of $K_2CO_3$, are carried out at 60° C. for step 1, and are derived from chiral resolution on a AD-H column (20×250 mm) and 95% (EtOH+0.1% diethylamine):heptane at 6.5 ml/min and 45° C.

Examples 126 and 127 use $Cs_2CO_3$ in place of $K_2CO_3$, are carried out at 60° C. for step 1, and are derived from chiral resolution on a AD-H column (20×250 mm) and 95% (EtOH+0.1% diethylamine):heptane at 6.5 ml/min and 45° C.

Method 12: Synthesis of 2-[4-(3-{1-[6-(2-aminopyrimidin-5-yl)pyridin-3-yl]-1-cyclopropylethyl}-1,2,4-oxadiazol-5-yl)-1H-pyrazol-1-yl]prop-2-en-1-ol (Example 65)

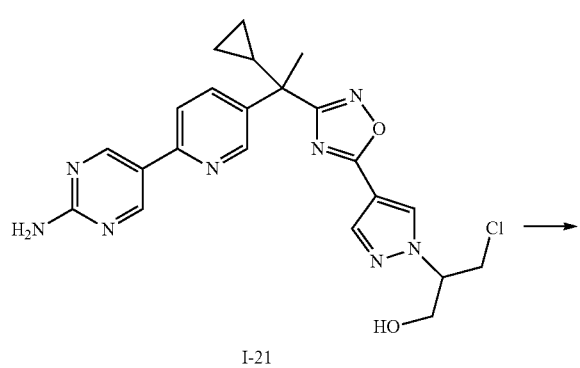

I-21

-continued

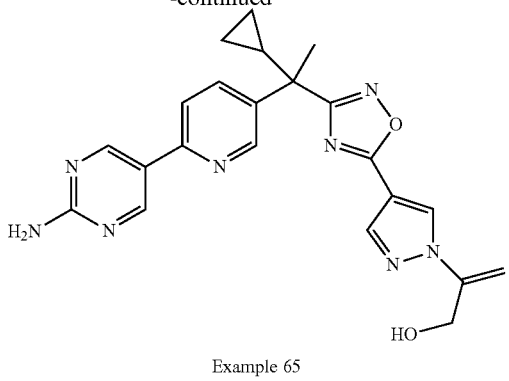

Example 65

A solution of I-21 (102.0 mg, 0.22 mmol) and KOH (14.4 mg, 0.22 mmol) in EtOH (1.0 mL) is refluxed for 30 minutes. The solution is cooled to room temperature, the solvent is removed under reduced pressure and the crude is purified via silica gel column chromatography to afford Example 65 (70.0 mg).

Method 13: Synthesis of 5-(5-{2-[5-(3-bromo-4-iodophenyl)-1,2,4-oxadiazol-3-yl]-3-methylbutan-2-yl}pyridin-2-yl)pyrimidin-2-amine (Example 69)

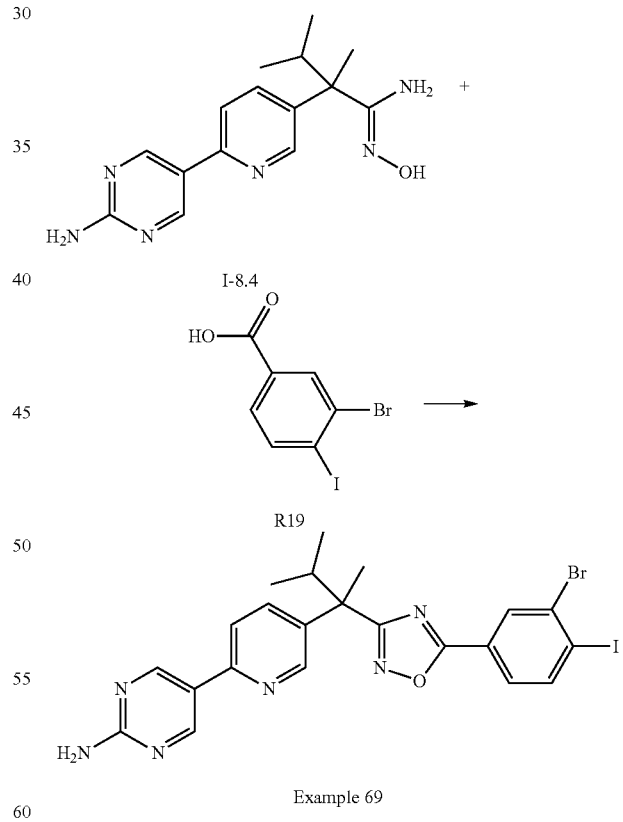

A suspension of R19 (163.3 mg, 0.50 mmol) and 1,1'-carbonyldiimidazole (81.0 mg, 0.50 mmol) in THF (2.0 mL) is heated at 50° C. for 30 min. I-8.4 (100.0 mg, 0.33 mmol) is added and the solution is heated under reflux for 3 hours. The mixture is cooled to room temperature and AcOH (0.2 mL) is added. The reaction mixture is stirred at 80° C. overnight.

After cooling to room temperature, the mixture is poured into water and extracted with EtOAc. The organic layers are combined, dried over anhydrous Na$_2$SO$_4$ and filtered. The solvent is removed under reduced pressure. Purification via silica gel column chromatography affords Example 69 (67.0 mg).

Method 14: Synthesis of 2-{[5-(3-{2-[6-(2-aminopyrimidin-5-yl)pyridin-3-yl]-3-methylbutan-2-yl}-1,2,4-oxadiazol-5-yl)pyridin-2-yl]amino}ethanol (Example 74)

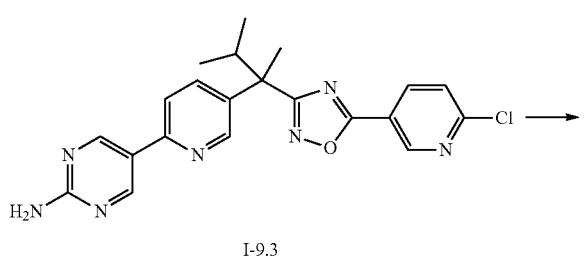

I-9.3

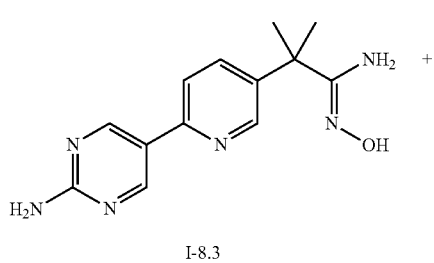

Example 74

A mixture of I-9.3 (200.0 mg, 0.38 mmol) and ethanolamine (1.0 mL) is stirred at 80° C. for 1 hour. The solvent is removed under reduced pressure, the crude purified via preparative HPLC to afford Example 74 (120.0 mg).

Method 15: Synthesis of 5-(5-{2-[5-(1H-pyrazol-4-yl)-1,2,4-oxadiazol-3-yl]propan-2-yl}pyridin-2-yl)pyrimidin-2-amine (Example 87)

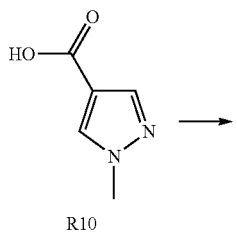

I-8.3

+

R10

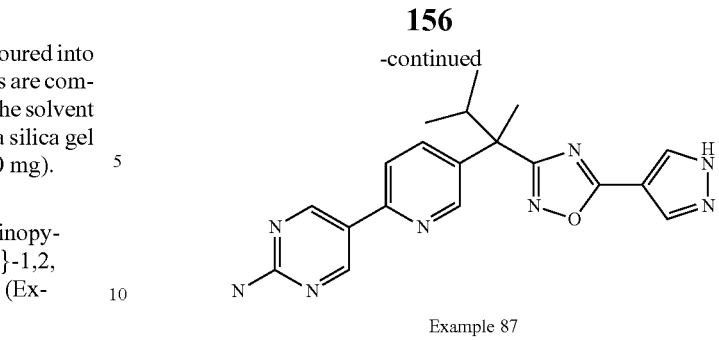

Example 87

This method is performed in accordance to the procedure reported for Method J. Examples listed in Table 13 have been synthesized in a similar manner.

Method 16: Synthesis of 1-[4-(3-{1-[6-(2-aminopyrimidin-5-yl)pyridin-3-yl]-1-cyclopropylethyl}-1,2,4-oxadiazol-5-yl)-1H-pyrazol-1-yl]-2-methylpropan-2-ol (Example 66)

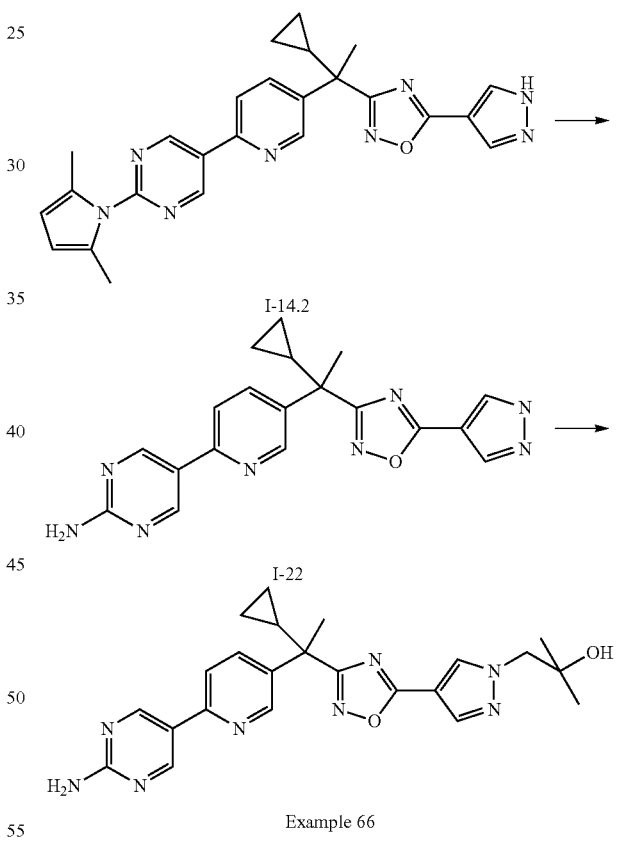

Step 1: Synthesis of Intermediate I-22

Performed according to Method 9. I-22, m/z: 375 [M+H]

Step 2: Synthesis of Example 66

Performed according to Method 4.
Examples listed in Table 13 have been synthesized in a similar manner, with the exception of Example 67 for which 2.0 eq of the corresponding chloride and potassium carbonate are employed and the reaction mixture is stirred at room temperature for two hours; for Example 68 the corresponding bromide is employed and the reaction mixture is heated at 80° C. for 18 hours; Example 75 and Example 76 are obtained from chiral resolution of Example 68 via a chiral column AD-H in 95% (EtOH+0.01% diethylamine) in Heptane at 8 mL/min; Example 81 and Example 82 are derived from chiral resolution of Example 66 via a chiral column AD-H column (4.6×250 mm) and 95% (EtOH+0.1% diethylamine):heptane at 0.4 ml/min and 40° C., or more recently a 2.1×250 mm column at 0.5 ml/min; Example 83 and Example 84 are obtained from chiral resolution of Example 67 on 4.6×100 mm ChiralPak AD-H from Chiral Technologies, $CO_2$ cosolvent+0.1% isopropilamine in methanol:isopropanol 9:1, 45% cosolvent at 4 mL/min, P=125 bar, T=25° C.

Method 17: Synthesis of 2-[4-(3-{1-[6-(2-Amino-pyrimidin-5-yl)-pyridin-3-yl]-1,2-dimethyl-propyl}-[1,2,4]oxadiazol-5-yl)-imidazol-1-yl]-N,N-dimethyl-acetamide (Example 135)

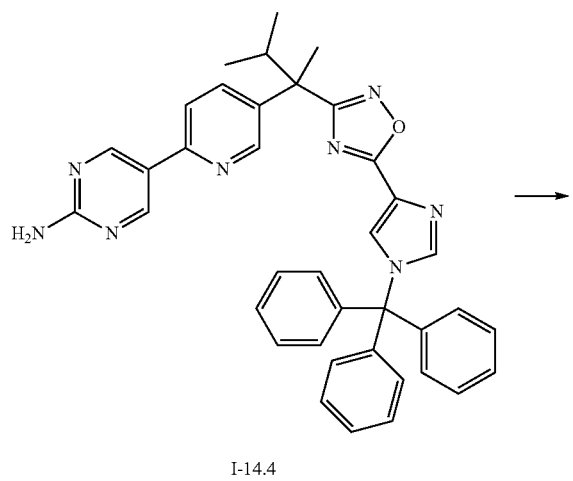

I-14.4

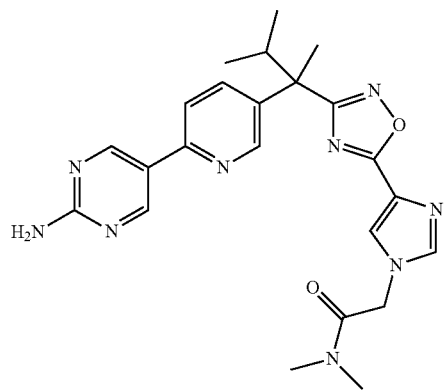

Example 135

Step 1: Synthesis of I-23

To a solution of I-14.4 (360 mg, 0.6 mmol) in $CH_2Cl_2$ is added TFA (0.13 mL, 1.7 mmol) at room temperature. The solution is stirred at the same temperature for 24 hours. The solution is concentrated under vacuum and the residue I-23 (180 mg) m/z: 377 [M+H] is used in the next step of the synthesis without further purification.

Step 2: Synthesis of Example 135

To a solution of I-23 (200 mg, 0.53 mmol) in DMF (15 mL) are added 2-chloro-N,N-dimethylacetamide (0.08 mL, 0.8 mmol) and $K_2CO_3$ (220 mg, 1.6 mmol) at room temperature. The mixture is stirred at room temperature for 48 hours. The solution is concentrated and the residue is purified by silica gel flash column chromatography to afford a mixture of regioisomer products. Further purification with preparative HPLC afford title compound (144 mg).

Method 18: Synthesis of 2-[4-(3-{(R)-[6-(5-Amino-pyrazin-2-yl)-pyridin-3-yl]-1,2-dimethyl-propyl}-[1,2,4]oxadiazol-5-yl)-pyrazol-1-yl]-N,N-dimethyl-acetamide (Example 112)

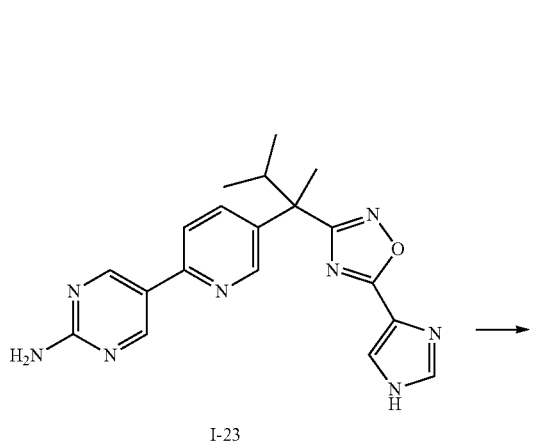

I-23

+

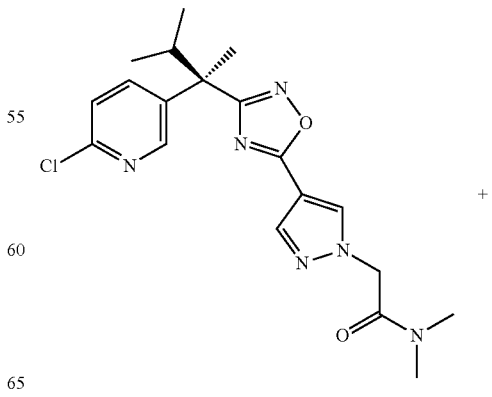

I-12.8

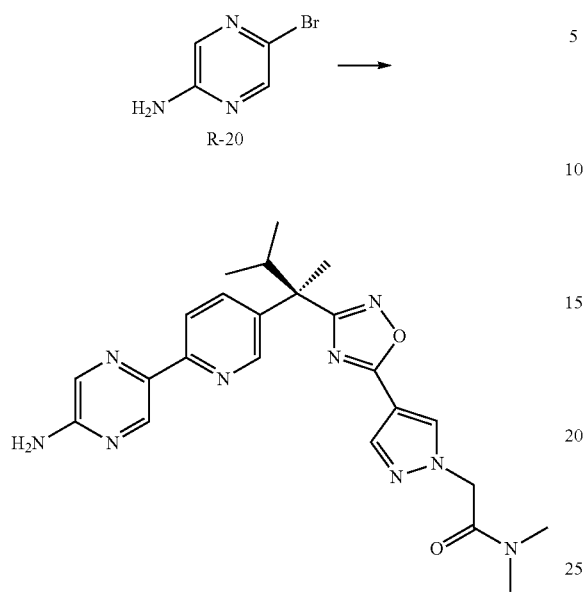

Example 112

In a 20 ml microwave vial is dissolved R-20 (100 mg, 0.575 mmol) in toluene (2.5 ml) and is added hexamethylditin (0.132 ml, 0.635 mmol) and is degassed with argon for 5 minutes. Pd(Ph$_3$P)$_4$ (33.2 mg, 0.050 mmol) is then added and the vial is capped and heated to 115° C. for 1 hour, then the reaction is cooled to room temperature. I-12.8 (277 mg, 0.690 mmol) is dissolved in toluene (2.5 ml) and is added to the reaction mixture follows by Pd(Ph$_3$P)$_4$. (33.2 mg, 0.05 mmol) The reaction vial is capped and stirred at 115° C. for 8 hours. The reaction mixture is concentrated in vacuo, and is purified by flash chromatography (SiO$_2$, 0-10% MeOH/DCM). The product is further purified by prep HPLC to yield the title compound (43 mg).

Method 19: Synthesis of 5-(5-{(R)-1-Cyclopropyl-1-[5-(3,4,5,6-tetrahydro-2H-[1,2']bipyrazinyl-5'-yl)-[1,2,4]oxadiazol-3-yl]-ethyl}-pyridin-2-yl)-pyrimidin-2-ylamine (Example 134)

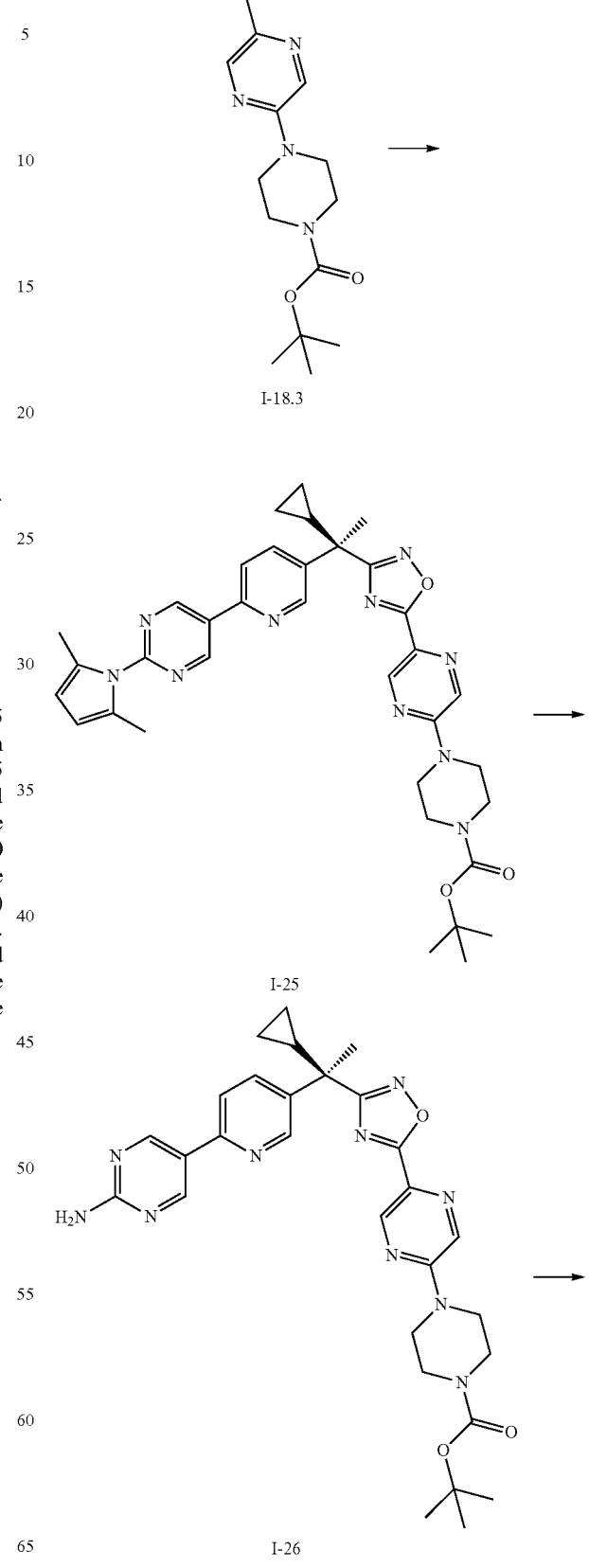

Method 20: Synthesis of 5-{1-Cyclopropyl-1-[5-(1H-pyrazol-4-yl)-[1,2,4]oxadiazol-3-yl]-ethyl}-[2,3']bipyridinyl-6'-ylamine (Example 98)

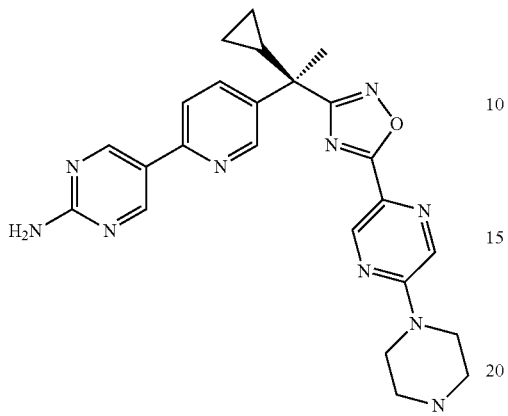

Example 134

Step 1: Synthesis of I-25

A suspension of I-18.3 (209 mg, 0.657 mmol) and CDI (102 mgs, 06328 mmol) in 1,4-dioxane (3 mL) in a sealed tube is stirred at 55° C. for one hour. A solution of I-8.10 (225 mg, 0.598 mmol) in dioxane (3 ml) is added and the reaction mixture is stirred at 120° C. for 18 hours. After cooling to room temperature, the reaction mixture is poured into brine and extracted with EtOAc (4×20 ml). The combined organic fractions are dried with sodium sulfate, filtered, and is concentrated in vacuo. The residue is purified by flash chromatography (SiO$_2$, Biotage SNAP 100 g, 0-5% MeOH/DCM) to yield I-25 (298 mg), m/z: 649 [M+H]

Step 2: Synthesis of I-26

I-26 is prepared in a manner similar to Method 9. m/z: 571.4 [M+1]

Step 3: Synthesis of example 134

4M HCl in dioxane (5 mL) is added to a solution of I-26 (55 mg, 0.096 mmol) in MeOH (3 mL) at 70° C. The reaction mixture is stirred at room temperature for 72 hours. The pH of the mixture is adjusted to 7 with 7N aq. NaOH and it is then concentrated in vacuo. The crude mixture is purified by flash chromatography (SiO$_2$, 0-25% MeOH/DCM) to afford the title compound (21 mg)

Example 137 is prepared with a similar procedure as the last step of method 19 (hydrolysis). The intermediate for that is prepared according to procedures described in Method 1.

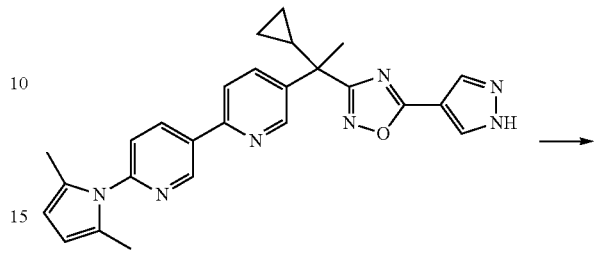

I-10.3

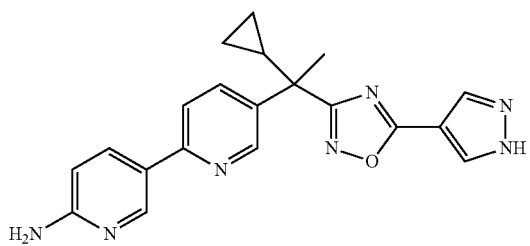

Example 98

Performed according to Method 9 with purification by preparative HPLC to afford the title compound.

Method 21: Synthesis of 1-[4-(3-{(R)-1-[6-(5-Amino-pyrazin-2-yl)-pyridin-3-yl]-1-cyclopropyl-ethyl}-[1,2,4]oxadiazol-5-yl)-pyrazol-1-yl]-2-methyl-propan-2-ol (Example 100) and 1-[4-(3-{(S)-1-[6-(5-Amino-pyrazin-2-yl)-pyridin-3-yl]-1-cyclopropyl-ethyl}-[1,2,4]oxadiazol-5-yl)-pyrazol-1-yl]-2-methyl-propan-2-ol (Example 101)

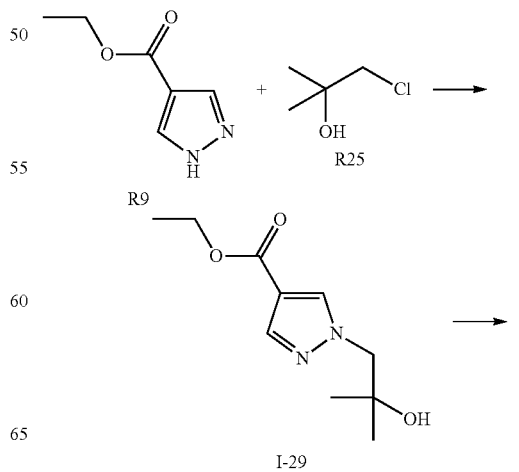

I-29

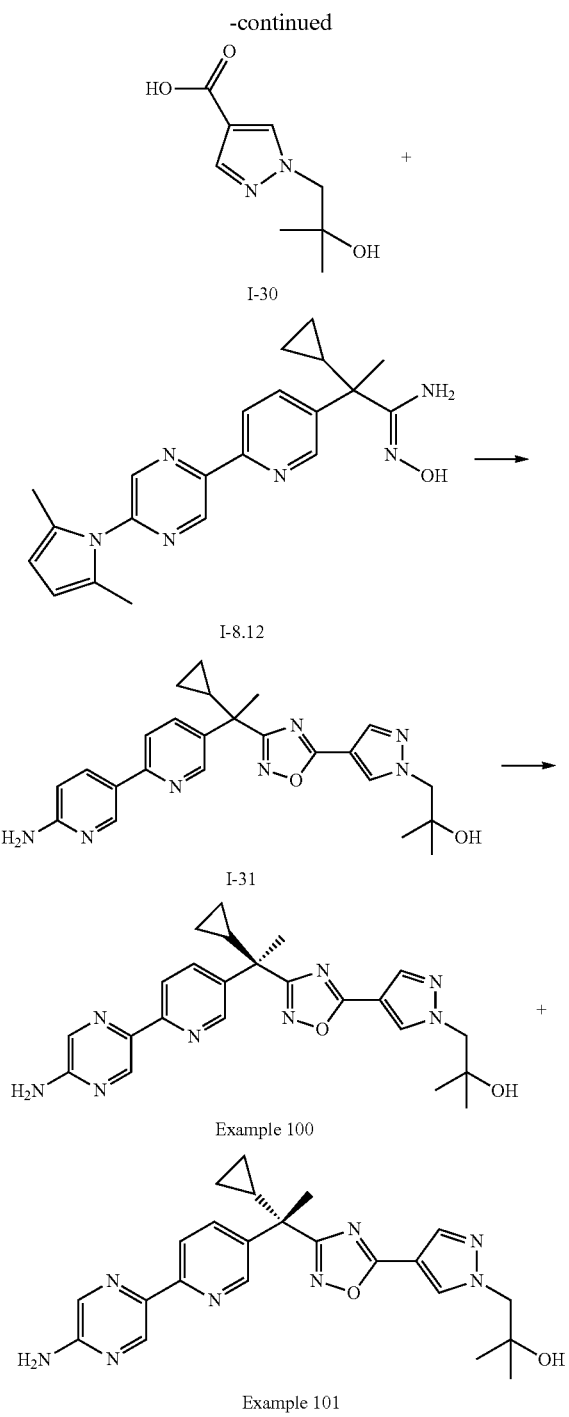

I-30

I-8.12

I-31

Example 100

Example 101

Step 1: Synthesis of I-29

R9 (2.00 g, 14.3 mmol) is treated with R25 (3.10 g, 28.5 mmol), K₂CO₃ (2.96 g, 21.4 mmol), and DMF (10 mL) and the reaction is stirred at 80° C. for 48 hours. The resulting mixture is diluted with EtOAc, washed with water and brine, dried over Na₂SO₄, filtered, and concentrated in vacuo. The resulting residue is purified by silica gel column chromatography (0-5% methanol in CH₂Cl₂) to yield I-29 (2.55 g); m/z 213 [M+H].

Step 2: Synthesis of I-30

I-29 (3.69 g, 17.4 mmol) is treated with THF (15 mL), NaOH (0.90 g, 22.5 mmol), water (7.0 mL), and methanol (5.0 mL) and the resulting mixture is stirred for 18 hours. The resulting mixture is then concentrated in vacuo and the residue partitioned between water and EtOAc. The layers are separated and the organics are washed with brine, collected, dried over Na₂SO₄, filtered, and concentrated in vacuo to yield I-30 (3.20 g); m/z 185 [M+H].

Step 3: Synthesis of I-31

This method is performed in accordance to the procedure reported for Method J; I-31, m/z: 525 [M+H].

Step 4: Synthesis of Examples 100 and 101

This method is performed according to the procedure reported for Method 9. Examples 100 and 101 are then obtained from chiral resolution on an AD-H column (20×250 mm) and 60% (EtOH+0.1% diethylamine):heptane at 4.5 ml/min and 40° C.

Method 22: Synthesis of 2-(4-{3-[(R)-1-(6'-Amino-[2,3']bipyridinyl-5-yl)-1-cyclopropyl-ethyl]-[1,2,4]oxadiazol-5-yl}-pyrazol-1-yl)-propane-1,3-diol (Example 114), 5-{(R)-1-Cyclopropyl-1-[5-(1-oxetan-3-yl-1H-pyrazol-4-yl)-[1,2,4]oxadiazol-3-yl]-ethyl}-[2,3']bipyridinyl-6'-ylamine (Example 115), and 5-{(S)-1-Cyclopropyl-1-[5-(1-oxetan-3-yl-1H-pyrazol-4-yl)-[1,2,4]oxadiazol-3-yl]-ethyl}-[2,3']bipyridinyl-6'-ylamine (Example 116)

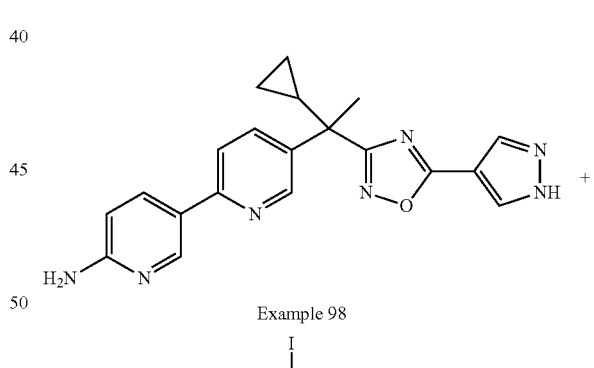

Example 98

R26

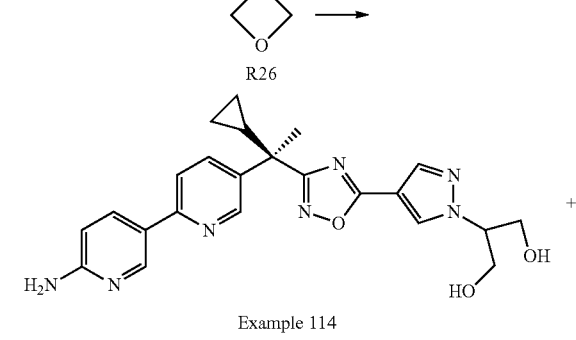

Example 114

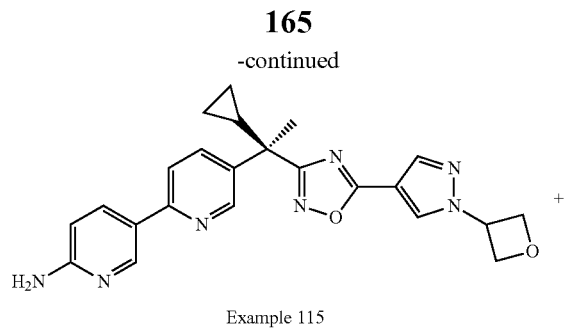

Example 115

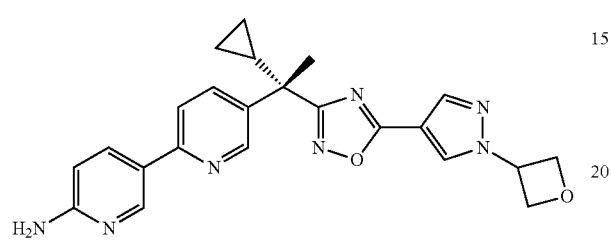

Example 116

Example 98 (120 mg, 0.321 mmol) is treated with R26 (88.7 mg, 0.482 mmol), Cs₂CO₃ (157 mg, 0.482 mmol), and DMF (1.50 mL) and the resulting mixture is stirred at 50° C. for 2 hours, then 80° C. for 4 hours. The resulting mixture is purified by reverse-phase preparative HPLC. Examples 115 (11 mg) and 116 (8 mg) are obtained from chiral resolution on an AD-H column (20×250 mm) and 80% (EtOH+0.1% diethylamine):heptane at 8 ml/min and 40° C., with Example 114 (6 mg) being obtained as a by-product from the chiral separation.

Method 23: Synthesis of 5-[5-((R)-1-{5-[1-(2-Methanesulfonyl-ethyl)-1H-pyrazol-4-yl]-[1,2,4]oxadiazol-3-yl}-1,2-dimethyl-propyl)-pyridin-2-yl]-pyrimidin-2-ylamine (Example 128)

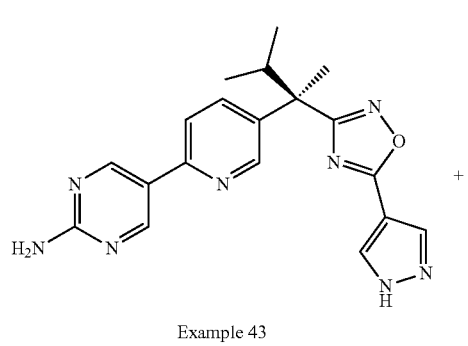

Example 43

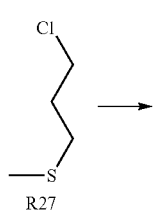

R27

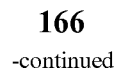

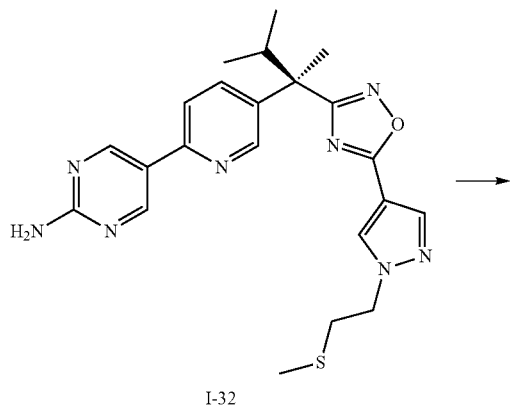

I-32

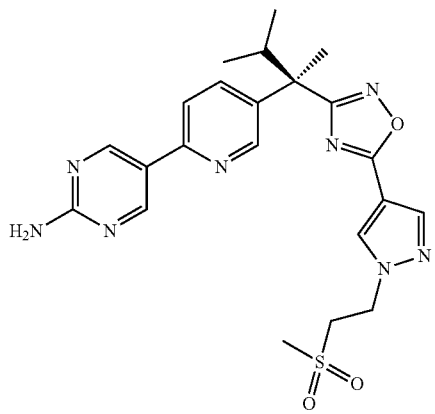

Example 128

Step 1: Synthesis of I-32

Prepared according to method 4 with Cs₂CO₃ in place of K₂CO₃, and is carried out at 60° C. for 1.5 hours with purification by reverse-phase preparative HPLC. The product is used as is without further purification.

Step 2: Synthesis of Example 128

I-32 (60.0 mg, 0.106 mmol) is treated with THF (3.0 mL), water (1.0 mL), and oxone (130 mg, 0.212 mmol) and the resulting mixture is stirred for 1 hour. Another charge of oxone (33.0 mg, 0.053 mmol) is added and the reaction is stirred for 2 hours. The resulting mixture is concentrated and the residue purified by reverse phase preparative HPLC to give Example 128 (11.0 mg).

167

Method 24: Synthesis of 2-[4-(3-{(R)-1-[6-(2-Amino-pyrimidin-5-yl)-pyridin-3-yl]-1,2-dimethyl-propyl}-1,2,4-oxadiazol-5-yl)-pyrazol-1-yl]-1-morpholin-4-yl-ethanone. (Example 151)

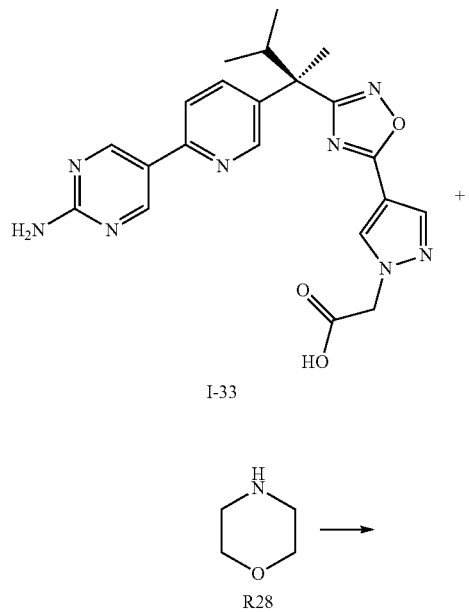

Example 151

Step 1: Synthesis of Intermediate I-33

Prepared according to method 8. I-33 m/z: 435 [M+H]

Step 2: Synthesis of Example 151

I-33 (43.4 mg, 0.10 mmol) is treated with R28 (13.1 mg, 0.15 mmol), HATU (68.4 mg, 0.18 mmol), DIEA (105 μL, 0.60 mmol), and DMA (1.80 mL) and the resulting mixture is heated at 60° C. for 16 hours. The reaction is purified directly by reverse phase preparative HPLC to give the title compound (20.9 mg).

168

Method 25: Synthesis of 2-Amino-5-[5-((R)-1-{5-[1-(2-hydroxy-2-methyl-propyl)-1H-pyrazol-4-yl]-[1,2,4]oxadiazol-3-yl}-1,2-dimethyl-propyl)-pyridin-2-yl]-3H-pyrimidin-4-one (Example 119)

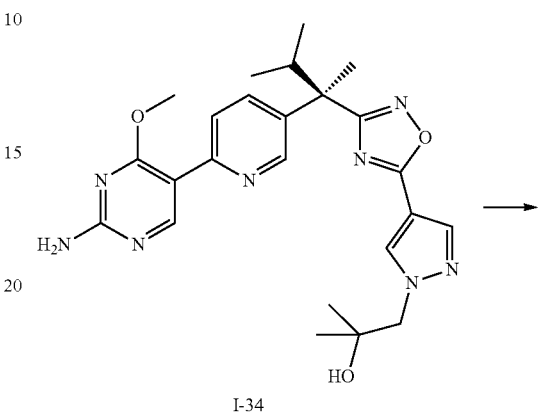

I-34

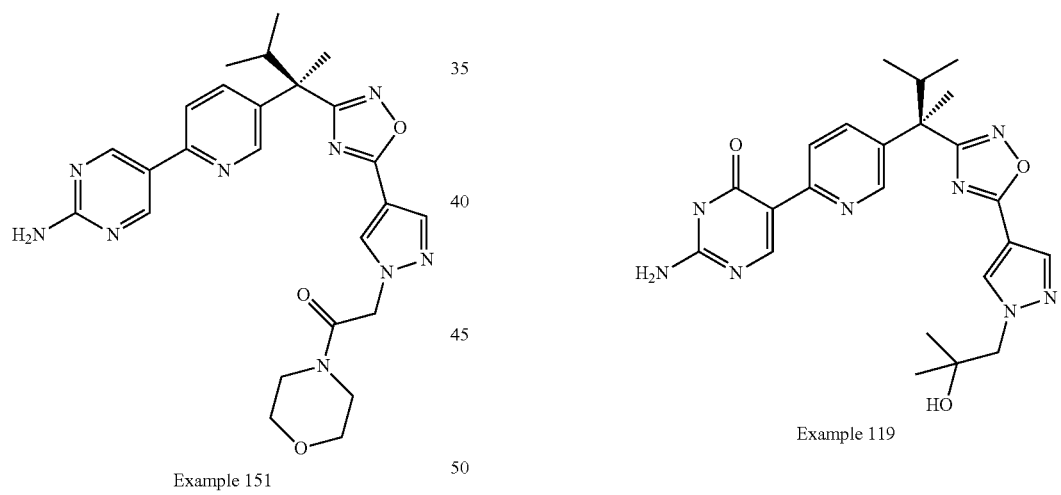

Example 119

Step 1: Synthesis of I-34

Prepared according to method 18. I-34, m/z: 479 [M+H]

Step 2: Synthesis of Example 119

To a solution of I-34 (8 mg, 0.02 mmol) in THF (0.5 mL) is added 48% HBr (0.15 mL). The mixture is heated to 70° C. for 24 hours. The solution is concentrated and the residue is purified by preparative HPLC to afford the title compound (4 mg).

Method 26: Synthesis of 1-[4-(3-{(R)-1-Cyclopropyl-1-[6-(3,4-dihydro-2H-pyrido[3,2-b][1,4]oxazin-7-yl)-pyridin-3-yl]-ethyl}-[1,2,4]oxadiazol-5-yl)-pyrazol-1-yl]-2-methyl-propan-2-ol (Example 167)

Method 27: Synthesis of {5-[5-((R)-1-Cyclopropyl-1-{5-[1-(tetrahydro-pyran-4-yl)-1H-pyrazol-4-yl]-[1,2,4]oxadiazol-3-yl}-ethyl)-pyridin-2-yl]-pyrimidin-2-yl}-methyl-amine (Example 169)

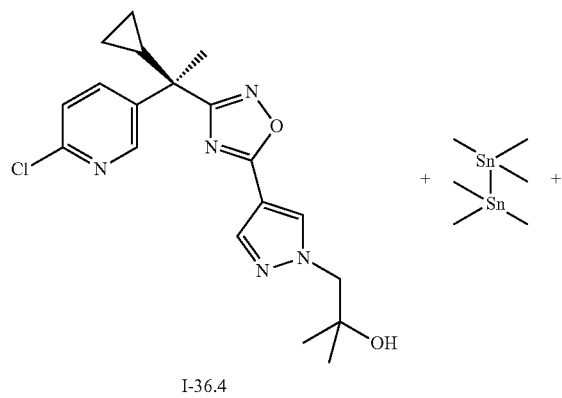
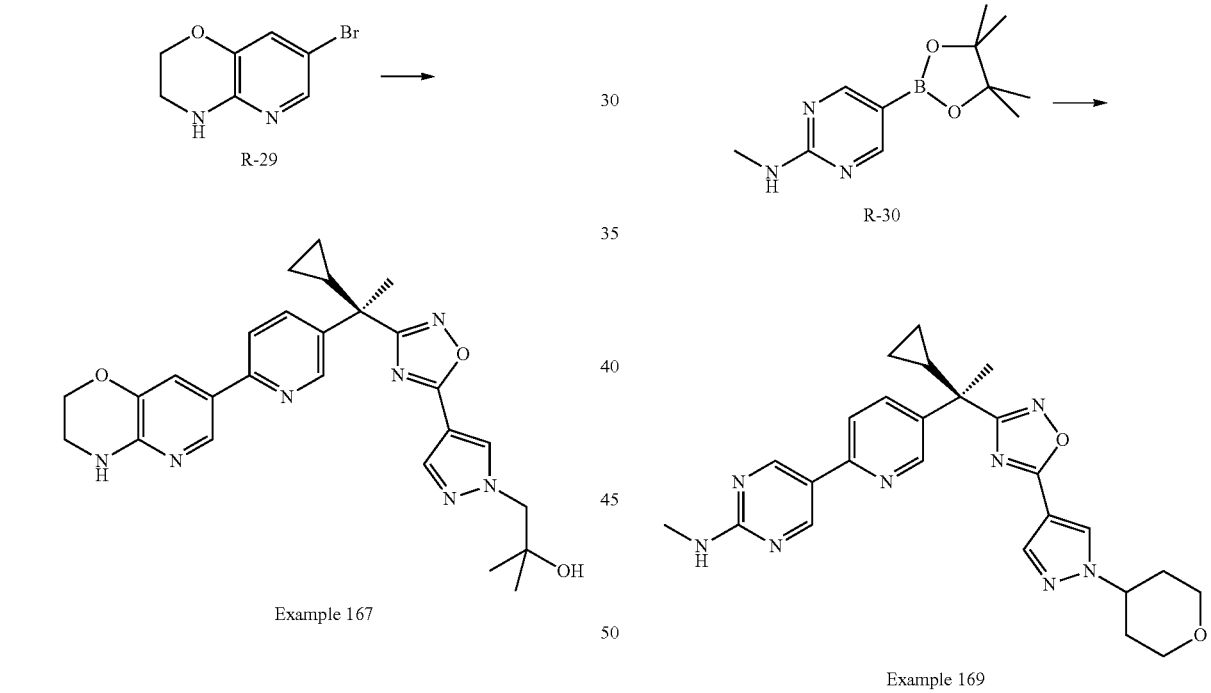

In a pressure tube is added I-36.4 (100 mg, 0.26 mmol), tetrakis(triphenylphosphine)palladium(0) (18 mg, 0.016 mmol), dichlorobis(triphenylphosphine)palladium(II) (15 mg, 0.021 mmol) and hexamethyldistannane (0.064 ml, 0.31 mmol) in 1,4-dioxane (3 ml). The reaction mixture is degassed with argon. The reaction mixture is stirred at 115° C. for 16 hours. The reaction mixture is cooled down to room temperature, followed by the addition of R-29 (67 mg, 0.312 mmol) and tetrakis(triphenylphosphine)palladium(0) (30 mg, 0.026 mmol). The reaction mixture is degassed with argone and is capped, and is stirred at 115° C. for 16 hours. The reaction mixture is concentrated in vacuo. The residue is purified by flash chromatography (SiO$_2$, 0-5% MeOH/CH$_2$Cl$_2$) to afford title compound (30 mg); m/z 488.4 [M+1]

To a pressure tube is added I-36.5 (213 mg, 0.53 mmol), R-30 (150 mg, 0.64 mmol), Tetrakis(triphenylphosphine)palladium (0) (61 mg, 0.053 mmol) and 2M aq. Na$_2$CO$_3$ (1 ml, 2 mmol) in THF (8 ml). The reaction mixture is stirred at 90° C. for 16 hours. The reaction mixture is concentrated in vacuo. The residue is diluted with EtOAc, is washed with water, brine, is dried under anhy. Na$_2$SO$_4$, and is filtered and concentrated. The residue is purified by flash chromatography (SiO$_2$, 0-5% MeOH/CH$_2$Cl$_2$) to afford the title compound (131 mg); m/z 473.4 [M+1]

Method 28: Synthesis of 1-[4-(3-{(R)-1-[6-(5-Amino-3-methyl-pyrazin-2-yl)-pyridin-3-yl]-1-cyclopropyl-ethyl}-[1,2,4]oxadiazol-5-yl)-pyrazol-1-yl]-2-methyl-propan-2-ol (Example 166)

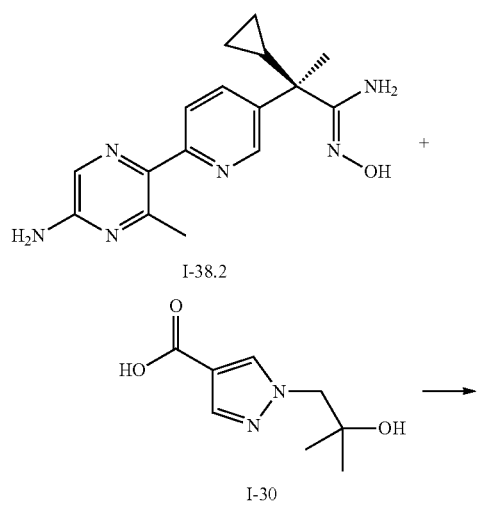

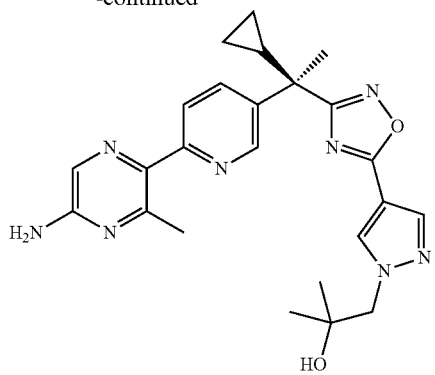

Example 166

To a scintillation vial is added I-30 (143 mg, 0.79 mmol) in 5 ml of 1,4-dioxane, followed by the addition of 1,1'-carbonyldiimidazole (120 mg, 0.74 mmol). The reaction mixture is stirred at 55° C. for 60 minutes. I-38.3 (165 mg, 0.53 mmol) is added to the reaction mixture, and is stirred at 120° C. for 6 hours. The reaction mixture is concentrated in vacuo. The residue is diluted with EtOAc, is washed with water, brine, dried under anhy. $Na_2SO_4$, and is filtered and concentrated. The residue is purified by HPLC (20-90% MeCN/water with 0.1% TFA), basified with sat. $NaHCO_3$, extracted with DCM, and concentrated in vacuo to afford the title compound (75 mg); m/z 461.1 [M+1]

TABLE 14

| Example # | Structure | Method | LC-MS Method | Retention Time | m/z [M + H] |
|---|---|---|---|---|---|
| 1 | 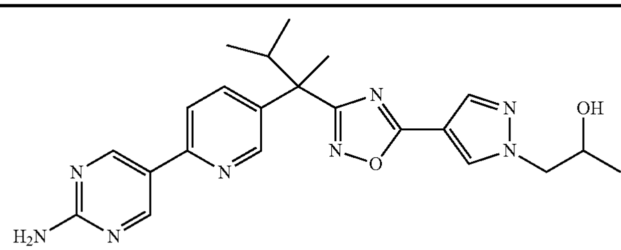 | 1 | A | 3.46 | 435.3 |
| 2 | 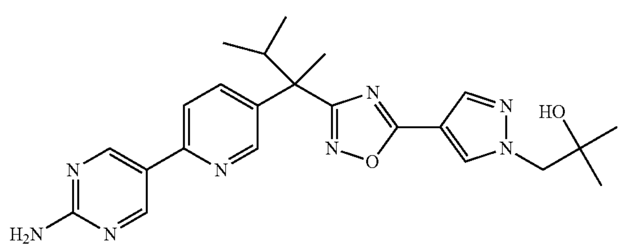 [SMILES: CC(C)C(C)(c1ccc(-c2cnc(N)nc2)nc1)c1noc(-c2cnn(CC(C)(C)O)c2)n1] | 4 | A | 3.59 | 449.3 |
| 3 | 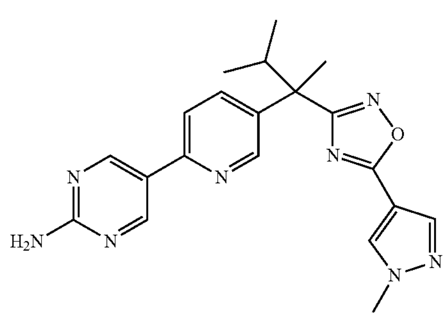 [SMILES: CC(C)C(C)(c1ccc(-c2cnc(N)nc2)nc1)c1noc(-c2cnn(C)c2)n1] | 1 | E | 4.97 | 391.6 |

TABLE 14-continued

| Example # | Structure | Method | LC-MS Method | Retention Time | m/z [M + H] |
|---|---|---|---|---|---|
| 4 | 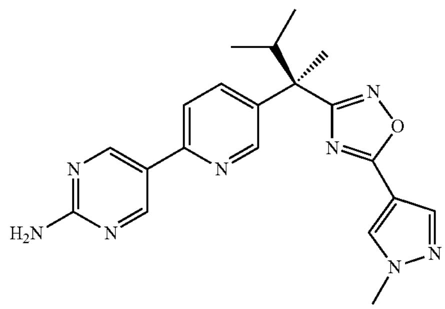 [SMILES: CC(C)[C@](C)(c1ccc(-c2cnc(N)nc2)nc1)c1noc(-c2cnn(C)c2)n1] | 2 | E | 4.98 | 391.3 |
| 5 | 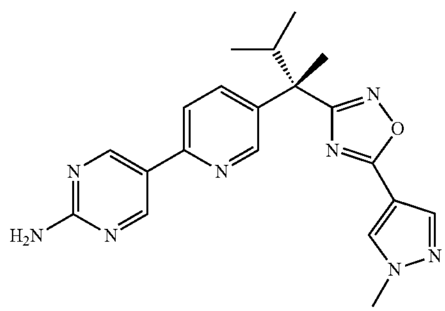 [SMILES: CC(C)[C@@](C)(c1ccc(-c2cnc(N)nc2)nc1)c1noc(-c2cnn(C)c2)n1] | 1 | E | 4.98 | 391.3 |
| 6 | 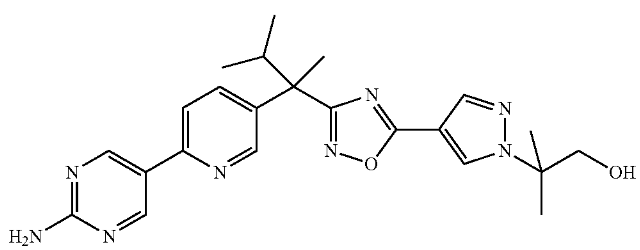 [SMILES: CC(C)C(C)(c1ccc(-c2cnc(N)nc2)nc1)c1noc(-c2cnn(C(C)(C)CO)c2)n1] | 1 | A | 3.76 | 449.3 |
| 7 | 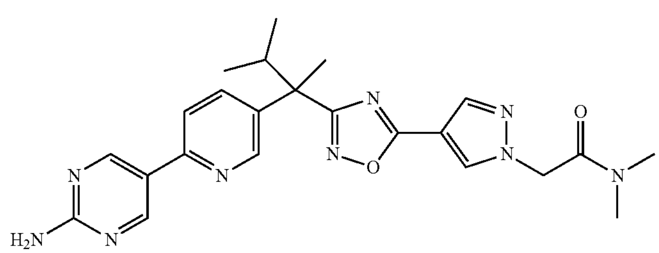 [SMILES: CC(C)C(C)(c1ccc(-c2cnc(N)nc2)nc1)c1noc(-c2cnn(CC(=O)N(C)C)c2)n1] | 1 | A | 3.36 | 462.2 |
| 8 | 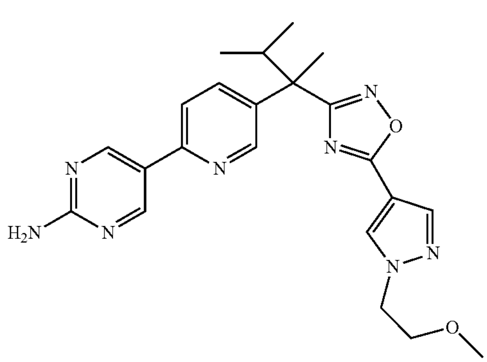 [SMILES: COCCn1cc(-c2nc(C(C)(c3ccc(-c4cnc(N)nc4)nc3)C(C)C)no2)cn1] | 1 | A | 3.78 | 435.3 |

TABLE 14-continued
| Example # | Structure | LC-MS Method | Method | Retention Time | m/z [M + H] |
|---|---|---|---|---|---|
| 9 | 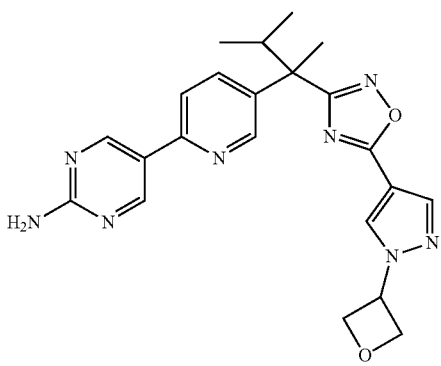 [SMILES: CC(C)C(C)(c1ccc(-c2cnc(N)nc2)nc1)c1noc(-c2cnn(C3COC3)c2)n1] | 1 | B | 3.6 | 433.3 |
| 10 | 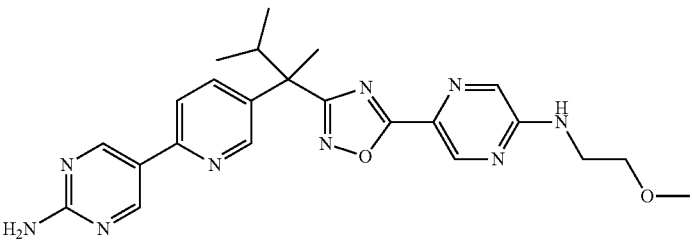 [SMILES: COCCNc1cnc(-c2nc(C(C)(c3ccc(-c4cnc(N)nc4)nc3)C(C)C)no2)cn1] | 1 | A | 3.61 | 462.3 |
| 11 | 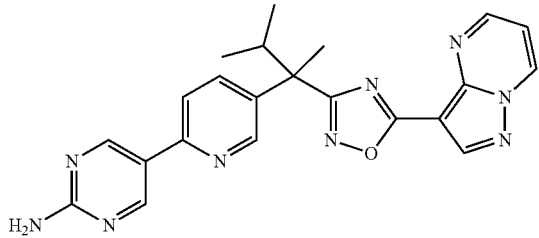 [SMILES: CC(C)C(C)(c1ccc(-c2cnc(N)nc2)nc1)c1noc(-c2cnn3cccnc23)n1] | 1 | A | 3.48 | 428.26 |
| 12 | 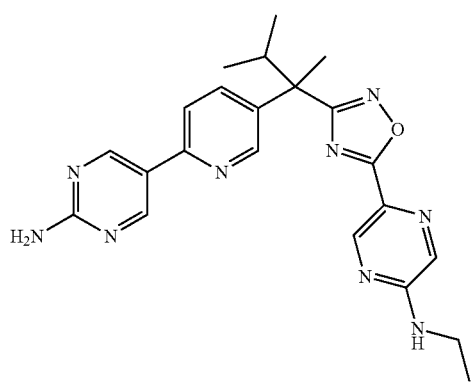 [SMILES: CCNc1cnc(-c2nc(C(C)(c3ccc(-c4cnc(N)nc4)nc3)C(C)C)no2)cn1] | 5 | A | 3.75 | 432.2 |

TABLE 14-continued

| Example # | Structure | LC-MS Method | Method | Retention Time | m/z [M + H] |
|---|---|---|---|---|---|
| 13 | 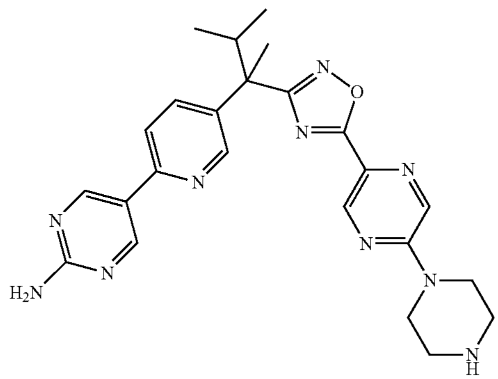 [SMILES: CC(C)C(C)(c1ccc(-c2cnc(N)nc2)nc1)c1noc(-c2cnc(N3CCNCC3)cn2)n1] | 6 | B | 1.47 | 473.24 |
| 14 | 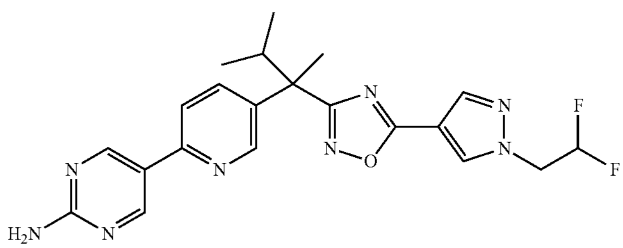 [SMILES: CC(C)C(C)(c1ccc(-c2cnc(N)nc2)nc1)c1noc(-c2cnn(CC(F)F)c2)n1] | 4 | A | 3.78 | 441.2 |
| 15 | 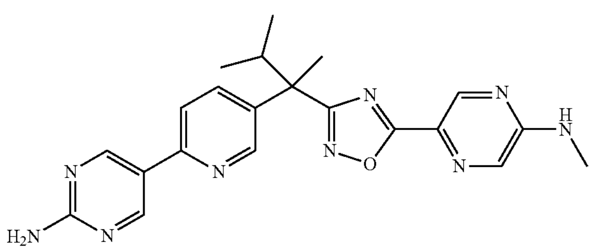 [SMILES: CNc1cnc(-c2nc(C(C)(c3ccc(-c4cnc(N)nc4)nc3)C(C)C)no2)cn1] | 6 | A | 3.55 | 418.2 |
| 16 | 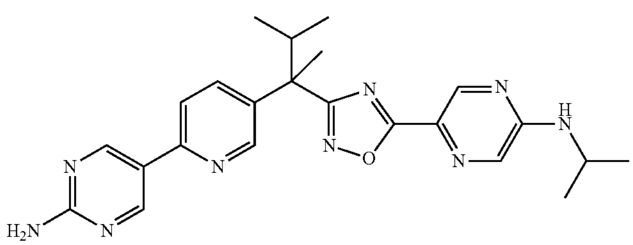 [SMILES: CC(C)Nc1cnc(-c2nc(C(C)(c3ccc(-c4cnc(N)nc4)nc3)C(C)C)no2)cn1] | 6 | A | 4.01 | 446.2 |
| 17 | 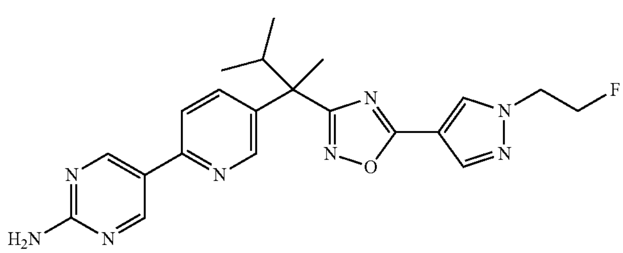 [SMILES: CC(C)C(C)(c1ccc(-c2cnc(N)nc2)nc1)c1noc(-c2cnn(CCF)c2)n1] | 4 | A | 3.68 | 423.2 |

TABLE 14-continued

| Example # | Structure | LC-MS Method | Method | Retention Time | m/z [M + H] |
|---|---|---|---|---|---|
| 18 | 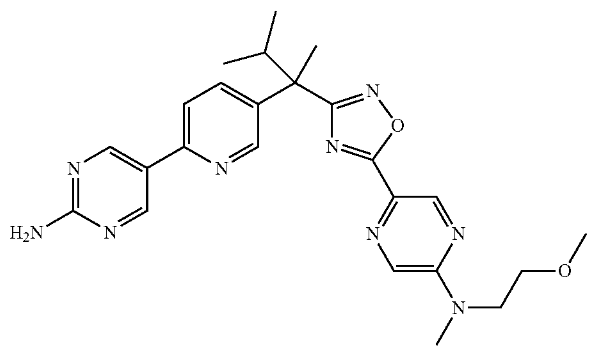 [SMILES: COCCN(C)c1cnc(-c2nc(C(C)(c3ccc(-c4cnc(N)nc4)nc3)C(C)C)no2)cn1] | 6 | A | 3.95 | 476.3 |
| 19 | 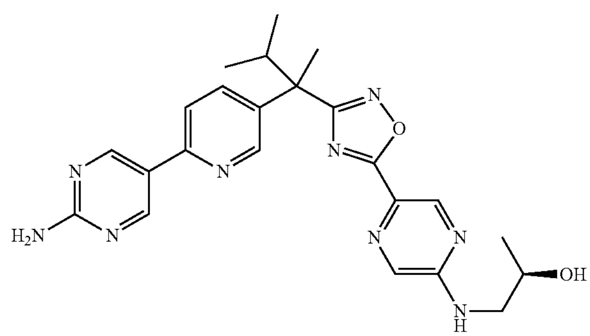 [SMILES: CC(C)C(C)(c1ccc(-c2cnc(N)nc2)nc1)c1noc(-c2cnc(NC[C@@H](C)O)cn2)n1] | 6 | B | 3.39 | 462.2 |
| 20 | 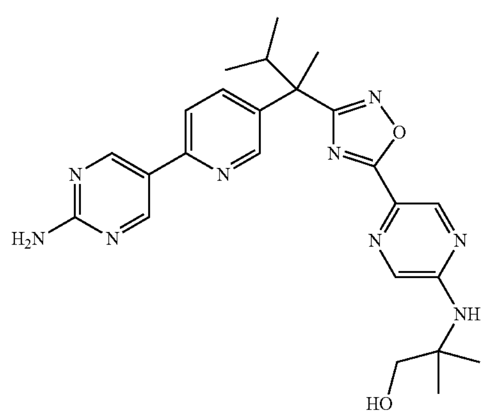 [SMILES: CC(C)C(C)(c1ccc(-c2cnc(N)nc2)nc1)c1noc(-c2cnc(NC(C)(C)CO)cn2)n1] | 6 | A | 3.72 | 476.2 |
| 21 | 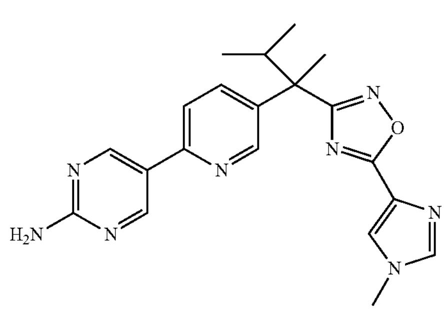 [SMILES: CC(C)C(C)(c1ccc(-c2cnc(N)nc2)nc1)c1noc(-c2cn(C)cn2)n1] | 2 | B | 1.63 | 391.4 |

TABLE 14-continued

| Example # | Structure | LC-MS Method | Method | Retention Time | m/z [M + H] |
|---|---|---|---|---|---|
| 22 | 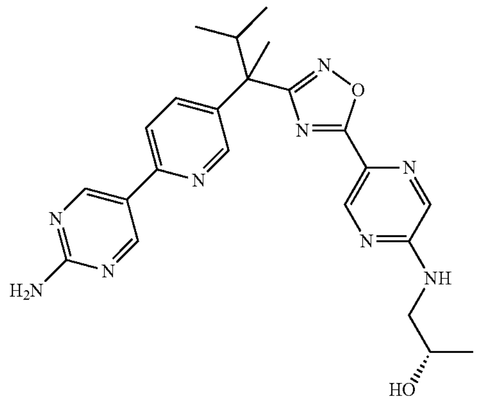 [SMILES: CC(C)C(C)(c1ccc(-c2cnc(N)nc2)nc1)c1noc(-c2cnc(NC[C@H](C)O)cn2)n1] | 6 | B | 1.7 | 462.2 |
| 23 | 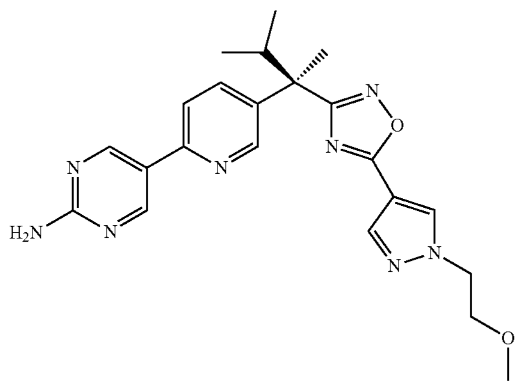 [SMILES: COCCn1cc(-c2nc([C@@](C)(c3ccc(-c4cnc(N)nc4)nc3)C(C)C)no2)cn1] | 1 | E | 5.16 | 435.3 |
| 24 | 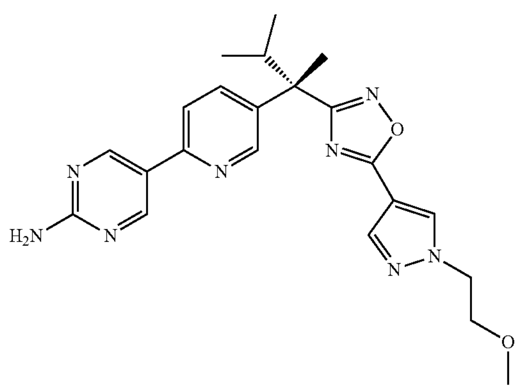 [SMILES: COCCn1cc(-c2nc([C@](C)(c3ccc(-c4cnc(N)nc4)nc3)C(C)C)no2)cn1] | 1 | E | 5.16 | 435.3 |
| 25 | 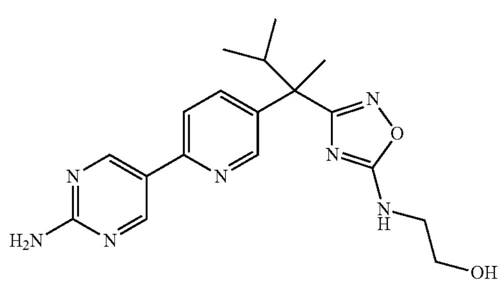 [SMILES: CC(C)C(C)(c1ccc(-c2cnc(N)nc2)nc1)c1noc(NCCO)n1] | 7 | G | 1.13 | 370.4 |

TABLE 14-continued
| Example # | Structure | LC-MS Method | Method | Retention Time | m/z [M + H] |
|---|---|---|---|---|---|
| 26 | 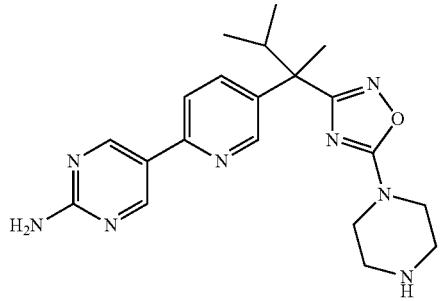 [SMILES: CC(C)C(C)(c1ccc(-c2cnc(N)nc2)nc1)c1noc(N2CCNCC2)n1] | 7 | G | 1.02 | 395.4 |
| 27 | 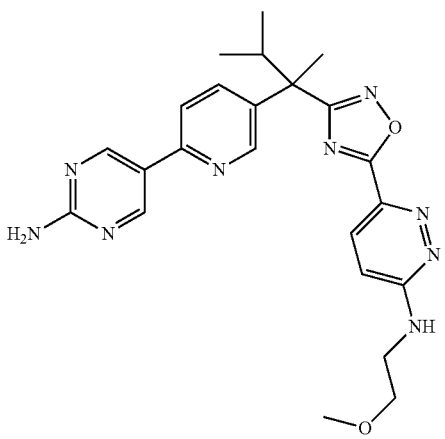 [SMILES: COCCNc1ccc(-c2nc(C(C)(c3ccc(-c4cnc(N)nc4)nc3)C(C)C)no2)nn1] | 6 | C | 2 | 462.4 |
| 28 | 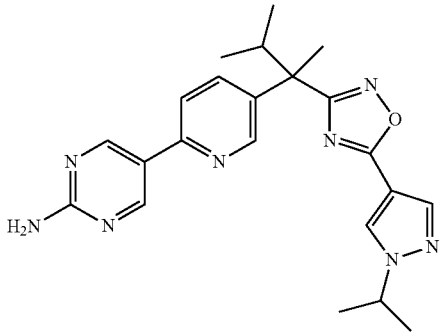 [SMILES: CC(C)n1cc(-c2nc(C(C)(c3ccc(-c4cnc(N)nc4)nc3)C(C)C)no2)cn1] | 4 | C | 2.5 | 419.4 |
| 29 | 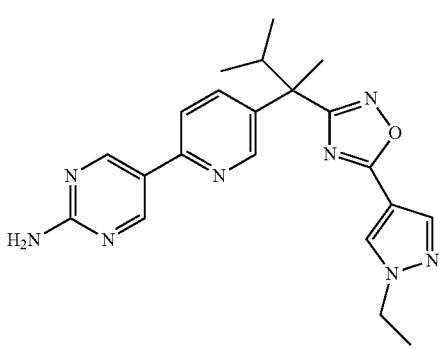 [SMILES: CCn1cc(-c2nc(C(C)(c3ccc(-c4cnc(N)nc4)nc3)C(C)C)no2)cn1] | 4 | D | 1.25 | 405.4 |

TABLE 14-continued

| Example # | Structure | Method | LC-MS Method | Retention Time | m/z [M + H] |
|---|---|---|---|---|---|
| 30 | 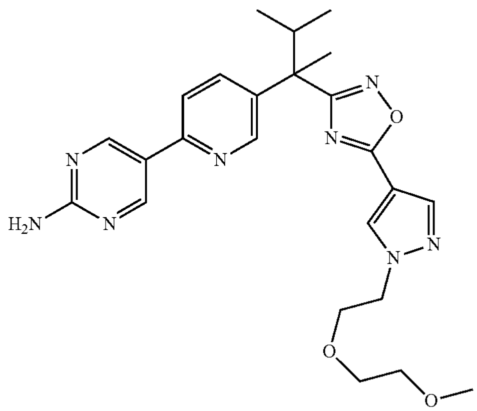 [SMILES: COCCOCCn1cc(-c2nc(C(C)(c3ccc(-c4cnc(N)nc4)nc3)C(C)C)no2)cn1] | 4 | D | 1.41 | 479.6 |
| 31 | 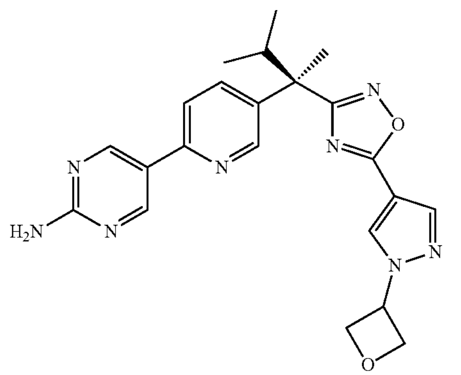 [SMILES: CC(C)[C@](C)(c1ccc(-c2cnc(N)nc2)nc1)c1noc(-c2cnn(C3COC3)c2)n1] | 4 | C | 2.05 | 433.4 |
| 32 | 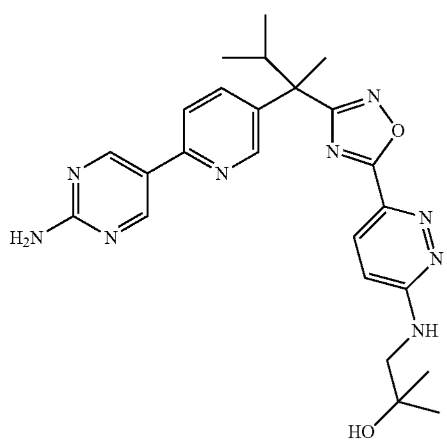 [SMILES: CC(C)C(C)(c1ccc(-c2cnc(N)nc2)nc1)c1noc(-c2ccc(NCC(C)(C)O)nn2)n1] | 6 | C | 1.95 | 476.4 |
| 33 | 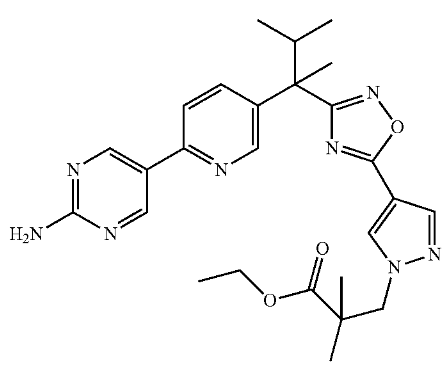 [SMILES: CCOC(=O)C(C)(C)Cn1cc(-c2nc(C(C)(c3ccc(-c4cnc(N)nc4)nc3)C(C)C)no2)cn1] | 4 | D | 1.42 | 505.4 |

TABLE 14-continued

| Example # | Structure | LC-MS Method | Method | Retention Time | m/z [M + H] |
|---|---|---|---|---|---|
| 34 | 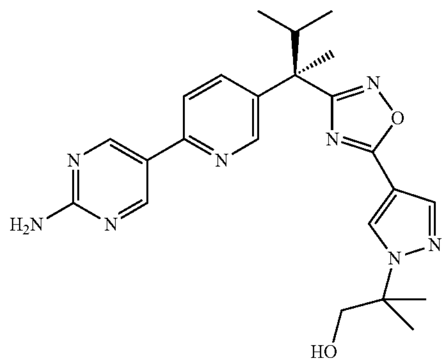 [SMILES: CC(C)[C@](C)(c1ccc(-c2cnc(N)nc2)nc1)c1noc(-c2cnn(C(C)(C)CO)c2)n1] | 1 | D | 1.2 | 449.4 |
| 35 | 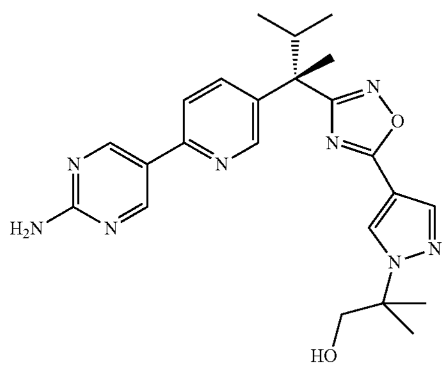 [SMILES: CC(C)[C@@](C)(c1ccc(-c2cnc(N)nc2)nc1)c1noc(-c2cnn(C(C)(C)CO)c2)n1] | 1 | D | 1.21 | 449.4 |
| 36 | 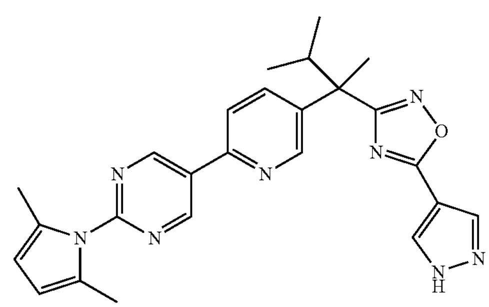 [SMILES: Cc1ccc(C)n1-c1ncc(-c2ccc(C(C)(c3noc(-c4cn[nH]c4)n3)C(C)C)cn2)cn1] | 2 | H | 1.94 | 455.5 |
| 37 | 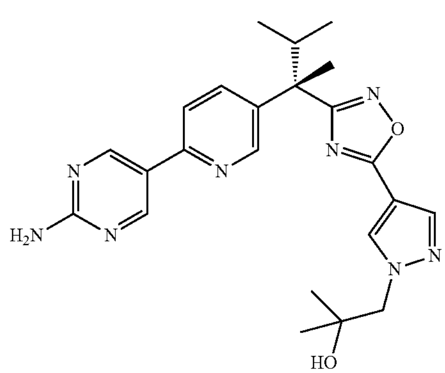 [SMILES: CC(C)[C@@](C)(c1ccc(-c2cnc(N)nc2)nc1)c1noc(-c2cnn(CC(C)(C)O)c2)n1] | 4 | D | 1.19 | 449.37 |

TABLE 14-continued

| Example # | Structure | Method | LC-MS Method | Retention Time | m/z [M + H] |
|---|---|---|---|---|---|
| 38 | 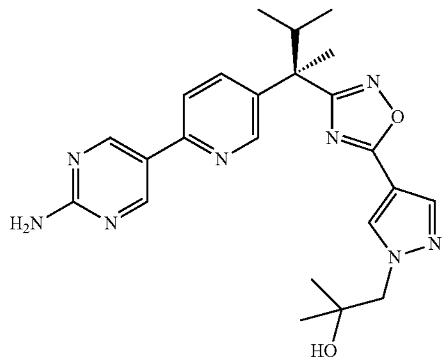 [SMILES: CC(C)[C@](C)(c1ccc(-c2cnc(N)nc2)nc1)c1noc(-c2cnn(CC(C)(C)O)c2)n1] | 4 | D | 1.18 | 449.37 |
| 39 | 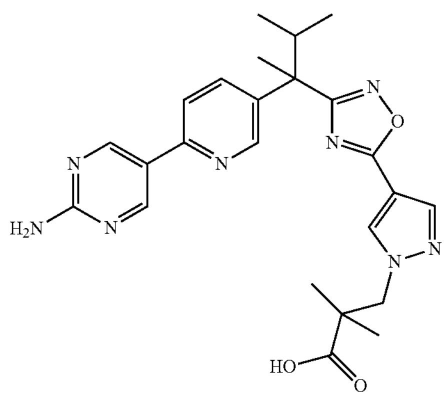 [SMILES: CC(C)C(C)(c1ccc(-c2cnc(N)nc2)nc1)c1noc(-c2cnn(CC(C)(C)C(=O)O)c2)n1] | 8 | D | 1.2 | 477.4 |
| 40 | 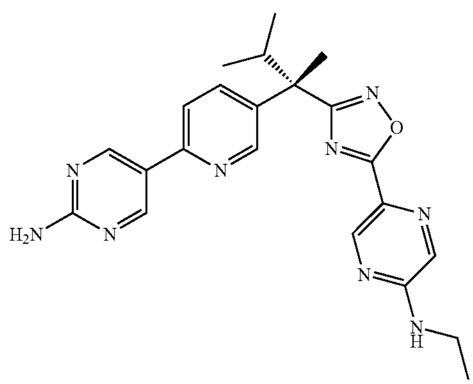 [SMILES: CCNc1cnc(-c2nc([C@](C)(c3ccc(-c4cnc(N)nc4)nc3)C(C)C)no2)cn1] | 5 | D | 1.25 | 432.4 |
| 41 | 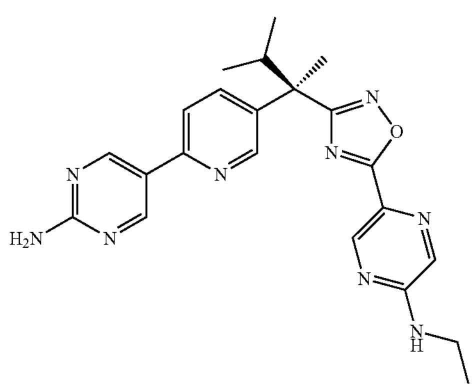 [SMILES: CCNc1cnc(-c2nc([C@@](C)(c3ccc(-c4cnc(N)nc4)nc3)C(C)C)no2)cn1] | 5 | D | 1.24 | 432.4 |

TABLE 14-continued

| Example # | Structure | LC-MS Method | Method | Retention Time | m/z [M + H] |
|---|---|---|---|---|---|
| 42 | 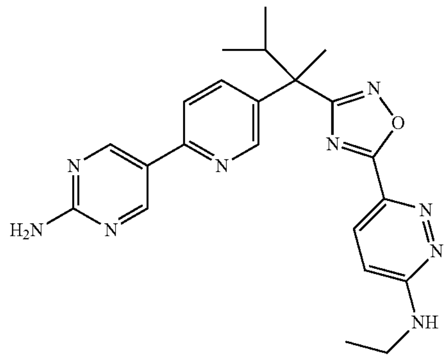 [SMILES: CCNc1ccc(-c2nc(C(C)(c3ccc(-c4cnc(N)nc4)nc3)C(C)C)no2)nn1] | 6 | C | 2.04 | 432.4 |
| 43 | 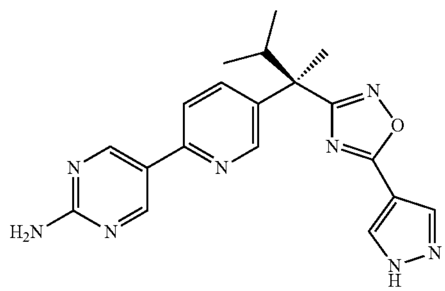 [SMILES: CC(C)[C@](C)(c1ccc(-c2cnc(N)nc2)nc1)c1noc(-c2cn[nH]c2)n1] | 3 | C | 1.86 | 377.4 |
| 44 | 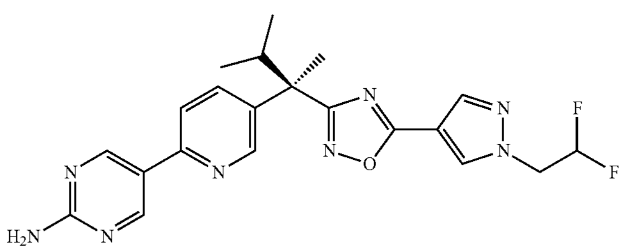 [SMILES: CC(C)[C@](C)(c1ccc(-c2cnc(N)nc2)nc1)c1noc(-c2cnn(CC(F)F)c2)n1] | 4 | D | 1.24 | 441.4 |
| 45 | 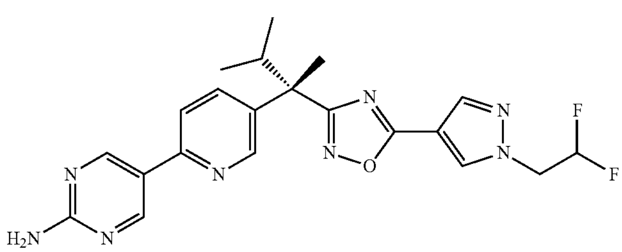 [SMILES: CC(C)[C@@](C)(c1ccc(-c2cnc(N)nc2)nc1)c1noc(-c2cnn(CC(F)F)c2)n1] | 4 | D | 1.24 | 441.4 |

TABLE 14-continued
| Example # | Structure | LC-MS Method | Retention Method | Retention Time | m/z [M + H] |
|---|---|---|---|---|---|
| 46 | 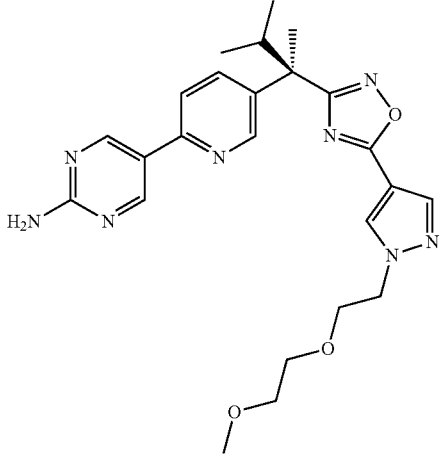 [SMILES: COCCOCCn1cc(-c2nc([C@@](C)(c3ccc(-c4cnc(N)nc4)nc3)C(C)C)no2)cn1] | 4 | D | 1.23 | 479.4 |
| 47 | 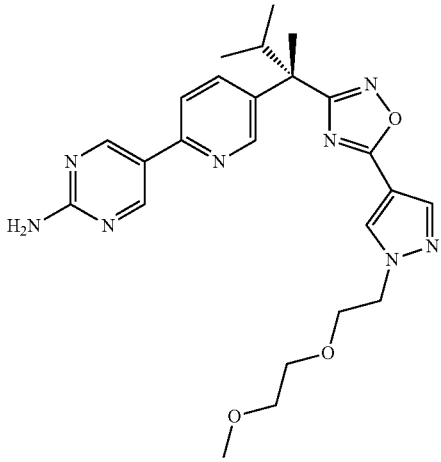 [SMILES: COCCOCCn1cc(-c2nc([C@](C)(c3ccc(-c4cnc(N)nc4)nc3)C(C)C)no2)cn1] | 4 | D | 1.22 | 479.4 |
| 48 | 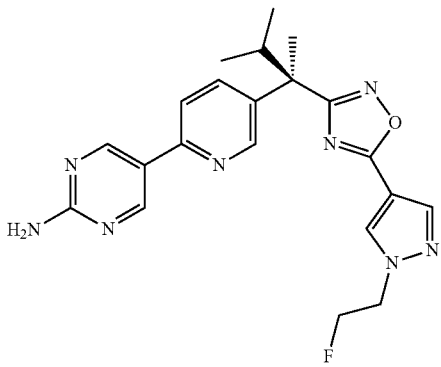 [SMILES: CC(C)[C@](C)(c1ccc(-c2cnc(N)nc2)nc1)c1noc(-c2cnn(CCF)c2)n1] | 4 | D | 1.21 | 423.4 |

TABLE 14-continued
| Example # | Structure | LC-MS Method | Method | Retention Time | m/z [M + H] |
|---|---|---|---|---|---|
| 49 | 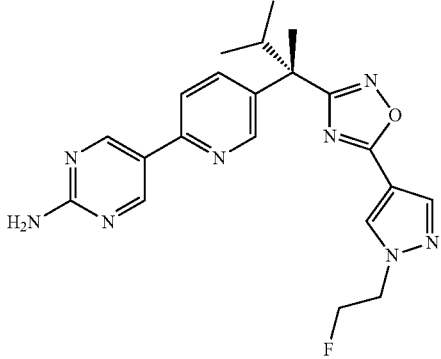 [SMILES: CC(C)[C@@](C)(c1ccc(-c2cnc(N)nc2)nc1)c1noc(-c2cnn(CCF)c2)n1] | 4 | D | 1.21 | 423.4 |
| 50 | 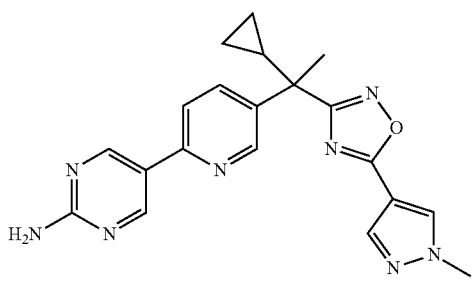 [SMILES: Cn1cc(-c2nc(C(C)(c3ccc(-c4cnc(N)nc4)nc3)C3CC3)no2)cn1] | 9 | H | 1.33 | 389.3 |
| 51 | 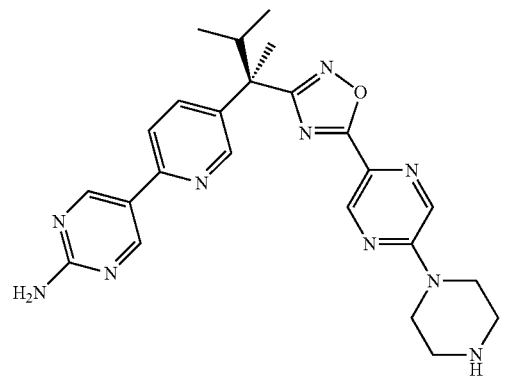 [SMILES: CC(C)[C@](C)(c1ccc(-c2cnc(N)nc2)nc1)c1noc(-c2cnc(N3CCNCC3)cn2)n1] | 6 | D | 0.92 | 473.4 |
| 52 | 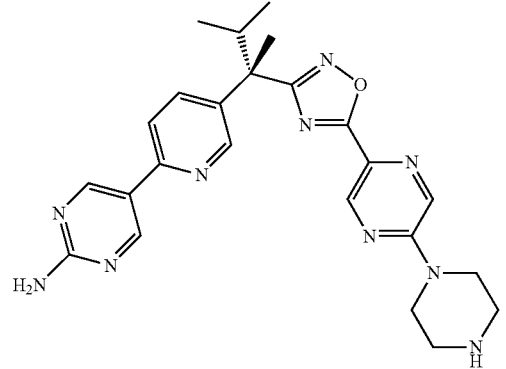 [SMILES: CC(C)[C@@](C)(c1ccc(-c2cnc(N)nc2)nc1)c1noc(-c2cnc(N3CCNCC3)cn2)n1] | 6 | D | 0.92 | 473.4 |

TABLE 14-continued

| Example # | Structure | Method | LC-MS Method | Retention Time | m/z [M + H] |
|---|---|---|---|---|---|
| 53 | 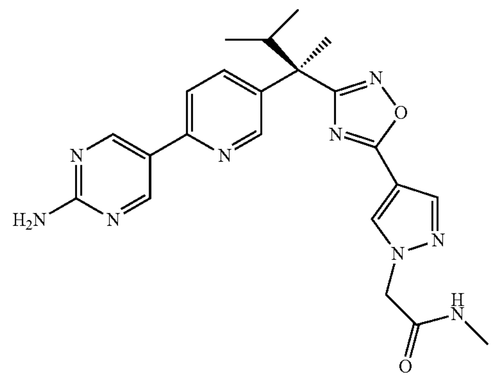 [SMILES: CNC(=O)Cn1cc(-c2nc([C@@](C)(c3ccc(-c4cnc(N)nc4)nc3)C(C)C)no2)cn1] | 1 | F | 1.26 | 448.4 |
| 54 | 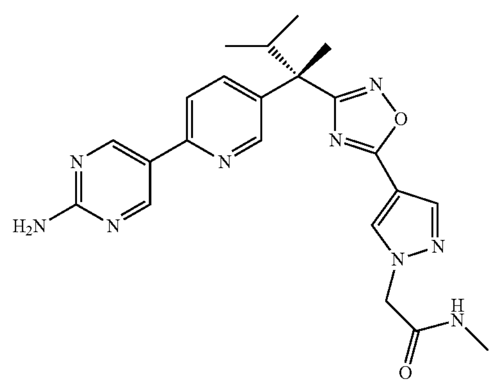 [SMILES: CNC(=O)Cn1cc(-c2nc([C@](C)(c3ccc(-c4cnc(N)nc4)nc3)C(C)C)no2)cn1] | 1 | F | 1.26 | 448.4 |
| 55 | 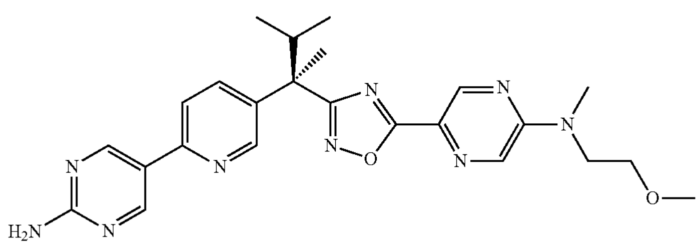 [SMILES: COCCN(C)c1cnc(-c2nc([C@@](C)(c3ccc(-c4cnc(N)nc4)nc3)C(C)C)no2)cn1] | 6 | F | 2.17 | 476.2 |
| 56 | 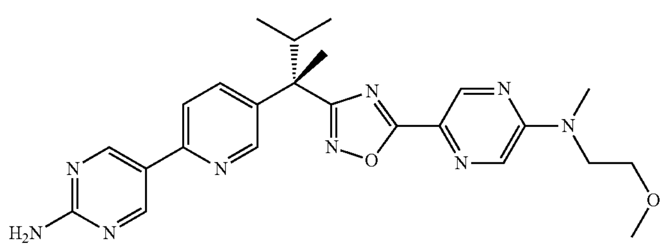 [SMILES: COCCN(C)c1cnc(-c2nc([C@](C)(c3ccc(-c4cnc(N)nc4)nc3)C(C)C)no2)cn1] | 6 | F | 2.23 | 476.2 |
| 57 | 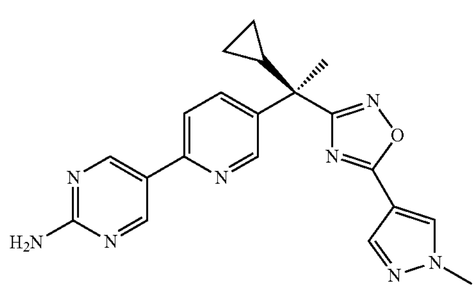 [SMILES: Cn1cc(-c2nc([C@@](C)(c3ccc(-c4cnc(N)nc4)nc3)C3CC3)no2)cn1] | 9 | H | 1.33 | 389.3 |

TABLE 14-continued

| Example # | Structure | LC-MS Method | Retention Method | Time | m/z [M + H] |
|---|---|---|---|---|---|
| 58 | 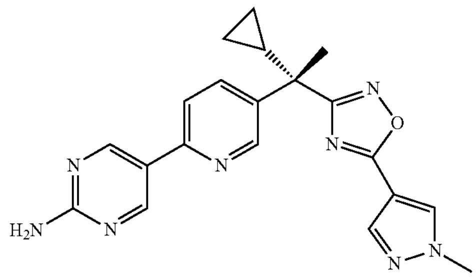 [SMILES: Cn1cc(-c2nc([C@](C)(c3ccc(-c4cnc(N)nc4)nc3)C3CC3)no2)cn1] | 9 | H | 1.33 | 389.3 |
| 59 | 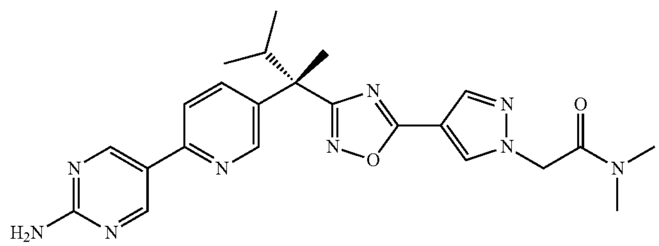 [SMILES: CC(C)[C@@](C)(c1ccc(-c2cnc(N)nc2)nc1)c1noc(-c2cnn(CC(=O)N(C)C)c2)n1] | 1 | F | 1.39 | 461.7 |
| 60 | 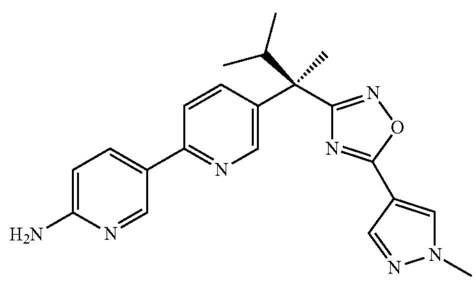 [SMILES: CC(C)[C@](C)(c1ccc(-c2ccc(N)nc2)nc1)c1noc(-c2cnn(C)c2)n1] | 2 | H | 1.49 | 390.4 |
| 61 | 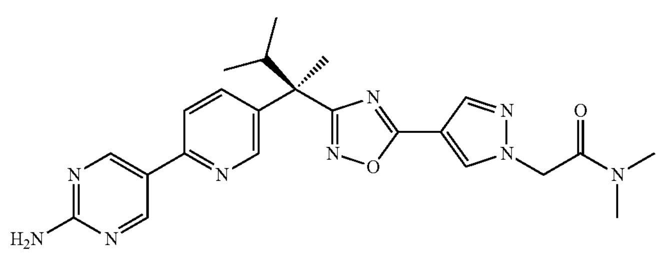 [SMILES: CC(C)[C@](C)(c1ccc(-c2cnc(N)nc2)nc1)c1noc(-c2cnn(CC(=O)N(C)C)c2)n1] | 1 | F | 1.38 | 461.7 |
| 62 | 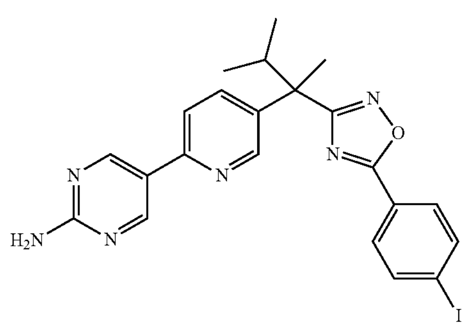 [SMILES: CC(C)C(C)(c1ccc(-c2cnc(N)nc2)nc1)c1noc(-c2ccc(I)cc2)n1] | 10 | D | 1.61 | 513.2 |

TABLE 14-continued
| Example # | Structure | LC-MS Method | Method | Retention Time | m/z [M + H] |
|---|---|---|---|---|---|
| 63 | 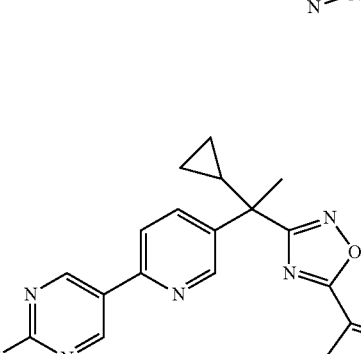 | 11 | G | 1.28 | 431.4 |
| 64 | 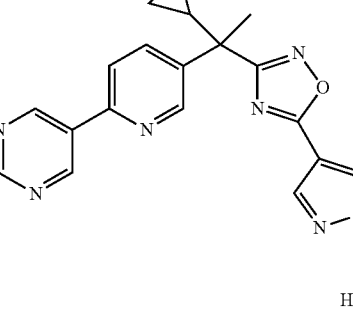 | 9 | H | 1.24 | 375.3 |
| 65 | 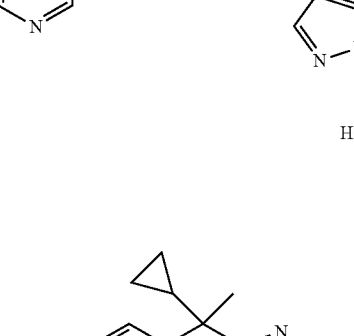 | 12 | G | 1.27 | 431.4 |
| 66 | 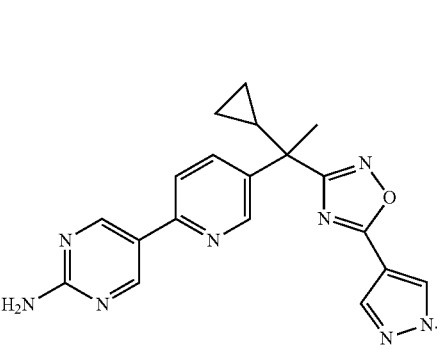 | 16 | E | 4.65 | 447.4 |

TABLE 14-continued

| Example # | Structure | Method | LC-MS Method | Retention Time | m/z [M + H] |
|---|---|---|---|---|---|
| 67 | 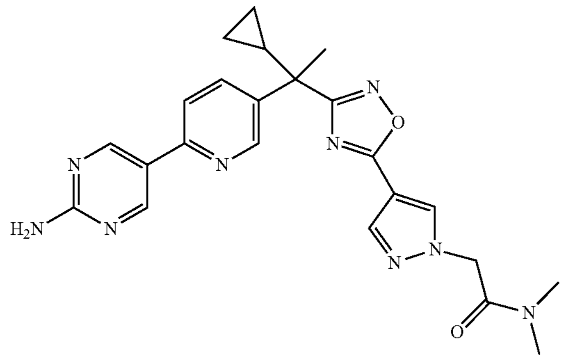 [SMILES: CN(C)C(=O)Cn1cc(-c2nc(C(C)(c3ccc(-c4cnc(N)nc4)nc3)C3CC3)no2)cn1] | 16 | H | 1.19 | 460.4 |
| 68 | 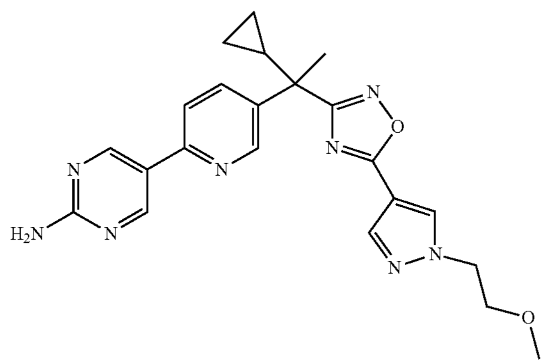 [SMILES: COCCn1cc(-c2nc(C(C)(c3ccc(-c4cnc(N)nc4)nc3)C3CC3)no2)cn1] | 16 | H | 1.32 | 433.3 |
| 69 | 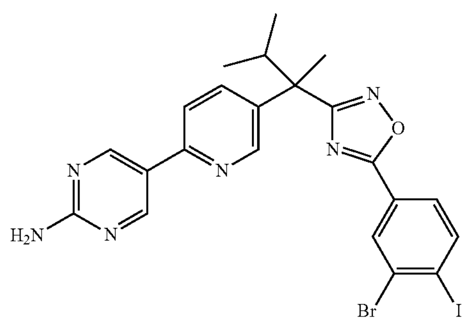 [SMILES: CC(C)C(C)(c1ccc(-c2cnc(N)nc2)nc1)c1noc(-c2ccc(I)c(Br)c2)n1] | 13 | D | 1.7 | 591593 M/M + 2 |
| 70 | 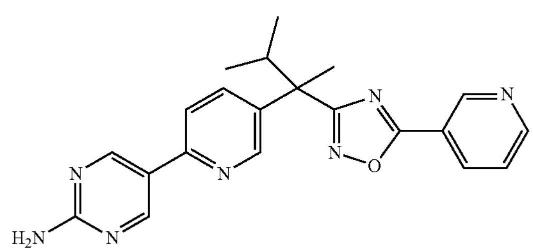 [SMILES: CC(C)C(C)(c1ccc(-c2cnc(N)nc2)nc1)c1noc(-c2cccnc2)n1] | 1 | A | 3.77 | 388.1 |
| 71 | 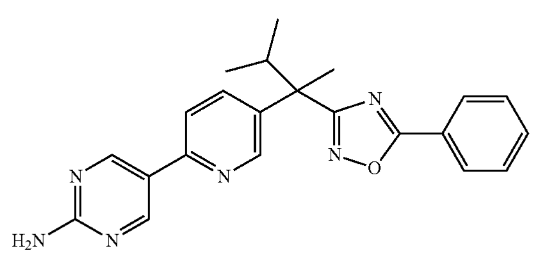 [SMILES: CC(C)C(C)(c1ccc(-c2cnc(N)nc2)nc1)c1noc(-c2ccccc2)n1] | 1 | A | 4.52 | 387.1 |

TABLE 14-continued

| Example # | Structure | Method | LC-MS Method | Retention Time | m/z [M + H] |
|---|---|---|---|---|---|
| 72 | 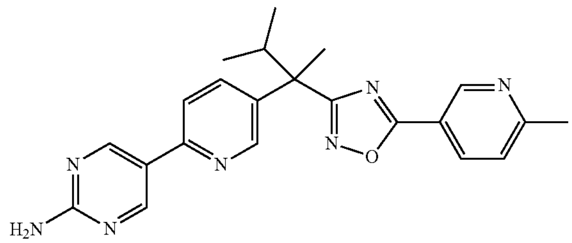 [SMILES: Cc1ccc(-c2nc(C(C)(c3ccc(-c4cnc(N)nc4)nc3)C(C)C)no2)cn1] | 1 | A | 3.9 | 402.1 |
| 73 | 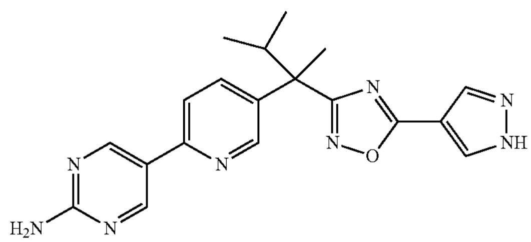 [SMILES: CC(C)C(C)(c1ccc(-c2cnc(N)nc2)nc1)c1noc(-c2cn[nH]c2)n1] | 1 | B | 1.61 | 377 |
| 74 | 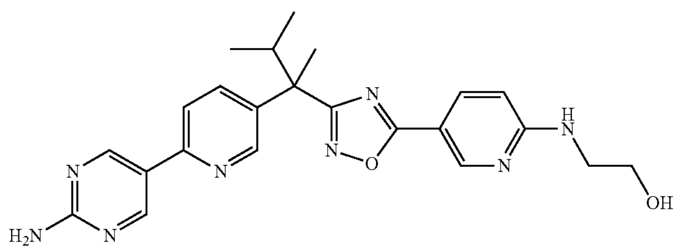 [SMILES: CC(C)C(C)(c1ccc(-c2cnc(N)nc2)nc1)c1noc(-c2ccc(NCCO)nc2)n1] | 14 | A | 3.38 | 447.3 |
| 75 | 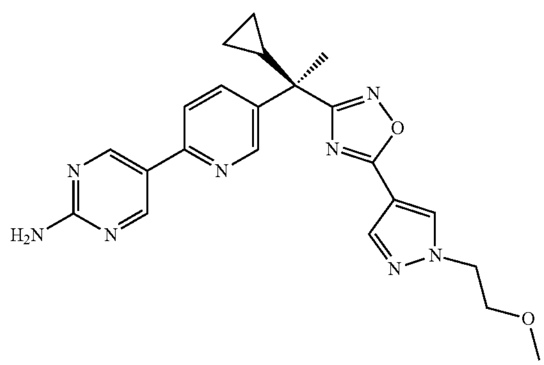 [SMILES: COCCn1cc(-c2nc([C@@](C)(c3ccc(-c4cnc(N)nc4)nc3)C3CC3)no2)cn1] | 4 | E | 4.87 | 433.3 |
| 76 | 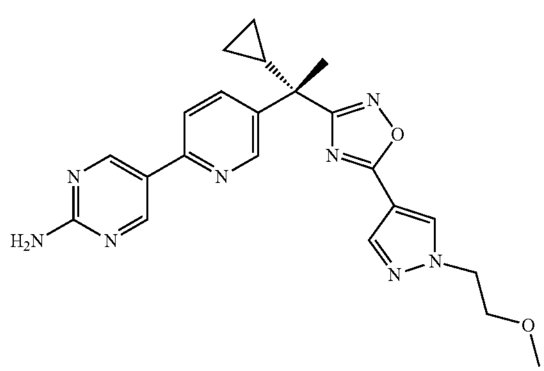 [SMILES: COCCn1cc(-c2nc([C@](C)(c3ccc(-c4cnc(N)nc4)nc3)C3CC3)no2)cn1] | 4 | E | 4.86 | 433.3 |

TABLE 14-continued

| Example # | Structure | LC-MS Method | Method | Retention Time | m/z [M + H] |
|---|---|---|---|---|---|
| 77 | 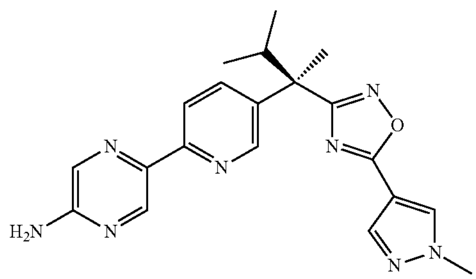 [SMILES: CC(C)[C@](C)(c1ccc(-c2cnc(N)cn2)nc1)c1noc(-c2cnn(C)c2)n1] | 2 | E | 4.53 | 391.3 |
| 78 | 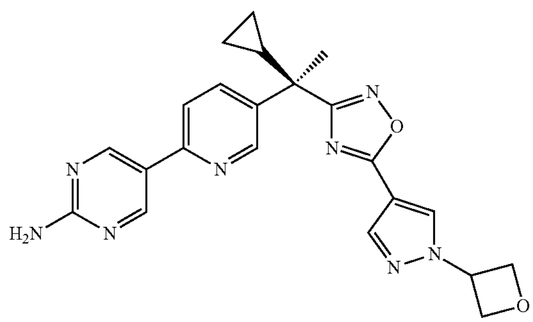 [SMILES: C[C@@](c1ccc(-c2cnc(N)nc2)nc1)(c1noc(-c2cnn(C3COC3)c2)n1)C1CC1] | 11 | G | 1.28 | 431.4 |
| 79 | 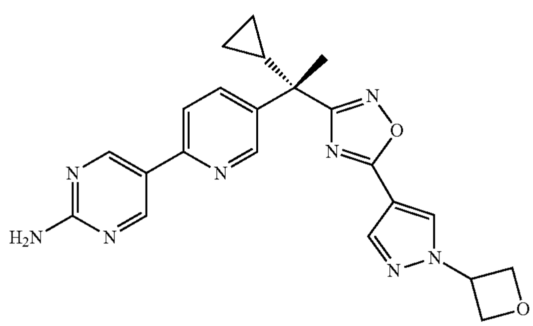 [SMILES: C[C@](c1ccc(-c2cnc(N)nc2)nc1)(c1noc(-c2cnn(C3COC3)c2)n1)C1CC1] | 11 | G | 1.28 | 431.4 |
| 80 | 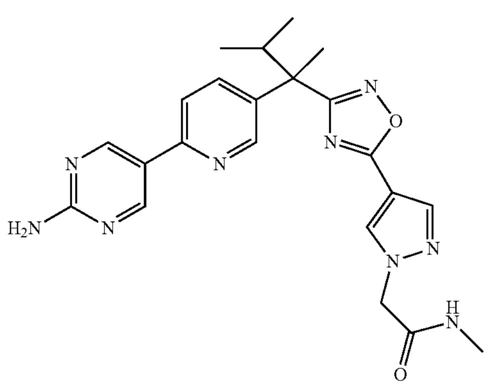 [SMILES: CNC(=O)Cn1cc(-c2nc(C(C)(c3ccc(-c4cnc(N)nc4)nc3)C(C)C)no2)cn1] | 1 | A | 3.27 | 448.3 |

TABLE 14-continued

| Example # | Structure | LC-MS Method | Retention Method | Time | m/z [M + H] |
|---|---|---|---|---|---|
| 81 | 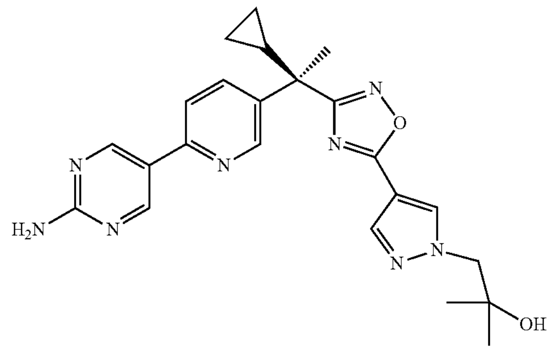 [SMILES: CC(C)(O)Cn1cc(-c2nc([C@@](C)(c3ccc(-c4cnc(N)nc4)nc3)C3CC3)no2)cn1] | 16 | F | 1.42 | 447.3 |
| 82 | 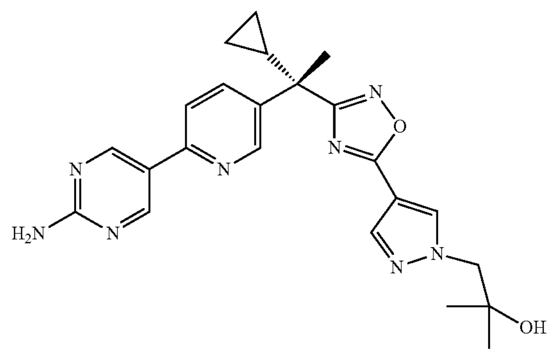 [SMILES: CC(C)(O)Cn1cc(-c2nc([C@](C)(c3ccc(-c4cnc(N)nc4)nc3)C3CC3)no2)cn1] | 16 | F | 1.42 | 447.3 |
| 83 | 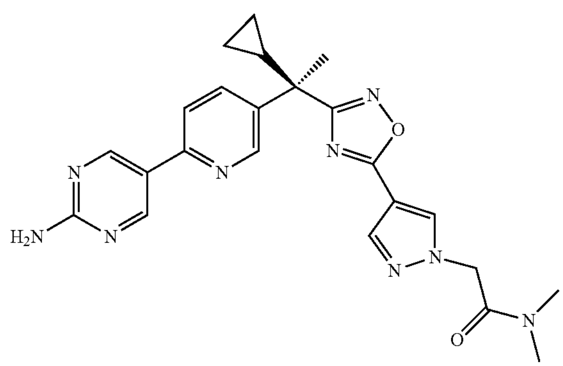 [SMILES: CN(C)C(=O)Cn1cc(-c2nc([C@@](C)(c3ccc(-c4cnc(N)nc4)nc3)C3CC3)no2)cn1] | 16 | G | 1.23 | 460.4 |
| 84 | 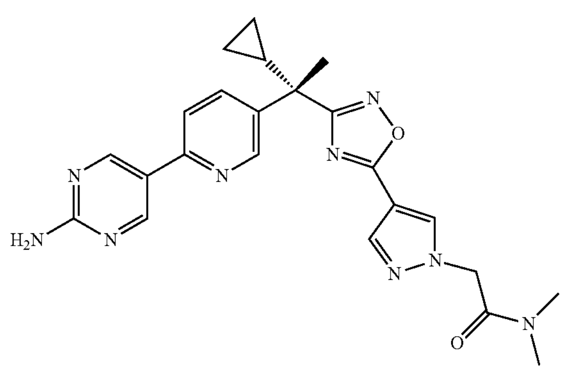 [SMILES: CN(C)C(=O)Cn1cc(-c2nc([C@](C)(c3ccc(-c4cnc(N)nc4)nc3)C3CC3)no2)cn1] | 16 | G | 1.24 | 460.4 |

TABLE 14-continued

| Example # | Structure | Method | LC-MS Method | Retention Time | m/z [M + H] |
|---|---|---|---|---|---|
| 85 | 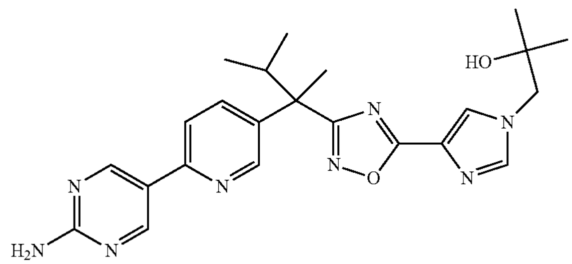 [SMILES: CC(C)C(C)(c1ccc(-c2cnc(N)nc2)nc1)c1noc(-c2cn(CC(C)(C)O)cn2)n1] | 1 | A | 3.24 | 449.2 |
| 86 | 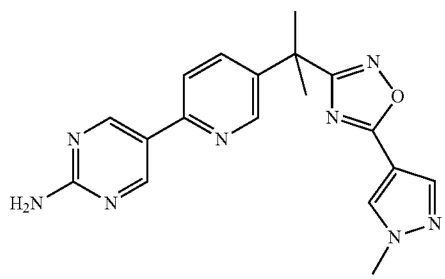 [SMILES: Cn1cc(-c2nc(C(C)(C)c3ccc(-c4cnc(N)nc4)nc3)no2)cn1] | 15 | D | 1.07 | 363.4 |
| 87 | 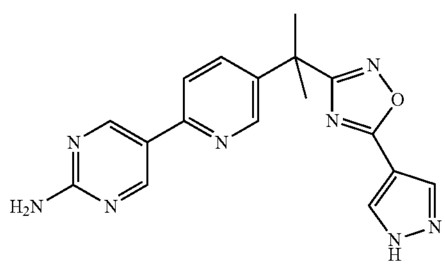 [SMILES: CC(C)(c1ccc(-c2cnc(N)nc2)nc1)c1noc(-c2cn[nH]c2)n1] | 15 | D | 0.99 | 349.4 |
| 88 | 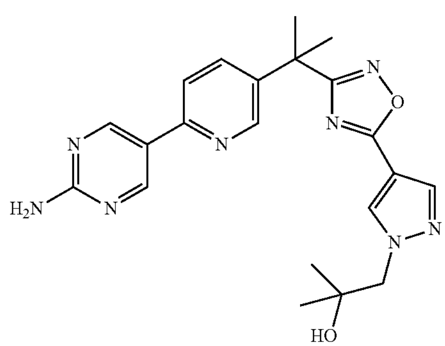 [SMILES: CC(C)(O)Cn1cc(-c2nc(C(C)(C)c3ccc(-c4cnc(N)nc4)nc3)no2)cn1] | 4 | D | 1.09 | 421.4 |
| 89 | 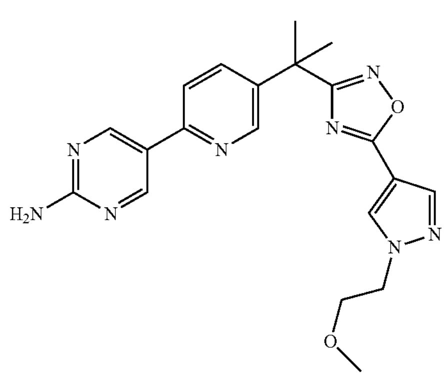 [SMILES: COCCn1cc(-c2nc(C(C)(C)c3ccc(-c4cnc(N)nc4)nc3)no2)cn1] | 4 | D | 1.11 | 407.4 |

TABLE 14-continued
| Example # | Structure | Method | LC-MS Method | Retention Time | m/z [M + H] |
|---|---|---|---|---|---|
| 90 | 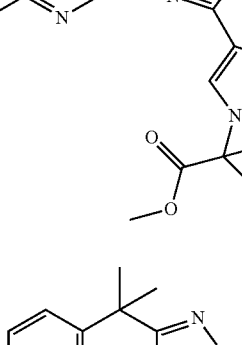 | 4 | D | 1.22 | 449.4 |
| 91 | 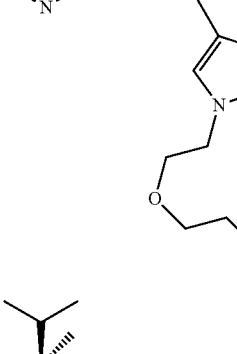 | 4 | D | 1.12 | 451.4 |
| 92 | 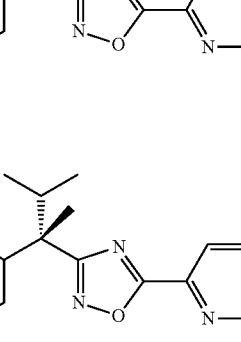 | 6 | F | 2.12 | 446 |
| 93 | 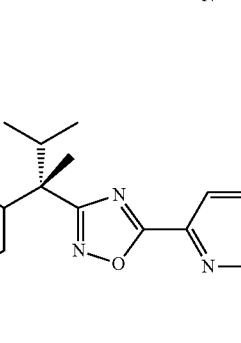 | 6 | F | 2.12 | 446 |
| 94 | 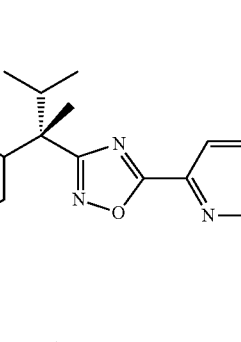 | 6 | F | 1.92 | 476 |

TABLE 14-continued

| Example # | Structure | LC-MS Method | Method | Retention Time | m/z [M + H] |
|---|---|---|---|---|---|
| 95 | 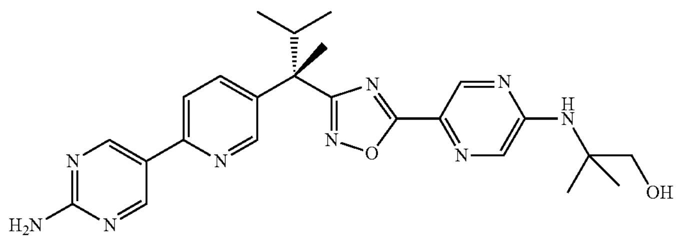 [SMILES: CC(C)[C@@](C)(c1ccc(-c2cnc(N)nc2)nc1)c1noc(-c2cnc(NC(C)(C)CO)cn2)n1] | 6 | F | 1.92 | 476 |
| 96 | 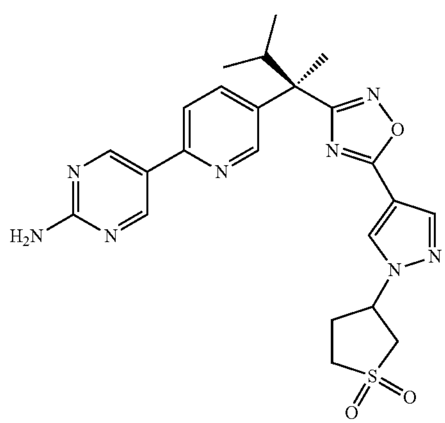 [SMILES: CC(C)[C@](C)(c1ccc(-c2cnc(N)nc2)nc1)c1noc(-c2cnn(C3CCS(=O)(=O)C3)c2)n1] | 4 | D | 1.15 | 495.4 |
| 97 | 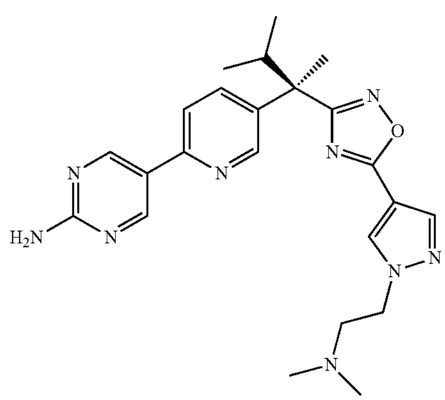 [SMILES: CC(C)[C@](C)(c1ccc(-c2cnc(N)nc2)nc1)c1noc(-c2cnn(CCN(C)C)c2)n1] | 4 | D | 0.97 | 448.4 |
| 98 | 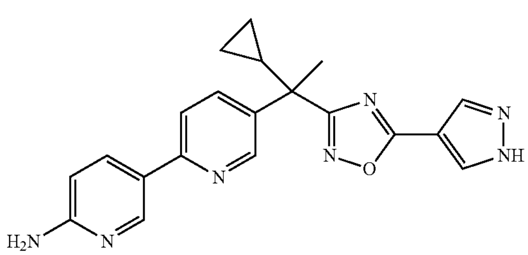 [SMILES: CC(c1ccc(-c2ccc(N)nc2)nc1)(c1noc(-c2cn[nH]c2)n1)C1CC1] | 20 | I | 0.56 | 374.2 |

TABLE 14-continued

| Example # | Structure | LC-MS Method | Method | Retention Time | m/z [M + H] |
|---|---|---|---|---|---|
| 99 | Chiral | 4 | I | 0.47 | 446.3 |
| 100 | 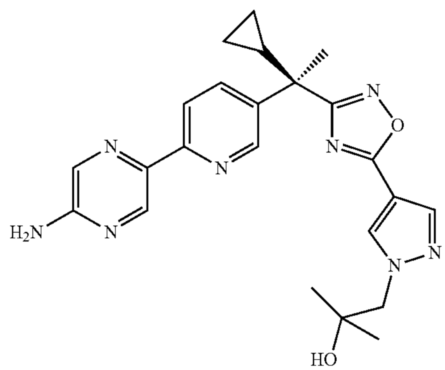 [SMILES: CC(C)(O)Cn1cc(-c2nc([C@@](C)(c3ccc(-c4cnc(N)cn4)nc3)C3CC3)no2)cn1] | 21 | I | 0.71 | 447.3 |
| 101 | 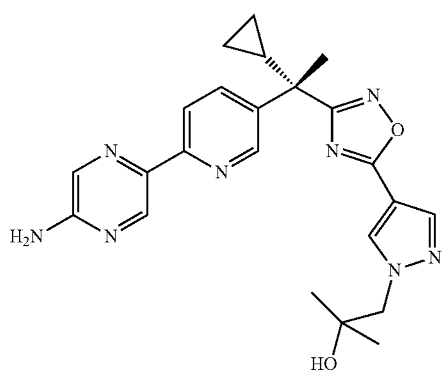 [SMILES: CC(C)(O)Cn1cc(-c2nc([C@](C)(c3ccc(-c4cnc(N)cn4)nc3)C3CC3)no2)cn1] | 21 | I | 0.71 | 447.3 |
| 102 | 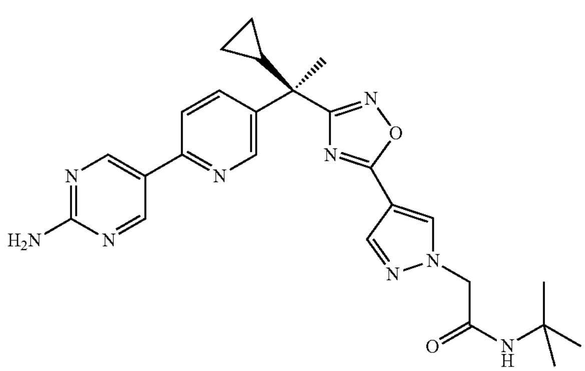 [SMILES: CC(C)(C)NC(=O)Cn1cc(-c2nc([C@@](C)(c3ccc(-c4cnc(N)nc4)nc3)C3CC3)no2)cn1] | 4 | I | 0.72 | 488.3 |

TABLE 14-continued

| Example # | Structure | LC-MS Method | Retention Method | Time | m/z [M + H] |
|---|---|---|---|---|---|
| 103 | Chiral | 4 | I | 0.75 | 414.3 |
| 104 | 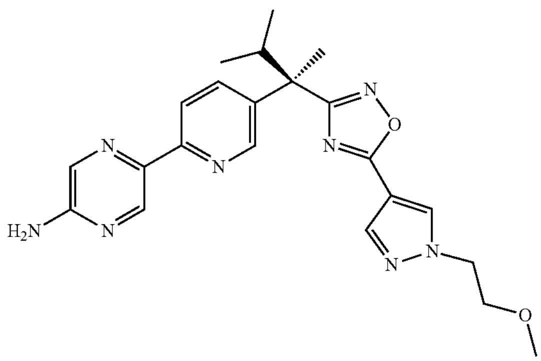 [SMILES: COCCn1cc(-c2nc([C@@](C)(c3ccc(-c4cnc(N)cn4)nc3)C(C)C)no2)cn1] | 18 | F | 1.6 | 435.3 |
| 105 | 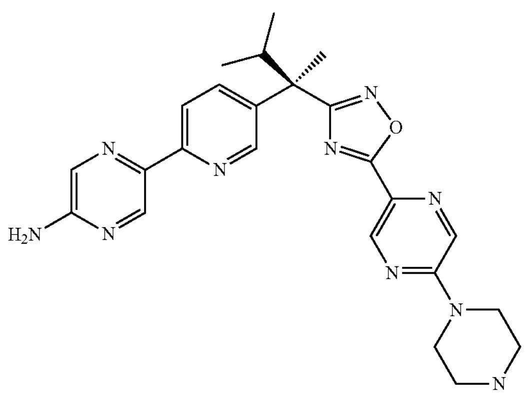 [SMILES: CC(C)[C@](C)(c1ccc(-c2cnc(N)cn2)nc1)c1noc(-c2cnc(N3CCNCC3)cn2)n1] | 18 | D | 0.94 | 473.4 |
| 106 | 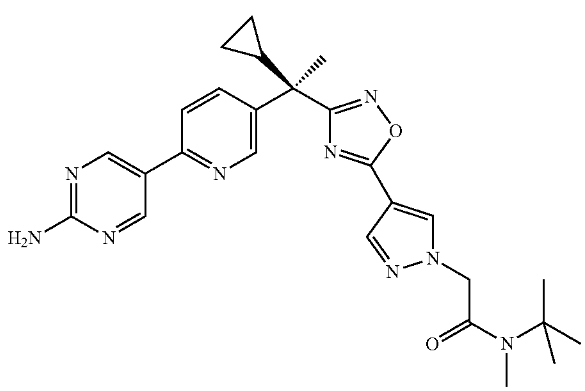 [SMILES: CN(C(=O)Cn1cc(-c2nc([C@@](C)(c3ccc(-c4cnc(N)nc4)nc3)C3CC3)no2)cn1)C(C)(C)C] | 4 | I | 0.82 | 502.3 |

TABLE 14-continued

| Example # | Structure | LC-MS Method | Method | Retention Time | m/z [M + H] |
|---|---|---|---|---|---|
| 107 | 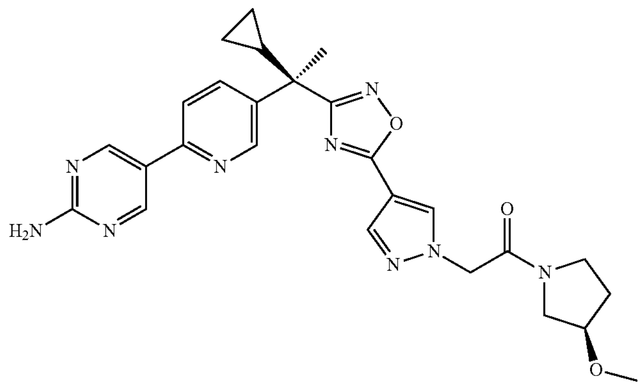 [SMILES: CO[C@@H]1CCN(C(=O)Cn2cc(-c3nc([C@@](C)(c4ccc(-c5cnc(N)nc5)nc4)C4CC4)no3)cn2)C1] | 4 | I | 0.68 | 516.3 |
| 108 | 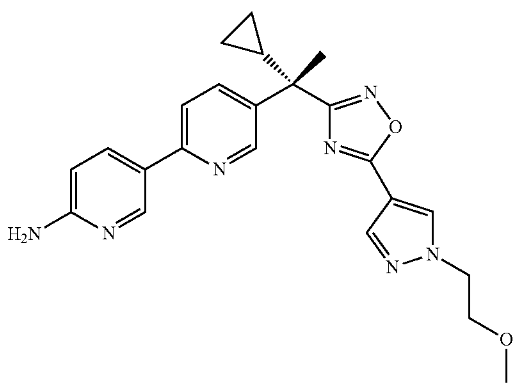 [SMILES: COCCn1cc(-c2nc([C@](C)(c3ccc(-c4ccc(N)nc4)nc3)C3CC3)no2)cn1] | 20 | I | 0.66 | 432.3 |
| 109 | 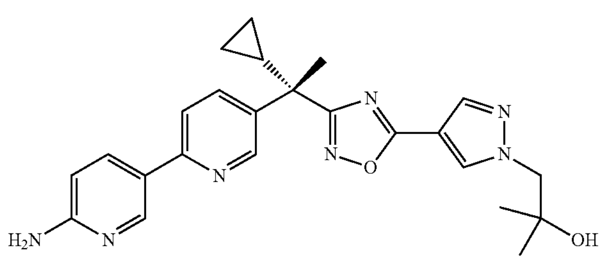 [SMILES: CC(C)(O)Cn1cc(-c2nc([C@](C)(c3ccc(-c4ccc(N)nc4)nc3)C3CC3)no2)cn1] | 11 | I | 0.64 | 446.3 |
| 110 | 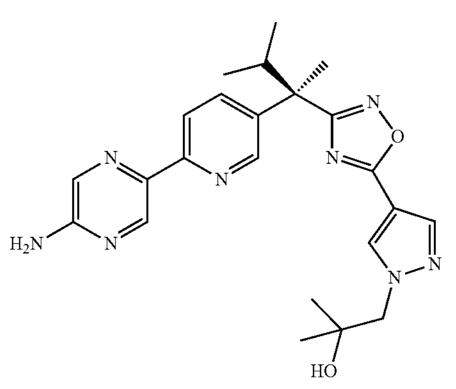 [SMILES: CC(C)[C@](C)(c1ccc(-c2cnc(N)cn2)nc1)c1noc(-c2cnn(CC(C)(C)O)c2)n1] | 18 | I | 0.73 | 449.3 |

TABLE 14-continued

| Example # | Structure | LC-MS Method | Method | Retention Time | m/z [M + H] |
|---|---|---|---|---|---|
| 111 | 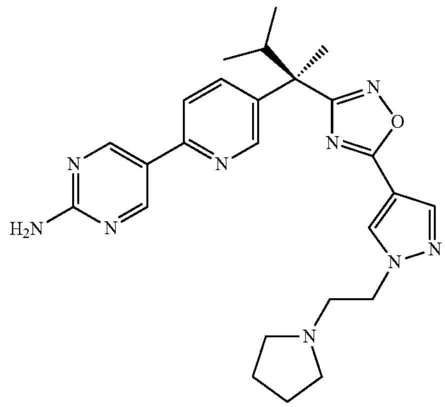 [SMILES: CC(C)[C@](C)(c1ccc(-c2cnc(N)nc2)nc1)c1noc(-c2cnn(CCN3CCCC3)c2)n1] | 4 | I | 0.64 | 474.4 |
| 112 | 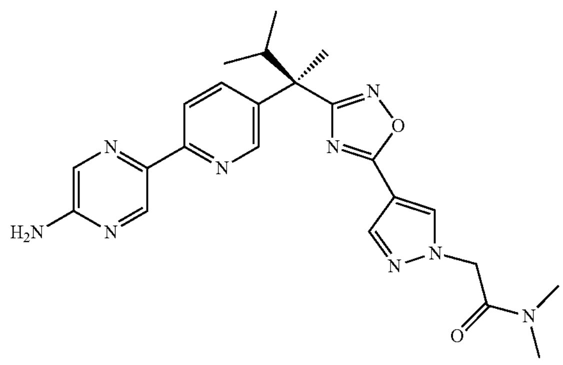 [SMILES: CC(C)[C@](C)(c1ccc(-c2cnc(N)cn2)nc1)c1noc(-c2cnn(CC(=O)N(C)C)c2)n1] | 18 | F | 1.39 | 462.5 |
| 113 | 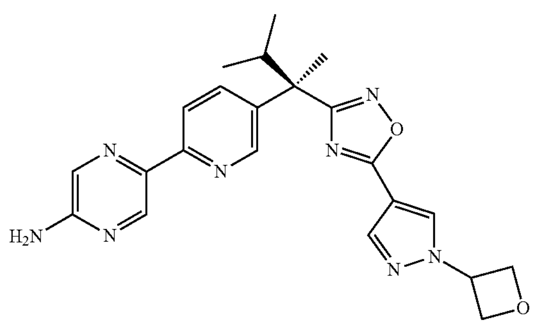 [SMILES: CC(C)[C@](C)(c1ccc(-c2cnc(N)cn2)nc1)c1noc(-c2cnn(C3COC3)c2)n1] | 18 | F | 1.55 | 43.3 |
| 114 | 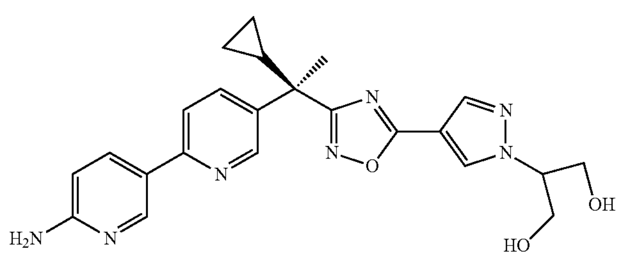 [SMILES: C[C@@](c1ccc(-c2ccc(N)nc2)nc1)(c1noc(-c2cnn(C(CO)CO)c2)n1)C1CC1] | 22 | I | 0.91 | 448.4 |

TABLE 14-continued

| Example # | Structure | LC-MS Method | Retention Method | Time | m/z [M + H] |
|---|---|---|---|---|---|
| 115 | 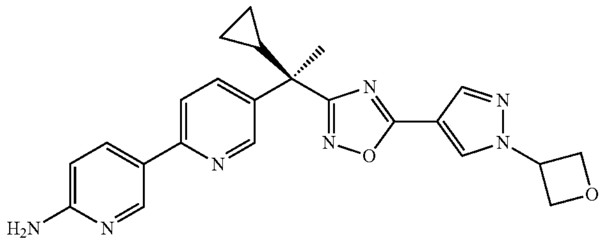 [SMILES: C[C@@](c1ccc(-c2ccc(N)nc2)nc1)(c1noc(-c2cnn(C3COC3)c2)n1)C1CC1] | 22 | I | 0.99 | 430.4 |
| 116 | 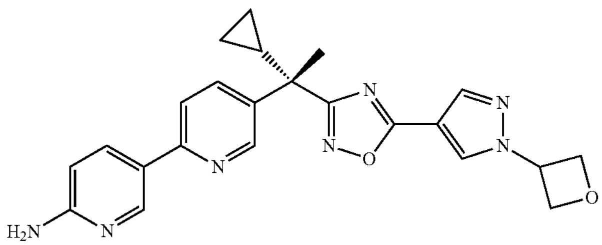 [SMILES: C[C@](c1ccc(-c2ccc(N)nc2)nc1)(c1noc(-c2cnn(C3COC3)c2)n1)C1CC1] | 22 | I | 0.99 | 430.4 |
| 117 | 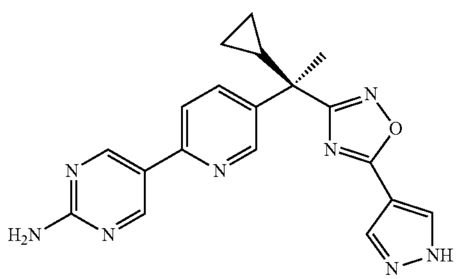 [SMILES: C[C@@](c1ccc(-c2cnc(N)nc2)nc1)(c1noc(-c2cn[nH]c2)n1)C1CC1] | 9 | I | 0.68 | 375.2 |
| 118 | 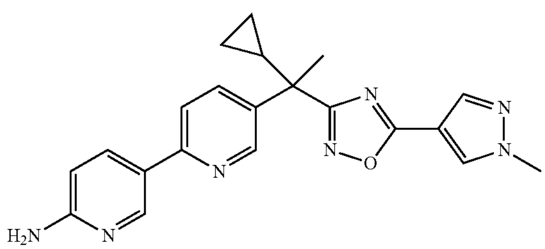 [SMILES: Cn1cc(-c2nc(C(C)(c3ccc(-c4ccc(N)nc4)nc3)C3CC3)no2)cn1] | 20 | D | 0.99 | 388.4 |
| 119 | 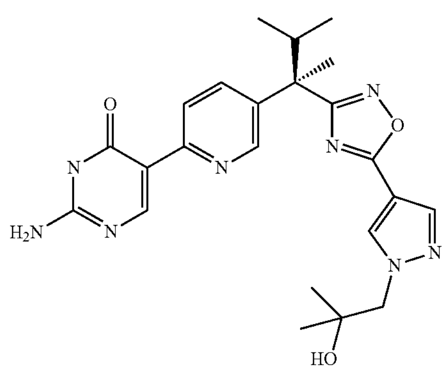 [SMILES: CC(C)[C@](C)(c1ccc(-c2cnc(N)[nH]c2=O)nc1)c1noc(-c2cnn(CC(C)(C)O)c2)n1] | 25 | I | 0.61 | 465.3 |

TABLE 14-continued

| Example # | Structure | Method | LC-MS Method | Retention Time | m/z [M + H] |
|---|---|---|---|---|---|
| 120 | 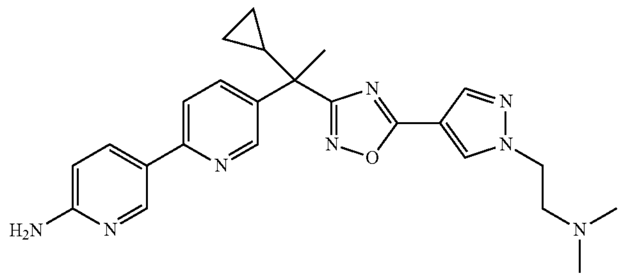 [SMILES: CN(C)CCn1cc(-c2nc(C(C)(c3ccc(-c4ccc(N)nc4)nc3)C3CC3)no2)cn1] | 11 | D | 0.79 | 445.4 |
| 121 | 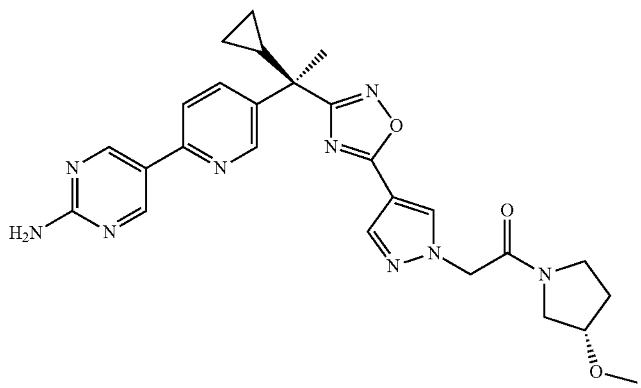 [SMILES: CO[C@H]1CCN(C(=O)Cn2cc(-c3nc([C@@](C)(c4ccc(-c5cnc(N)nc5)nc4)C4CC4)no3)cn2)C1] | 4 | I | 0.65 | 516.3 |
| 122 | 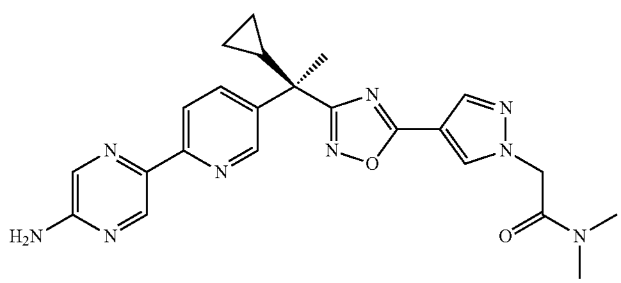 [SMILES: CN(C)C(=O)Cn1cc(-c2nc([C@@](C)(c3ccc(-c4cnc(N)cn4)nc3)C3CC3)no2)cn1] | 11 | I | 0.56 | 460.3 |
| 123 | 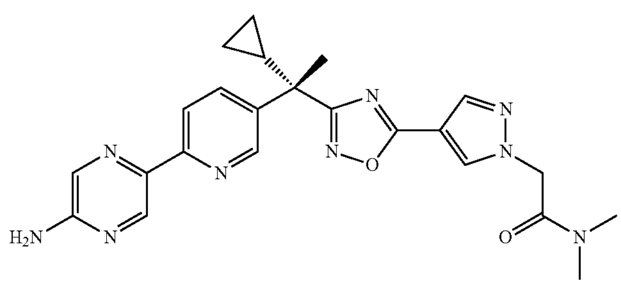 [SMILES: CN(C)C(=O)Cn1cc(-c2nc([C@](C)(c3ccc(-c4cnc(N)cn4)nc3)C3CC3)no2)cn1] | 11 | I | 0.56 | 460.3 |
| 124 | 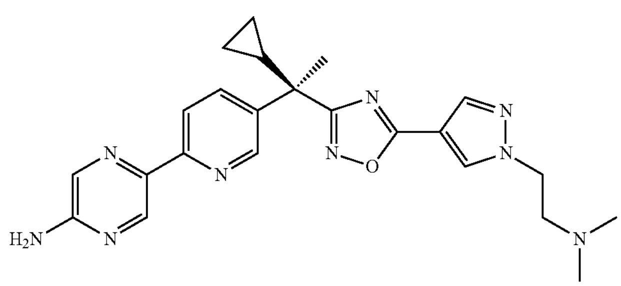 [SMILES: CN(C)CCn1cc(-c2nc([C@@](C)(c3ccc(-c4cnc(N)cn4)nc3)C3CC3)no2)cn1] | 11 | D | 0.89 | 4 |

TABLE 14-continued
| Example # | Structure | Method | LC-MS Method | Retention Time | m/z [M + H] |
|---|---|---|---|---|---|
| 125 | 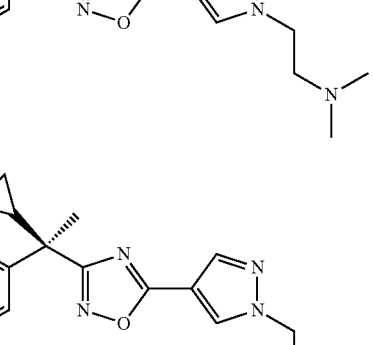 | 11 | I | 0.52 | 446.3 |
| 126 | 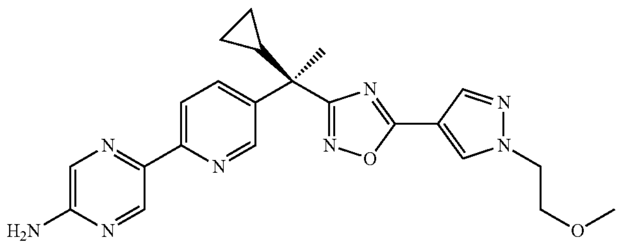 [SMILES: COCCn1cc(-c2nc([C@@](C)(c3ccc(-c4cnc(N)cn4)nc3)C3CC3)no2)cn1] | 11 | I | 0.75 | 433.3 |
| 127 | 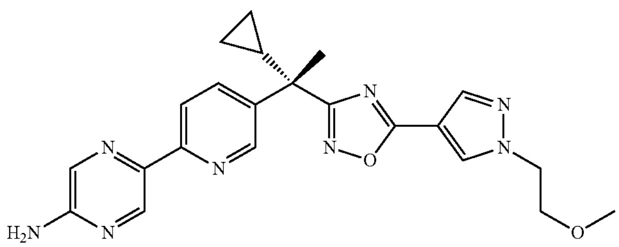 [SMILES: COCCn1cc(-c2nc([C@](C)(c3ccc(-c4cnc(N)cn4)nc3)C3CC3)no2)cn1] | 11 | I | 0.75 | 433.3 |
| 128 | 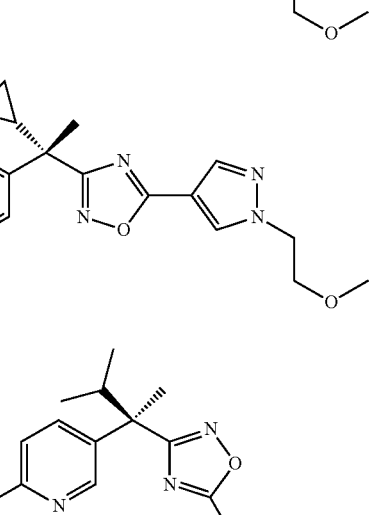 | 23 | D | 1.1 | 483.4 |
| 129 | 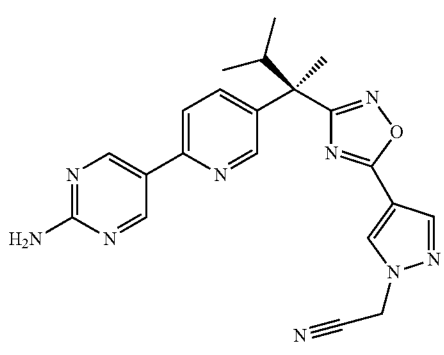 [SMILES: CC(C)[C@](C)(c1ccc(-c2cnc(N)nc2)nc1)c1noc(-c2cnn(CC#N)c2)n1] | 4 | D | 1.16 | 416.4 |

TABLE 14-continued

| Example # | Structure | LC-MS Method | Method | Retention Time | m/z [M + H] |
|---|---|---|---|---|---|
| 130 | 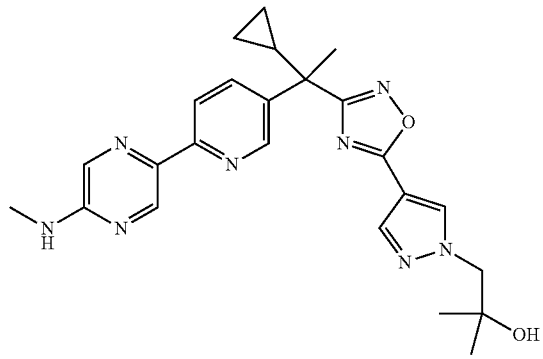 [SMILES: CNc1cnc(-c2ccc(C(C)(c3noc(-c4cnn(CC(C)(C)O)c4)n3)C3CC3)cn2)cn1] | 21 | I | 0.74 | 461.4 |
| 131 | 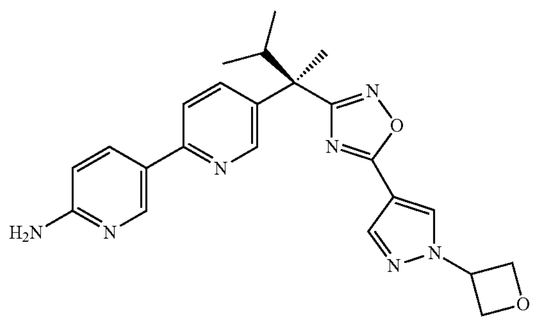 [SMILES: CC(C)[C@](C)(c1ccc(-c2ccc(N)nc2)nc1)c1noc(-c2cnn(C3COC3)c2)n1] | 1 | I | 0.66 | 432.3 |
| 132 | 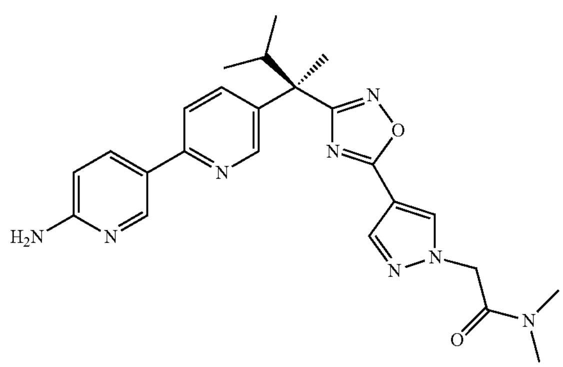 [SMILES: CC(C)[C@](C)(c1ccc(-c2ccc(N)nc2)nc1)c1noc(-c2cnn(CC(=O)N(C)C)c2)n1] | 1 | I | 0.62 | 461.4 |
| 133 | 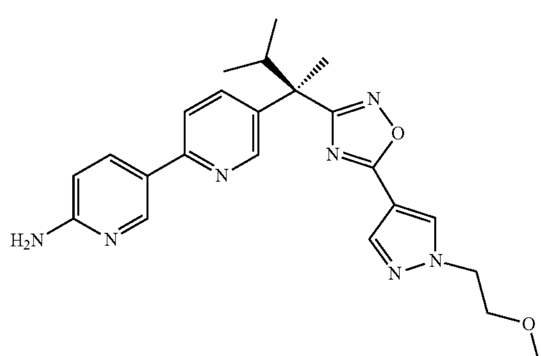 | 1 | F | 1.3 | 434.3 |

TABLE 14-continued

| Example # | Structure | Method | LC-MS Method | Retention Time | m/z [M + H] |
|---|---|---|---|---|---|
| 134 | 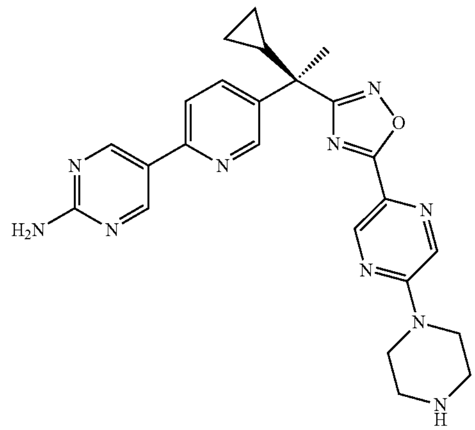 [SMILES: C[C@@](c1ccc(-c2cnc(N)nc2)nc1)(c1noc(-c2cnc(N3CCNCC3)cn2)n1)C1CC1] | 19 | I | 0.53 | 471.3 |
| 135 | 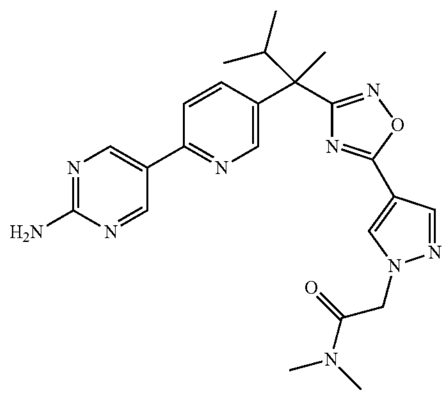 [SMILES: CC(C)C(C)(c1ccc(-c2cnc(N)nc2)nc1)c1noc(-c2cnn(CC(=O)N(C)C)c2)n1] | 17 | I | 0.58 | 462.31 |
| 136 | 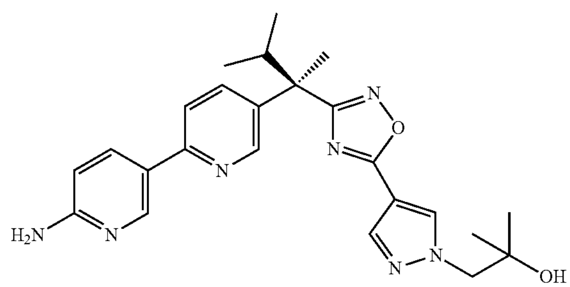 [SMILES: CC(C)[C@](C)(c1ccc(-c2ccc(N)nc2)nc1)c1noc(-c2cnn(CC(C)(C)O)c2)n1] | 1 | I | 0.68 | 448.4 |
| 137 | 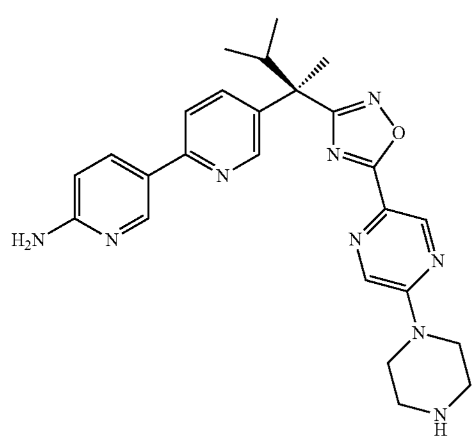 [SMILES: CC(C)[C@](C)(c1ccc(-c2ccc(N)nc2)nc1)c1noc(-c2cnc(N3CCNCC3)cn2)n1] | 19 | I | 0.49 | 472.4 |

TABLE 14-continued

| Example # | Structure | LC-MS Method | Method | Retention Time | m/z [M + H] |
|---|---|---|---|---|---|
| 138 | 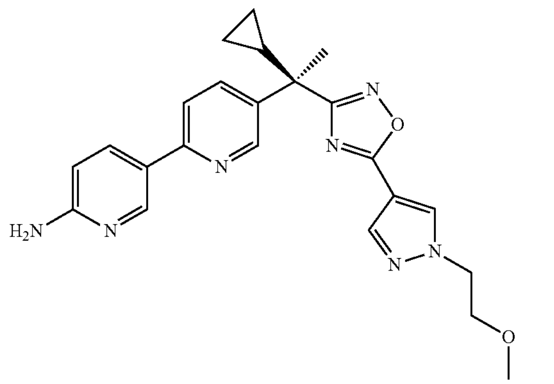 [SMILES: COCCn1cc(-c2nc([C@@](C)(c3ccc(-c4ccc(N)nc4)nc3)C3CC3)no2)cn1] | 11 | I | 0.66 | 432.3 |
| 139 | 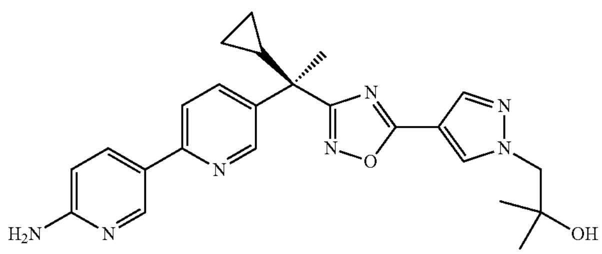 [SMILES: CC(C)(O)Cn1cc(-c2nc([C@@](C)(c3ccc(-c4ccc(N)nc4)nc3)C3CC3)no2)cn1] | 11 | I | 0.64 | 446.3 |
| 140 | 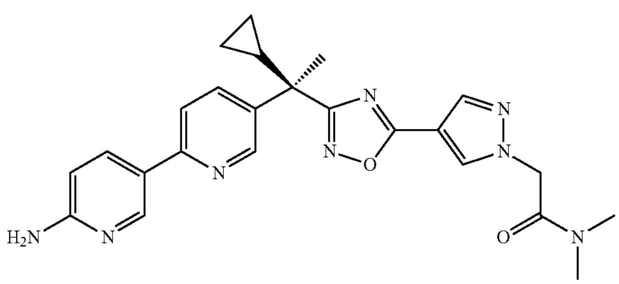 [SMILES: CN(C)C(=O)Cn1cc(-c2nc([C@@](C)(c3ccc(-c4ccc(N)nc4)nc3)C3CC3)no2)cn1] | 4 | I | 0.54 | 459.2 |
| 141 | 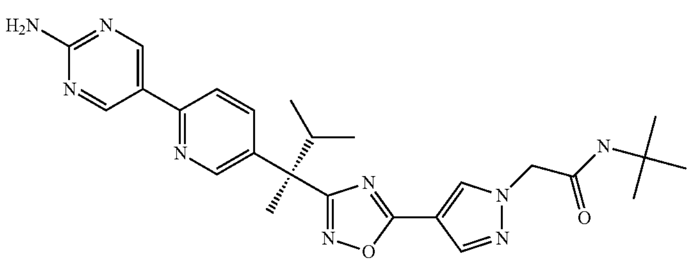 [SMILES: CC(C)[C@](C)(c1ccc(-c2cnc(N)nc2)nc1)c1noc(-c2cnn(CC(=O)NC(C)(C)C)c2)n1] | 24 | I | 0.98 | 490.4 |
| 142 | 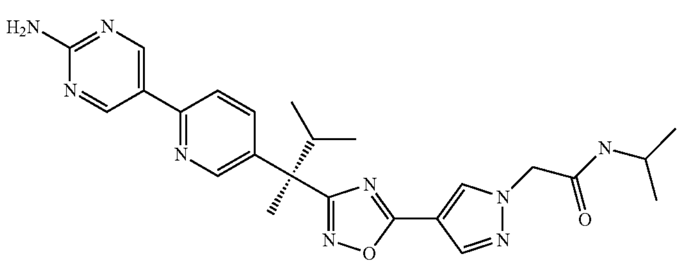 | 24 | I | 0.91 | 476.3 |

TABLE 14-continued

| Example # | Structure | Method | LC-MS Method | Retention Time | m/z [M + H] |
|---|---|---|---|---|---|
| 143 | 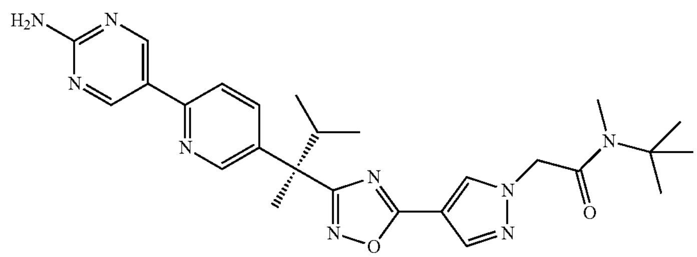 [SMILES: CC(C)[C@](C)(c1ccc(-c2cnc(N)nc2)nc1)c1noc(-c2cnn(CC(=O)N(C)C(C)(C)C)c2)n1] | 24 | I | 1.02 | 504.4 |
| 144 | 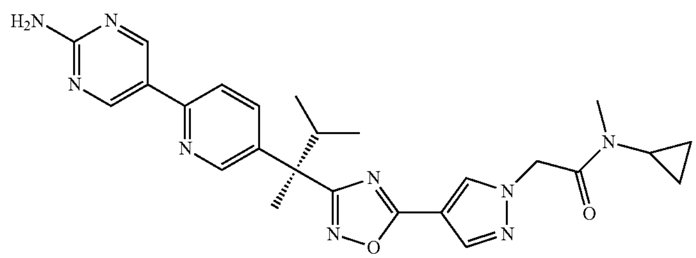 | 24 | I | 0.93 | 488.3 |
| 145 | 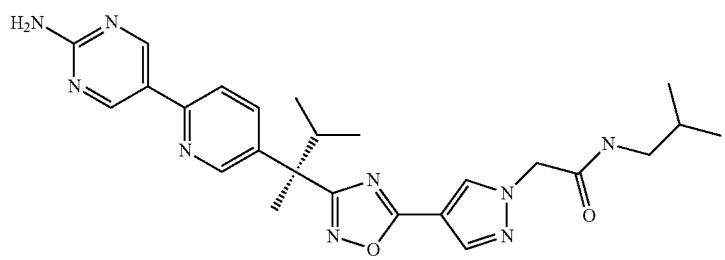 [SMILES: CC(C)CNC(=O)Cn1cc(-c2nc([C@@](C)(c3ccc(-c4cnc(N)nc4)nc3)C(C)C)no2)cn1] | 24 | I | 0.96 | 490.3 |
| 146 | 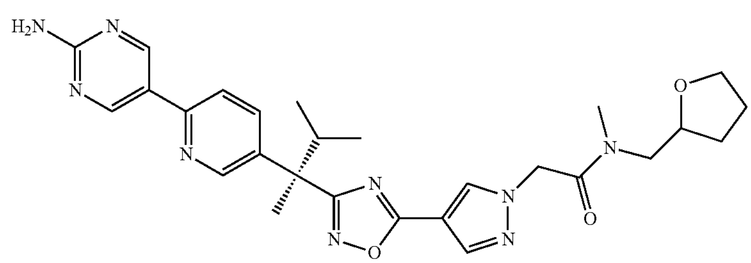 [SMILES: CC(C)[C@](C)(c1ccc(-c2cnc(N)nc2)nc1)c1noc(-c2cnn(CC(=O)N(C)CC3CCCO3)c2)n1] | 24 | I | 0.91 | 532.4 |
| 147 | 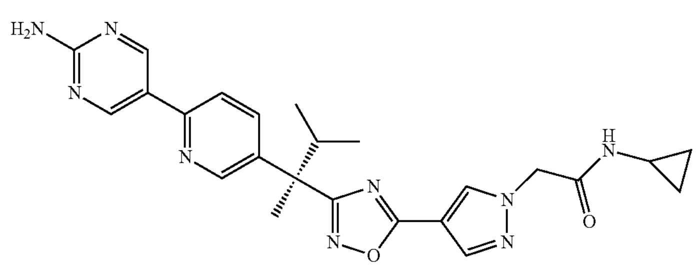 [SMILES: CC(C)[C@](C)(c1ccc(-c2cnc(N)nc2)nc1)c1noc(-c2cnn(CC(=O)NC3CC3)c2)n1] | 24 | I | 0.79 | 474.3 |
| 148 | 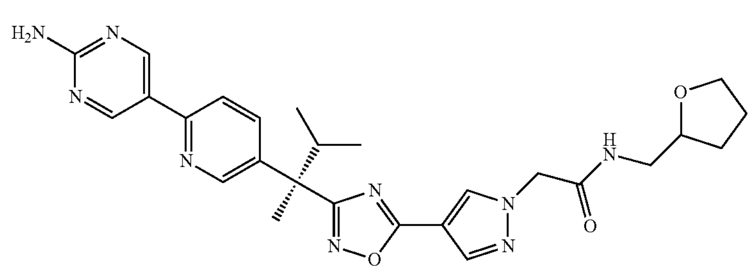 [SMILES: CC(C)[C@](C)(c1ccc(-c2cnc(N)nc2)nc1)c1noc(-c2cnn(CC(=O)NCC3CCCO3)c2)n1] | 24 | I | 0.8 | 518.4 |

TABLE 14-continued

| Example # | Structure | Method | LC-MS Method | Retention Time | m/z [M + H] |
|---|---|---|---|---|---|
| 149 | 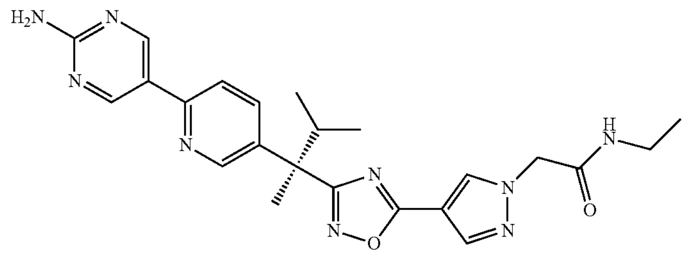 [SMILES: CCNC(=O)Cn1cc(-c2nc([C@@](C)(c3ccc(-c4cnc(N)nc4)nc3)C(C)C)no2)cn1] | 24 | I | 0.78 | 462.3 |
| 150 | 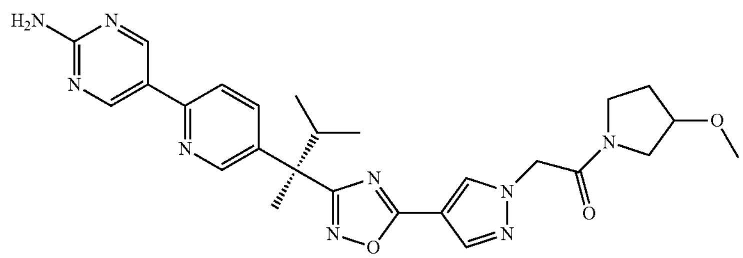 [SMILES: COC1CCN(C(=O)Cn2cc(-c3nc([C@@](C)(c4ccc(-c5cnc(N)nc5)nc4)C(C)C)no3)cn2)C1] | 24 | I | 0.79 | 518.4 |
| 151 | 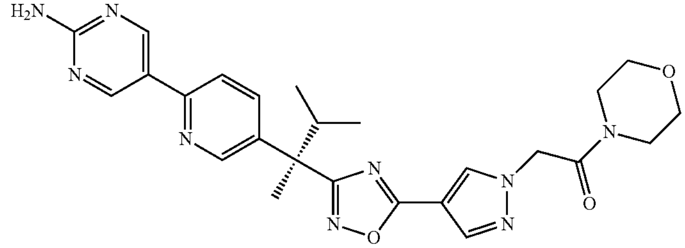 [SMILES: CC(C)[C@](C)(c1ccc(-c2cnc(N)nc2)nc1)c1noc(-c2cnn(CC(=O)N3CCOCC3)c2)n1] | 24 | I | 0.77 | 504.3 |
| 152 | 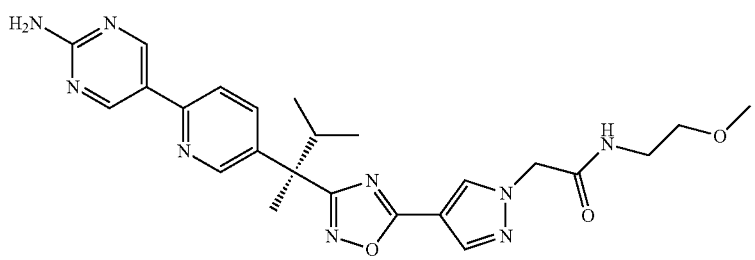 [SMILES: COCCNC(=O)Cn1cc(-c2nc([C@@](C)(c3ccc(-c4cnc(N)nc4)nc3)C(C)C)no2)cn1] | 24 | I | 0.78 | 492.4 |
| 153 | 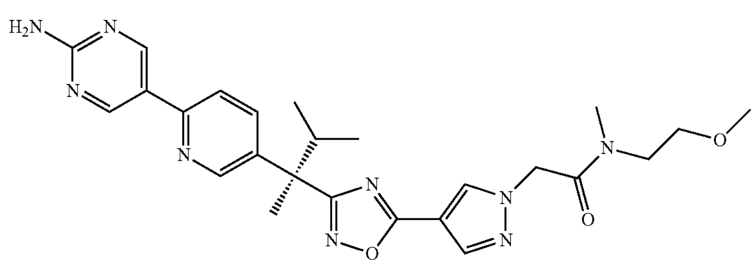 [SMILES: COCCN(C)C(=O)Cn1cc(-c2nc([C@@](C)(c3ccc(-c4cnc(N)nc4)nc3)C(C)C)no2)cn1] | 24 | I | 0.82 | 506.4 |
| 154 | 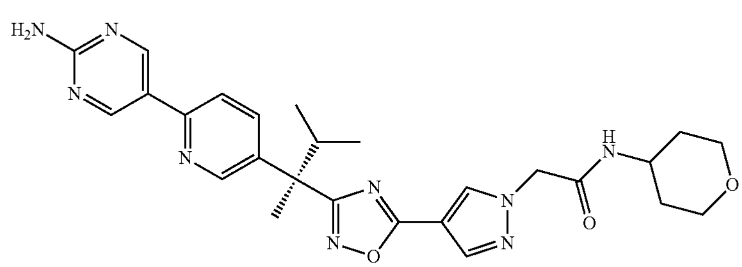 [SMILES: CC(C)[C@](C)(c1ccc(-c2cnc(N)nc2)nc1)c1noc(-c2cnn(CC(=O)NC3CCOCC3)c2)n1] | 24 | I | 0.79 | 518.4 |

TABLE 14-continued

| Example # | Structure | LC-MS Method | Method | Retention Time | m/z [M + H] |
|---|---|---|---|---|---|
| 155 | 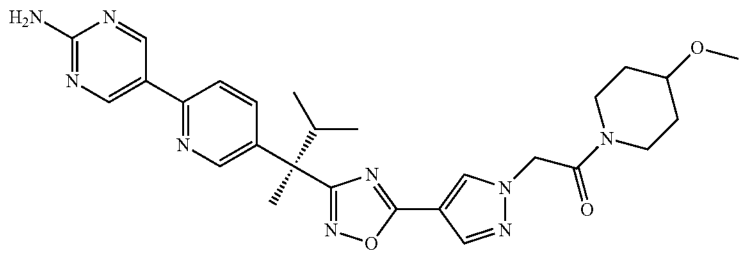 [SMILES: COC1CCN(C(=O)Cn2cc(-c3nc([C@@](C)(c4ccc(-c5cnc(N)nc5)nc4)C(C)C)no3)cn2)CC1] | 24 | I | 0.83 | 532.3 |
| 156 | 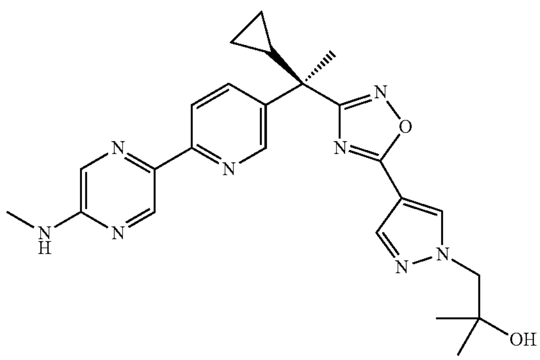 [SMILES: CNc1cnc(-c2ccc([C@](C)(c3noc(-c4cnn(CC(C)(C)O)c4)n3)C3CC3)cn2)cn1] | 21 | I | 0.75 | 461.3 |
| 157 | 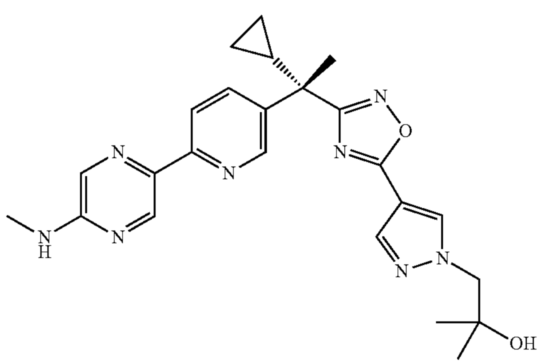 [SMILES: CNc1cnc(-c2ccc([C@@](C)(c3noc(-c4cnn(CC(C)(C)O)c4)n3)C3CC3)cn2)cn1] | 21 | I | 0.75 | 461.3 |
| 158 | 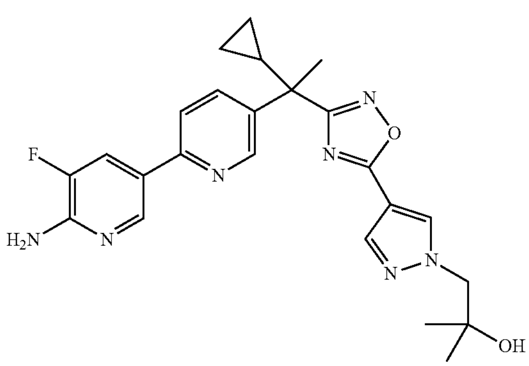 [SMILES: CC(C)(O)Cn1cc(-c2nc(C(C)(c3ccc(-c4cnc(N)c(F)c4)nc3)C3CC3)no2)cn1] | 18 | I | 0.8 | 464.3 |

TABLE 14-continued
| Example # | Structure | LC-MS Method | Method | Retention Time | m/z [M + H] |
|---|---|---|---|---|---|
| 159 | 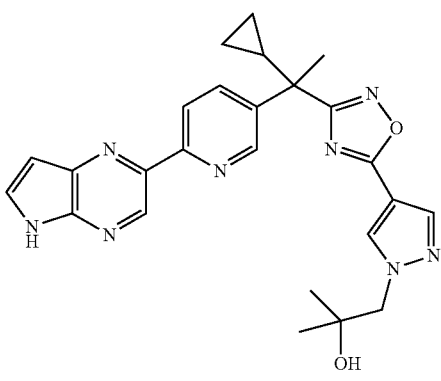 [SMILES: CC(C)(O)Cn1cc(-c2nc(C(C)(c3ccc(-c4cnc5[nH]ccc5n4)nc3)C3CC3)no2)cn1] | 2 | F | 2 | 471.4 |
| 160 | 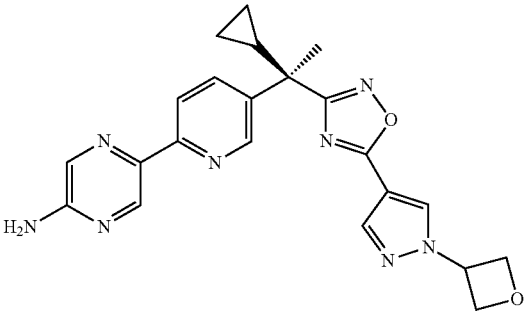 [SMILES: C[C@@](c1ccc(-c2cnc(N)cn2)nc1)(c1noc(-c2cnn(C3COC3)c2)n1)C1CC1] | 16 | I | 0.67 | M − H = 429.3 |
| 161 | 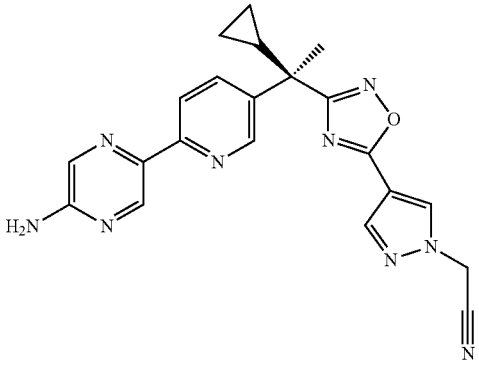 [SMILES: C[C@@](c1ccc(-c2cnc(N)cn2)nc1)(c1noc(-c2cnn(CC#N)c2)n1)C1CC1] | 16 | I | 0.69 | M − H = 412.3 |
| 162 | 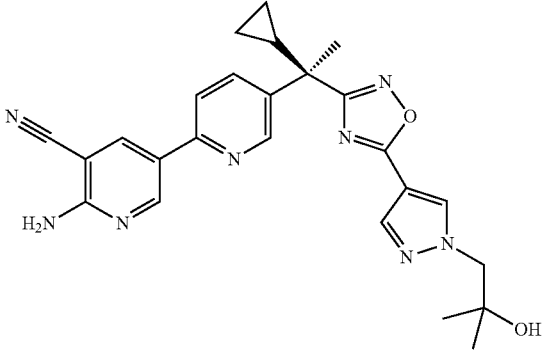 [SMILES: CC(C)(O)Cn1cc(-c2nc([C@@](C)(c3ccc(-c4cnc(N)c(C#N)c4)nc3)C3CC3)no2)cn1] | 18 | I | 0.8 | 471.4 |

TABLE 14-continued

| Example # | Structure | LC-MS Method | Retention Method | Time | m/z [M + H] |
|---|---|---|---|---|---|
| 163 | 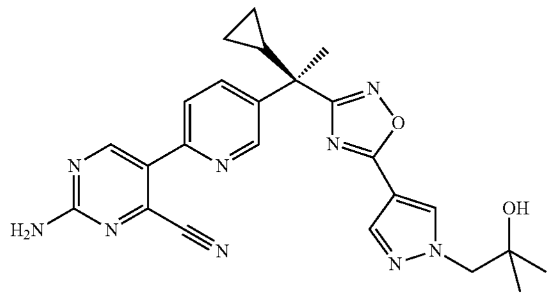 [SMILES: CC(C)(O)Cn1cc(-c2nc([C@@](C)(c3ccc(-c4cnc(N)nc4C#N)nc3)C3CC3)no2)cn1] | 26 | I | 0.79 | 472.3 |
| 164 | 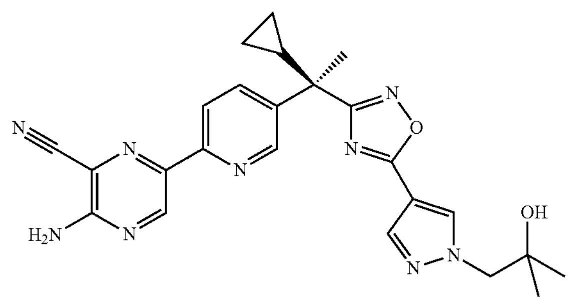 [SMILES: CC(C)(O)Cn1cc(-c2nc([C@@](C)(c3ccc(-c4cnc(N)c(C#N)n4)nc3)C3CC3)no2)cn1] | 18 | I | 0.86 | 472.3 |
| 165 | 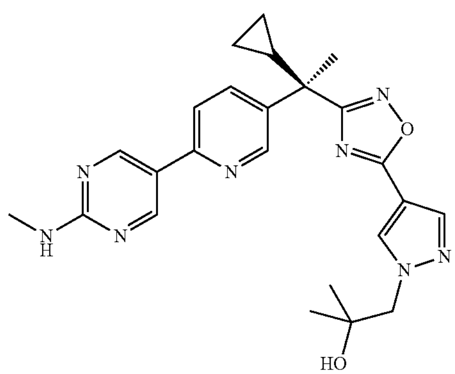 [SMILES: CNc1ncc(-c2ccc([C@](C)(c3noc(-c4cnn(CC(C)(C)O)c4)n3)C3CC3)cn2)cn1] | 1 | F | 1.57 | 461.2 |
| 166 | 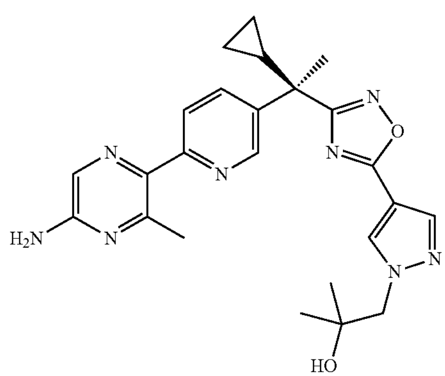 [SMILES: Cc1nc(N)cnc1-c1ccc([C@](C)(c2noc(-c3cnn(CC(C)(C)O)c3)n2)C2CC2)cn1] | 28 | F | 1.22 | 461.1 |

TABLE 14-continued
| Example # | Structure | LC-MS Method | Method | Retention Time | m/z [M + H] |
|---|---|---|---|---|---|
| 167 | 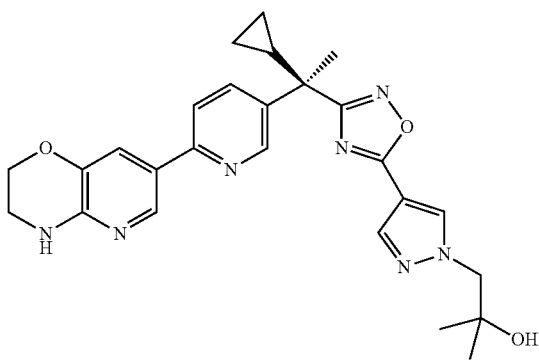 [SMILES: CC(C)(O)Cn1cc(-c2nc([C@@](C)(c3ccc(-c4cnc5c(c4)OCCN5)nc3)C3CC3)no2)cn1] | 26 | I | 0.64 | 488.4 |
| 168 | 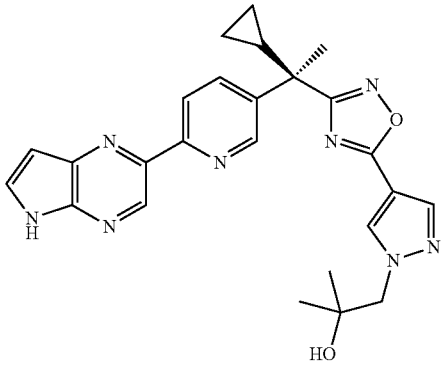 [SMILES: CC(C)(O)Cn1cc(-c2nc([C@@](C)(c3ccc(-c4cnc5[nH]ccc5n4)nc3)C3CC3)no2)cn1] | 18 | F | 1.64 | 471.3 |
| 169 | 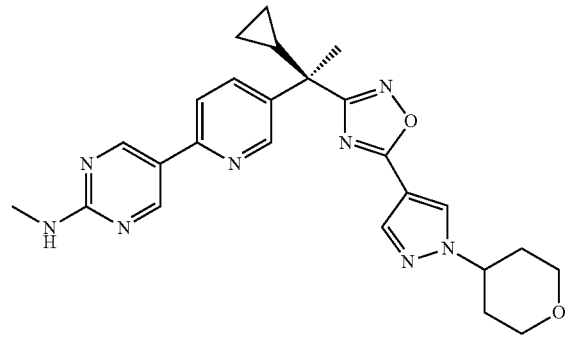 [SMILES: CNc1ncc(-c2ccc([C@](C)(c3noc(-c4cnn(C5CCOCC5)c4)n3)C3CC3)cn2)cn1] | 27 | I | 0.82 | 473.4 |
| 170 | 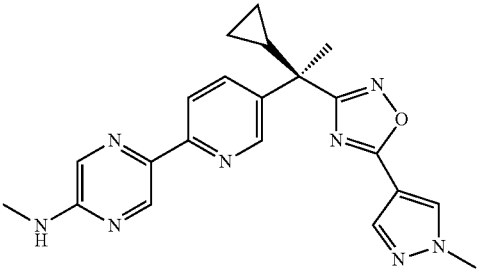 | 18 | I | 0.68 | 403.7 |

TABLE 14-continued

| Example # | Structure | LC-MS Method | Retention Method | Time | m/z [M + H] |
|---|---|---|---|---|---|
| 171 | 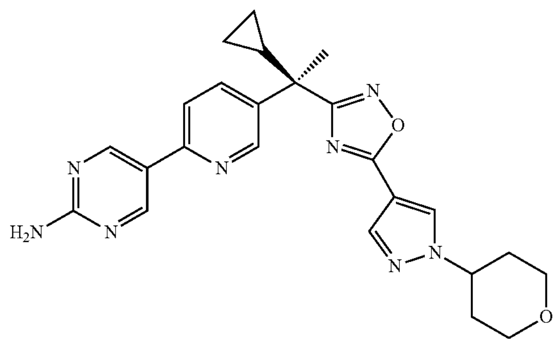 [SMILES: C[C@@](c1ccc(-c2cnc(N)nc2)nc1)(c1noc(-c2cnn(C3CCOCC3)c2)n1)C1CC1] | 23 | I | 0.75 | 459.4 |
| 172 | 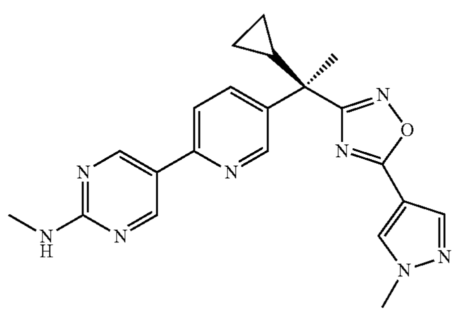 [SMILES: CNc1ncc(-c2ccc([C@](C)(c3noc(-c4cnn(C)c4)n3)C3CC3)cn2)cn1] | 1 | F | 1.53 | 403 |
| 173 | 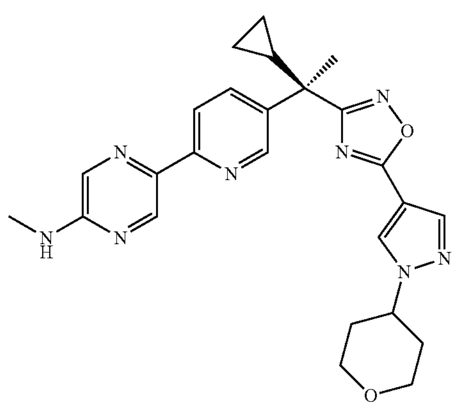 [SMILES: CNc1cnc(-c2ccc([C@](C)(c3noc(-c4cnn(C5CCOCC5)c4)n3)C3CC3)cn2)cn1] | 18 | F | 1.5 | 473.1 |
| 174 | 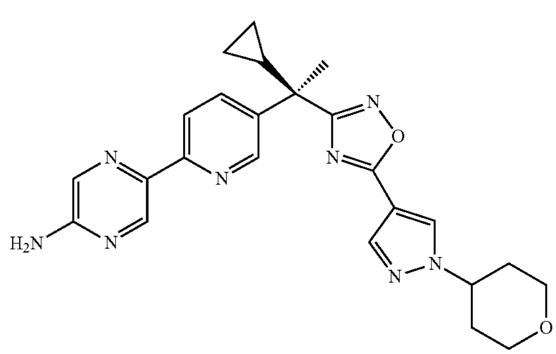 [SMILES: C[C@@](c1ccc(-c2cnc(N)cn2)nc1)(c1noc(-c2cnn(C3CCOCC3)c2)n1)C1CC1] | 16 | I | 0.7 | 459.1 |

TABLE 14-continued

| Example # | Structure | LC-MS Method | Method | Retention Time | m/z [M + H] |
|---|---|---|---|---|---|
| 175 | 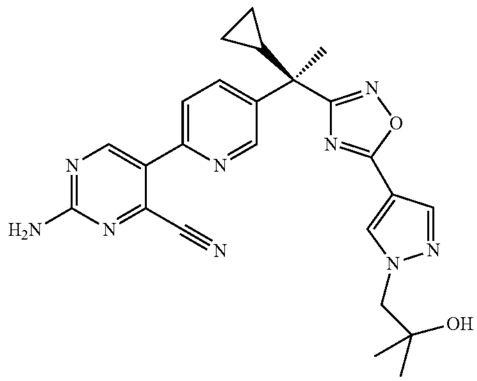 [SMILES: CC(C)(O)Cn1cc(-c2nc([C@@](C)(c3ccc(-c4cnc(N)nc4C#N)nc3)C3CC3)no2)cn1] | 26 | I | 0.8 | 472.3 |
| 176 | 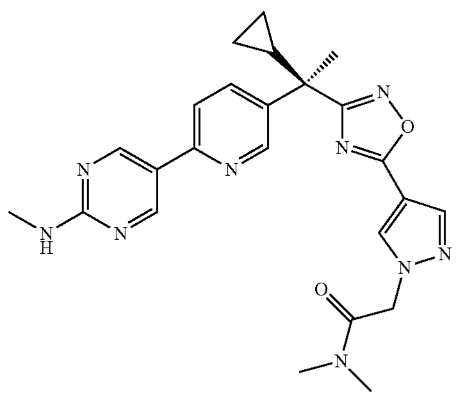 [SMILES: CNc1ncc(-c2ccc([C@](C)(c3noc(-c4cnn(CC(=O)N(C)C)c4)n3)C3CC3)cn2)cn1] | 1 | F | 1.25 | 474.3 |
| 177 | 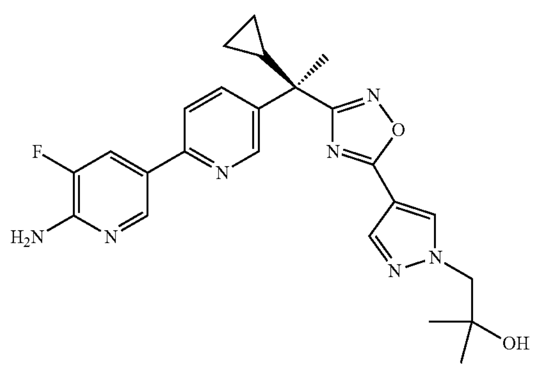 [SMILES: CC(C)(O)Cn1cc(-c2nc([C@@](C)(c3ccc(-c4cnc(N)c(F)c4)nc3)C3CC3)no2)cn1] | 21 | I | 0.92 | 464.3 |
| 178 | 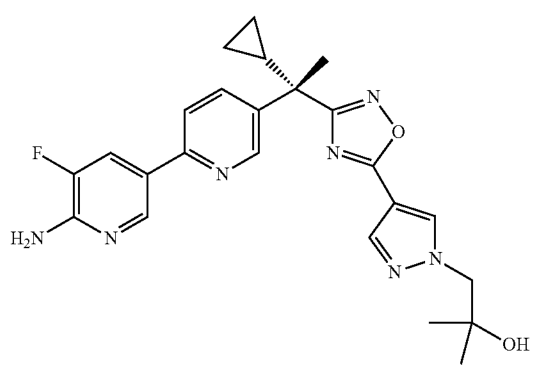 [SMILES: CC(C)(O)Cn1cc(-c2nc([C@](C)(c3ccc(-c4cnc(N)c(F)c4)nc3)C3CC3)no2)cn1] | 21 | I | 0.92 | 464.3 |

TABLE 14-continued

| Example # | Structure | Method | LC-MS Method | Retention Time | m/z [M + H] |
|---|---|---|---|---|---|
| 179 | 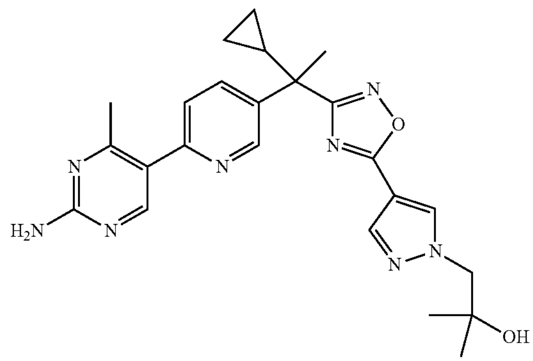 [SMILES: Cc1nc(N)ncc1-c1ccc(C(C)(c2noc(-c3cnn(CC(C)(C)O)c3)n2)C2CC2)cn1] | 27 | I | 0.88 | 461.3 |
| 180 | 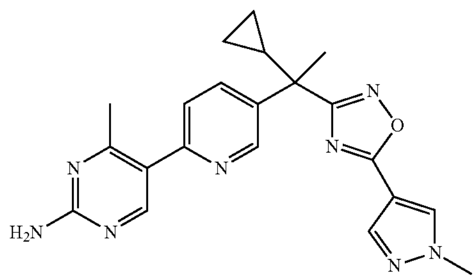 [SMILES: Cc1nc(N)ncc1-c1ccc(C(C)(c2noc(-c3cnn(C)c3)n2)C2CC2)cn1] | 27 | I | 0.62 | 403.2 |
| 181 | 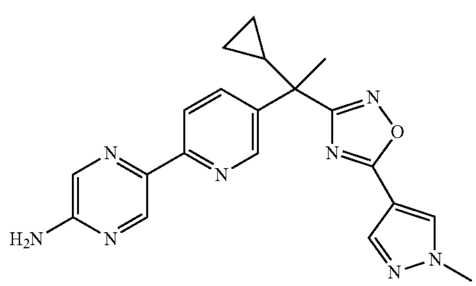 [SMILES: Cn1cc(-c2nc(C(C)(c3ccc(-c4cnc(N)cn4)nc3)C3CC3)no2)cn1] | 18 | I | 0.6 | 389.2 |

ASSESSMENT OF BIOLOGICAL PROPERTIES

1. Binding Assay

Compounds are assessed for the ability to bind to FLAP in a binding assay that measures compound-specific displacement of an iodinated ($^{125}$I) FLAP inhibitor via a Scintillation Proximity Assay format (adapted from S. Charleson et al., Mol. Pharmacol., 1992, 41, 873-879).

Cell pellets produced from sf9 insect cells expressing recombinant human FLAP protein are resuspended in buffer A [15 mM Tris-HCl (pH 7.5), 2 mM MgCl$_2$, 0.3 mM EDTA, 1 mM PMSF]. The cells are lysed with a Dounce homogenizer and the material is centrifuged at 10,000×g for 10 minutes. The supernatant is then collected and centrifuged at 100,000×g for 60 minutes. To prepare membrane protein for an assay, an aliquot of the 100,000×g pellet is resuspended in 1 ml of buffer A, Dounce homogenized, and finally subjected to polytron mixing (30 seconds). Membrane protein (25 µl, 5 µg) is mixed with WGA SPA beads (Amersham) and stirred for 1 h. To an assay plate (Perkin Elmer FlexiPlate) is added 25 µl of test compound prepared in Binding buffer [100 mM Tris (pH 7.5), 140 mM NaCl, 5% glycerol, 2 mM EDTA, 0.5 mM TCEP, 0.05% Tween 20], 25 µl of [$^{125}$I]L-691,831 (an iodinated analog of MK-591, Charleson et al. Mol. Pharmacol., 41, 873-879, 1992) and finally 50 µl of the bead/protein mixture. (final concentrations: beads, 200 µg/well; protein, 5 µg/well; [$^{125}$I] probe, 0.08 nM/well (17 nCi/well). The plates are shaken for 2 h before reading on a Microbeta plate reader. Non-specific binding is determined by the addition of 10 µM cold L-691,831 compound.

In general, the preferred potency range (IC$_{50}$) of compounds in the above assay is between 0.1 nM to 10 µM, the more preferred potency range is 0.1 nM to 1 µM, and the most preferred potency range is 0.1 nM to 100 nM.

2. Whole Blood Assay

Compounds are additionally tested in a human whole blood assay to determine their ability to inhibit the synthesis of LTB$_4$ in a cellular system. Compounds are combined with heparinized human whole blood and incubated for 15 minutes at 37° C. Calcimycin (20 µM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma LTB$_4$ concentrations are then measured using an antibody-based homogenous time-resolved fluorescence method (CisBio, Bedford, Mass.).

In general, the preferred potency range (IC$_{50}$) of compounds in the above assay is between 10 nM to 10 µM, the more preferred potency range is 10 nM to 1 μM, and the most preferred potency range is 10 nM to 100 nM.

METHOD OF USE

The compounds of the invention are effective inhibitors of 5-lipoxygenase activating protein (FLAP) and thus inhibit leukotriene production. Therefore, in one embodiment of the invention, there is provided methods of treating leukotriene-mediated disorders using compounds of the invention. In another embodiment, there is provided methods of treating cardiovascular, inflammatory, allergic, pulmonary and fibrotic diseases, renal diseases and cancer using compounds of the invention.

Without wishing to be bound by theory, by inhibiting the activity of FLAP, the compounds of the invention block the production of LTs resulting from the oxidation of arachidonic acid by 5-LO and subsequent metabolism. Thus, the inhibition of FLAP activity is an attractive means for preventing and treating a variety of diseases mediated by LTs. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease, multiple sclerosis, inflammatory pain, systemic lupus erythematosus, transplant rejection, inflammatory and allergic ocular diseases;

Cancer including solid tumors, leukemias and lymphomas; and

Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound of formula I:

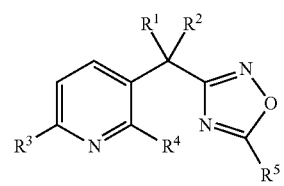

wherein:

$R^1$ and $R^2$ are each independently hydrogen, $C_{1-7}$ alkyl or $C_{3-10}$ carbocycle, with the proviso that both $R^1$ and $R^2$ are not hydrogen;

$R^3$ is a 5-11 membered heteroaryl ring containing one to three heteroatoms selected from nitrogen, oxygen and sulfur, wherein the heteroaryl ring is optionally independently substituted with one to three groups selected from $C_{1-5}$ alkyl, $C_{1-5}$ alkoxy, $C_{1-3}$ alkylhydroxy, amino, $C_{1-3}$ alkylamino, $C_{1-3}$ dialkylamino, oxo, —CN, halogen, and 5-6 membered heteroaryl optionally substituted with one to three methyl groups;

$R^4$ is hydrogen, $C_{1-3}$ alkyl, halogen or nitrile;

$R^5$ is $C_{1-6}$ alkyl, $C_{3-10}$ carbocycle, 5-11 membered heterocycle, aryl, 5-11 membered heteroaryl, —C(O)—$R^6$ or —NR$^7$R$^8$, wherein each R$^5$ is optionally independently substituted with one to three groups selected from R$^9$, R$^{10}$ and R$^{11}$;

R$^6$ is C$_{3-8}$ heterocycle or —NH-5-6 membered heterocycle, each optionally independently substituted with one to three groups selected from R$^9$, R$^{10}$ and R$^{11}$;

R$^7$ and R$^8$ are each independently hydrogen or C$_{1-6}$ alkyl, wherein the alkyl group is optionally substituted with —OH or C$_{1-3}$alkoxy;

R$^9$, R$^{10}$ and R$^{11}$ are independently selected from
(a) —H,
(b) —OH,
(c) halogen,
(d) —CN,
(e) —CF$_3$,
(f) C$_{1-6}$alkyl optionally substituted with one to three —OH, —N(R$^{12}$)(R$^{13}$), 3-6 membered heterocycle, C$_{1-6}$alkoxy, halogen, CN, —CO$_2$R$^{12}$, —O—C$_{1-6}$alkyl-O—C$_{1-3}$alkyl, —C(O)N(R$^{12}$)(R$^{13}$) or —S(O)$_n$C$_{1-6}$alkyl,
(g) C$_{1-6}$alkoxy,
(h) —N(R$^{12}$)(R$^{13}$),
(i) —S(O)$_n$—C$_{1-6}$alkyl,
(j) —CO$_2$R$^{12}$,
(k) —C(O)N(R$^{12}$)(R$^{13}$),
(l) —S(O)$_2$N(R$^{12}$)(R$^{13}$),
(m) a 3-10 membered heterocyclic group optionally substituted with one to three C$_{1-6}$ alkyl groups or oxo,
(n') oxo,
(o) —C(O)—C$_{1-3}$ alkyl;
(p) C$_{1-6}$alkenyl substituted optionally substituted with a —OH;

R$^{12}$ and R$^{13}$ are each independently selected from —H, —C$_{1-6}$alkyl, C(O)C$_{1-6}$alkyl C$_{3-6}$ carbocycle and a 3-6 membered heterocyclic group, each of which is optionally independently substituted with one to three C$_{1-6}$alkyl groups, halogen, —OH, C$_{1-6}$alkoxy, —C(O)N(R$^{14}$)(R$^{15}$), —S(O)—C$_{1-6}$alkyl, CN, a 3-6 membered heterocyclic group, —OC$_{1-6}$alkyl, CF$_3$, or;

R$^{12}$ and R$^{13}$ taken together with the nitrogen ring to which they are attached form a heterocyclyl ring optionally substituted with one to three —OH, CN, —OC$_{1-6}$alkyl or oxo;

R$^{14}$ and R$^{15}$ are each independently selected from —H and —C$_{1-6}$alkyl;

n is 0, 1 or 2;

or a pharmaceutically acceptable salt thereof.

2. A compound according to claim 1, wherein:

R$^1$ and R$^2$ are each independently hydrogen, methyl, ethyl, propyl, isopropyl, butyl, isobutyl, tert. butyl, pentyl, hexyl, cyclopropyl, cyclobutyl, cyclopentyl or cyclohexyl, with the proviso that both R$^1$ and R$^2$ are not hydrogen;

R$^3$ is pyridinyl, pyrimidinyl, pyrazinyl, pyridazinyl, pyrrolyl, imidazolyl, thienyl, furanyl or thiazolyl, wherein each heteroaryl ring is optionally independently substituted with one to three groups selected from C$_{1-3}$ alkyl, C$_{1-3}$ alkoxy, C$_{1-3}$ alkylhydroxy, amino, C$_{1-3}$ alkylamino and C$_{1-3}$ dialkylamino, oxo, —CN, halogen and 5-6 membered heteroaryl optionally substituted with one to three methyl groups; or R$^3$ is pyrrolopyrazinyl or pyrido-oxazinyl;

R$^4$ is hydrogen, methyl or fluoro;

R$^5$ is methyl, ethyl, propyl, isopropyl, butyl, isobutyl, tert-butyl, pentyl, hexyl, cyclopropyl, cyclobutyl, cyclopentyl, cyclohexyl, cycloheptyl, cyclooctyl, phenyl, piperidinyl, piperazinyl, morpholinyl, thiomorpholinyl, pyrrolidinyl, tetrahydropyranyl, pyrrolyl, thienyl, furanyl, thiazolyl, oxazolyl, isoxazolyl, pyrazolyl, imidazolyl, triazolyl, pyridinyl, pyrimidinyl, pyrazinyl, pyridazinyl, quinolinyl, isoquinolinyl, indolyl, pyrrolopyridinyl, pyrrolopyrimidinyl, pyrazolopyrimidinyl, pyrazolopyridinyl, —C(O)—R$^6$ or —NR$^7$R$^8$, wherein each R$^5$ is optionally independently substituted with one to three groups selected from R$^9$, R$^{10}$ and R$^{11}$;

R$^6$ is piperidinyl, piperazinyl, tetrahydropyranyl, morpholinyl, thiomorpholinyl or —NH-piperadinyl each optionally independently substituted with one to three groups selected from R$^9$, R$^{10}$ and R$^{11}$;

R$^7$ and R$^8$ are each independently hydrogen or C$_{1-5}$ alkyl wherein the alkyl group is optionally substituted with —OH or C$_{1-3}$alkoxy;

R$^9$, R$^{10}$ and R$^{11}$ are independently selected from
(a) —H,
(b) —OH,
(c) halogen,
(d) —CN,
(e) —CF$_3$,
(f) C$_{1-6}$alkyl optionally substituted with one to three —OH, —N(R$^{12}$)(R$^{13}$), 3-6 membered heterocycle, C$_{1-6}$alkoxy, halogen, CN, —CO$_2$R$^{12}$, —O—C$_{1-6}$alkyl-O—C$_{1-3}$alkyl, —C(O)N(R$^{12}$)(R$^{13}$) or —S(O)$_n$C$_{1-6}$alkyl,
(g) C$_{1-6}$alkoxy,
(h) —N(R$^{12}$)(R$^{13}$),
(i) —S(O)$_n$C$_{1-6}$alkyl,
(j) —CO$_2$R$^{12}$,
(k) —C(O)N(R$^{12}$)(R$^{13}$),
(l) —S(O)$_2$N(R$^{12}$)(R$^{13}$),
(m) a 3-8 membered heterocyclic group optionally substituted with one to three C$_{1-6}$ alkyl groups or oxo,
(n') oxo,
(o) —C(O)—C$_{1-3}$ alkyl,
(p) C$_{1-6}$alkenyl substituted optionally substituted with a —OH;

R$^{12}$ and R$^{13}$ are each independently selected from —H, —C$_{1-6}$alkyl, C(O)C$_{1-6}$alkyl, C$_{3-6}$ carbocycle, and a 3-6 membered heterocyclic group, each of which is optionally independently substituted with one to three C$_{1-6}$alkyl groups, halogen, —OH, C$_{1-6}$alkoxy, —C(O)N(R$^{14}$)(R$^{15}$), —S(O)$_n$C$_{1-6}$alkyl, CN, a 3-6 membered heterocyclic group, —OC$_{1-6}$alkyl, CF$_3$; or, R$^{12}$ and R$^{13}$ taken together with the nitrogen ring to which they are attached can form a heterocyclyl ring optionally substituted with one to three —OH, CN, —OC$_{1-6}$alkyl or oxo;

R$^{14}$ and R$^{15}$ are each independently selected from —H and —C$_{1-4}$alkyl;

n is 1 or 2;

or a pharmaceutically acceptable salt thereof.

3. A compound according to claim 1, wherein:

R$^1$ and R$^2$ are each independently hydrogen, methyl, ethyl, propyl, isopropyl, tert-butyl, cyclopropyl or cyclobutyl, with the proviso that both R$^1$ and R$^2$ are not hydrogen;

or a pharmaceutically acceptable salt thereof.

4. A compound of formula (I) according to claim 1, wherein:

R$^3$ is pyridinyl, pyrazinyl, pyridazinyl or pyrimidinyl, wherein each heteroaryl ring is optionally independently substituted with one to two groups selected from C$_{1-3}$ alkyl, C$_1$-C$_3$ alkoxy, C$_{1-2}$ alkylhydroxy, dimethylpyrrole, oxo, —CN, halogen, C$_{1-3}$ alkylamino and amino; or R³ is pyrrolopyrazinyl or pyrido-oxazinyl;
or a pharmaceutically acceptable salt thereof.

5. A compound of formula (I) according to claim 1, wherein:
R⁵ is methyl, ethyl, propyl, isopropyl, butyl, pentyl, hexyl, cyclopropyl, cyclobutyl, cyclopentyl, cyclohexyl, phenyl, piperidinyl, piperazinyl, morpholinyl, tetrahydropyranyl, thiazolyl, oxazolyl, isoxazolyl, pyrazolyl, imidazolyl, pyridinyl, pyrimidinyl, pyrazinyl, pyridazinyl, quinolinyl, isoquinolinyl, pyrrolopyridinyl, pyrrolopyrimidinyl, pyrazolopyrimidinyl, pyrazolopyridinyl, —C(O)-piperizinyl, —C(O)-piperidinyl, —C(O)—NH-piperidinyl or —NR⁷R⁸, wherein each R⁵ is optionally independently substituted with one to three groups selected from R⁹, R¹⁰ and R¹¹;
R⁷ and R⁸ are each independently hydrogen or $C_1$-$C_5$ alkyl wherein the alkyl group is optionally substituted with —OH or $C_{1-3}$alkoxy;
R⁹, R¹⁰ and R¹¹ are independently selected from
(a) —H,
(b) —OH,
(c) halogen,
(d) —CN,
(e) —CF₃,
(f) $C_{1-6}$alkyl optionally substituted with one to three —OH, halogen, CN, —CO₂R¹², —O—$C_{1-6}$alkyl-O—$C_{1-3}$alkyl, —N(R¹²)(R¹³), morpholinyl, piperazinyl, $C_{1-6}$alkoxy, —SO₂$C_{1-3}$alkyl or —C(O)N(R¹²)(R¹³),
(g) $C_{1-3}$alkoxy,
(h) —N(R¹²)(R¹³),
(i) —S(O)₂$C_{1-6}$alkyl,
(j) —CO₂R¹²,
(k) —C(O)N(R¹²)(R¹³),
(l) —S(O)₂N(R¹²)(R¹³),
(m) morpholinyl, piperazinyl, piperidinyl, tetrahydropyranyl, tetrahydrothienyl, dioxotetrahydrothienyl or oxetanyl each optionally substituted with a methyl group,
(n') oxo,
(o) —C(O)—CH₃,
(p) $C_{1-6}$alkenyl substituted optionally substituted with a —OH;
R¹² and R¹³ are each independently selected from —H, $C_{3-6}$ carbocycle, 3-6 membered heterocycle and —$C_{1-6}$ alkyl, wherein the alkyl group is optionally substituted with one to three halogen, —OH, $C_{1-6}$alkoxy, 5-6 membered heterocyclic group, —C(O)N(R¹⁴)(R¹⁵) or —S(O)₂$C_{1-6}$alkyl; or
R¹² and R¹³ taken together with the nitrogen ring to which they are attached form a heterocyclyl ring selected from pyrrolidinyl, piperidinyl and morpholinyl, wherein each heterocyclic ring is optionally substituted with one to three —OH, CN, —O$C_{1-6}$alkyl or oxo;
R¹⁴ and R¹⁵ are each independently selected from —H and —$C_{1-4}$alkyl;
or a pharmaceutically acceptable salt thereof.

6. A compound according to claim 1, wherein:
R¹ and R² are each independently hydrogen, methyl, isopropyl, or cyclopropyl, with the proviso that both R¹ and R² are not hydrogen;
R³ is pyridinyl, pyrazinyl, pyridazinyl or pyrimidinyl, wherein each heteroaryl ring is optionally independently substituted with one to two groups selected from $C_{1-3}$ alkyl, methoxy, —CH₂OH, amino, —NH—CH₃, oxo, —CN, fluoro and 2,5-dimethylpyrrole; or R³ is pyrrolopyrazinyl or pyrido-oxazinyl;
R⁴ is hydrogen;
R⁵ is pyrazolyl, imidazolyl, pyridinyl, pyrimidinyl, pyrazinyl, pyridazinyl, piperazinyl, pyrazolopyrimidinyl, phenyl or —NR⁷R⁸, wherein each R⁵ is optionally independently substituted with one to three groups selected from R⁹, R¹⁰ and R¹¹;
R⁷ and R⁸ are each independently hydrogen, methyl or ethyl optionally substituted with hydroxy;
R⁹, R¹⁰ and R¹¹ are independently selected from
(a) —H,
(b) —OH,
(c) halogen,
(d) —CN,
(e) —CF₃,
(f) $C_{1-6}$alkyl optionally substituted with one to three —OH, —N(R¹²)(R¹³), morpholinyl, piperazinyl, $C_{1-3}$alkoxy, halogen, CN, —CO₂R¹², —O—$C_{1-6}$alkyl-O—$C_{1-3}$alkyl, —SO₂CH₃ or —C(O)N(R¹²)(R¹³),
(g) $C_{1-3}$alkoxy,
(h) —N(R¹²)(R¹³),
(i) —S(O)₂$C_{1-2}$alkyl,
(j) —CO₂R¹²,
(k) —C(O)N(R¹²)(R¹³),
(l) —S(O)₂N(R¹²)(R¹³),
(m) morpholinyl, piperazinyl, tetrahydropyranyl, dioxotetrahydrothienyl or oxetanyl each optionally substituted with a methyl group,
(n') oxo,
(o) —C(O)—CH₃,
(p) $C_{1-4}$alkenyl substituted optionally substituted with a —OH;
R¹² and R¹³ are each independently selected from —H, cyclopropyl, tetrahydrofuranyl, tetrahydropyranyl and —$C_{1-6}$alkyl, wherein the alkyl group is optionally independently substituted with one to three halogen, —OH, $C_{1-6}$alkoxy, tetrahydrofuranyl, tetrahydropyranyl, —C(O)N(R¹⁴)(R¹⁵), or —S(O)₂$C_{1-6}$alkyl; or
R¹² and R¹³ taken together with the nitrogen ring to which they are attached form a heterocyclyl ring selected from pyrrolidinyl, piperidinyl and morpholinyl, wherein each heterocyclic ring is optionally substituted with one to three —OH, CN, —O$C_{1-6}$alkyl or oxo;
R¹⁴ and R¹⁵ are each independently selected from —H and —$C_{1-4}$alkyl;
or a pharmaceutically acceptable salt thereof.

7. A compound according to claim 6 above, wherein:
R¹ is methyl,
R² is selected from methyl, isopropyl and cyclopropyl;
or a pharmaceutically acceptable salt thereof.

8. A compound according to claim 6, wherein:
R³ is selected from

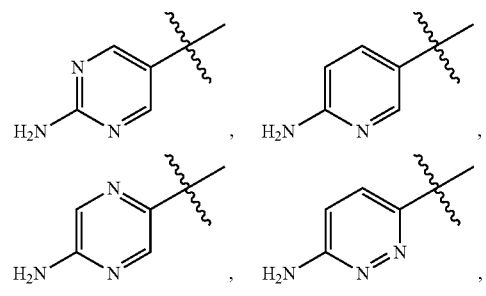

-continued

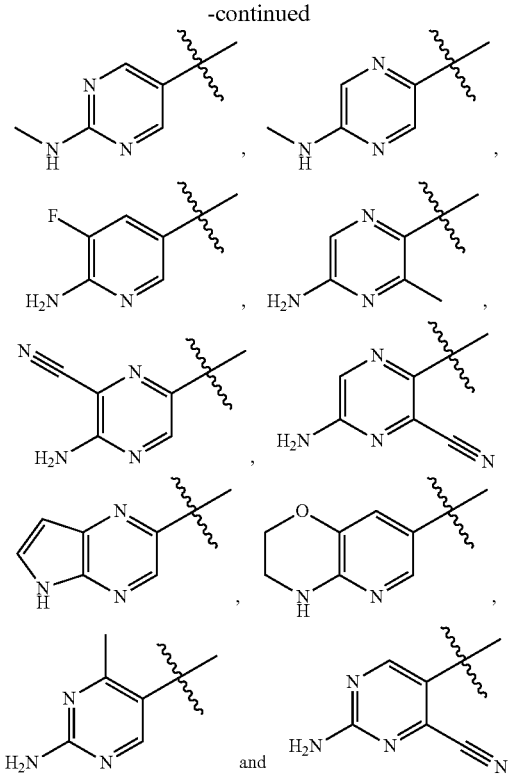

or a pharmaceutically acceptable salt thereof.

9. A compound according to claim 6, wherein:
$R^5$ is pyrazolyl optionally independently substituted with one to three groups selected from $R^9$, $R^{10}$ and $R^{11}$;
or a pharmaceutically acceptable salt thereof.

10. A compound according to claim 6, wherein:
$R^1$ is methyl,
$R^2$ is selected from methyl, isopropyl and cyclopropyl;
$R^3$ is selected from

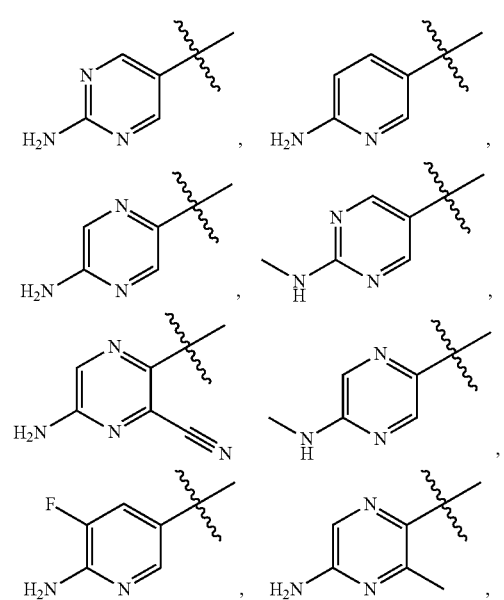

-continued

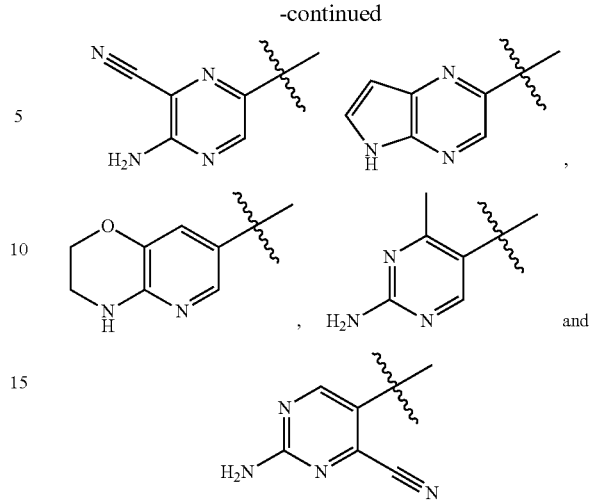

$R^4$ is hydrogen,
$R^5$ is selected from

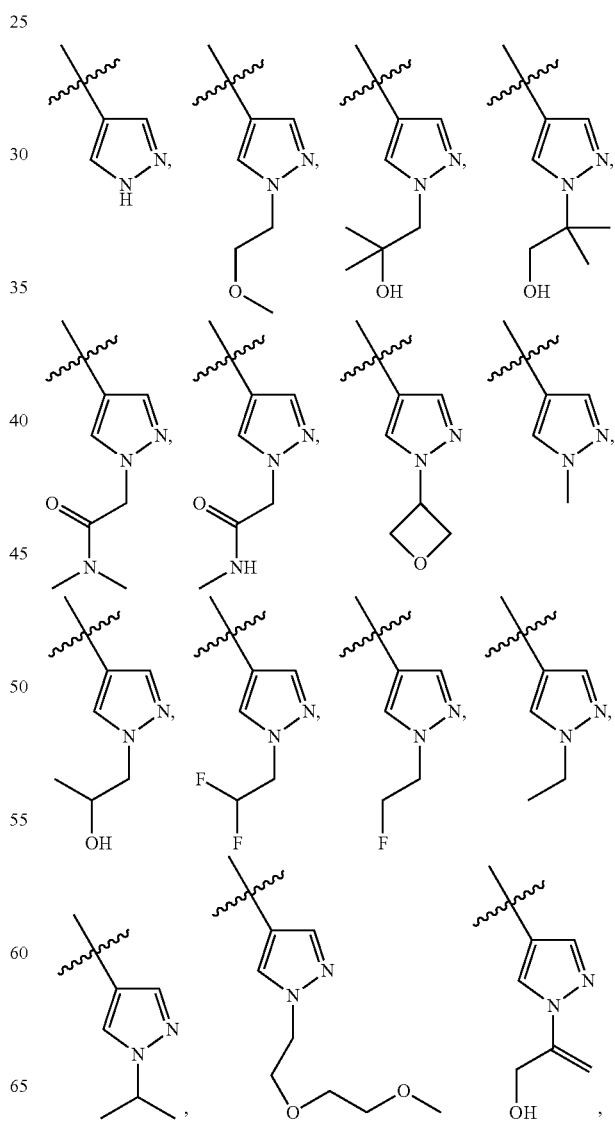

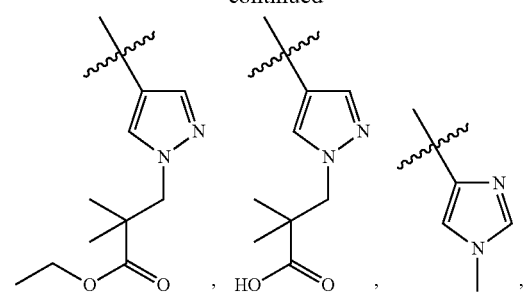
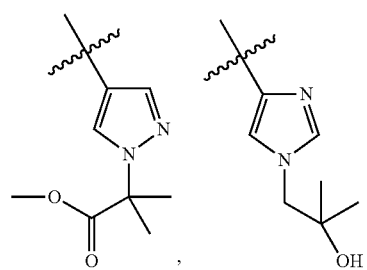
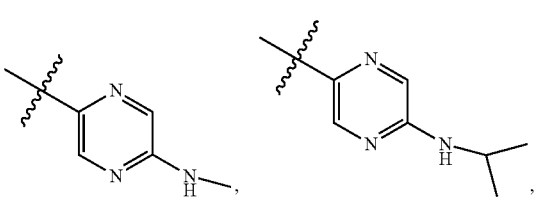
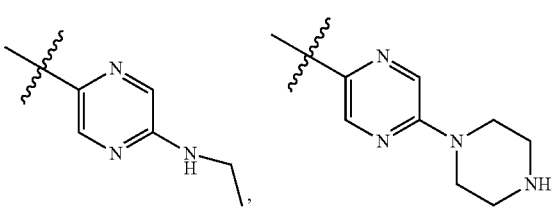
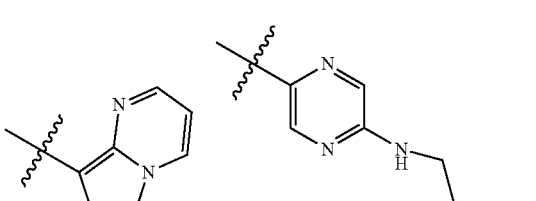
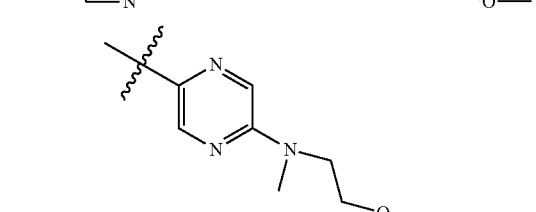
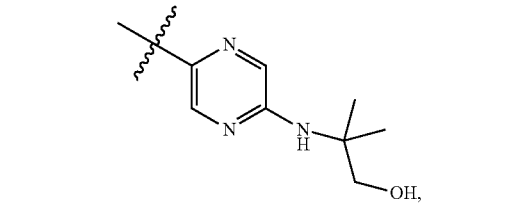
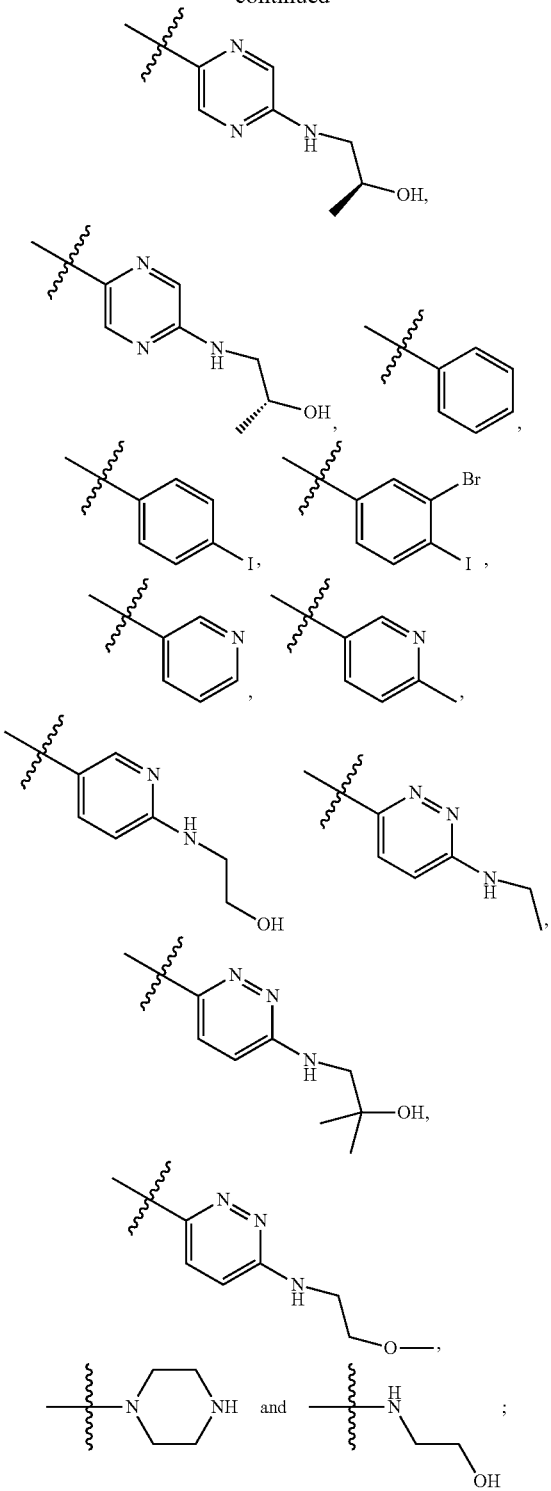
or pharmaceutically acceptable salts thereof.
11. A compound according to claim 10 above, wherein: $R^2$ is cyclopropyl;
or a pharmaceutically acceptable salt thereof.
12. A compound according to claim 10, wherein: $R^2$ is selected from methyl and isopropyl;
or a pharmaceutically acceptable salt thereof.

13. A compound selected from a group consisting of:
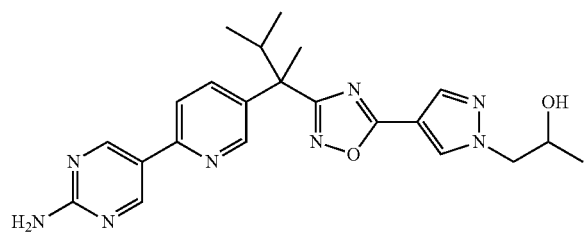
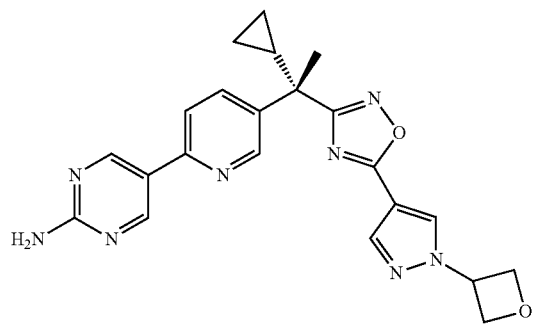
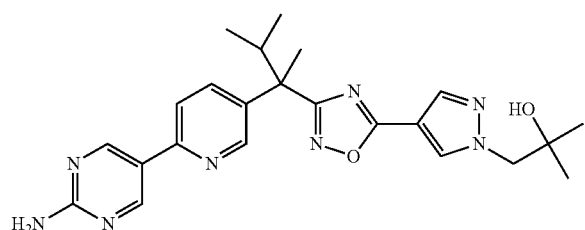
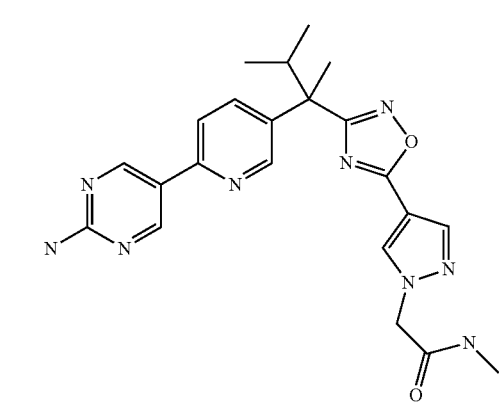
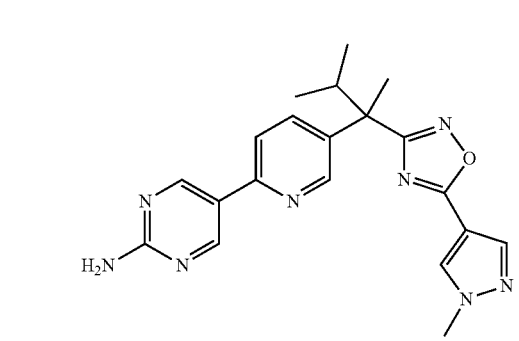
-continued
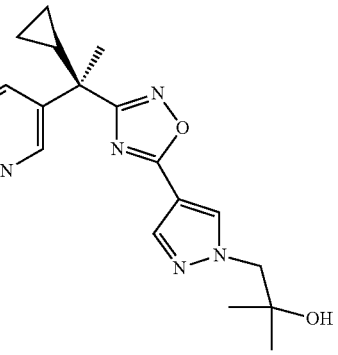
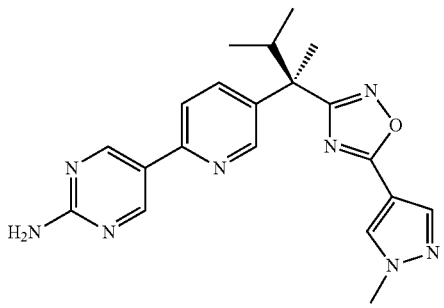
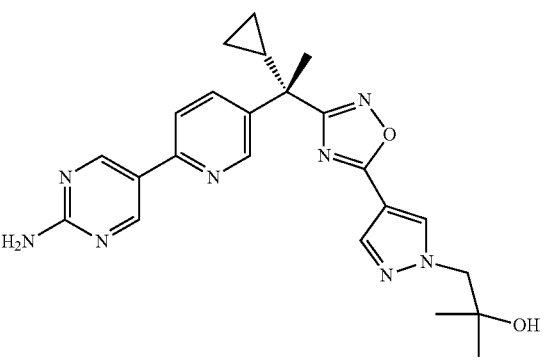
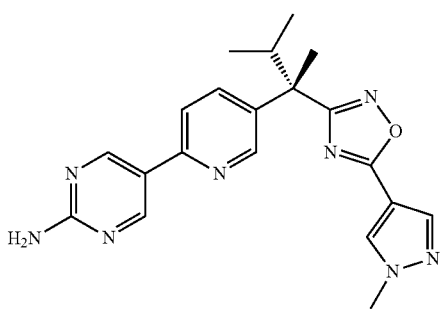
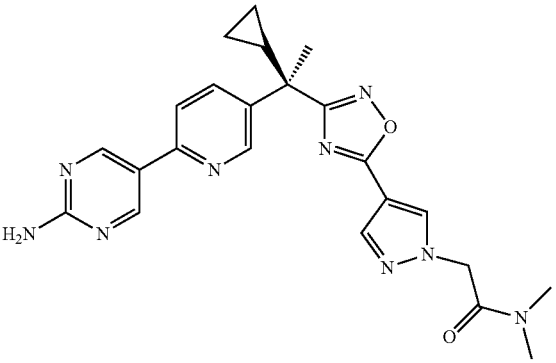

267
-continued
268
-continued
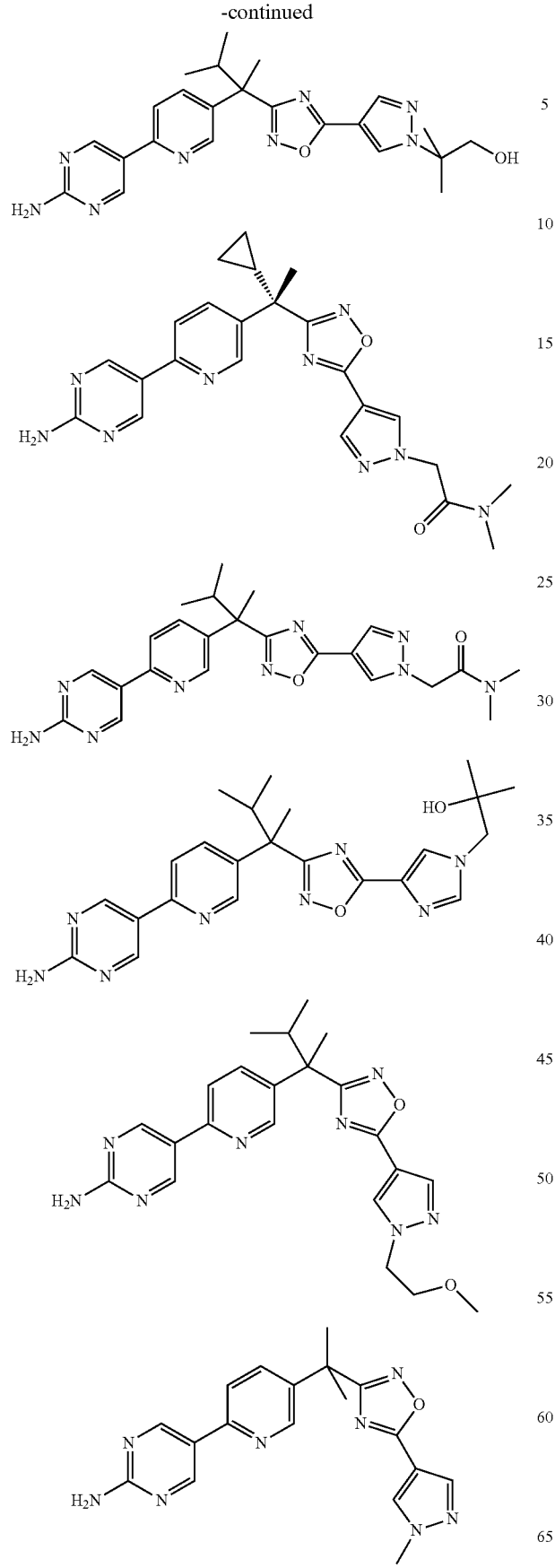
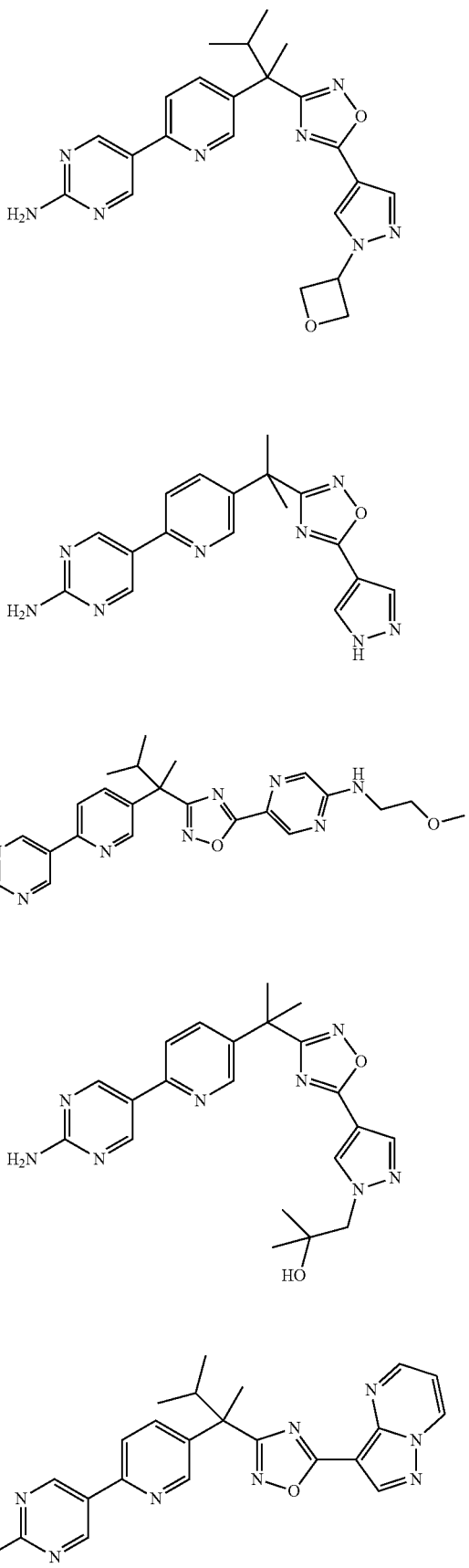

269
-continued
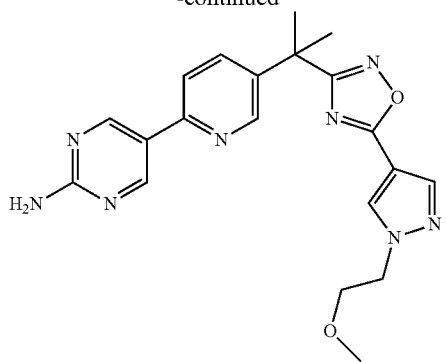
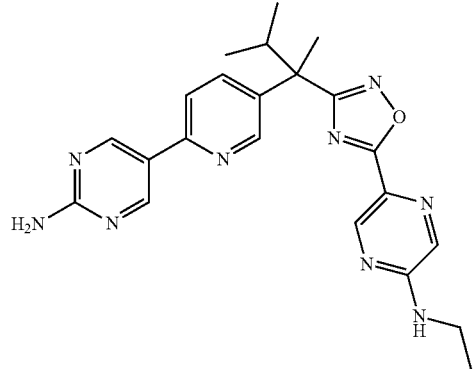
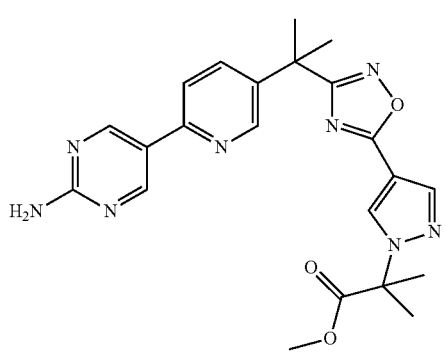
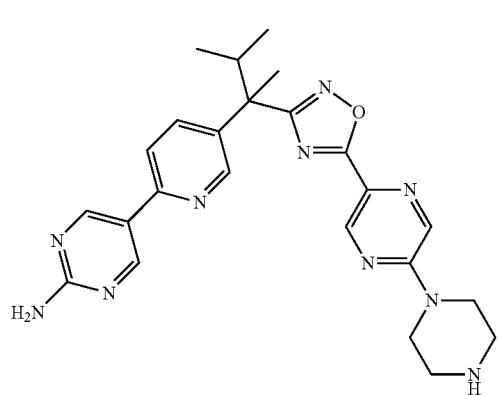
270
-continued
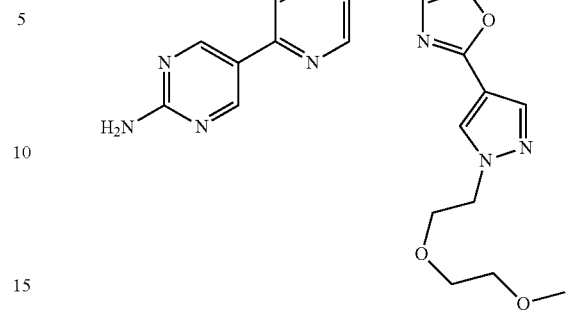
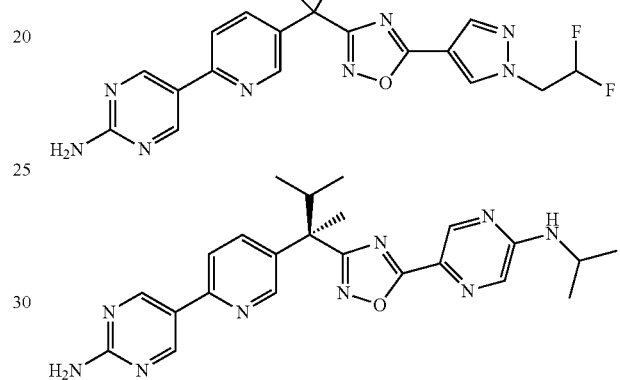
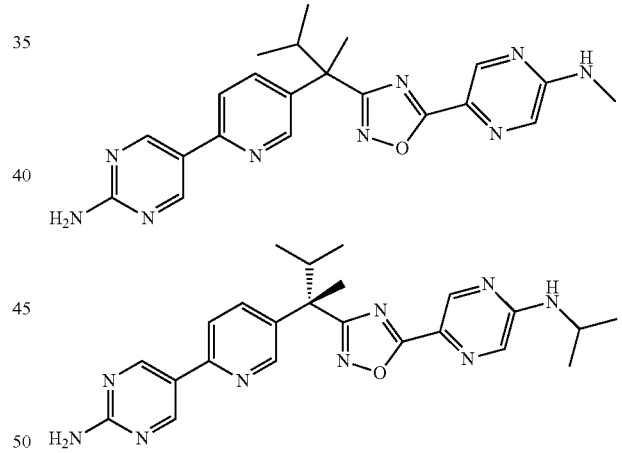
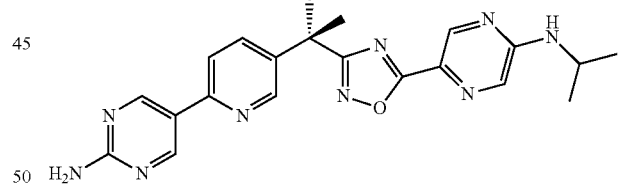
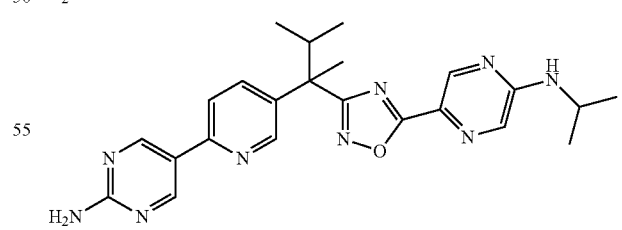
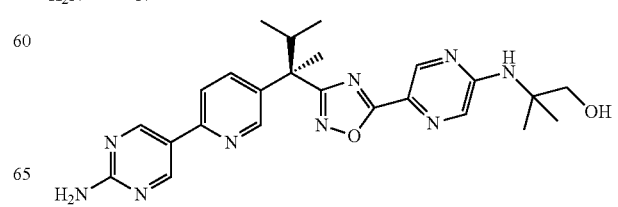

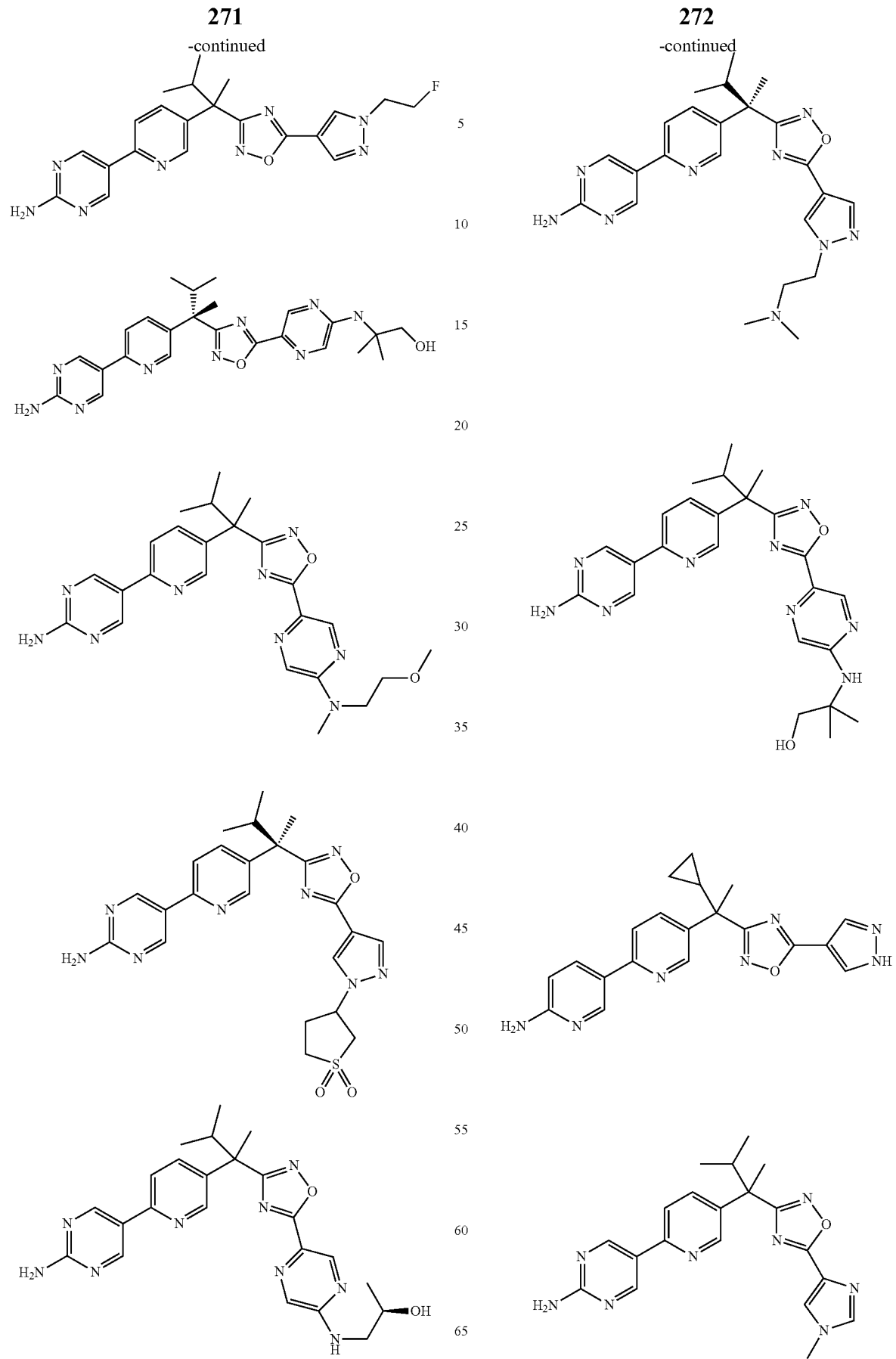

273
-continued
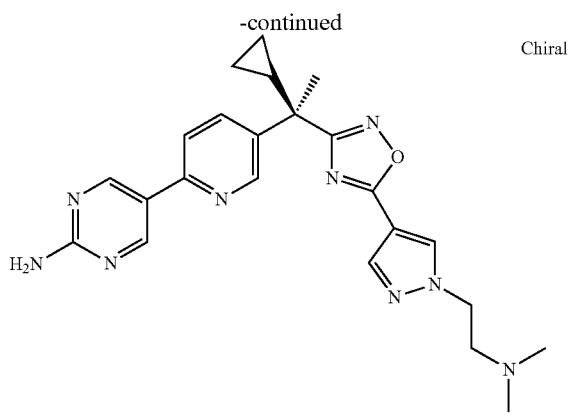
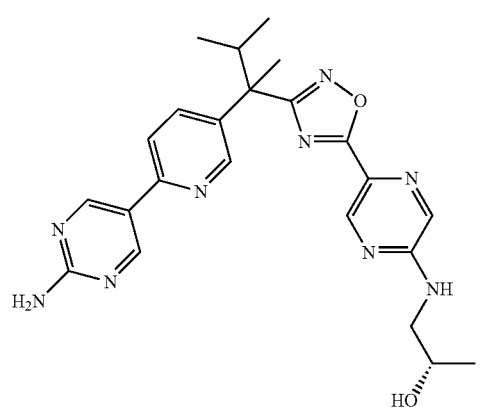
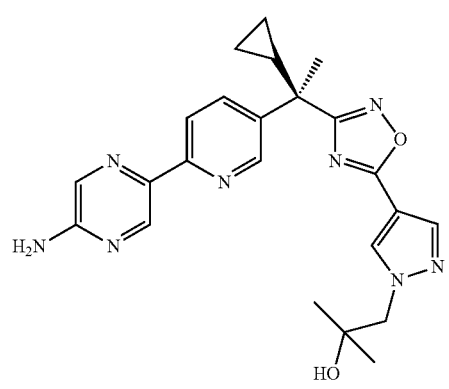
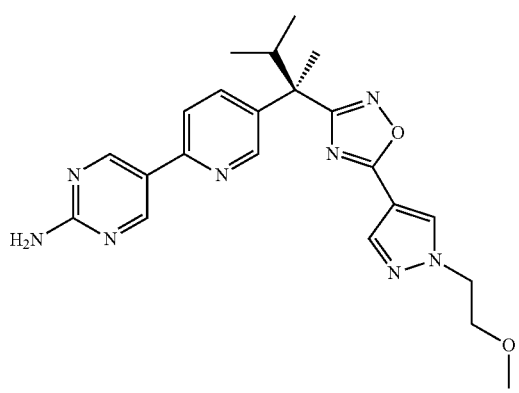
274
-continued
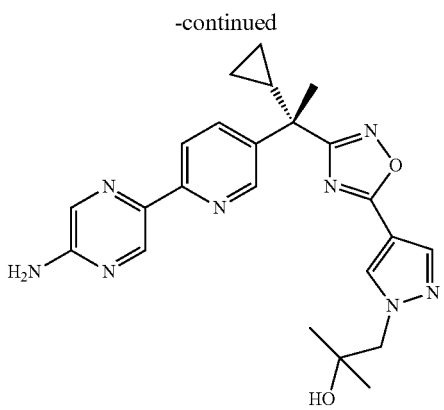
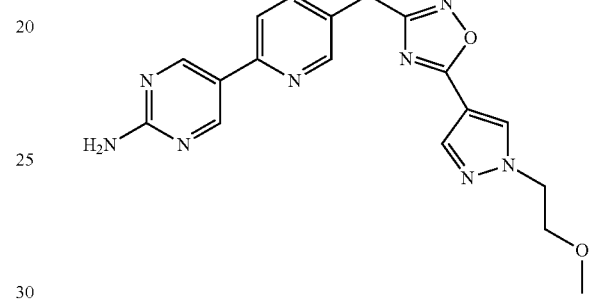
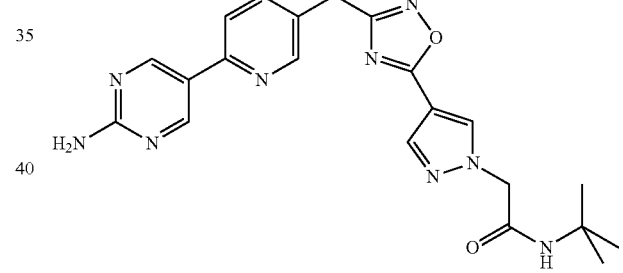
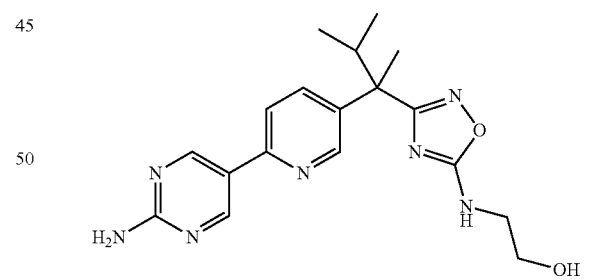
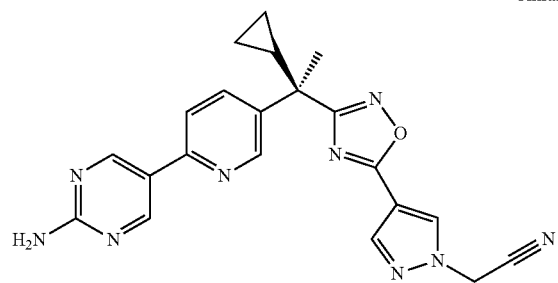

275
-continued
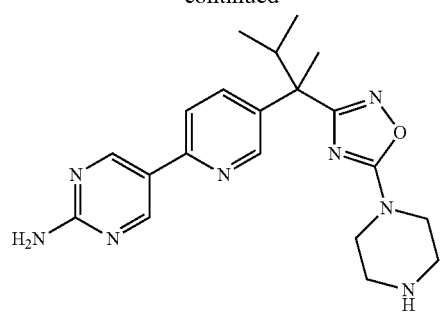
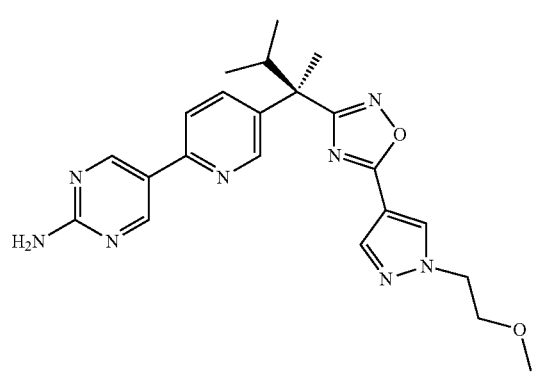
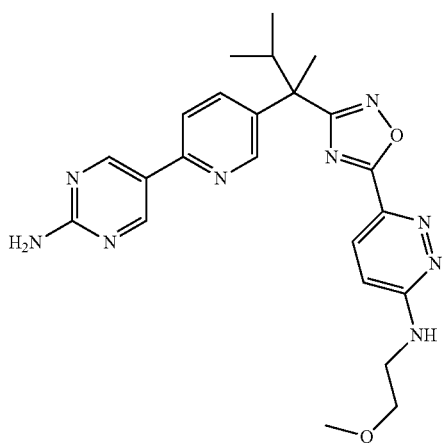
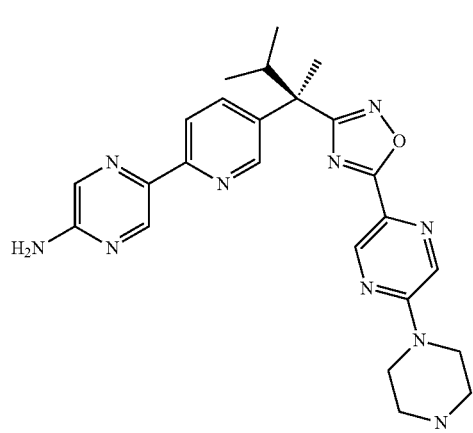
276
-continued
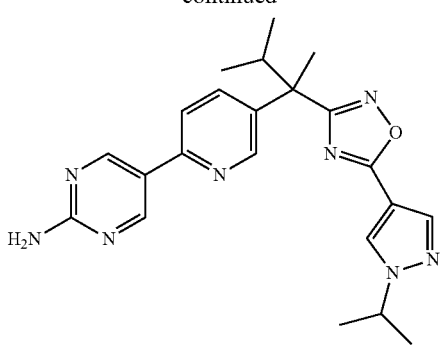
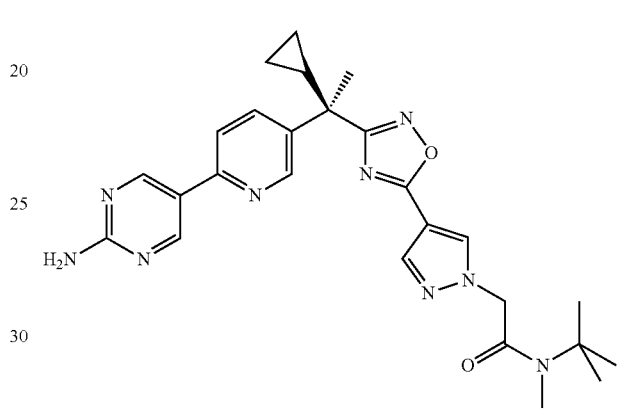
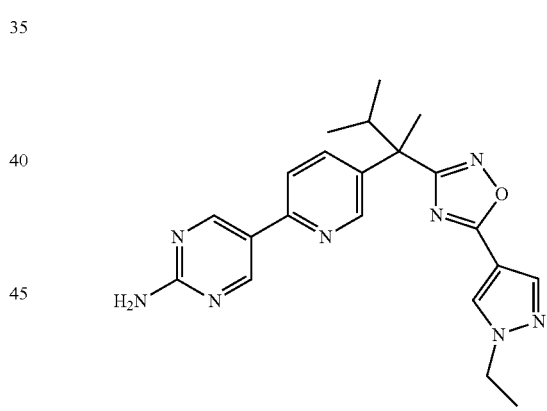
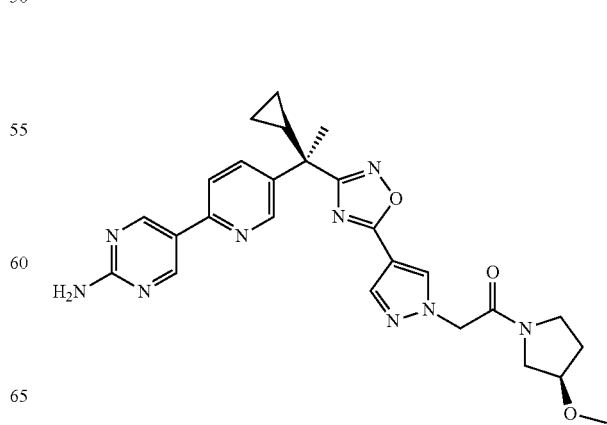

277
-continued
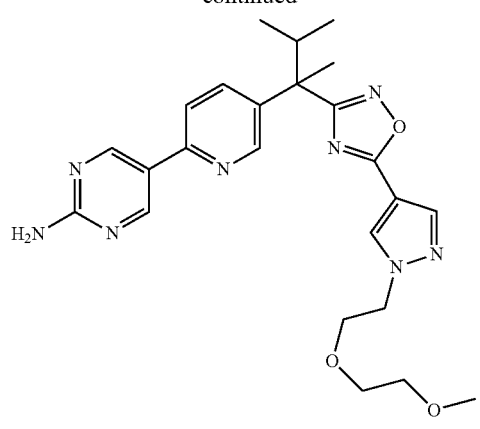
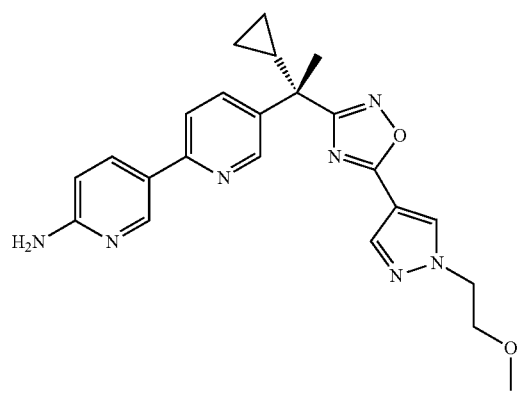
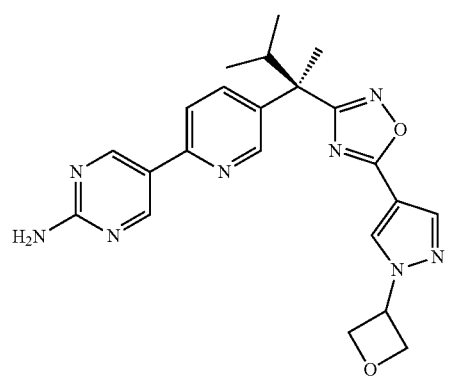
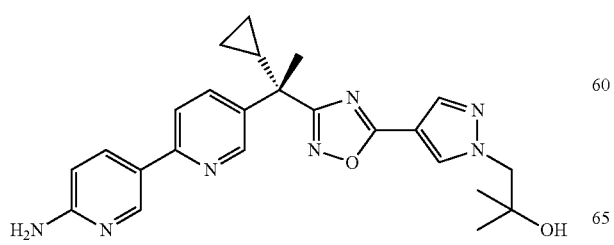
278
-continued
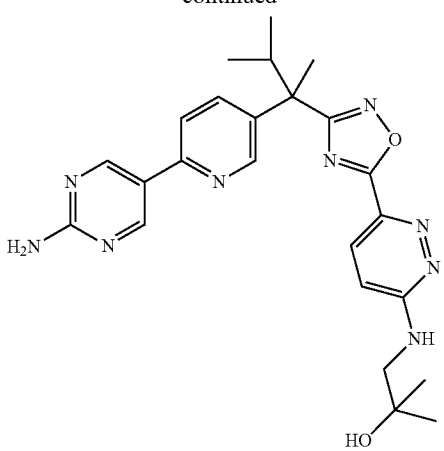
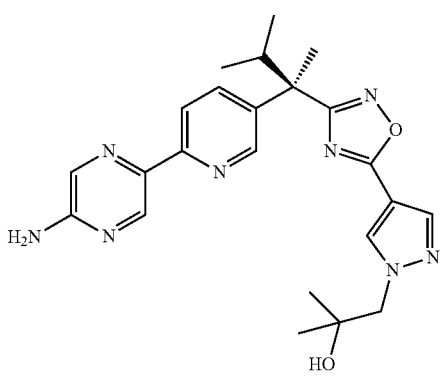
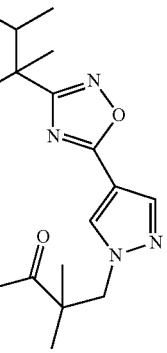
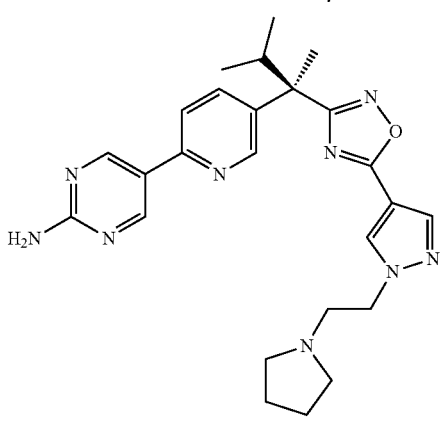

279
-continued
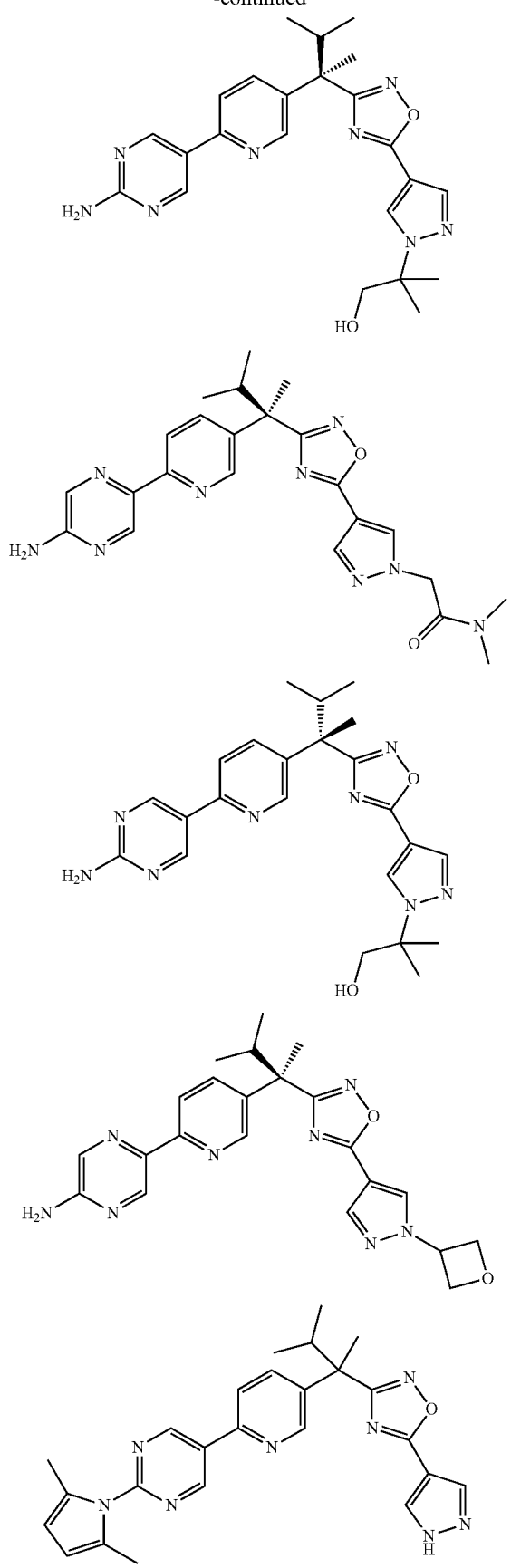
280
-continued
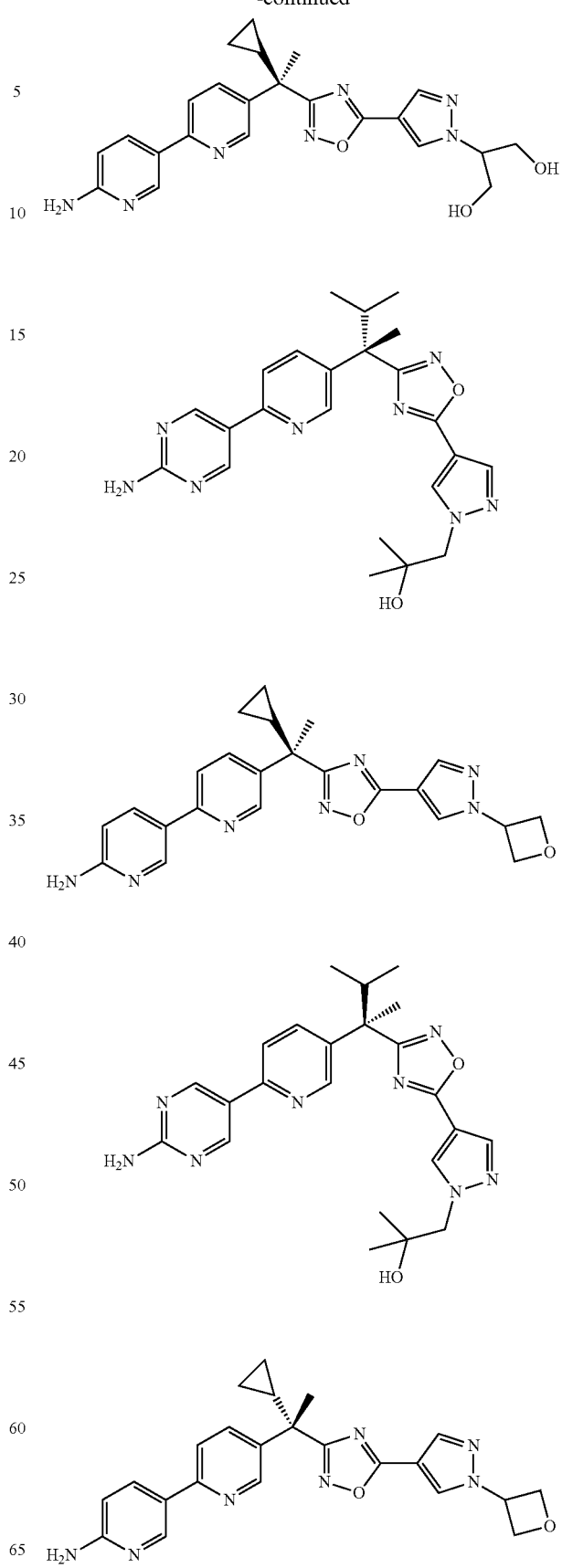

-continued
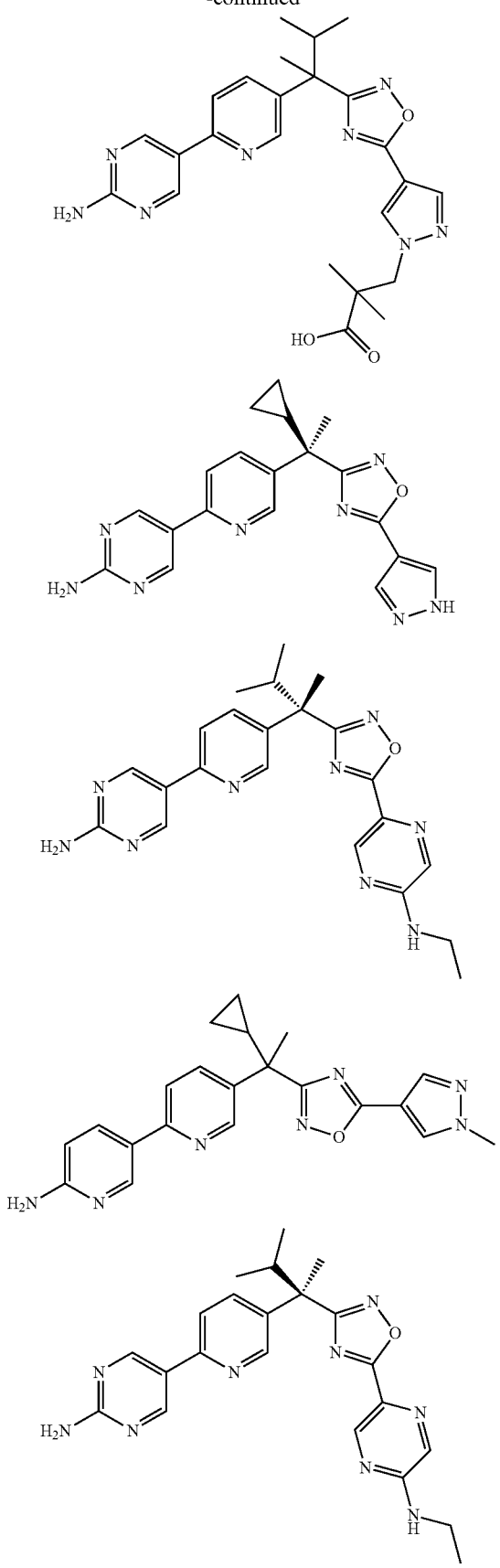
-continued
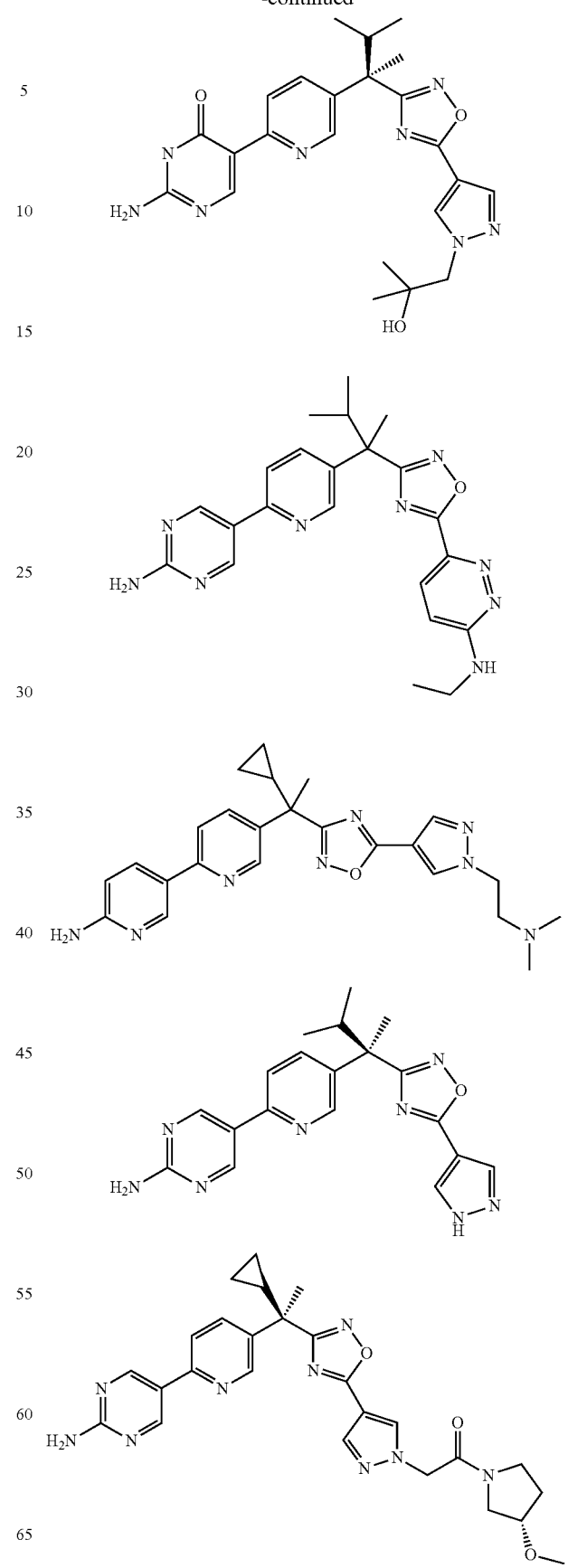

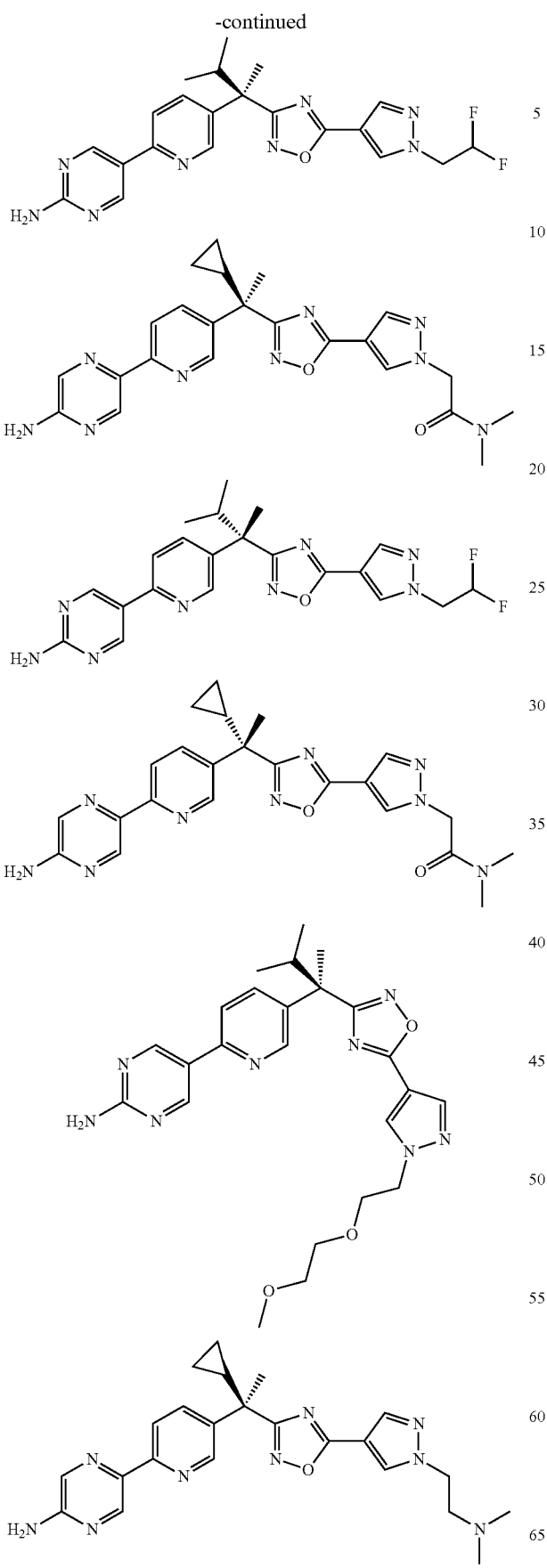
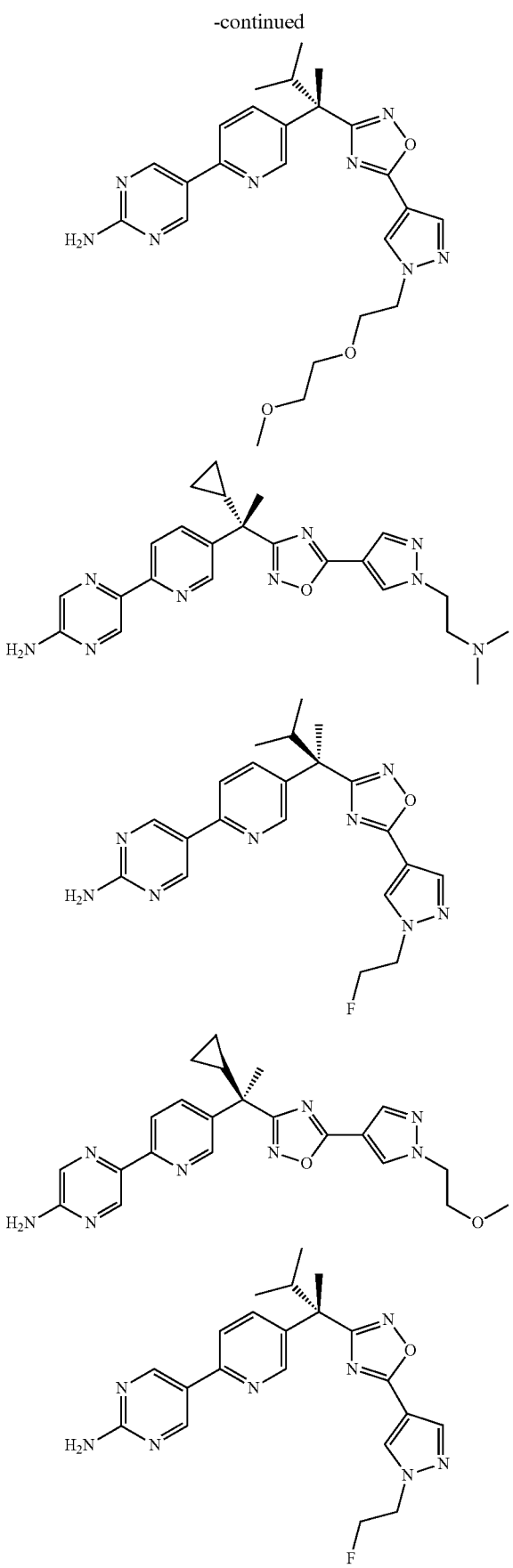

285
-continued
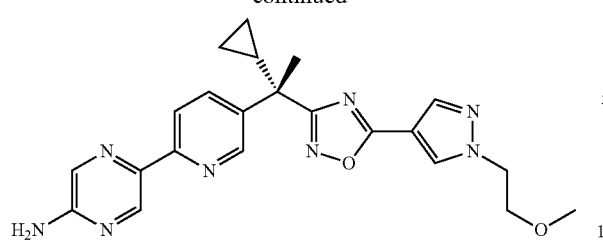
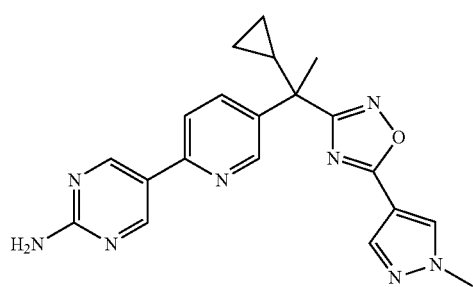
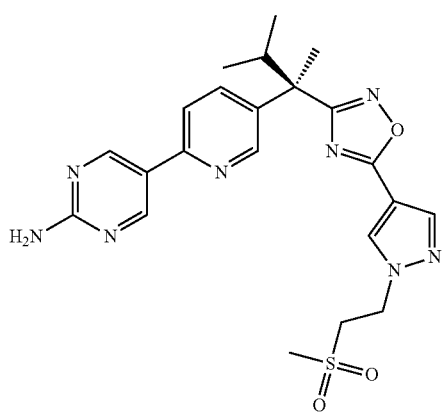
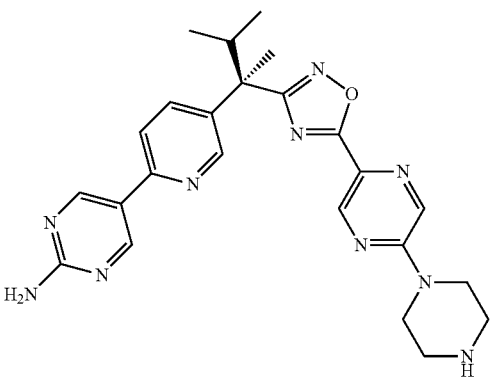
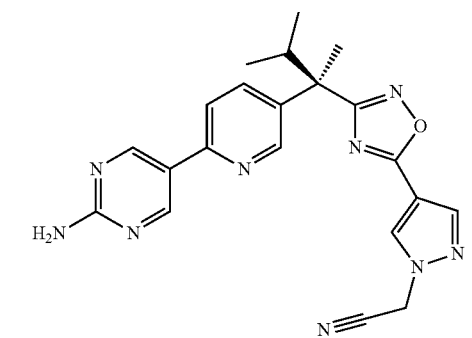
286
-continued
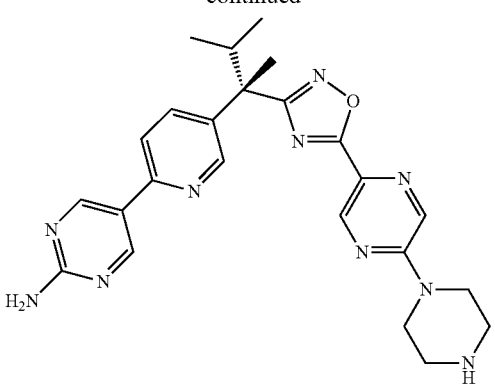
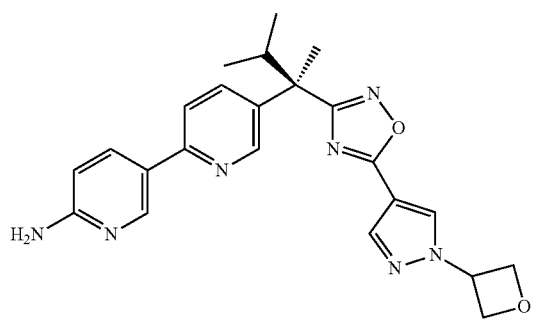
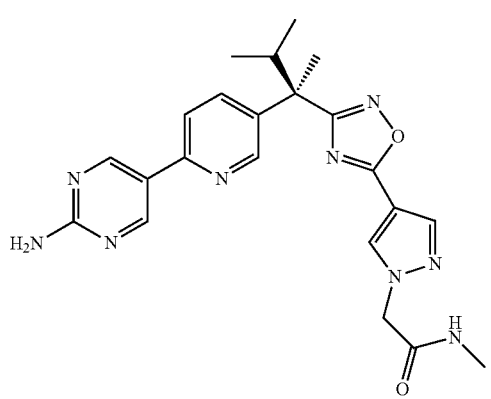
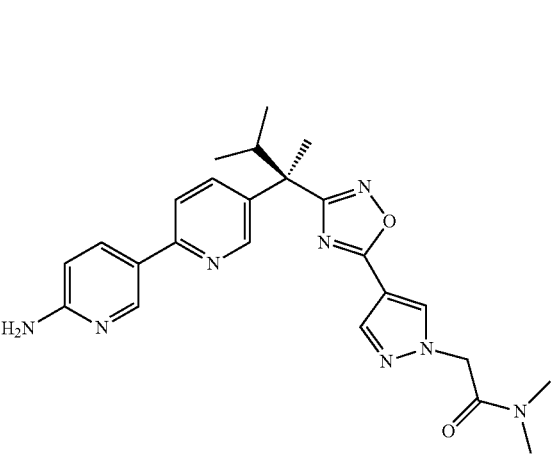

287
-continued
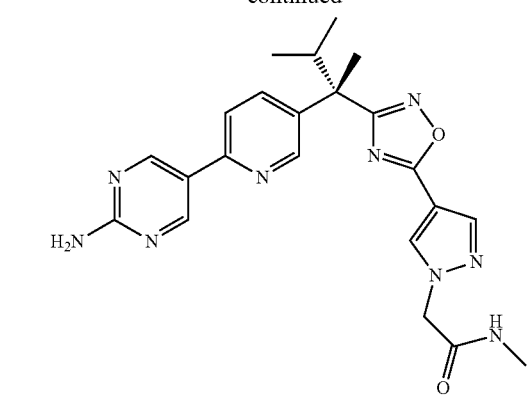
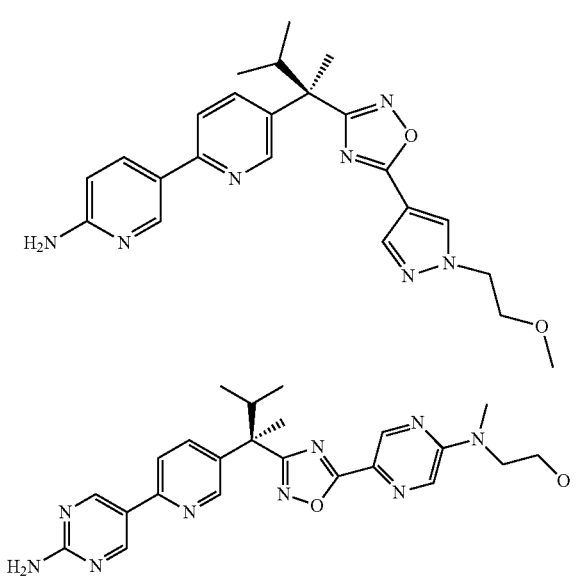
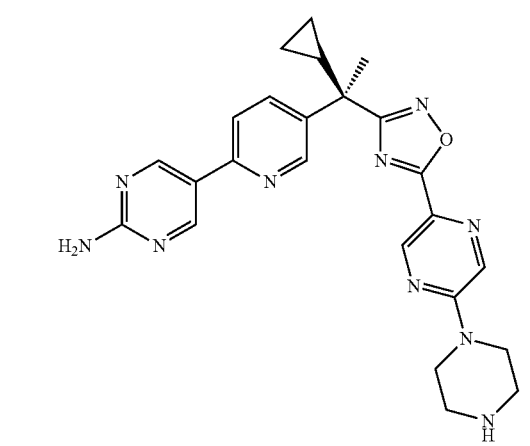
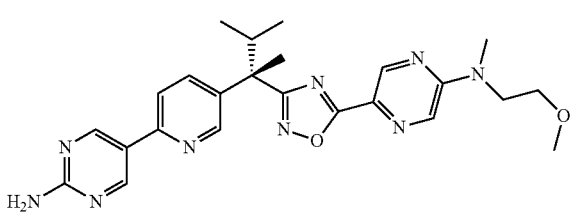
288
-continued
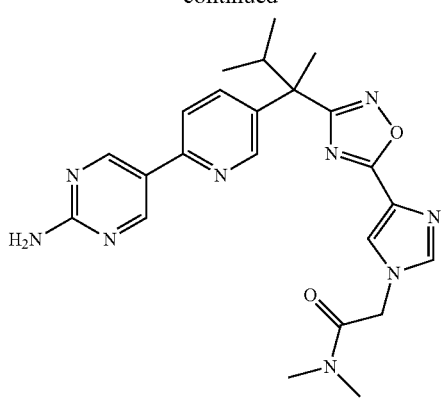
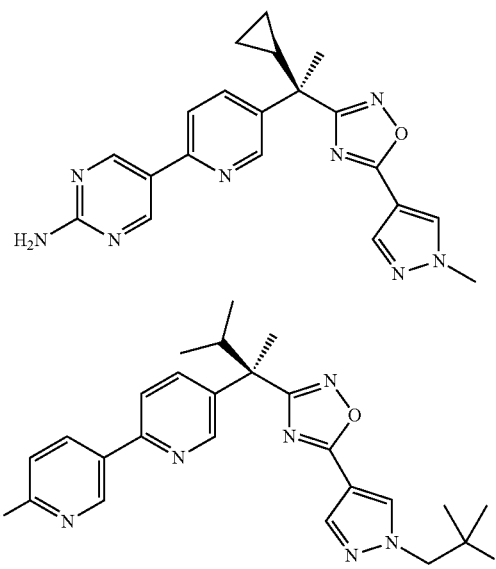
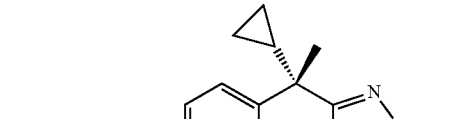
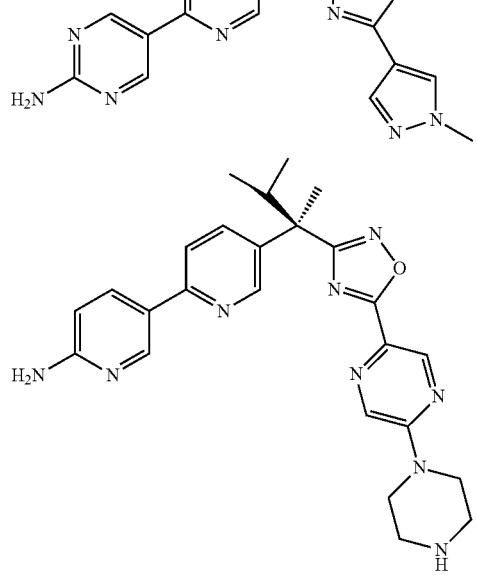

289
-continued
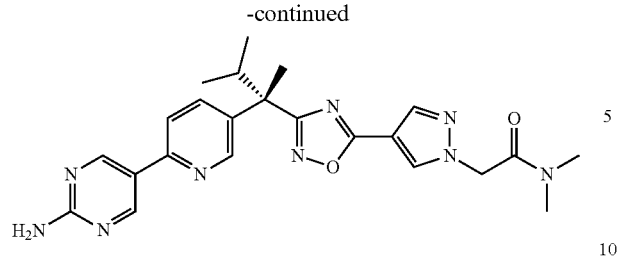
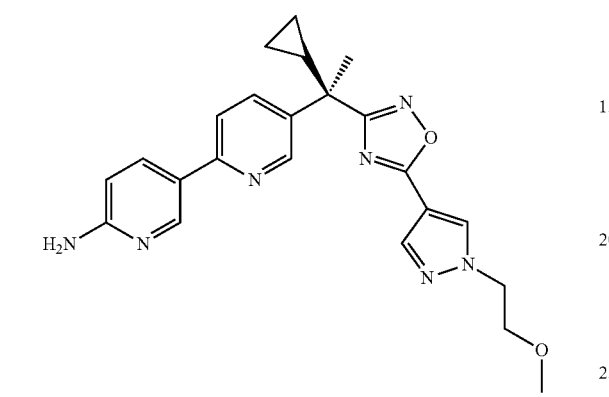
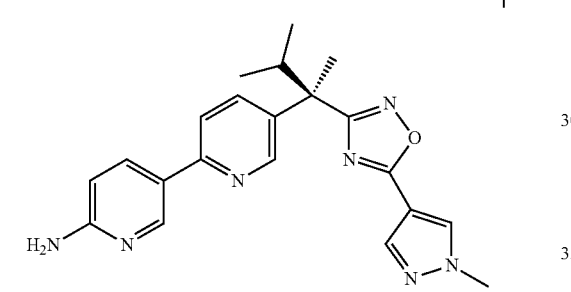
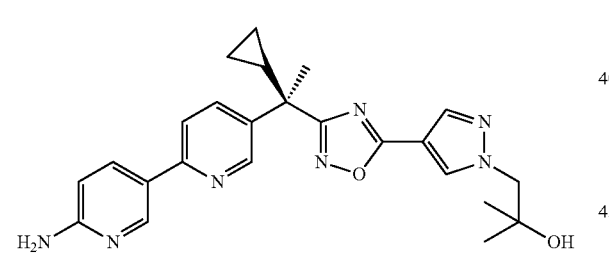
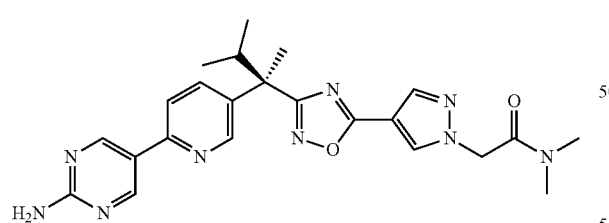
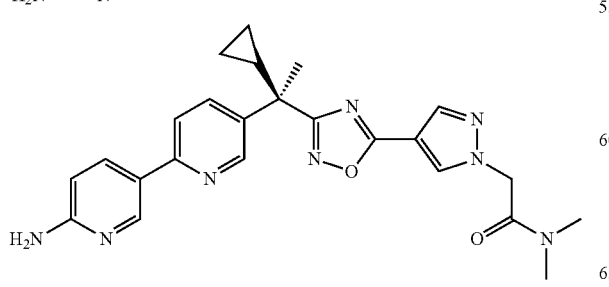
290
-continued
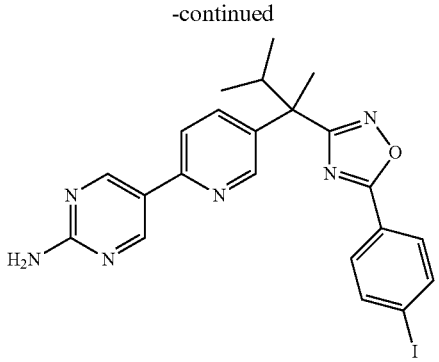
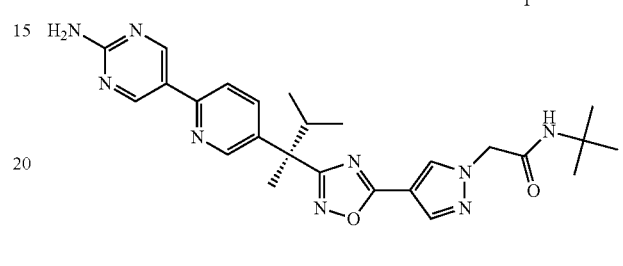
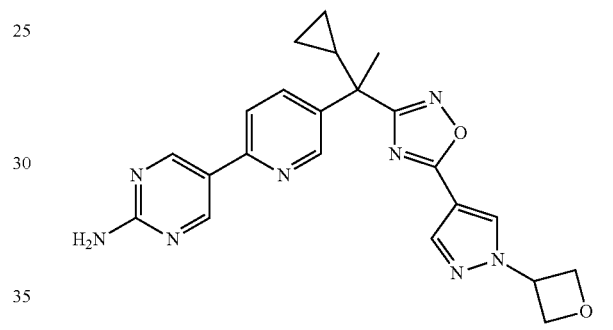
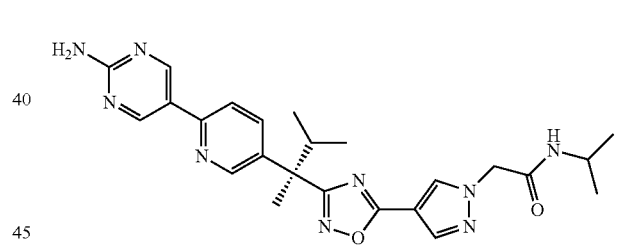
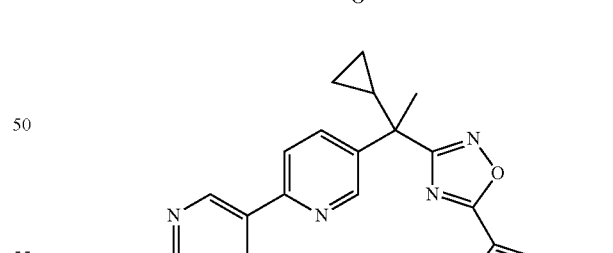
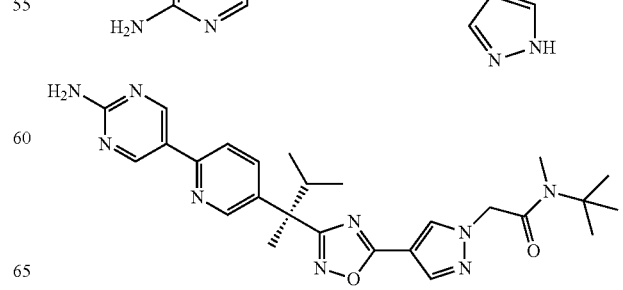

291
-continued
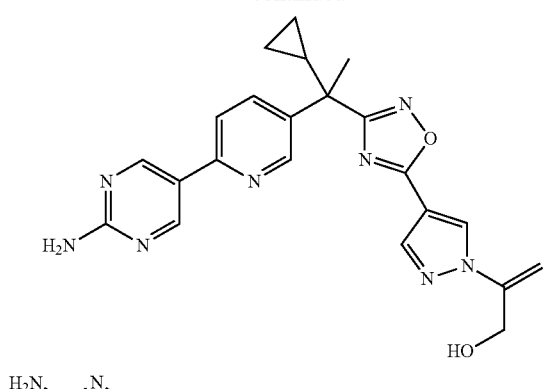
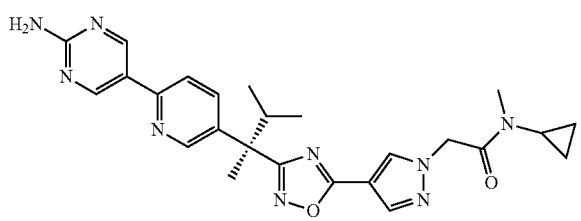
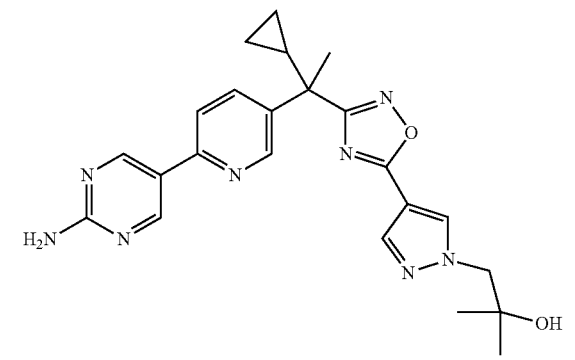
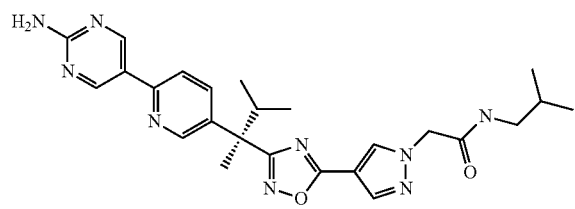
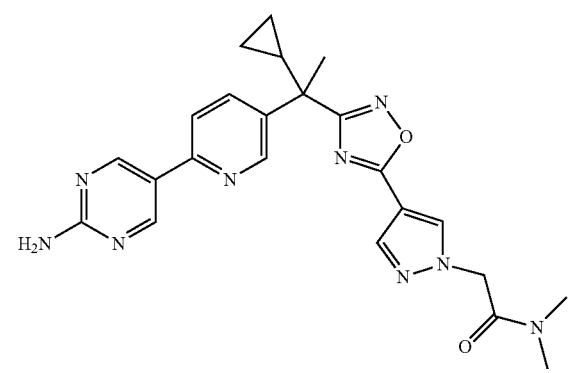
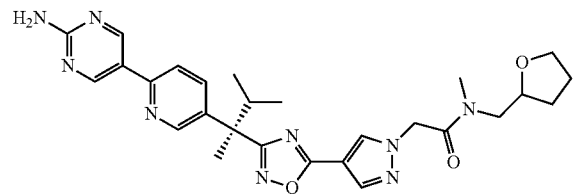
292
-continued
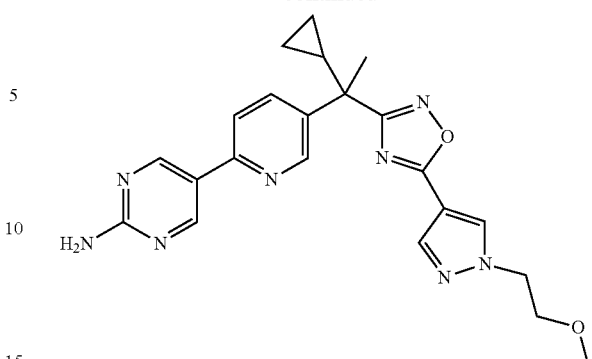
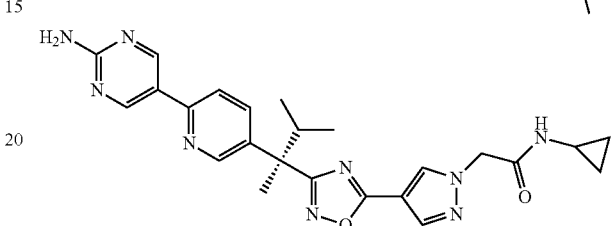
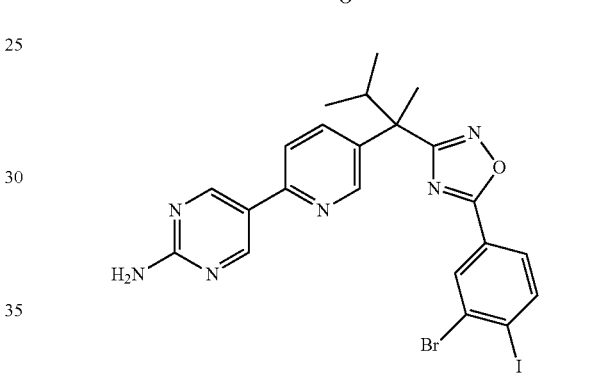
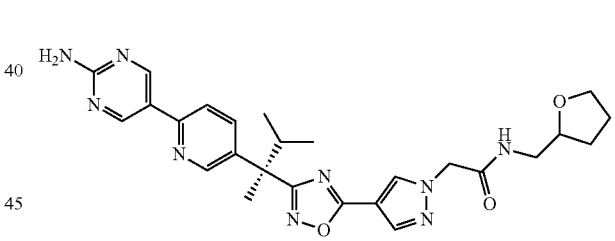
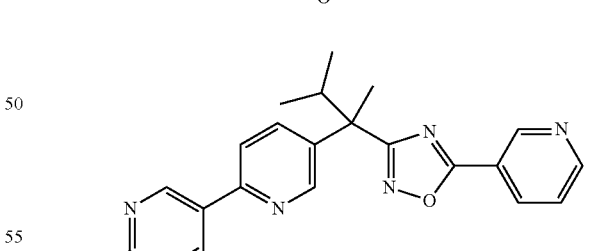
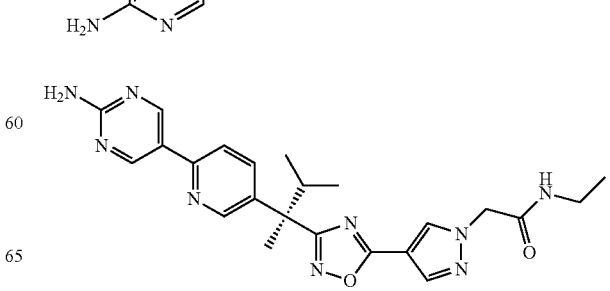

293
-continued
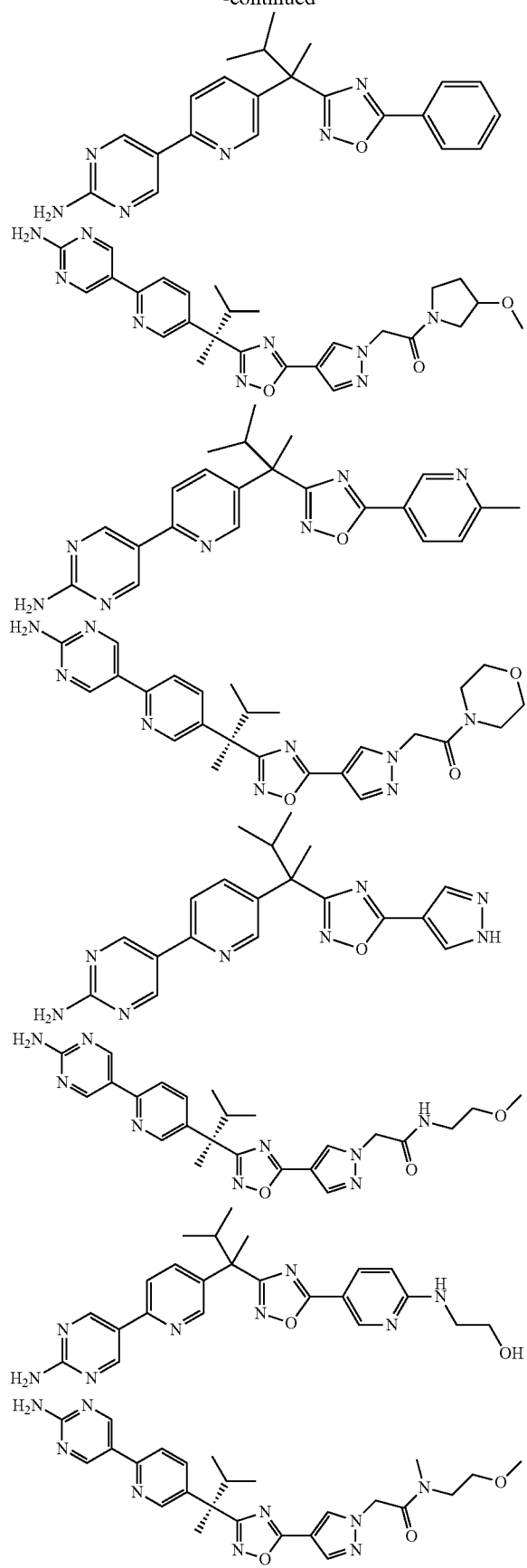
294
-continued
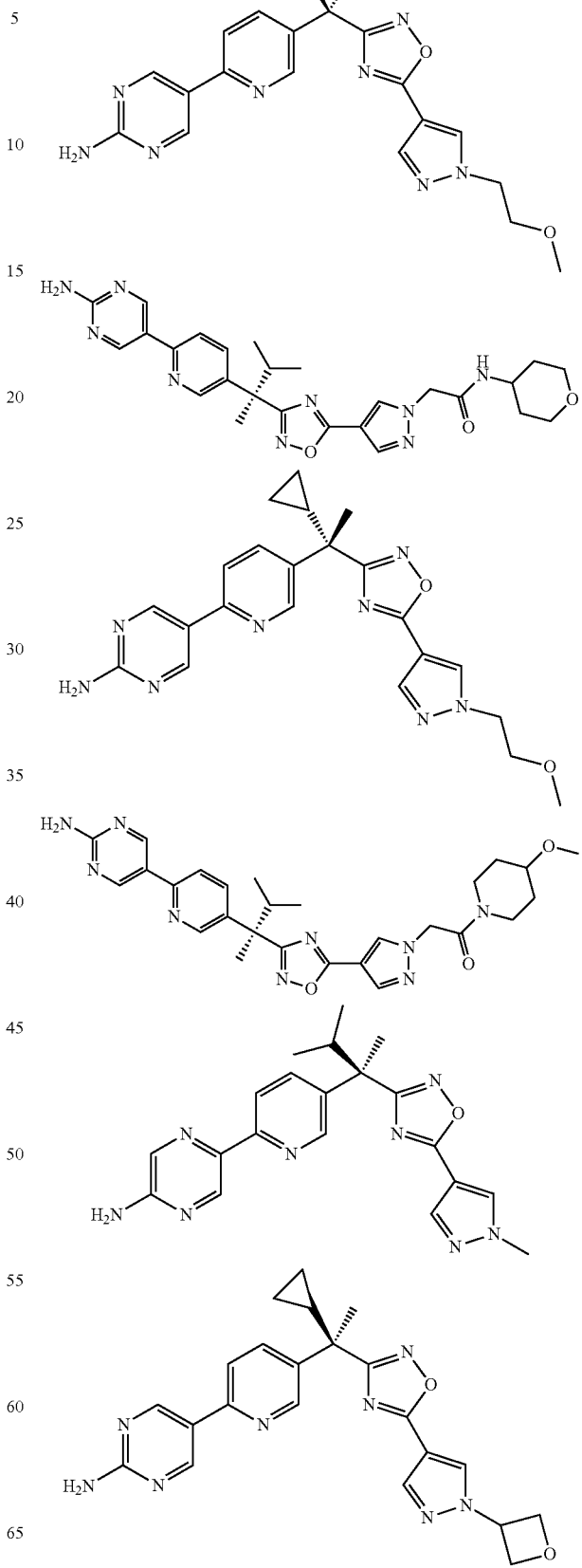

295
-continued
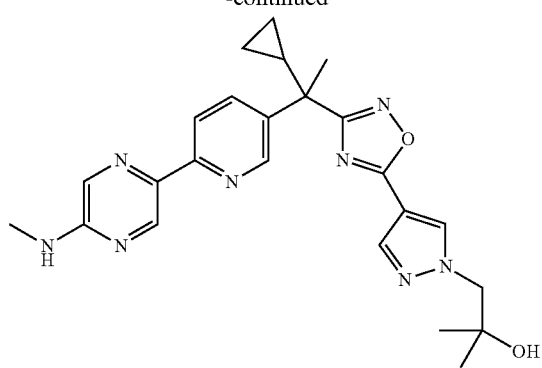
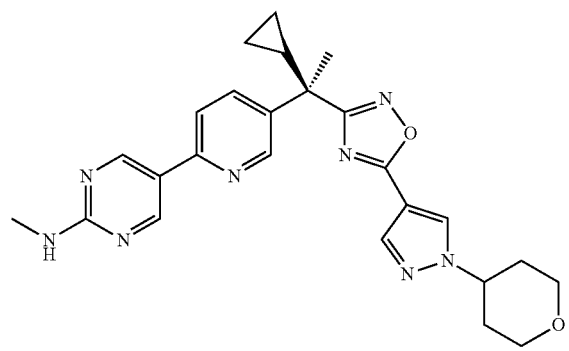
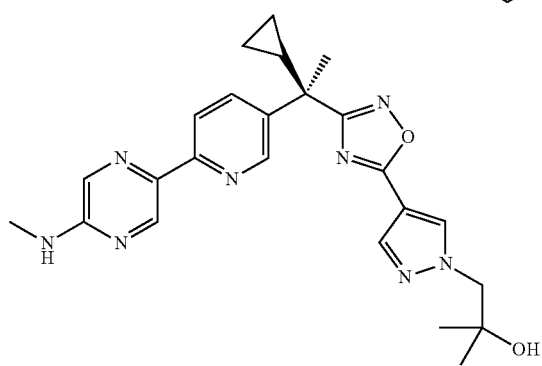
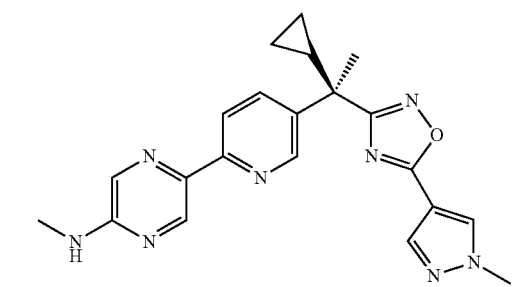
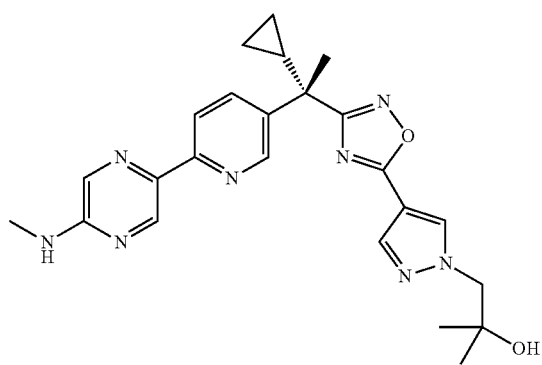
296
-continued
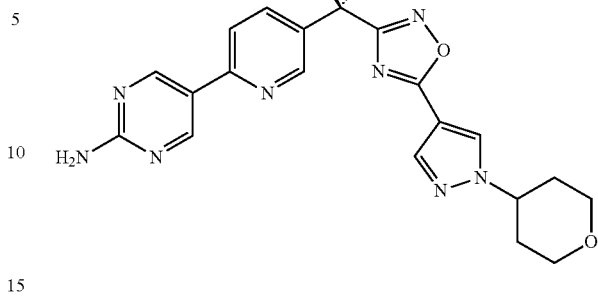
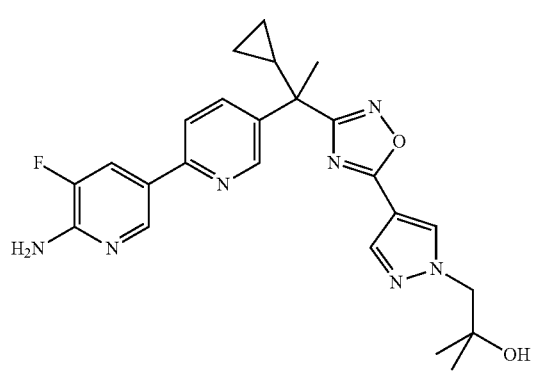
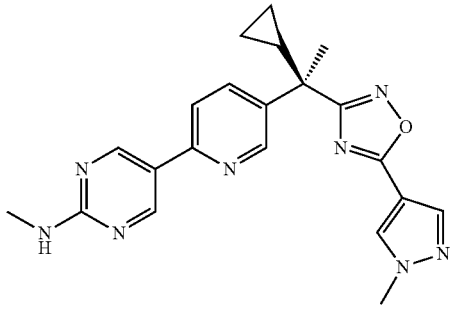
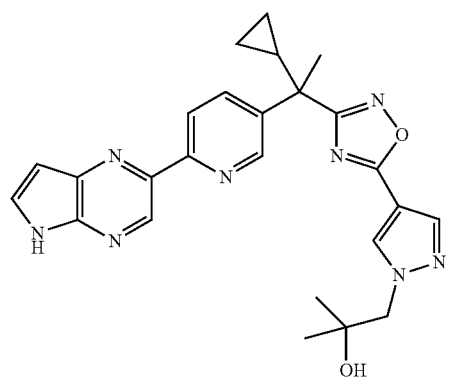

297
-continued
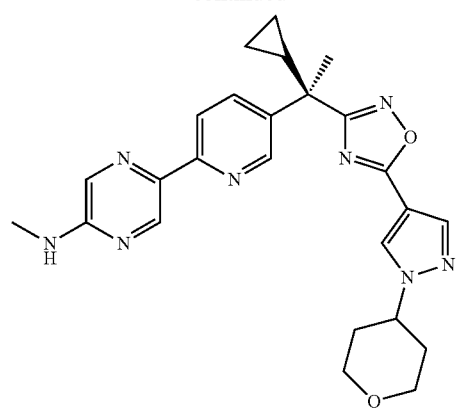
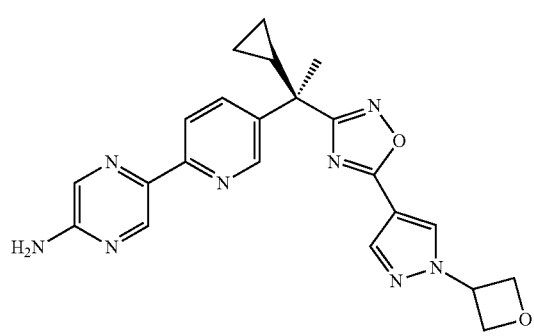
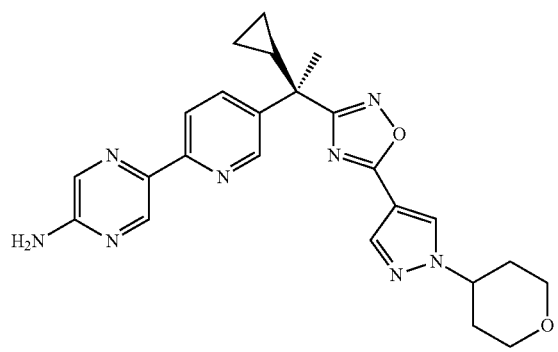
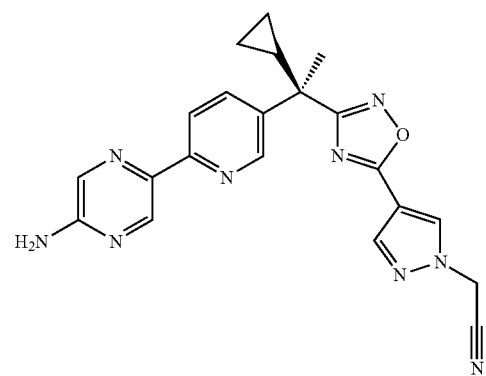
298
-continued
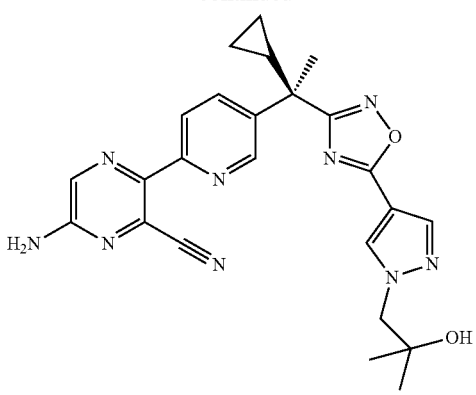
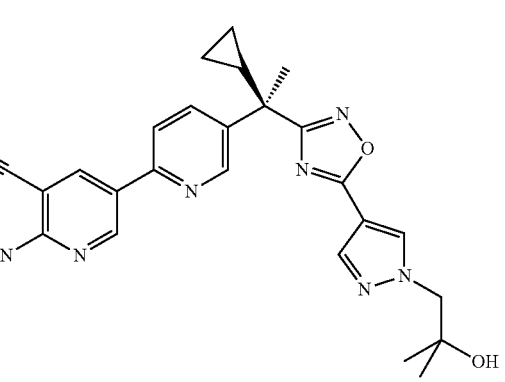
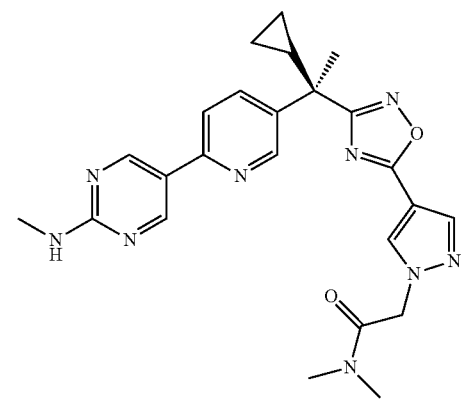
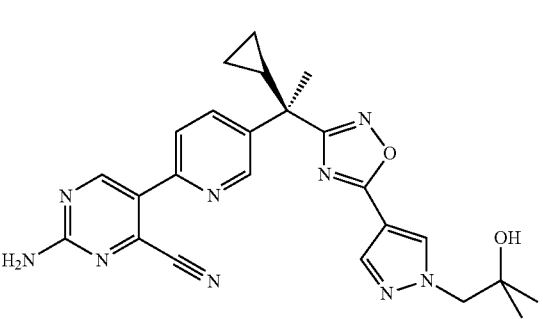

299
-continued
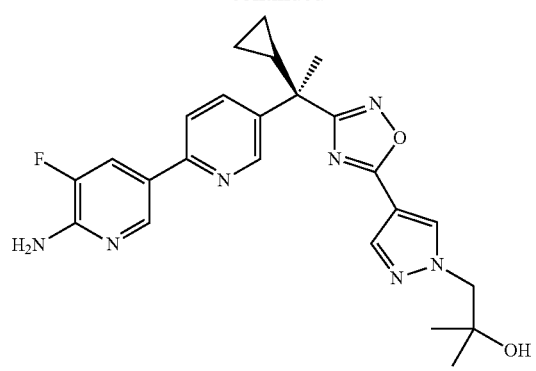
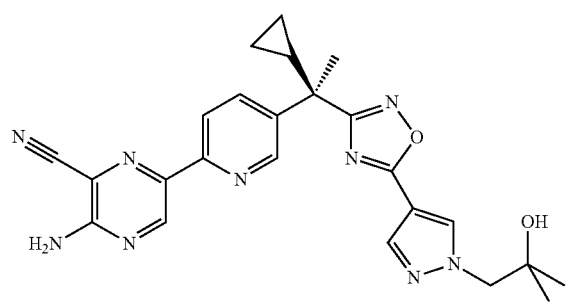
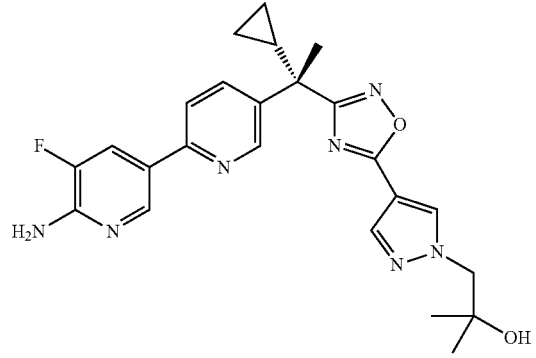
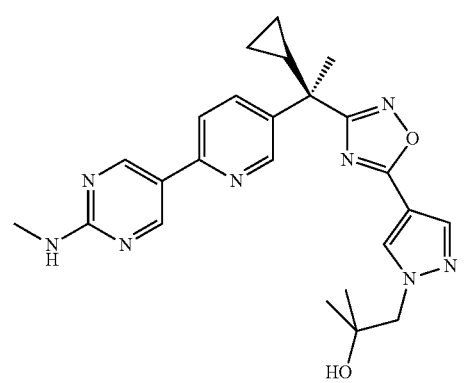
300
-continued
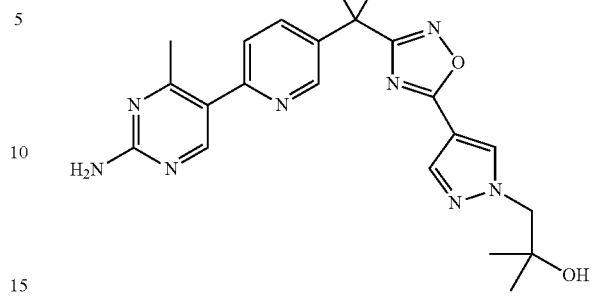
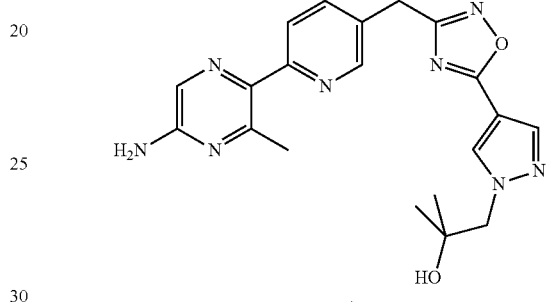
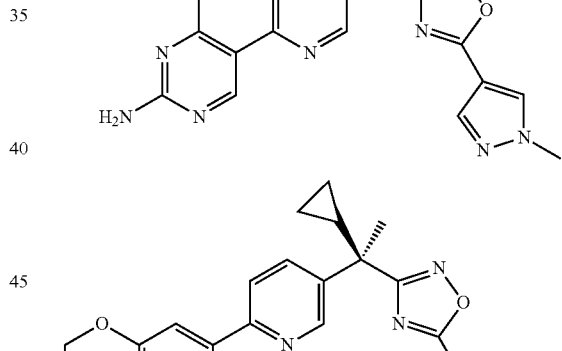
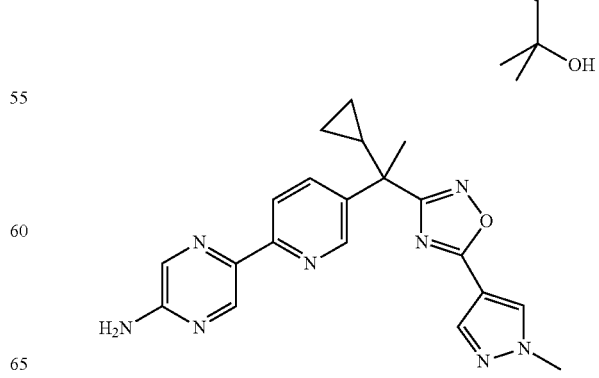

301
-continued
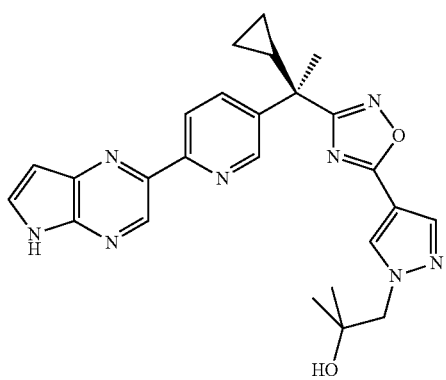
or pharmaceutically acceptable salts thereof.
14. A compound according to claim 13, selected from a group consisting of:
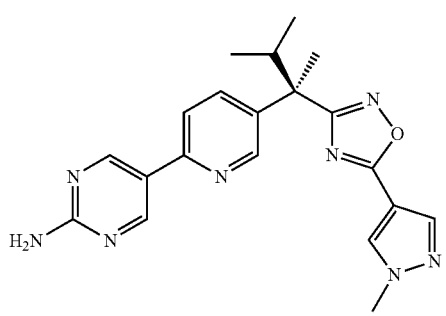
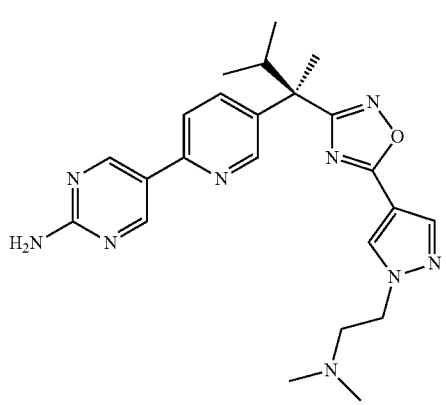
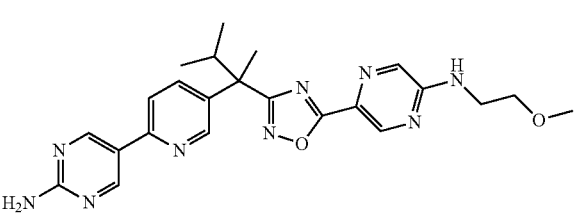
302
-continued
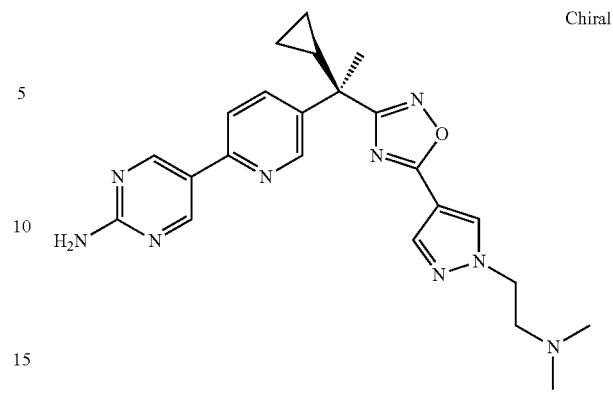
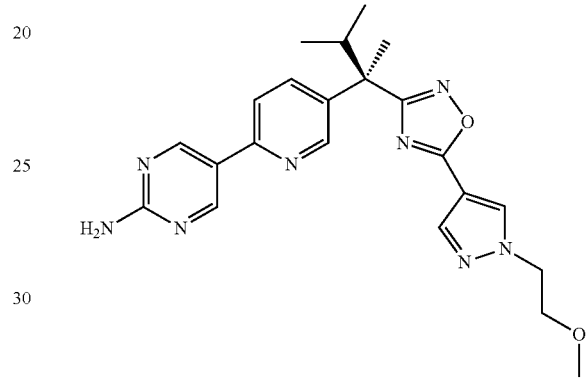
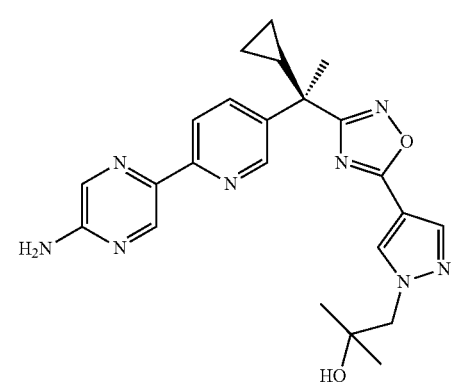
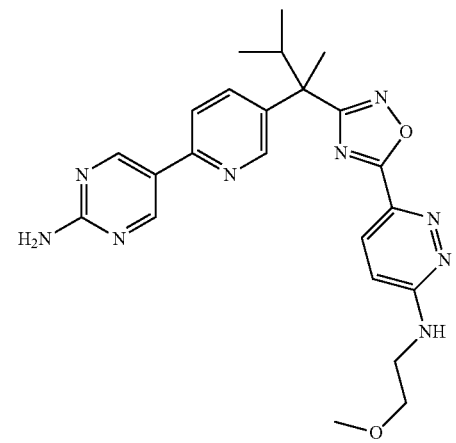

303
-continued
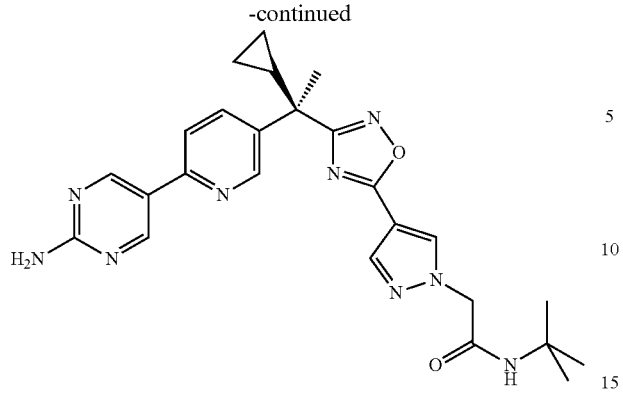
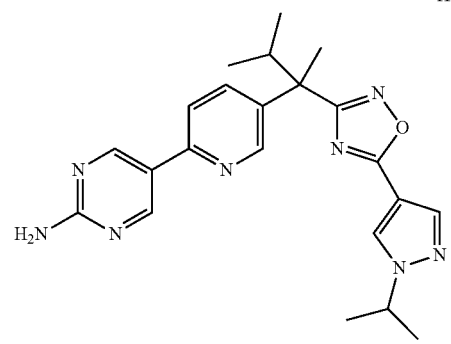
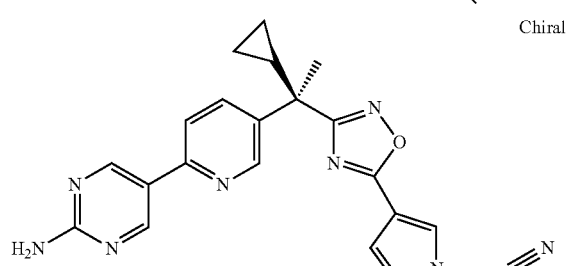
Chiral
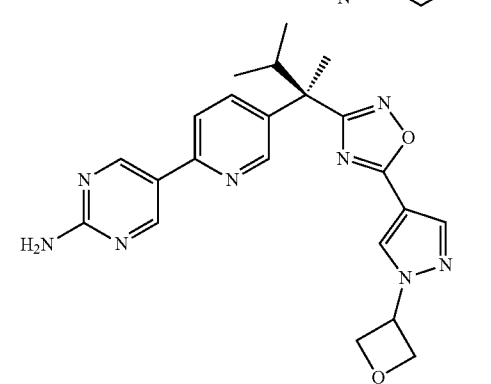
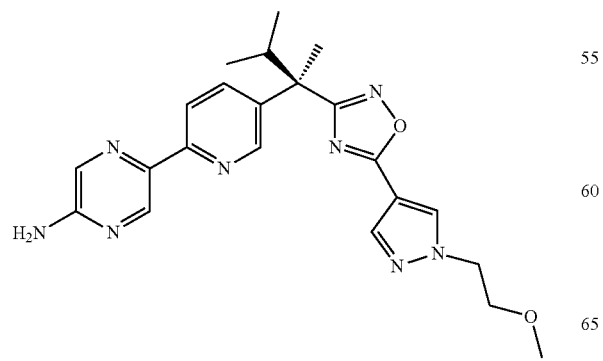
304
-continued
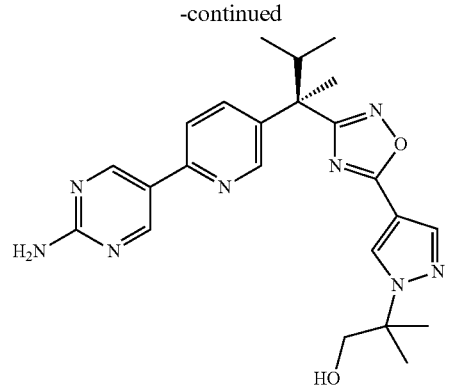
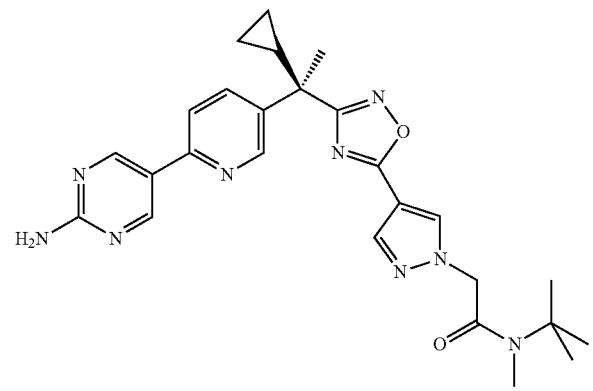
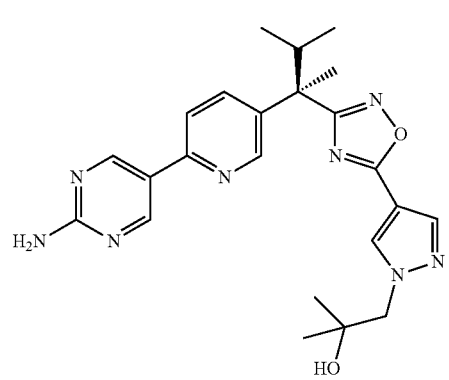
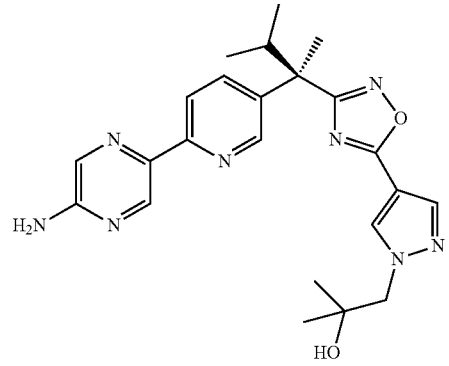

305
-continued
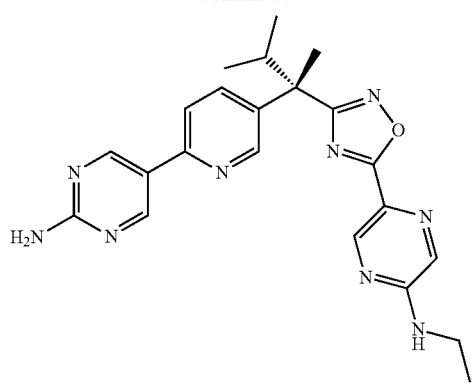
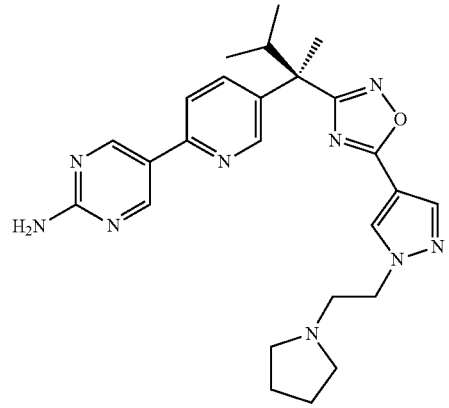
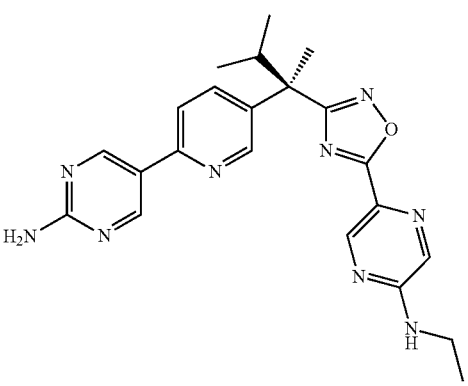
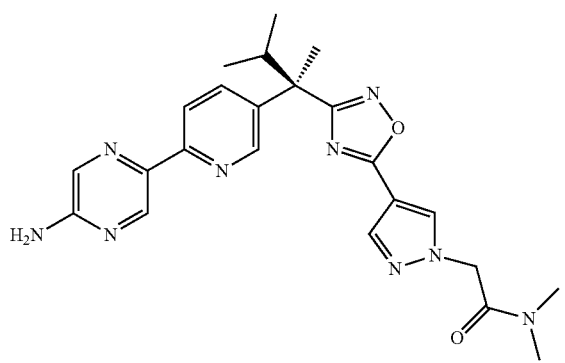
306
-continued
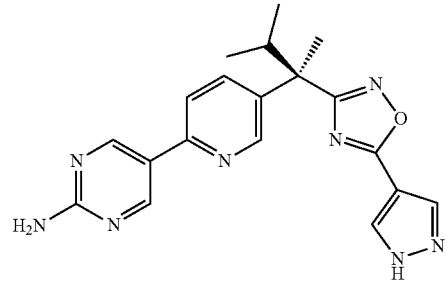
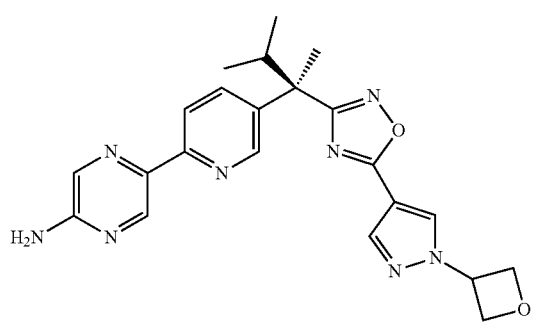
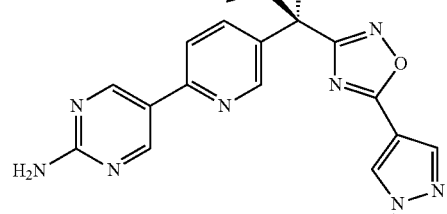
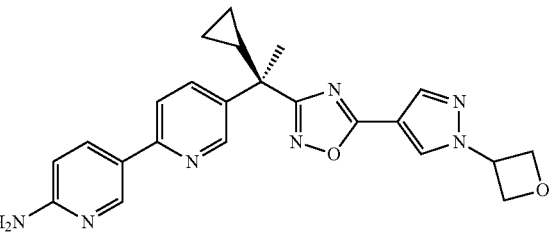
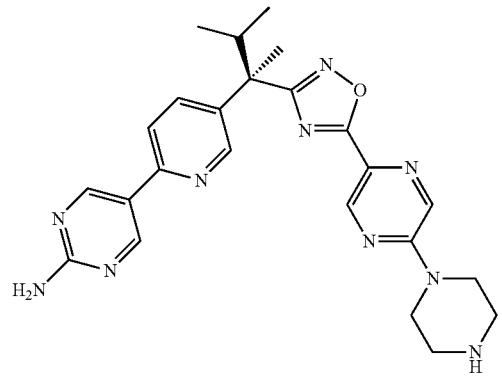

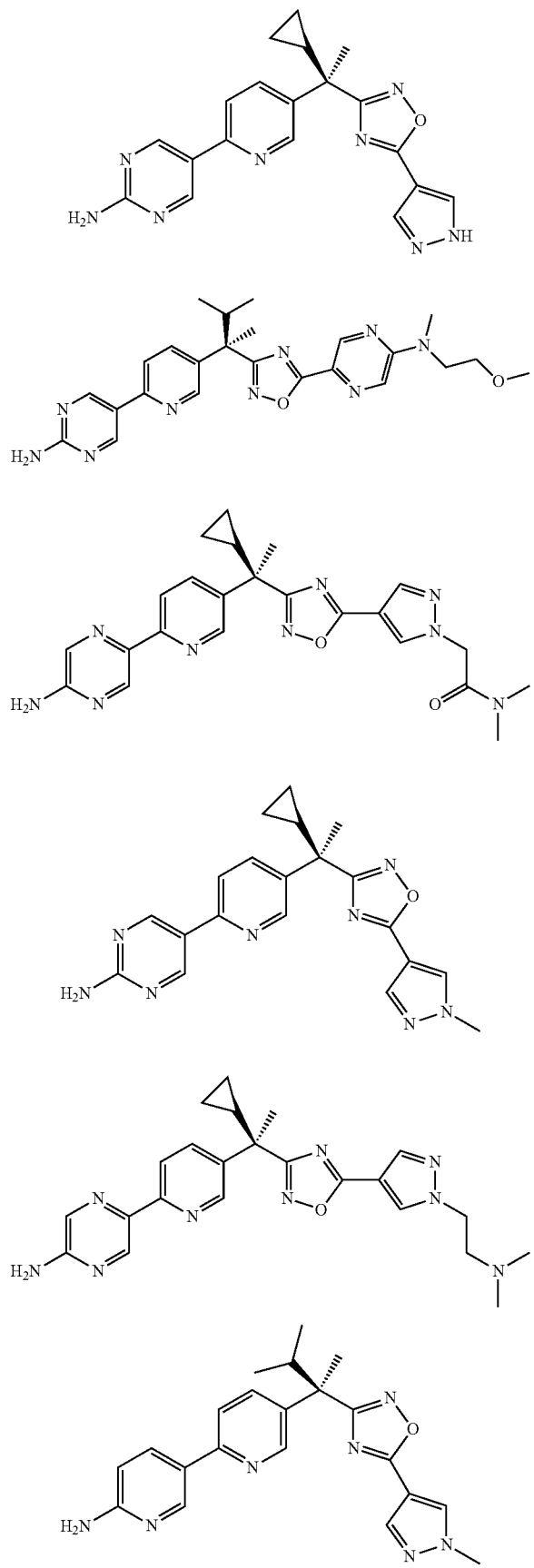
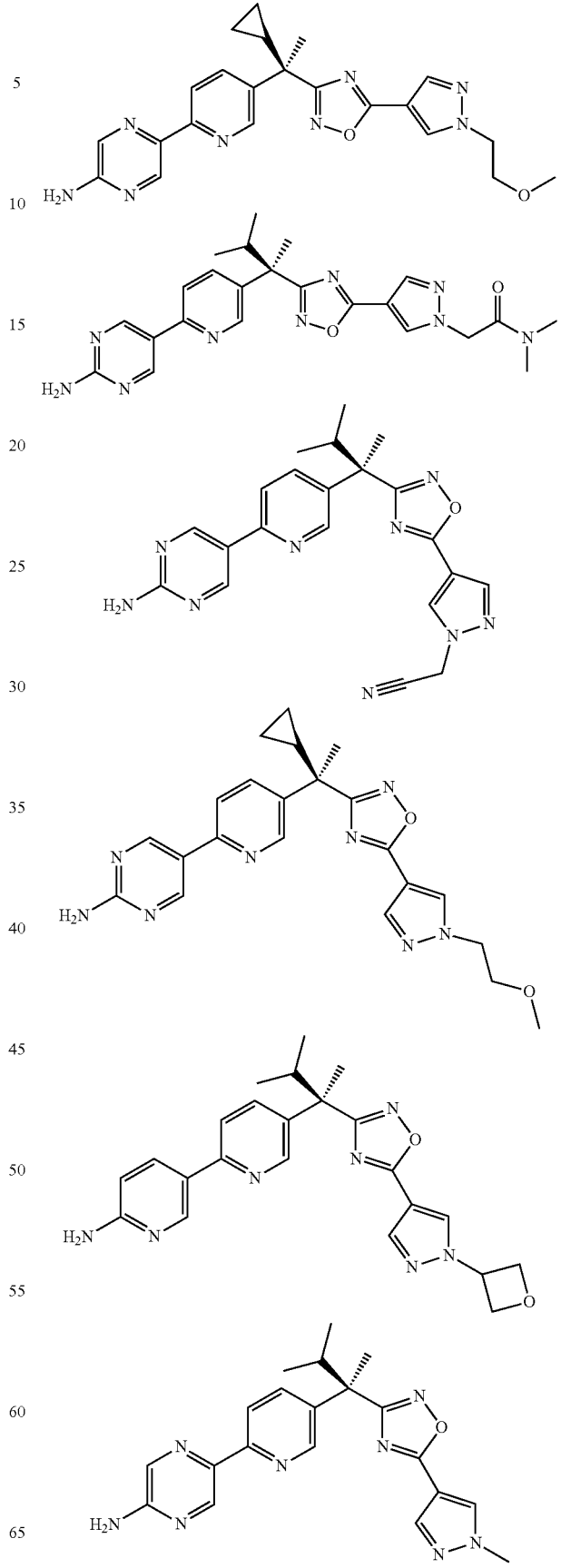

309
-continued
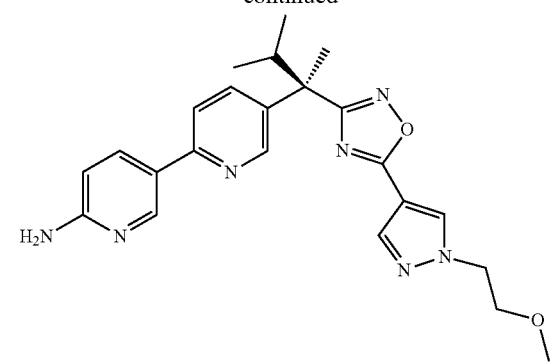
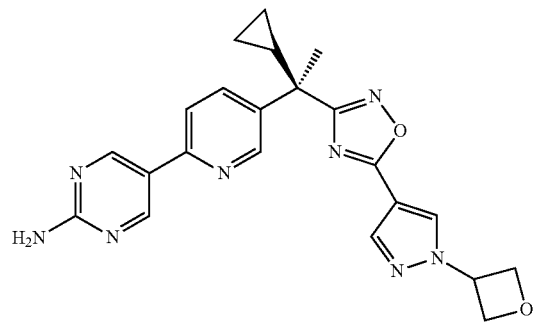
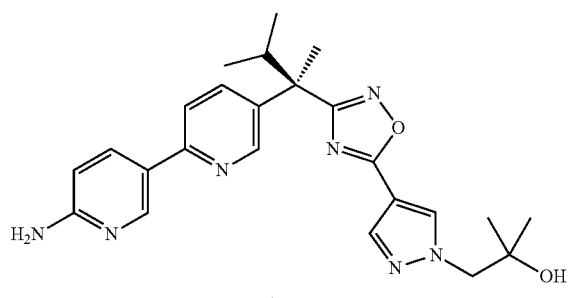
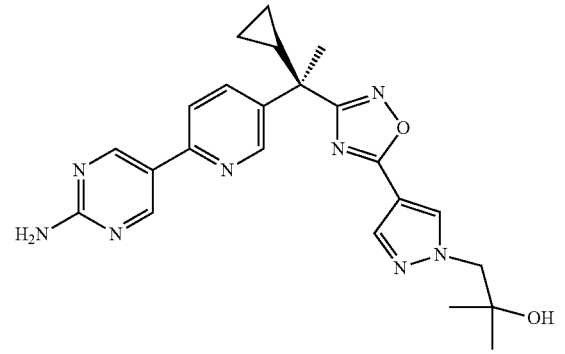
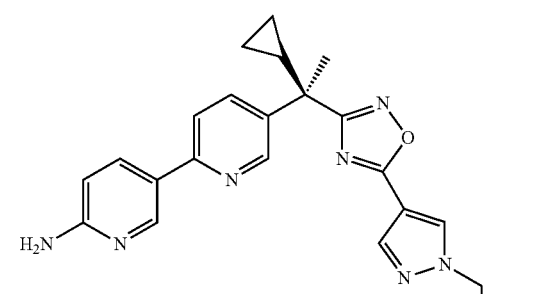
310
-continued
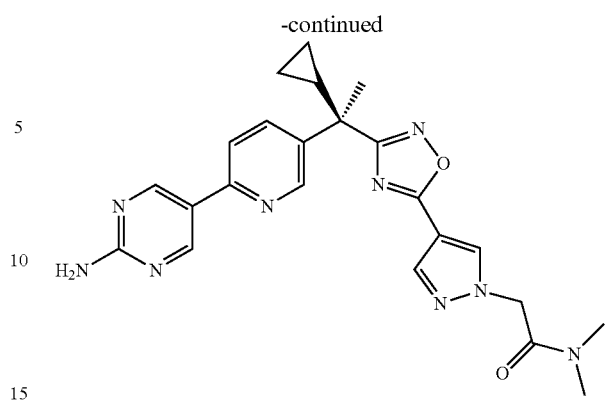
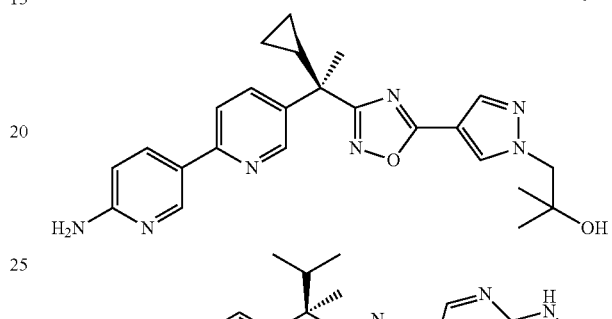
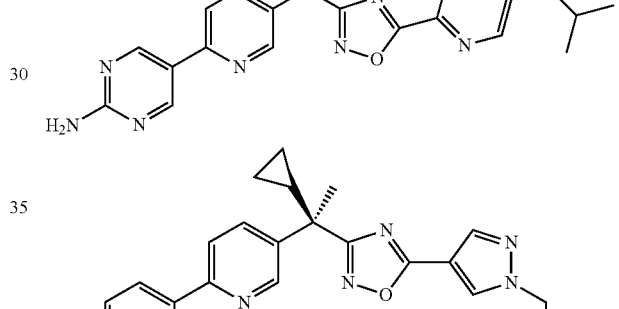
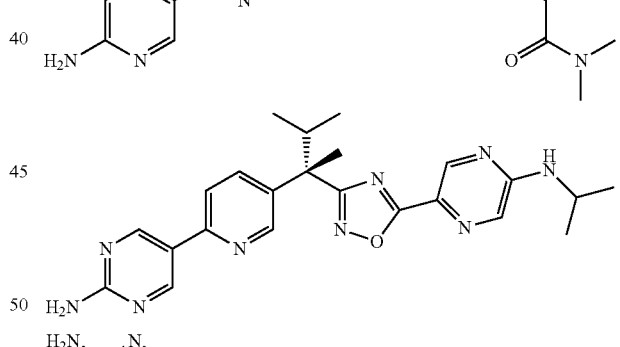
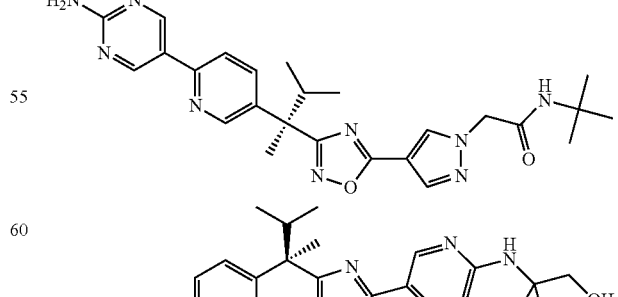
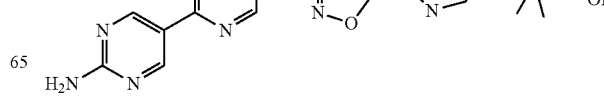

311
-continued
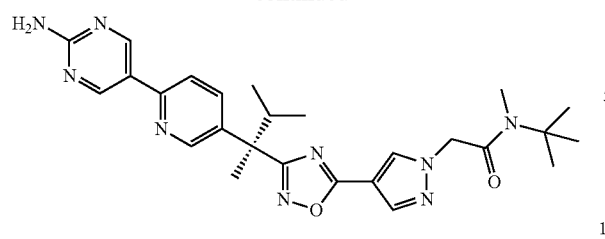
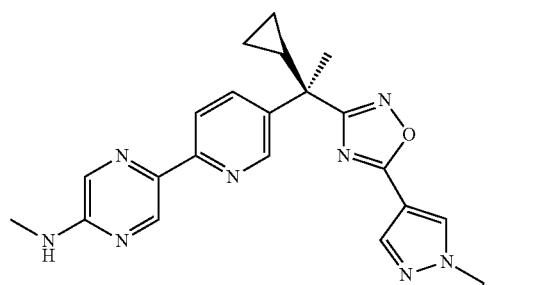
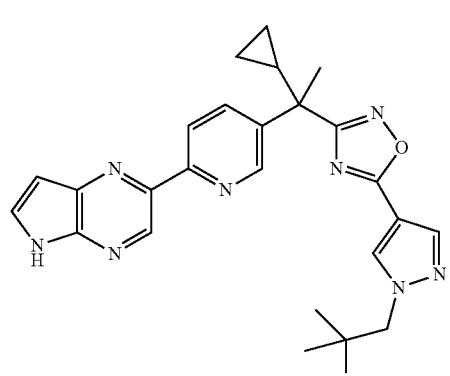
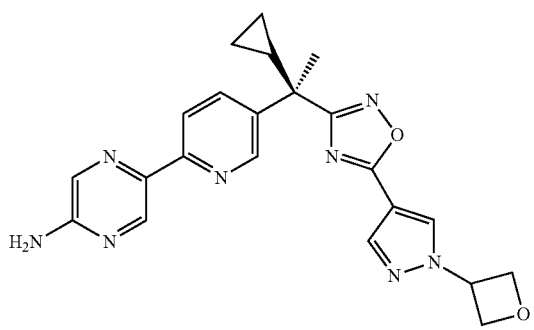
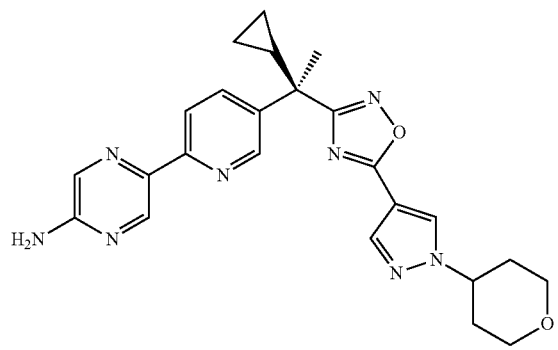
312
-continued
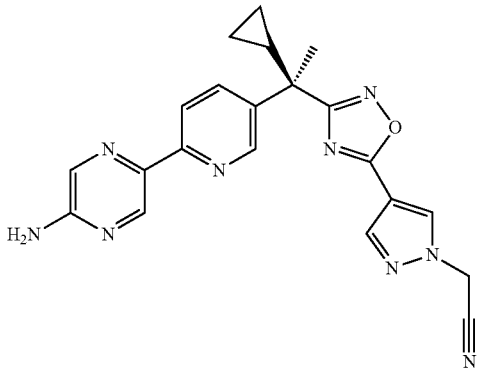
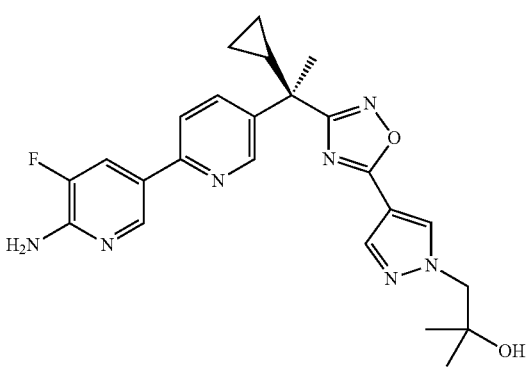
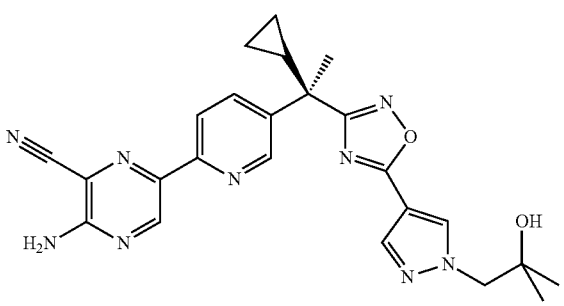
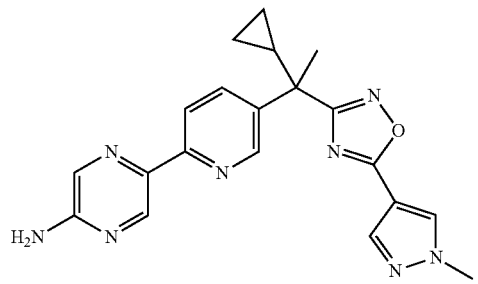

313
-continued

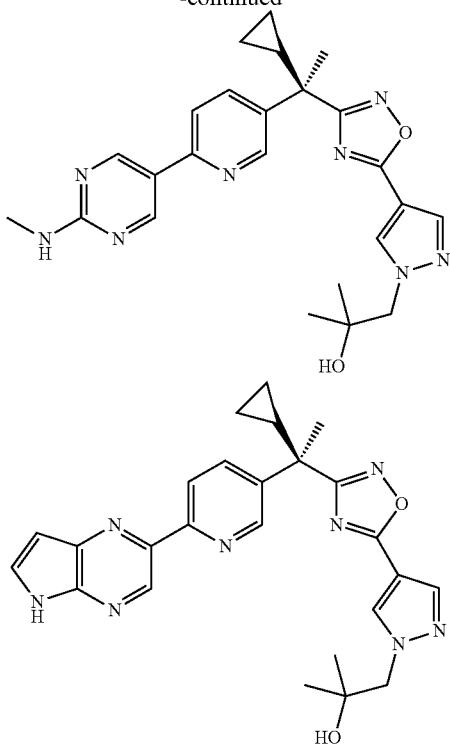

314
-continued

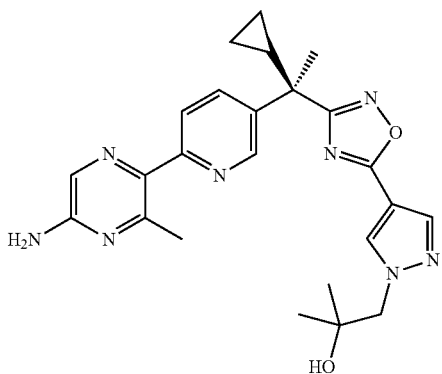

or pharmaceutically acceptable salts thereof.

15. A pharmaceutical composition comprising a compound according to claim 1, or a pharmaceutically acceptable salt thereof, and a pharmaceutically acceptable excipient and/or carrier.

16. A method of treating atherosclerosis comprising administering an effective amount of a compound according to claim 1 or a pharmaceutically acceptable salt thereof, to a patient in need thereof.

* * * * *